United States Patent
Fevre et al.

(10) Patent No.: US 12,280,080 B2
(45) Date of Patent: Apr. 22, 2025

(54) ANTIBACTERIAL COMPOSITION AND USES THEREOF

(71) Applicant: ERYTECH PHARMA, Lyons (FR)

(72) Inventors: Cindy Fevre, Paris (FR); Hélène Blois, Paris (FR); Mathieu Medina, Saint Denis (FR)

(73) Assignee: ERYTECH PHARMA, Lyons (FR)

( * ) Notice: Subject to any disclaimer, the term of this patent is extended or adjusted under 35 U.S.C. 154(b) by 0 days.

(21) Appl. No.: 18/344,924

(22) Filed: Jun. 30, 2023

(65) Prior Publication Data

US 2024/0024391 A1 Jan. 25, 2024

Related U.S. Application Data

(63) Continuation of application No. 16/491,176, filed as application No. PCT/EP2018/055629 on Mar. 7, 2018, now Pat. No. 11,690,885.

(30) Foreign Application Priority Data

Mar. 8, 2017 (EP) .................................. 17305245

(51) Int. Cl.
| | | |
|---|---|---|
| A61K 35/76 | (2015.01) | |
| A01N 63/40 | (2020.01) | |
| A61P 31/04 | (2006.01) | |
| C07K 14/005 | (2006.01) | |
| C12N 7/00 | (2006.01) | |
| C12Q 1/18 | (2006.01) | |
| A61K 38/00 | (2006.01) | |

(52) U.S. Cl.
CPC .............. *A61K 35/76* (2013.01); *A01N 63/40* (2020.01); *A61P 31/04* (2018.01); *C07K 14/005* (2013.01); *C12N 7/00* (2013.01); *C12Q 1/18* (2013.01); *A61K 38/00* (2013.01); *C12N 2795/10122* (2013.01); *C12N 2795/10131* (2013.01); *C12N 2795/10132* (2013.01); *C12N 2795/10171* (2013.01); *C12N 2795/10222* (2013.01); *C12N 2795/10231* (2013.01); *C12N 2795/10232* (2013.01); *C12N 2795/10271* (2013.01)

(58) Field of Classification Search
None
See application file for complete search history.

(56) References Cited

U.S. PATENT DOCUMENTS

| | | |
|---|---|---|
| 10,077,431 B2 | 9/2018 | Pouillot et al. |
| 10,260,051 B2 | 4/2019 | Pouillot et al. |
| 10,898,530 B2 | 1/2021 | Pouillot et al. |
| 10,918,680 B2 | 2/2021 | Pouillot et al. |
| 11,690,885 B2 | 7/2023 | Fevre et al. |
| 2010/0203019 A1 | 8/2010 | Yoon et al. |
| 2021/0060100 A1 | 3/2021 | Pouillot et al. |
| 2021/0228659 A1 | 7/2021 | Pouillot et al. |

FOREIGN PATENT DOCUMENTS

| | | |
|---|---|---|
| KR | 20130-142820 | 12/2013 |
| WO | WO 2009/087356 | 7/2009 |
| WO | WO 2010/033546 | 3/2010 |
| WO | WO 2017/015652 | 1/2017 |

OTHER PUBLICATIONS

Deghorain, M. et al. "The Staphylococci Phages Family: An Overview" *Viruses*, 2012, pp. 3316-3335, vol. 4, No. 12.
Database EMBL [Online] Accession No. AB626963, "*Staphylococcus* phage S13' DNA, complete genome" Dec. 22, 2011, pp. 1-10, XP-002770466.
Hsieh, S.-E. et al. "Genomic analysis of *Staphylococcus* phage Stau2 isolated from medical specimen" *Virus Genes*, 2016, pp. 107-116, vol. 52, No. 1.
Written Opinion in International Application No. PCT/EP2018/055629, Jun. 4, 2018, pp. 1-11.
El Haddad, L. et al. "Efficacy of two *Staphylococcus aureus* phage cocktails in cheese production" *International Journal of Food Microbiology*, 2016 (available online Oct. 5, 2015), pp. 7-13, vol. 217.
Gibson, D. G. et al. "Creation of a Bacterial Cell Controlled by a Chemically Synthesized Genome" *Science*, pp. 1-7, supplemental pp. 1-5, May 20, 2010, vol. 329, No. 5987.
Smith, H. O. et al. "Generating a synthetic genome by whole genome assembly: ΦX174 bacteriophage from synthetic oligonucleotides" *PNAS*, Dec. 23, 2003, pp. 15440-15445, vol. 100, No. 26.
EMBL Database No. JX846613, *Staphylococcus* phage vB_SauM_Romulus, complete genome, Mar. 12, 2013, pp. 1-75.
EMBL Database No. JX846612, *Staphylococcus* phage vB_SauM_Romulus, complete genome, Aug. 15, 2013, pp. 1-78.
EMBL Database No. JX194239, *Staphylococcus* phage SA11, complete genome, Aug. 1, 2012, pp. 1-68.
EMBL Database No. KX532239, *Staphylococcus* phage StAP1, complete genome, Jan. 20, 2017, pp. 1-78.
EMBL Database No. KP881332, *Staphylococcus* phage Stau2, complete genome, Jan. 7, 2016, pp. 1-78.

*Primary Examiner* — Nicole Kinsey White
(74) *Attorney, Agent, or Firm* — SALIWANCHIK, LLOYD & EISENSCHENK

(57) ABSTRACT

The present invention relates to bacteriophage therapy. More particularly, the present invention relates to novel bacteriophages having a high specificity against *Staphylococcus aureus* strains, their manufacture, components thereof, compositions comprising the same and the uses thereof in phage therapy and as companion diagnostic.

11 Claims, No Drawings
Specification includes a Sequence Listing.

ANTIBACTERIAL COMPOSITION AND USES THEREOF

CROSS-REFERENCE TO RELATED APPLICATIONS

This application is a continuation of U.S. application Ser. No. 16/491,176, filed Sep. 5, 2019, now U.S. Pat. No. 11,690,885, which is the U.S. national stage application of International Patent Application No. PCT/EP2018/055629, filed Mar. 7, 2018.

The Sequence Listing for this application is labeled "Seq-List.xml" which was created on Jun. 16, 2023 and is 311,655 bytes. The entire content of the sequence listing is incorporated herein by reference in its entirety.

The present invention relates to novel bacteriophage compositions, their manufacture and the uses thereof. The invention is particularly suited for the treatment of an infection in human and animals.

BACKGROUND OF THE INVENTION

Bacteriophages (or phages) are small viruses displaying the ability to infect and kill bacteria while they do not affect cells from other organisms. Initially described a century ago by William Twort, and independently discovered shortly thereafter by Felix d'Herelle, more than 6000 different bacteriophages have been exposed so far and described morphologically, including bacterial and archeal viruses. The vast majority of these viruses are tailed, while a small proportion is polyhedral, filamentous or pleomorphic. They may be classified according to their morphology, their genetic content (DNA vs. RNA), their specific host, the place where they live (marine virus vs. other habitats), and their life cycle. As intra-cellular parasites of bacterial cells, phages display different life cycles within the bacterial host: lytic, lysogenic and pseudo-lysogenic (Weinbauer, 2004; Drulis-Kawa, 2012). Lytic phages cause lysis of the host bacterial cell as a normal part of their life cycles. Lysogenic phages (also termed temperate phages) can either replicate by means of the lytic life cycle and cause lysis of the host bacterium, or they can incorporate their DNA into the host bacterial DNA and become noninfectious prophages. Pseudolysogeny can be defined as the stage of stalled development of a bacteriophage in a host cell without multiplication or replication (M Łoś, 2012). Whatever the type of phage cycle, the first step is the attachment to receptors of the bacterial cell wall before phage genetic material may enter into the bacteria. This specific process defines the spectrum of bacteria that a phage interacts with.

Bacteriophages are commonly used as research tools to modify bacteria in laboratory experiments.

Because of their target host cell specificity, the use of phages as a therapy to treat acute and chronic infections has been considered, particularly in dermatology, ophthalmology, urology, stomatology, pediatrics, otolaryngology or surgery. This concept of therapeutic use of phages to treat bacterial infections was, however, highly controversial from the very beginning and not widely accepted by the public or medical community. Early studies were widely criticized for lacking appropriate controls and inconsistent results. The lack of reproducibility and many conflicting results obtained in various published studies led the Council on Pharmacy and Chemistry of the American Medical Association to conclude that the evidence for the therapeutic value of lytic filtrates was for the most part contradictory, unconvincing, and recommended additional research to confirm its purported benefits.

Since the introduction of antibiotics in the 1940s, little attention was paid to this field of therapeutics, especially in the Western world. But the extensive use of antibiotics has led to the widespread emergence of antibiotic-resistant bacteria around the world, causing increasingly serious problems. It has therefore become a major challenge to overcome the remaining limited therapeutic options, which are still available to treat major multi-drug resistant microbes.

*Staphylococcus aureus* (*S. aureus*) is a gram-positive cocci bacterium which is frequently found in the nose, respiratory tract, and on the skin. *S. aureus* distinguishes from other staphylococcal species on the basis of the gold colonies pigmentation and positive results of coagulase, mannitol-fermentation, and deoxyribonuclease test. *S. aureus* is one of the most important pathogens worldwide and has emerged as a prominent organism infecting critically ill persons.

*S. aureus* can be a commensal but also a dangerous pathogen. Approximately 30% of the human population is colonized with *S. aureus*. *S. aureus* infection is a major cause of skin, soft-tissue, respiratory, bone, joint and endovascular disease like for example skin abscesses, wound infections, endocarditis, osteomyelitis, pneumonia, and toxic shock syndrome. *S. aureus* is particularly adept at infecting foreign bodies within the human host. In those cases, *S. aureus* typically forms a biofilm on the surface of a foreign device (such as implantable cardiac devices, intravascular catheter, prostheses, stents), making eradication of the infection without surgical removal of the device all but impossible. *S. aureus* can acclimatize to live inside cells, where it finds protection from host defense mechanisms and from most antibiotics.

The number of staphylococcal infections continues to increase while the treatment of these infections becomes even more difficult because of the emergence of staphylococcal strains resistant to multiple antibiotics, including methicillin or vancomycin. In the United States and United Kingdom, 40% to 60% of nosocomial *S. aureus* strains are multidrug resistant.

Therefore, there is a great need for new antibacterial agents or compositions that can be used to destroy or control *S. aureus* strains, suitable for use in human or animal therapy as well as for decontaminating materials.

Experimental phage therapy against *S. aureus* has been tested in mice (Capparelli et al., 2007), without development for human use. Therefore, in view of the high resistance-acquisition potency of *S. aureus*, there is a need for new antibacterial agents or compositions that can be used to kill *S. aureus* strains including the troublesome methicillin-resistant strains (MRSA).

SUMMARY OF THE INVENTION

The inventors have isolated and characterized new bacteriophages presenting strong lytic activity against *Staphylococcus aureus* (*S. aureus*) strains. These bacteriophages, alone or in combinations, provide very potent antibacterial effect and can be used as active agents in pharmaceutical or veterinary preparations, particularly to treat *S. aureus* bacterial infections.

An object of the invention is to provide antibacterial compositions comprising at least one bacteriophage having lytic activity against at least one *Staphylococcus aureus* (*S. aureus*) strain, said at least one bacteriophage being selected from the bacteriophages having a genome comprising a nucleotide sequence of anyone of SEQ ID NOs: 1 to 4 or a sequence having at least 90% identity thereto.

A further object of the invention relates to a bacteriophage having lytic activity to a *S. aureus* strain and having a genome comprising a nucleotide sequence selected from anyone of SEQ ID NOs: 1 to 4 or a sequence having at least 95% identity thereto.

The invention further concerns an isolated nucleic acid molecule contained in a bacteriophage of the invention, preferably an isolated nucleic acid molecule comprising a nucleotide sequence selected from anyone of SEQ ID NOs: 1 to 4 or a sequence having at least 95% identity thereto, as well as an isolated polypeptide encoded by said nucleic acid.

Another object of the invention is a composition comprising a nucleic acid or polypeptide as defined above.

The compositions of the invention typically further comprise a pharmaceutically or veterinary acceptable excipient or carrier. They may be liquid, semi-liquid, solid or lyophilized.

Another object of the invention relates to a bacteriophage, nucleic acid, polypeptide or composition as defined above, for use in the treatment of an infection in humans and animals, for modifying the microbial flora of the human or animal, for decontaminating a material, for killing or controlling a *S. aureus* bacterium, and/or for compromising the integrity of a bacterial biofilm generated by a *S. aureus* bacterium, and/or for decontaminating food and beverage.

The invention also relates to a bacteriophage, nucleic acid, polypeptide or composition as defined above, for use to improve a subject condition by modifying the microbial flora in said subject. The microbial flora may be modified by correcting, adapting or restoring a proper balance of microorganisms in said flora.

The invention also relates to a method for treating an infection in humans or animals, comprising the administration to said humans or animals of at least one bacteriophage, nucleic acid, polypeptide or composition as defined above.

The invention also relates to a method for treating a surface or material suspected of being contaminated with a *S. aureus* bacterium, comprising applying to said surface or material at least one bacteriophage, nucleic acid, polypeptide or composition as defined above. The surface or material may be a surface of any device, vessel, laboratory material, clothing, footwear, military equipment, air cooling systems, housings, etc.

A further object of the invention relates to a kit comprising a composition as defined above and a mean for applying the same to a subject or a surface.

The invention may be used on and in any human or animal, preferably human beings, or to treat any material, including laboratory materials or medical devices inside or outside human or animals.

Another object of the invention relates to a method for determining a cocktail of bacteriophages effective against a *S. aureus* strain target, comprising:

a) separately contacting a targeted *S. aureus* strain, or a sample containing said strain, with (i) a bacteriophage having a genome comprising a nucleotide sequence of SEQ ID NO: 1 or a sequence having at least 90% identity thereto, and/or (ii) a bacteriophage having a genome comprising a nucleotide sequence of SEQ ID NO: 2 or a sequence having at least 90% identity thereto, and/or (iii) a bacteriophage having a genome comprising a nucleotide sequence of SEQ ID NO: 3 or a sequence having at least 90% identity thereto, and/or (iv) a bacteriophage having a genome comprising a nucleotide sequence of SEQ ID NO: 4 or a sequence having at least 90% identity thereto, and (v) one or more combinations thereof, b) selecting bacteriophage(s) which exhibit(s) lytic activity on the strain, c) optionally further selecting active bacteriophages which, when combined together, exhibit synergistic activity on the strain; and/or d) optionally further selecting active bacteriophages which, when combined together, exhibit no antagonism; and/or e) optionally selecting active bacteriophages which belong to different genus; and f) combining said selected bacteriophages.

DETAILED DESCRIPTION OF THE INVENTION

The present invention relates to novel bacteriophages, components thereof, compositions comprising the same, their manufacture, and the uses thereof as antibacterial agents, particularly for the treatment of an infection in humans or animals or for improving a subject condition by modifying the microbial flora in said subject.

Definitions

To facilitate understanding of the invention, a number of terms are defined below.

As used herein, the term "bacteriophage" or "phage" refers to a functional phage particle comprising a nucleic acid genome packaged in a proteinaceous envelope or capsid. The term also refers to portions of the bacteriophage, including, e.g., a head portion, or an assembly of phage components, which provide substantially the same functional activity.

The term "phenotypic characteristic" designates more preferably the morphology and/or host-range of a bacteriophage. Methods for phenotyping bacteriophages are well known per se in the part and include, for example, determining bacterial host range and/or activity against the biofilm produced by certain bacterial strains.

The term "lytic activity" as used in the invention designates the property of a bacteriophage to cause lysis of a bacterial cell. The lytic activity of a bacteriophage can be tested on *S. aureus* strains according to techniques known per se in the art (see also experimental section).

The term "variant" of a reference bacteriophage designates a bacteriophage having variation(s) in the genomic sequence and/or polypeptide(s) encoded thereby as compared to said reference bacteriophage. Said variants may have different phenotypic characteristics such as a different bacterial host range compared to the reference bacteriophage. In a particular aspect, a variant may be obtained by directed evolution (also called phage training) which allows the variant to acquire a lytic activity on one or several bacterial strains. Variants typically exhibit the same morphology compared to the reference bacteriophage. Typically, the reference bacteriophage has a nucleic acid sequence comprising a sequence selected from anyone of SEQ ID NOs: 1-4. Variants typically comprise e.g., silent mutations, conservative mutations, minor deletions, and/or minor replications of genetic material. In a preferred embodiment, variants according to the invention retain any observable characteristic or property that is dependent upon the genome of the bacteriophage of the invention, e.g., phenotypic characteristics of said bacteriophage and/or lytic activity against the *S. aureus* strains. Preferred variants have less than 5% nucleic acid variation as compared to the genome of the reference bacteriophage, even more preferably less than 4%, more preferably less than 2%. Alternatively, or in combination, variants have preferably less than 5% amino acid variation in a coded polypeptide sequence as compared to a polypeptide of the reference bacteriophage.

The term "specific" or "specificity" in relation to a bacteriophage refers to the type of host that said bacteriophage is able to infect. A bacteriophage "specific" for S. aureus more preferably designates a bacteriophage which can infect one or several S. aureus strains and which essentially does not infect non-S. aureus bacteria under physiological conditions.

As used herein, the term "polypeptide" refers to polypeptides of any size, including small peptides of e.g., from 5 to 20 amino acids, longer polypeptides, proteins or fragments thereof.

In the context of the present specification, the term "isolated bacteriophage" should be considered to mean a bacteriophage that is removed from its natural environment and/or separated from a component of its natural environment and or is issued from directed evolution. The term designates, particularly, a phage that is e.g., cultivated in vitro, purified, and/or formulated with any suitable product for formulation, such as diluent(s) or excipient(s). In relation to a nucleic acid or polypeptide, the term "isolated" designates e.g., a nucleic acid molecule or polypeptide which is separated from at least one component of its natural environment such as, e.g., a protein, lipid, carbohydrate and/or nucleic acid.

The terms "pharmaceutically or veterinary acceptable" as used herein refers to any material (e.g., carrier, excipient or diluent) that is compatible for use in a human or animal subject. Such includes physiologically acceptable solutions or vehicles that are harmless or do not cause any significant specific or non-specific immune reaction to an organism or do not abrogate the biological activity of the active compound. For formulation of the composition into a liquid preparation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If necessary, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, or powdered formulations, and aerosolized formulations such as liquids or powders.

As used herein, "PFU" means plaque forming unit, as it is well defined in the art. Lytic bacteriophages lyse the host cell, causing a zone of clearing (or plaque) on a culture plate. Theoretically, each plaque is formed by one phage and the number of plaques multiplied by the dilution factor is equal to the total number of phages in a test preparation.

As used herein, "CFU" means colony forming unit, as it is well defined in the art for estimating the number of viable bacteria in a sample.

The term "treatment" or "therapy" designates a curative or a prophylactic treatment of a disease. A curative treatment is defined as a treatment that results in a cure of a disease, or a treatment that alleviates, reduces, stabilizes, or eliminates the symptoms of a disease or the suffering that it causes, directly or indirectly, or that improves a subject condition or reduces progression of a disease. A prophylactic treatment comprises a treatment resulting in the prevention of a disease, and/or a treatment reducing and/or delaying the incidence of a disease or the risk of its occurrence.

The term "biofilm" as used herein designates a heterogeneous bacterial formation growing on various surfaces; preferably a bacterial community growing embedded in an exopolysaccharide matrix adhered onto solid biological or non-biological surfaces.

The term "compromise" as used herein refers to any alteration of the integrity. By compromising a bacterial biofilm, it is understood a denaturation and/or a penetration of the biofilm by bacteriophage, an infection of biofilm-associated bacteria and/or a lysis thereof and/or a partial or an entire clearing of the biofilm (i.e., by stopping colonization and/or disrupting biofilms).

The term "sample", as used herein, means any sample, such as biological samples, particularly samples containing cells. Examples of samples include body fluids such as blood, plasma, saliva, faeces or urine, as well as biopsies, organs, tissues or cell samples. The sample may be treated.

As used herein, the term "subject" or "patient" refers to an animal, preferably a human, including adult and child. The term "subject" also encompasses animals, such as and not limited to pets (e.g., dogs, cats), farm species, such as horses, cows, goats, pigs, sheep, poultry, non-human primates, and fishes, shells, shrimps etc. . . . .

The term "efficacy" of treatment or "response" to a bacteriophage therapy as used herein refers to a treatment which results in a decrease in the number of S. aureus strains in a subject after bacteriophage treatment when compared to the number of S. aureus strains before treatment. A "good responder" subject refers to a subject who shows or will show a clinically significant recovery when treated with a bacteriophage therapy.

The term "cocktail" of bacteriophages designates a combination of different bacteriophages. The bacteriophages in a cocktail are preferably formulated together in a same vessel or packaging, although they may be used as kits of parts wherein some of the bacteriophages are formulated or packaged separately and combined when used or administered.

The term "sequence identity" as used herein is determined by comparing two optimally aligned sequences over a comparison window, where the fragment of the polynucleotide in the comparison window may comprise additions or deletions (e.g., gaps or overhangs) as compared to the reference sequence, which does not comprise additions or deletions, for optimal alignment of the two sequences. The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BEST-FIT, BLAST, PASTA, and TFASTA in the Wisconsin Genetics Software Package, Genetics Computer Group (GCG), 575 Science Dr., Madison, WI), or by inspection.

Description of Embodiments

The present invention is related to novel bacteriophage therapies of *S. aureus* infections. More particularly, the present invention relates to novel bacteriophages having high lytic activity against *S. aureus* strains, their manufacture, components thereof, compositions comprising the same and the uses thereof in phage therapy.

Bacteriophages

In a first aspect, the invention discloses the isolation and characterization of novel bacteriophages having lytic activity against *S. aureus* strains and which exhibit, either alone or in combination(s), remarkable host range spectrum of lytic activity. These bacteriophages have been isolated, sequenced, and characterized. They are, individually and in combination(s), active against *S. aureus* strains. They are remarkably effective against pathogenic *S. aureus* strains, including antibiotic-resistant *S. aureus* strains such as a Methicillin-Resistant *Staphylococcus aureus* (MRSA) strain. These bacteriophages can be combined and formulated in conditions suitable for use as pharmaceutical or veterinary agents to exhibit very potent antibacterial effect against a controlled spectrum of *S. aureus* strains.

More specifically, the following bacteriophages have been isolated. Their corresponding nucleic acid sequence is also indicated.

TABLE 1

| Bacteriophage | SEQ ID |
| --- | --- |
| PN1137 | SEQ ID NO: 1 |
| PN1493 | SEQ ID NO: 2 |
| PN1815 | SEQ ID NO: 3 |
| PN1957 | SEQ ID NO: 4 |

The lytic profile of these bacteriophages has been determined on a wide range of *S. aureus* strains. The results show a broad spectrum of activity (specific and total) for the four bacteriophages of the invention. These four bacteriophages are members of the Caudovirales order.

The bacteriophage PN1137 is a member of the Podoviridae family and has the nucleic acid sequence of SEQ ID NO: 1 which comprises 17,213 nucleotides. It exhibits a specific lytic activity on 46 out of the 109 *S. aureus* strains tested, which represents 42.2% of the strains. Further, bacteriophage PN1137 exhibits a total lytic activity on 81 of the 109 strains tested, which represents 74.31% of the strains.

The bacteriophage PN1493 is a member of the Myoviridae family and has the nucleic acid sequence of SEQ ID NO: 2 which comprises 134,876 nucleotides. It exhibits a specific lytic activity on 86 out of the 109 *S. aureus* strains tested, which represents 78.9% of the strains. Further, bacteriophage PN1493 exhibits a total lytic activity on 108 of the 109 strains tested, which represents 99.08% of the strains.

The bacteriophage PN1815 is a member of the Myoviridae family and has the nucleic acid sequence of SEQ ID NO: 3 which comprises 136,156 nucleotides. It exhibits a specific lytic activity on 59 out of the 109 *S. aureus* strains tested, which represents 54.13% of the strains. Further, bacteriophage PN1815 exhibits a total lytic activity on 108 of the 109 strains tested, which represents 99.08% of the strains.

The bacteriophage PN1957 is a member of the Podoviridae family and has the nucleic acid sequence of SEQ ID NO: 4 which comprises 17,629 nucleotides. It exhibits a specific lytic activity on 71 out of the 109 *S. aureus* strains tested, which represents 65.14% of the strains. Further, bacteriophage PN1957 exhibits a total lytic activity on 95 of the 109 strains tested, which represents 87.16% of the strains.

Combinations of those bacteriophages have a specific lytic activity which covers at least 74 of the strains (67%). Particularly, together bacteriophages PN1493 and PN1957 have a specific lytic activity which covers 98 of the *S. aureus* strains (89.9%) and a total lytic activity which covers 100% of the *S. aureus* strains.

A particular object of the invention thus resides in a bacteriophage having lytic activity to a *S. aureus* strain and having a genome comprising a nucleotide sequence selected from anyone of SEQ ID NOs: 1 to 4 or a sequence having at least 95% identity thereto, preferably at least 96%, 97%, 98% or 99% identity thereto.

The bacteriophages of the invention can be prepared by standard culture, isolation and purification methods. For example, *S. aureus* producing bacteria are cultured, infected by a sample of a bacteriophage, and then treated to remove bacterial cells and debris. The enriched bacteriophage solution can be plated in a medium, for example agar medium, with embedded susceptible host strains of *S. aureus* to obtain plaques. Then, single plaque can be picked out for subsequent bacteriophage purification and amplification. One or more cycles of selective amplification of bacteriophages of the invention may be performed, for example by mixing bacteriophages with the competent *S. aureus*, followed by addition of a growth medium and incubation at selected test growing conditions. Following centrifugation, the cleared amplified supernatant is filtered through filter and subjected to another cycle of selective amplification or tested for presence of lytic activity.

The titration of bacteriophages in a suspension and the visualization of plaque morphology of bacteriophages of the invention may then be assessed by known methods, for example by plaque counting. Additionally, processing bacteriophages of the invention in various forms (liquid, lyophilized, etc.) for short-, long-, freeze- or any other kind of storage can be carried out by any suitable method as it is well-known in the art (see e.g., Clark, 1962).

The lytic activity of the bacteriophages of the invention can be assessed by methods well-known in the art, such as plaque assay also known as double agar method, based on the growing of bacteriophage with potential host bacteria and followed by assessing their ability to kill the host bacterial cell. In the plaque assay method, the bacteriophage induces lysis of target *S. aureus* strains after a period of incubation in soft agar medium, resulting in zones of clearing on the plate known as plaques.

The bacteriophages of the invention may be cultured, expanded, isolated, purified, and used in e.g., phage therapy of *S. aureus*-mediated disorders, as will be disclosed in more details below. Furthermore, variants of these bacteriophages retaining a phenotypic character (e.g., lytic activity) of the bacteriophages can be produced and/or isolated by techniques known per se in the art.

Nucleic Acids and Polypeptides

The invention relates to a nucleic acid contained in a bacteriophage of the invention, or any fragment of such a nucleic acid. The term fragment designates, more preferably, a fragment containing (or consisting of) an open reading frame. The nucleic acid may be DNA or RNA, single- or double-stranded.

The nucleic acid can be isolated from the deposited bacteriophages, or produced using recombinant DNA technology (e.g., polymerase chain reaction (PCR) amplification, cloning), enzymatic or chemical synthesis, or combinations thereof, according to general techniques known per se in the art. Also included are homologous sequences and fragments thereof including, but not limited to, natural allelic variants and modified nucleic acid sequences in which nucleotides have been inserted, deleted, substituted, and/or inverted.

In a particular embodiment, the invention relates to a nucleic acid comprising a sequence selected from anyone of SEQ ID NOs: 1-4, or a sequence having at least 95%, 96%, 97%, 98%, 99% or more sequence identity to anyone of SEQ ID NOs: 1-4.

The nucleic acid of the invention can be in free form, or cloned in a vector, such as a plasmid, viral vector, expression cassette, cosmid, etc.

In a further aspect, the invention also relates to an isolated polypeptide encoded by a nucleic acid sequence as defined above, preferably a nucleic acid sequence selected from SEQ ID NO: 1, SEQ ID NO: 2, SEQ ID NO: 3, or SEQ ID NO: 4. The polypeptide(s) may be produced by techniques known per se in the art such as synthesis, recombinant technology, or combinations thereof. The polypeptides may be isolated or purified, and used as antibacterial agents or as reagents for in vitro analyses.

Compositions of the Invention

One aspect of the invention relates to compositions comprising at least one bacteriophage as described above, more preferably at least two or more and, optionally, a pharmaceutically or veterinary acceptable excipient. As described, the bacteriophages of the invention have very potent lytic activity against *S. aureus* strains. Combinations of these bacteriophages may be produced to expand the host spectrum and produce highly effective antibacterial compositions.

More particularly, the invention relates to an antibacterial composition comprising at least one bacteriophage having lytic activity against a *S. aureus* strain, said at least one bacteriophage being selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

In one aspect, a bacteriophage having a genome comprising a nucleotide sequence having at least 90% identity to anyone of SEQ ID NOs: 1-4, for example at least 91%, 92%, 93%, 94%, 95%, 96%, 97%, 98% or 99% identity to anyone of SEQ ID NOs: 1 to 4 may have the same phenotypic characteristics than the reference bacteriophage having the sequence of anyone of SEQ ID NOs: 1-4. Typically, said bacteriophage has the same bacteria host range. Such a bacteriophage typically comprises e.g., silent mutations, conservative mutations, minor deletions, and/or minor replications of genetic material.

In another aspect, a bacteriophage having a genome comprising a nucleotide sequence having at least 90% identity to anyone of SEQ ID NOs: 1 to 4, for example at least 91%, 92%, 93%, 94%, 95%, 96%, 97%, 98% or 99% identity to anyone of SEQ ID NOs: 1-4 may result from directed evolution (phage training) and may have a different bacteria host range. Typically, said bacteriophage has an activity on more bacteria strains compared to the reference bacteriophage having the sequence of anyone of SEQ ID NOs: 1-4.

Even more particularly, the invention relates to an antibacterial composition comprising at least two bacteriophages having lytic activity against a *S. aureus* strain, said at least two bacteriophages being selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

In another particular embodiment, the compositions of the invention comprise at least three, even more preferably at least four distinct bacteriophages selected from the bacteriophages having a genome comprising a nucleotide sequence of anyone of SEQ ID NOs: 1 to 4 or a sequence having at least 90% identity thereto, for example at least 91%, 92%, 93%, 94%, 95%, 96%, 97%, 98% or 99% identity thereto.

Specific examples of compositions of the invention comprise:

a bacteriophage having a genome comprising a nucleotide sequence of SEQ ID NO: 1 or a sequence having at least 90% identity thereto, and a bacteriophage having a genome comprising a nucleotide sequence of SEQ ID NO: 2 or a sequence having at least 90% identity thereto;

a bacteriophage having a genome comprising a nucleotide sequence of SEQ ID NO: 1 or a sequence having at least 90% identity thereto, and a bacteriophage having a genome comprising a nucleotide sequence of SEQ ID NO: 3 or a sequence having at least 90% identity thereto;

a bacteriophage having a genome comprising a nucleotide sequence of SEQ ID NO: 1 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 2 or a sequence having at least 90% identity thereto, and a bacteriophage having a genome comprising a nucleotide sequence of SEQ ID NO: 3 or a sequence having at least 90% identity thereto;

a bacteriophage having a genome comprising a nucleotide sequence of SEQ ID NO: 2 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 1 or a sequence having at least 90% identity thereto, a bacteriophage having a genome comprising a nucleotide sequence of SEQ ID NO: 2 or a sequence having at least 90% identity thereto, and a bacteriophage having a genome comprising a nucleotide sequence of SEQ ID NO: 3 or a sequence having at least 90% identity thereto;

a bacteriophage having a genome comprising a nucleotide sequence of SEQ ID NO: 1 or a sequence having at least 90% identity thereto, a bacteriophage having a genome comprising a nucleotide sequence of SEQ ID NO: 2 or a sequence having at least 90% identity thereto, and a bacteriophage having a genome comprising a nucleotide sequence of SEQ ID NO: 4 or a sequence having at least 90% identity thereto;

a bacteriophage having a genome comprising a nucleotide sequence of SEQ ID NO: 1 or a sequence having at least 90% identity thereto, a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto; or a bacteriophage having a genome comprising a nucleotide sequence of SEQ ID NO: 2 or a sequence having at least 90% identity thereto, a bacteriophage having a genome comprising a nucleotide sequence of SEQ ID NO: 3 or a sequence having at least 90% identity thereto, and a bacteriophage having a genome comprising a nucleotide sequence of SEQ ID NO: 4 or a sequence having at least 90% identity thereto.

In a specific embodiment, the compositions of the invention comprise at least:

a bacteriophage having a genome comprising a nucleotide sequence of SEQ ID NO: 1 or a sequence having at least 90% identity thereto;

a bacteriophage having a genome comprising a nucleotide sequence of SEQ ID NO: 2 or a sequence having at least 90% identity thereto;

a bacteriophage having a genome comprising a nucleotide sequence of SEQ ID NO: 3 or a sequence having at least 90% identity thereto; and a bacteriophage having a genome comprising a nucleotide sequence of SEQ ID NO: 4 or a sequence having at least 90% identity thereto.

The compositions of the invention may comprise the cocktails of bacteriophages as presented in Table 2:

TABLE 2

Cocktails of bacteriophages of the invention

| Cocktail | Bacteriophages |
|---|---|
| 1 | PN1137 + PN1493 |
| 2 | PN1137 + PN1815 |
| 3 | PN1137 + PN1957 |
| 4 | PN1493 + PN1815 |
| 5 | PN1493 + PN1957 |
| 6 | PN1815 + PN1957 |
| 7 | PN1137 + PN1493 + PN1815 |
| 8 | PN1137 + PN1493 + PN1957 |
| 9 | PN1137 + PN1815 + PN1957 |
| 10 | PN1493 + PN1815 + PN1957 |
| 11 | PN1137 + PN1493 + PN1815 + PN1957 |

The compositions of the invention may further comprise additional antibacterial agents, particularly other bacteriophages having distinct host specificity.

Most preferred compositions of the invention are lytic against more that 70% of all of the 109 bacterial strains of the panel determined by the Centre National de Référence des Staphylocoques de Lyon. This collection contains a vast number and variety of S. aureus strains which are those with the highest incidence in Europe and the United States of America.

The compositions of the invention may comprise any effective amount of the selected bacteriophage(s). Preferably, they comprise between $10^{e1}$ and $10^{e12}$ PFU/ml of each of said bacteriophages, preferably between $10^{e4}$ and $10^{e11}$ PFU/ml. The relative amounts of each type of bacteriophage in a composition of the invention may be adjusted by a skilled artisan. Typically, when the antibacterial composition comprises several (n) distinct bacteriophages as defined above, the total relative amount % A of each bacteriophage in the composition is more preferably % $A=(100/n_i) \times V$, wherein $n_i$ represents the number of distinct bacteriophages and V is a variability factor comprised between 0.2 and 5. Most preferably, V is comprised between 0.3 and 3, even more preferably between 0.5 and 2, generally between 0.8 and 1.5. In a preferred typical embodiment, each type of bacteriophage is present in a composition of the invention in approximately equal relative amounts.

The antibacterial compositions of the invention may be in various forms, such as liquid, semi-liquid, solid or lyophilized formulations. The compositions of the invention preferably comprise a suitable diluent or carrier, such as a pharmaceutically or veterinary acceptable excipient or carrier. Compositions according to the present invention may include any excipient or carrier, such as thickeners, diluents, buffers, preservatives, surface active agents and the like, in addition to the bacteriophage(s) of choice. Such includes physiologically acceptable solutions or vehicles that are harmless or do not cause any significant specific or non-specific immune reaction to an organism or do not abrogate the biological activity of the bacteriophage. For liquid formulation, saline, sterile water, Ringer's solution, buffered physiological saline, albumin infusion solution, dextrose solution, maltodextrin solution, glycerol, ethanol, and mixtures thereof may be used as a pharmaceutically or veterinary acceptable excipient or carrier. If appropriate, other conventional additives such as thickeners, diluents, buffers, preservatives, surface active agents, antioxidants and bacteriostatic agents may be added. Further, diluents, dispersants, surfactants, binders and lubricants may be additionally added to the composition to prepare injectable formulations such as aqueous solutions, suspensions, and emulsions, oral formulations such as pills, capsules, granules, or tablets, powdered formulations with dry or/and extruded powders, aerosolized formulations with liquid or dry aerosols. Formulations for topical administration may include, bandage, dressings, patches, films, ointments, lotions, creams, gels, drops, suppositories, sprays, tampons, sanitary towels, liquids and powders. Formulations for decontamination or for medical use may also include aerosols or sprays.

The compositions of the invention may be used in the medical field, including the human or veterinary medical areas, for e.g. the treatment of a subject infection or for improving a subject's condition. The compositions may be used to reduce or kill S. aureus bacteria in an organism for treating an infection. The composition may also be used for improving the condition of a subject by modifying the microbial flora in said subject. In particular, the compositions of the invention can specifically remove S. aureus strains on the skin or mucous membranes of a subject, thus modifying its microbial flora and restoring a proper balance.

In a particular embodiment, the invention also relates to a method for treating an infection in a subject comprising the administration to said subject of a composition or bacteriophages or nucleic acids or polypeptides as defined above.

The invention also relates to the use of a composition of bacteriophages, nucleic acids or polypeptides as described for manufacturing a medicament for treating an infection in a subject, or for restoring microbial flora in said subject.

The compositions of the invention may be used to treat various S. aureus-mediated infections, particularly diabetic or non-diabetic foot ulcer infections, or bone such as and not limited to osteomyelitis, or septic arthritis, or joint infections, or prosthetic joint infections, or skin infections such as and not limited to atopic dermatitis, acne, impetigo, Staphylococcal scalded skin syndrome, or soft tissue infections, or pleuropulmonary infections, or other clinical syndromes such as and not limited to meningitis or urinary tract infections or septicemia or endocarditis or otitis.

The compositions of the invention may be administered by any convenient route, including intravenous, oral, transdermal, subcutaneous, mucosal, intramuscular, intrapulmonary, intranasal, parenteral, rectal, vaginal and topical. The bacteriophages or compositions may be administered by intrapulmonary or intranasal instillation or nebulisation, as well. The compositions may be administered directly or indirectly, e.g., via a support or a device (e.g. a nebulizer, a bandage . . . ). In this regard, the compositions may, for example, be applied or sprayed to the afflicted area. Compositions of the invention can also be administered by oral or parenteral routes. The dosage suitable for applying, spraying, or administrating the compositions of the present invention can be adjusted by the skilled person depending on a variety of factors including formulation, mode of administration, age, weight, sex, condition, diet of the subject being treated at the time of administration, route of administration, and reaction sensitivity. A physician or veterinarian having ordinary skills in the art can readily determine and prescribe the effective amount of the composition required.

The dosing can also be adjusted by the skilled person so that a lytic activity against antibiotic-resistant $S.$ $aureus$ strains is obtained. An efficient dose to obtain a lytic activity in vivo typically includes a concentration of at least $10^{e4}$ PFU/ml, preferably from about $10^{e2}$ to $10^{e12}$ PFU/ml, depending on the administration route.

In a particular embodiment, the bacteriophages, compositions, and cocktails of the invention are used for treating diabetic or non-diabetic foot ulcer infections, bone and joint infections, prosthetic joint infections or respiratory tract infections.

In the case of diabetic foot ulcers infected, for example, by methicillin-resistant or susceptible $S.$ $aureus$ (MRSA or MSSA), patients may receive dressings impregnated with a phage(s) solution at $10^4$ to $10^{10}$ PFU/ml with a frequency of application comprised between every day and every ten days, for example between every two days and every nine days, preferably between every three days and every eight days, more preferably every seven days, with or without antibiotic(s), until wound closure. The efficacy of the treatment may be measured by the relative reduction in bacterial load.

In the case of relapsing $S.$ $aureus$ (MRSA or MSSA) prosthetic joint infections of, for example, hip or knee, patients may receive phage therapy associated to standard surgery, with and without antibiotics. The content of a phage(s) solution at $10^4$ to $10^{10}$ PFU/ml may be scattered in the operative field in the osseous barrels, the articular space and/or the muscular tissues, at the end of explanation. A second identical preparation may be used for a second dispersal just after the reimplantation and before surgical site closure. Additional applications when the wound is still open may be done, for example at the time of wound dressing. Complementary oral phage administration at $10^4$ to $10^{10}$ PFU/ml may be used to support the local treatment.

In the case of plastic surgery with $S.$ $aureus$ (MRSA or MSSA) infected bone, a bone curettage may be followed by the placement of a compress imbibed with $10^4$ to $10^{10}$ PFU/ml of bacteriophage(s) at the bottom of the surgical site, in contact with the infected curetted bone. The rest of the cavity may be filled with other sterile compresses and the surgical site occluded by waterproof dressing. In addition, a Vacuum-Assisted Closure (VAC) system may be used, following a cycle of drainage to remove blood or serous fluid from the wound or operation site, followed by phage instillation ($10^4$ to $10^{10}$ PFU/ml) with or without antibiotics. The phages remain during several hours before drainage is reinitiated. The cycle may be repeated several times during the days following operation.

In the case of respiratory tract infection, a $10^4$ to $10^{10}$ PFU/ml phage solution may be applied using a nebulizing device. Nebulization may be carried out with a portable inhaler or with an add-on nebulizer to a medical mechanical ventilator. A phage solution volume ranging for instance from 1 to 20 ml may be nebulized at various time intervals and during the treatment period. Before starting the first nebulization and according to the pathology, lung washing may be performed with the same phage solution.

As shown in the experimental section, the bacteriophages and compositions of the invention are able to effectively kill a broad range of $S.$ $aureus$ bacteria. Compositions can destroy mixtures of different $S.$ $aureus$ bacteria, even at low dosage. Also, the compositions and bacteriophages of the invention are strictly unable to affect eukaryotic cells, and are therefore specific and devoid of side effects when applied to humans and animals.

The invention also relates to the use of a composition, bacteriophage, nucleic acid or polypeptide of the invention for decontaminating a material. Due to their potent antibacterial effect, and to their ability to even compromise the integrity of a bacterial biofilm, the compositions of the invention can be used as decontaminating agent, to eliminate or at least cause a reduction in bacterial numbers on a material. Such methods may be applied for the treatment of a variety of biological or non-biological surfaces in both medical and non-medical contexts, including solid materials or devices such as, for example, contact lenses, surfaces of devices to be implanted into the body, pipes, ducts, laboratory vessels, textiles, clothing, footwear, housing, military equipment, etc.

The invention also relates to a method for preparing a composition of the invention, wherein the composition comprises at least two bacteriophages, said method comprising separately producing said at least two bacteriophages, and combining said bacteriophages with a suitable carrier or excipient.

The composition of the invention may be used in combination with at least one antibiotic. Such a co-administration allows to reduce the amount of antibiotic used, to restore the efficacy of an antibiotic or to make a bacterium embedded in a biofilm susceptible to an antibiotic.

Diagnostic/Predictive Tests of the Invention-Companion Diagnostic:

The invention also concerns a method for predicting or determining the efficacy of a bacteriophage therapy in a subject, wherein the method comprises a step of determining a lytic activity of one or more bacteriophages of the invention to a $S.$ $aureus$ strain from a sample from said subject, such a lytic activity being indicative of an efficient treatment. In a preferred aspect, the method further optionally comprises a step of treating said subject by one or more bacteriophages having a lytic activity to a $S.$ $aureus$ strain from a sample of said subject.

In another aspect, the invention provides a method for selecting a subject or determining whether a subject is susceptible to benefit from a bacteriophage therapy, wherein the method comprises the step of determining a lytic activity of one or more bacteriophages of the invention to a $S.$ $aureus$ strain from a sample of said subject, a lytic activity of one or more bacteriophages of the invention to at least one $S.$ $aureus$ strain indicating a responder subject.

Another object of the invention relates to a method for predicting the response of a subject to a bacteriophage therapy, wherein the method comprises the step of determining a lytic activity of one or more bacteriophage of the invention to a *S. aureus* strain from a sample of said subject, a lytic activity of one or more bacteriophage of the invention to at least one *S. aureus* strain being indicative of a good response to said therapy.

In another aspect, the invention provides a method for assessing the sensitivity of a *S. aureus* strain to a bacteriophage selected from the bacteriophages having a genome comprising a nucleotide sequence of anyone of SEQ ID NO: 1 to 4 or a sequence having at least 90% identity thereto and/or at least one cocktail of bacteriophages of Table 2, comprising:
  a) contacting the *S. aureus* strain with said at least one bacteriophage and/or said at least one cocktail of bacteriophages, and
  b) determining the lytic activity of the bacteriophage and/or of the cocktail on the strain, thereby assessing the sensitivity of the strain to the bacteriophage and/or to the cocktail. Step a) may be carried out in vitro by bringing into contact, exposing or mixing a *S. aureus* strain with the at least one bacteriophage and/or at least one cocktail of bacteriophage in any medium adapted for such step (e.g. a solid or a liquid medium).

In a preferred embodiment, the determination of the lytic activity of the bacteriophage and/or of the cocktail comprises measuring the amplification of the bacteriophage in the *S. aureus* strain, wherein an augmentation of the bacteriophage concentration is indicative of the lytic activity of the bacteriophage and/or of the cocktail on the strain.

The bacteriophage concentration may be measured by any technical well-known from the person skilled in the art, such as plaque forming, Polymorphism Chain reaction (PCR), bioluminescence, etc.

Additionally or alternatively, the determination of the lytic activity of the bacteriophage and/or the cocktail comprises a determination of the apparition of a plaque in a plaque assay.

However, a bacteria strain may also be considered as sensitive to a bacteriophage when in a solid medium culture of the bacteria in presence of the bacteriophage, complete or partial lysis of a bacterial mat is observed.

Other techniques well-known from the person skilled in the art may be used to assess the lytic activity of the bacteriophage and/or of the cocktail.

Another object of the invention relates to a method for determining a cocktail of bacteriophages effective against a target *S. aureus* strain, comprising:
  a) separately contacting the target *S. aureus* strain, or a sample containing said strain, with (i) a bacteriophage having a genome comprising a nucleotide sequence of SEQ ID NO: 1 or a sequence having at least 90% identity thereto, and/or (ii) a bacteriophage having a genome comprising a nucleotide sequence of SEQ ID NO: 2 or a sequence having at least 90% identity thereto, and/or (iii) a bacteriophage having a genome comprising a nucleotide sequence of SEQ ID NO: 3 or a sequence having at least 90% identity thereto, and/or (iv) a bacteriophage having a genome comprising a nucleotide sequence of SEQ ID NO: 4 or a sequence having at least 90% identity thereto, and/or (v) one or more combinations thereof,
  b) selecting bacteriophages which exhibit lytic activity on the strain,
  c) optionally further selecting active bacteriophages which, when combined together, exhibit synergistic activity on the strain; and/or
  d) optionally further selecting active bacteriophages which, when combined together, exhibit no antagonism; and/or
  e) optionally selecting active bacteriophages which belong to different genus; and
  f) combining said selected bacteriophages.

This method may be used as a phagogram in order to determine which cocktail has the best lytic activity on a particular *S. aureus* strain.

Further aspects and advantages of the invention will be disclosed in the following experimental section, which is illustrative only.

EXAMPLES

Methods
Taxonomic Identification of the Phage Families.

Four phages of the invention (PN1137, PN1493, PN1815 and PN1957) were studied using electron microscopy. The results show that the bacteriophages belong to the Caudovirales order and to the Podovirae and Myoviridae families, as described hereinafter:
  PN1137: Podovirae,
  PN1483: Myoviridae,
  PN1815: Myoviridae,
  PN1957: Podovirae.

Sequencing and Analysis of Phage Genomes.

Phage DNA was isolated by extraction with phenol:chloroform:isoamyl alcohol (25:24:1, V/V), ethanol precipitation and resolution in water. Whole genome sequencing was done and the BLAST algorithm was used to determine the similarity to described genes in the National Center for Biotechnology Information (NCBI) database. The genomes were scanned for potential open reading frames (ORFs). The nucleic acid sequences are shown as SEQ ID NOs: 1-4. Sequences alignments using databases lead to the same taxonomic identifications than those using electron microscopy.

Example 1: In Vitro Characterization: Host Range

Two different kinds of bacterial lysis are possible. Bacterial lysis resulting from bacteria cell wall hydrolysis by bacteriophage's enzymes (termed "aspecific" lysis) and bacterial lysis resulting of phage amplification (termed "specific" lysis). Both types of lysis are relevant to the utility of the phages. Both the specific and aspecific lysis were determined for each of the bacteriophages using two methods.
Phage Amplification in a Solid Medium This method allows to assess the capacity of a bacteriophage to lyse bacteria by amplification.

The method consists in depositing a range of dilution (ratio 10) of a bacteriophage suspension at the surface of a bacteria-containing agar. This agar is then incubated at 37° C. for 18 h for allowing the development of a bacterial mat. Deposition areas are analyzed. The following situations are possible:
  Case 1: absence of lysis of the bacterial mat at the deposition area,
  Case 2: complete lysis of the bacterial mat at the deposition area,
  Case 3: partial lysis of the bacterial mat at the deposition area, and Case 4: observation of a plaque (plaque-forming unit (PFU)) at the deposition area.

It is only the formation of a plaque (Case 4) that attests the capacity of a phage to amplify in the bacteria strain and to effectively lyse the bacteria.

If cases 1, 2 and/or 3 is observed in absence of case 4, the strain is tested in liquid medium.

Phage Amplification in a Liquid Medium

This method allows to assess the capacity of a bacteria to produce a bacteriophage.

The method consists in culturing a bacterial strain and a bacteriophage at 37° C. for 18 h. Bacteriophage concentration in the supernatant is then determined. If the bacteriophage concentration after culturing is superior to the initial bacteriophage concentration, this indicates that the bacteriophage has been amplified by the bacterium.

The capacity of a bacterium to produce a bacteriophage depends on, inter alia, the multiplicity of infection (MOI), i.e., the bacteriophage/bacteria ratio. Several MOI have been tested.

Phage titration after culturing is determined using a method analog to the spot test. A range of dilution (ratio 10) of the culture supernatant is deposited on one hand on an agar surface containing the production strain of the bacteriophage and on the other hand on an agar surface containing the strain of a patient. This agar is then incubated at 37° C. for 18 h. The number of plaques on a depositing area correlated to the dilution factor allows the determination of bacteriophage concentration.

Specific Activity

The spectrum of specific activity, i.e., the capacity of each bacteriophage to lyse by amplification the strains of a panel, has been assessed. A bacteriophage is considered to be amplified by a bacterial strain when:
- in solid medium test, observation of case 4 was made, and
- in liquid medium test, the concentration of the bacteriophage after culturing was 50-fold increased with respect to the initial concentration.

The panel of *S. aureus* was determined by the Centre National de Référence des Staphylocoques de Lyon. It comprises the 109 *S. aureus* strains having the highest incidence in Europe and in the United States of America.

In the following Table 3, the capacity of the bacteriophages of the invention to be amplified by a bacterial strain is represented by a "+" and the incapacity of a bacteriophage to be amplified by a bacterial strain is represented by a "−".

TABLE 3

Spectrum of specific activity of PN1137, PN1493, PN1815 and PN1957 on a panel of 109 *S. aureus* strains.

| # | S. aureus strain | PN1137 | PN1493 | PN1815 | PN1957 |
|---|---|---|---|---|---|
| 1 | HOCIL001 | + | + | + | + |
| 2 | HOCIL002 | − | + | + | − |
| 3 | HOCIL003 | + | + | + | + |
| 4 | HOCIL004 | + | + | + | + |
| 5 | HOCIL005 | + | + | + | + |
| 6 | HOCIL006 | − | + | + | + |
| 7 | HOCIL007 | − | + | − | + |
| 8 | HOCIL008 | + | + | + | + |
| 9 | HOCIL009 | + | − | − | + |
| 10 | HOCIL010 | − | − | − | + |
| 11 | HOCIL011 | − | + | + | − |
| 12 | HOCIL012 | + | + | + | + |
| 13 | HOCIL013 | − | + | + | + |
| 14 | HOCIL014 | + | + | + | + |
| 15 | HOCIL015 | + | + | + | + |
| 16 | HOCIL016 | + | + | − | + |
| 17 | HOCIL017 | + | + | + | + |
| 18 | HOCIL018 | + | + | + | + |
| 19 | HOCIL020 | − | + | + | − |
| 20 | HOCIL022 | + | + | + | + |
| 21 | HOCIL093 | − | + | − | + |
| 22 | HOCIL095 | + | + | + | − |
| 23 | HOCIL099 | + | + | + | + |
| 24 | HOCIL106 | − | + | − | − |
| 25 | HOCIL117 | − | − | − | + |
| 26 | HOCIL118 | − | − | − | − |
| 27 | HOCIL124 | − | − | − | + |
| 28 | HOCIL 129 | − | − | − | + |
| 29 | HOCIL137 | − | − | − | − |
| 30 | HOCIL139 | − | + | + | + |
| 31 | HOCIL140 | − | − | − | + |
| 32 | HOCIL 145 | + | + | + | + |
| 33 | HOCIL 148 | − | + | − | − |
| 34 | HOCIL155 | + | + | − | + |
| 35 | HOCIL156 | + | + | − | + |
| 36 | HOCIL 161 | − | + | + | − |
| 37 | HOCIL163 | − | − | − | − |
| 38 | HOCIL165 | + | + | + | + |
| 39 | HOCIL 167 | + | − | − | + |
| 40 | HOCIL172 | + | + | − | + |
| 41 | HOCIL174 | + | + | − | + |
| 42 | HOCIL175 | − | − | + | + |
| 43 | HOCIL176 | − | − | − | − |
| 44 | HOCIL183 | + | + | − | + |
| 45 | HOCIL184 | + | + | − | + |
| 46 | HOCIL185 | + | + | + | + |
| 47 | HOCIL186 | − | + | − | + |
| 48 | HOCIL187 | − | + | − | − |
| 49 | HOCIL188 | + | + | + | + |
| 50 | HOCIL 189 | − | + | − | − |
| 51 | HOCIL190 | − | + | + | + |
| 52 | HOCIL191 | + | + | + | + |
| 53 | HOCIL 192 | − | − | − | + |
| 54 | HOCIL193 | + | + | + | + |
| 55 | HOCIL194 | + | + | + | + |
| 56 | HOCIL195 | − | − | − | − |
| 57 | HOCIL196 | − | − | − | − |
| 58 | HOCIL197 | + | + | + | + |
| 59 | HOCIL 198 | + | + | + | + |
| 60 | HOCIL 199 | − | + | − | + |
| 61 | HOCIL200 | − | + | + | + |
| 62 | HOCIL201 | + | + | + | + |
| 63 | HOCIL202 | − | − | − | − |
| 64 | HOCIL203 | + | + | + | + |
| 65 | HOCIL204 | + | + | + | + |
| 66 | HOCIL205 | + | + | + | + |
| 67 | HOCIL206 | + | + | + | − |
| 68 | HOCIL207 | + | + | + | + |
| 69 | HOCIL210 | − | + | − | − |
| 70 | HOCIL211 | + | + | + | + |
| 71 | HOCIL212 | + | + | + | + |
| 72 | HOCIL213 | − | + | + | + |
| 73 | HOCIL214 | − | + | − | + |
| 74 | HOCIL215 | − | − | − | + |
| 75 | HOCIL216 | − | + | + | + |
| 76 | HOCIL217 | − | − | − | − |
| 77 | HOCIL218 | − | + | − | + |
| 78 | HOCIL219 | + | + | + | + |
| 79 | HOCIL220 | − | − | − | + |
| 80 | HOCIL221 | − | + | + | − |
| 81 | HOCIL222 | − | + | + | − |
| 82 | HOCIL223 | − | + | + | − |
| 83 | HOCIL224 | − | + | − | − |
| 84 | HOCIL225 | − | + | + | − |
| 85 | HOCIL226 | + | + | + | + |
| 86 | HOCIL227 | − | + | − | + |
| 87 | HOCIL228 | + | + | + | + |
| 88 | HOCIL229 | + | + | + | + |
| 89 | HOCIL230 | + | + | + | + |
| 90 | HOCIL231 | − | + | − | − |
| 91 | HOCIL232 | − | + | + | − |

TABLE 3-continued

Spectrum of specific activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 92 | HOCIL233 | − | + | − | + |
| 93 | HOCIL234 | − | + | − | − |
| 94 | HOCIL235 | − | + | − | + |
| 95 | HOCIL236 | − | + | + | + |
| 96 | HOCIL237 | + | + | − | + |
| 97 | HOCIL238 | + | + | + | + |
| 98 | HOCIL239 | − | − | − | − |
| 99 | HOCIL240 | + | − | − | + |
| 100 | HOCIL241 | − | + | + | − |
| 101 | HOCIL242 | − | + | + | − |
| 102 | HOCIL243 | − | + | − | − |
| 103 | HOCIL244 | + | + | − | − |
| 104 | HOCIL245 | − | − | − | − |
| 105 | HOCIL246 | − | + | + | − |
| 106 | HOCIL248 | − | − | − | − |
| 107 | HOCIL249 | + | + | − | + |
| 108 | HOCIL250 | + | + | + | − |
| 109 | HOCIL251 | − | + | + | − |

PN1493 and PN1957 exhibit a specific activity respectively on 86 and 71 of the 109 *S. aureus* strains, which represent 78.9% and 65.14% respectively.

PN1137 and PN1815 also present a broad range of specific activity. They exhibit a specific activity respectively on 46 and 59 of the strains, which represent 42.2% and 54.13% respectively.

Total Lytic Activity

The spectrum of total lytic activity, i.e., the capacity of each bacteriophage to lyse strains either with or without bacteriophage production, has been evaluated. The bacteriophage is considered active on the *S. aureus* strain either when:
- in solid medium test, observations of cases 2, 3 or 4 were made, or
- in liquid medium test, the concentration of the bacteriophage after culturing was 50-fold increase with respect to the initial concentration.

In the following Table 5, the positive lytic activity of a bacteriophage on a bacterial strain is represented by a "+" and the absence of lytic activity of a bacteriophage on a bacterial strain is represented by a "−".

TABLE 5

Spectrum of total activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 1 | HOCIL001 | + | + | + | + |
| 2 | HOCIL002 | + | + | + | + |
| 3 | HOCIL003 | + | + | + | + |
| 4 | HOCIL004 | + | + | + | + |
| 5 | HOCIL005 | + | + | + | + |
| 6 | HOCIL006 | + | + | + | + |
| 7 | HOCIL007 | + | + | + | + |
| 8 | HOCIL008 | + | + | + | + |
| 9 | HOCIL009 | + | + | + | + |
| 10 | HOCIL010 | + | + | + | + |
| 11 | HOCIL011 | + | + | + | + |
| 12 | HOCIL012 | + | + | + | + |
| 13 | HOCIL013 | + | + | + | + |
| 14 | HOCIL014 | + | + | + | + |
| 15 | HOCIL015 | + | + | + | + |
| 16 | HOCIL016 | + | + | + | + |
| 17 | HOCIL017 | + | + | + | + |
| 18 | HOCIL018 | + | + | + | + |
| 19 | HOCIL020 | + | + | + | − |
| 20 | HOCIL022 | + | + | + | + |
| 21 | HOCIL093 | + | + | + | + |
| 22 | HOCIL095 | + | + | + | + |
| 23 | HOCIL099 | + | + | + | + |
| 24 | HOCIL106 | + | + | + | + |
| 25 | HOCIL117 | + | + | + | + |
| 26 | HOCIL118 | + | + | + | + |
| 27 | HOCIL124 | + | + | + | + |
| 28 | HOCIL 129 | + | + | + | + |
| 29 | HOCIL137 | + | + | + | + |
| 30 | HOCIL139 | + | + | + | + |
| 31 | HOCIL140 | + | + | + | + |
| 32 | HOCIL 145 | + | + | + | + |
| 33 | HOCIL 148 | + | + | + | + |
| 34 | HOCIL155 | + | + | + | + |
| 35 | HOCIL156 | + | + | + | + |
| 36 | HOCIL161 | + | + | + | + |
| 37 | HOCIL163 | + | + | + | + |
| 38 | HOCIL165 | + | + | + | + |
| 39 | HOCIL167 | + | + | + | + |
| 40 | HOCIL172 | + | + | + | + |
| 41 | HOCIL174 | + | + | + | + |
| 42 | HOCIL175 | + | + | + | + |
| 43 | HOCIL176 | + | + | + | + |
| 44 | HOCIL183 | + | + | + | + |
| 45 | HOCIL184 | + | + | + | + |
| 46 | HOCIL185 | + | + | + | + |
| 47 | HOCIL186 | + | + | + | + |
| 48 | HOCIL187 | + | + | + | + |
| 49 | HOCIL188 | + | + | + | + |
| 50 | HOCIL189 | + | + | + | + |
| 51 | HOCIL190 | + | + | + | + |
| 52 | HOCIL191 | + | + | + | + |
| 53 | HOCIL 192 | − | − | − | + |
| 54 | HOCIL193 | + | + | + | + |
| 55 | HOCIL194 | + | + | + | + |
| 56 | HOCIL 195 | + | + | + | + |
| 57 | HOCIL 196 | − | + | + | + |
| 58 | HOCIL 197 | + | + | + | + |
| 59 | HOCIL198 | + | + | + | + |
| 60 | HOCIL 199 | + | + | + | + |
| 61 | HOCIL200 | + | + | + | + |
| 62 | HOCIL201 | + | + | + | + |
| 63 | HOCIL202 | + | + | + | + |
| 64 | HOCIL203 | + | + | + | + |
| 65 | HOCIL204 | + | + | + | + |
| 66 | HOCIL205 | + | + | + | + |
| 67 | HOCIL206 | + | + | + | + |
| 68 | HOCIL207 | + | + | + | + |
| 69 | HOCIL210 | − | + | + | − |
| 70 | HOCIL211 | − | + | + | + |
| 71 | HOCIL212 | + | + | + | + |
| 72 | HOCIL213 | + | + | + | + |
| 73 | HOCIL214 | + | + | + | + |
| 74 | HOCIL215 | − | + | + | + |
| 75 | HOCIL216 | + | + | + | + |
| 76 | HOCIL217 | − | + | + | + |
| 77 | HOCIL218 | − | + | + | + |
| 78 | HOCIL219 | + | + | + | + |
| 79 | HOCIL220 | + | + | + | + |
| 80 | HOCIL221 | − | + | + | − |
| 81 | HOCIL222 | − | + | + | − |
| 82 | HOCIL223 | − | + | + | − |
| 83 | HOCIL224 | + | + | + | + |
| 84 | HOCIL225 | − | + | + | − |
| 85 | HOCIL226 | + | + | + | + |
| 86 | HOCIL227 | − | + | + | + |
| 87 | HOCIL228 | − | + | + | + |
| 88 | HOCIL229 | + | + | + | + |
| 89 | HOCIL230 | − | + | + | + |
| 90 | HOCIL231 | − | + | + | + |
| 91 | HOCIL232 | + | + | + | + |
| 92 | HOCIL233 | − | + | + | + |
| 93 | HOCIL234 | − | + | + | + |
| 94 | HOCIL235 | − | + | + | + |

TABLE 5-continued

Spectrum of total activity of PN1137, PN1493, PN1815 and PN1957 on a panel of 109 *S. aureus* strains.

| # | *S. aureus* strain | PN1137 | PN1493 | PN1815 | PN1957 |
|---|---|---|---|---|---|
| 95 | HOCIL236 | − | + | + | + |
| 96 | HOCIL237 | + | + | + | + |
| 97 | HOCIL238 | + | + | + | + |
| 98 | HOCIL239 | − | + | + | − |
| 99 | HOCIL240 | + | + | + | + |
| 100 | HOCIL241 | − | + | + | − |
| 101 | HOCIL242 | − | + | + | − |
| 102 | HOCIL243 | − | + | + | + |
| 103 | HOCIL244 | − | + | + | + |
| 104 | HOCIL245 | − | + | + | − |
| 105 | HOCIL246 | − | + | + | − |
| 106 | HOCIL248 | − | + | + | − |
| 107 | HOCIL249 | + | + | + | + |
| 108 | HOCIL250 | + | + | + | − |
| 109 | HOCIL251 | − | + | + | − |

Those results show a very broad spectrum of activity for the four bacteriophages tested which all present a lytic activity on more than 70% of the 109 *S. aureus* strains. Particularly, bacteriophages PN1493 and PN1815 show very good results with an activity on 108 of the 109 *S. aureus* strains, which represents more than 99% of the strains of the panel. PN1137 and PN1957 also exhibit a broad range of lytic activity. They are effective respectively on 81 and 95 of the strains from the panel (74.31% and 87.16% respectively). Every *S. aureus* strain from the panel is lysed by at least one of the bacteriophages. Further, 79 of the strains are lysed by the four bacteriophages.

Example II: Production of Cocktails

Cocktail 5: PN1493 and PN1957

Those two bacteriophages have a complementary range of lytic activity. Indeed, together they exhibit a specific activity on 98 of the tested *S. aureus* strains which represents 89.9% of the strains. Moreover, their total lytic activity covers all of the tested *S. aureus* strains. A preferred cocktail comprises these two bacteriophages in a 1:1 ratio.

Cocktail 6: PN1815 and PN1957

As for cocktail 5, those two bacteriophages have a complementary range of lytic activity. Together they exhibit a specific activity on 87 of the tested *S. aureus* strains (79.8%). Moreover, their total lytic activity covers all of the tested *S. aureus* strains. A preferred cocktail comprises these two bacteriophages in a 1:1 ratio.

Cocktail 1 (PN1137 and PN1493) and Cocktail 4 (PN1493 and PN1815)

Those two cocktail also present a broad range of lytic activity on the tested bacterial strains. Cocktail 1 and 4 have a specific lytic activity respectively on 89 and 87 of the strains (respectively 81.6% and 79.8%). Moreover, they both exhibit a total lytic activity on 108 of the strains, which represents a lytic activity on more than 99% of the tested *S. aureus* strains. Preferred cocktails comprise the two bacteriophages in a 1:1 ratio.

Cocktails 3, 5, 6, 8, 9, 10 and 11

Those cocktails exhibit a total lytic activity on 100% of the strains.

Example II: In Vivo Efficacy

Two mice models are used to assess the efficacy of cocktail of bacteriophages of the invention.

The first model reproduces *S. aureus* infections of a diabetic or non-diabetic foot ulcer. It is based on *S. aureus* hind paw infection of naive mice or diabetic mice.

The second model reproduces *S. aureus* bone and joint infections (BJI) as well as prosthetic joint infection (PJI).

Diabetic Foot Ulcer Model (DFU)

Diabetes are induced using Streptozotocin. The diabetes status of the mice is based on blood glucose around 5 g/l seven days after the induction and on an impaired *S. aureus* blood killing assay.

*S. aureus* Strain

A clinical strain isolated from prosthetic infection is chosen based on the ability of the strain to persist and multiply in situ. The best inoculum is chosen based on a sustained bacterial load 14 days p.i. in diabetic mice with the highest survival rate.

Experimental Design

Diabetes is induced by two injections of Streptozotocin at 48 h interval. One hind paw is infected 14 days after the first Streptozotocin injection. Four groups are compared:

bacteriophage cocktail-treated. The cocktail is administered locally (SC injection) 30 min p.i. at multiplicity of infection of 1 (MOI 1).

bacteriophage cocktail-treated. The cocktail is administered locally (SC injection) 30 min p.i. at MOI 10.

antibiotic-treated. Linezolid is administered systemically (IP injection) 30 min p.i. at 25 mg/kg.

Untreated control. PBS is administered locally (SC injection) 30 min p.i.

Thirty mice per group are studied.

At six time points p.i., mice are euthanized, the number of colony-forming unit (CFU) and plaque-forming unit (PFU) is numerated in the soft tissue and bone of the infected hind paw. Macroscopic observation of the oedema and lesion is scored as mentioned in Chhibber et al. The myeloperoxidase (MPO) level is determined to follow the inflammatory reaction and histology of the hind paw is performed at day 5 to assess the inflammatory reaction differences between the 4 groups.

This model allows to assess the efficacy of a bacteriophage or a cocktail of bacteriophages of the invention on a *S. aureus* infections of a diabetic foot ulcer.

Non-Diabetic Foot Ulcer Model

*S. aureus* Strain

The strain used in the diabetic foot ulcer model is also used in the non-diabetic foot ulcer model. The same inoculum is used.

Experimental Design

One hind paw is infected in naïve mice. The groups compared in the diabetic foot ulcer model are also studied in the non-diabetic foot ulcer model. The same criteria were studied.

This model allows to assess the efficacy of a bacteriophage or a cocktail of bacteriophages of the invention on a *S. aureus* infection of a non-diabetic foot ulcer.

Bone and Joint Infection Model

*S. aureus* Strain

A clinical strain isolated from prosthetic infection is chosen based on the ability of the strain to persist and multiply in situ. The best inoculum is chosen based on a sustained bacterial load 7 days p.i. with the highest survival rate.

Experimental Design

Naive mice are infected through the knee. Seven groups are compared:

bacteriophage cocktail-treated. The cocktail is administered systemically 30 min p.i. at a high dose.

bacteriophage cocktail-treated. The cocktail is administered systemically 30 min p.i. at a low dose.
bacteriophage cocktail-treated. The cocktail is administered locally 30 min p.i. at a high dose.
bacteriophage cocktail-treated. The cocktail is administered locally 30 min p.i. at a low dose.
antibiotic-treated.
antibiotic+bacteriophage-treated.
untreated control.
Thirty mice per group are studied.

The bacterial load and phage load, the clinical status of the mice, such as the weight, food and water consumption are followed along the course of the infection.

This model allows to assess the efficacy of a bacteriophage or a cocktail of bacteriophages of the invention on a *S. aureus* bone and joint infection.

Prosthetic Joint Infection Model

*S. aureus* Strain

The strain is similar to the BJI model as well as the inoculum.

Experimental Design

A K-wire is inserted into the femoral cavity of naive mice. The mice are then infected through the knee next to the K-wire. The groups comparison and readouts are similar to the bone and joint infection model.

This model allows to assess the efficacy of a bacteriophage or a cocktail of bacteriophages of the invention on a *S. aureus* prosthetic joint infection.

REFERENCES

Capparelli R, et al. Antimicrob Agents Chemother. Experimental Phage Therapy against *Staphylococcus aureus* in Mice. 2007 August; 51(8): 2765-2773.

Clark W A, 1962, Appl Microbiol. Comparison of several methods for preserving bacteriophages. 1962 September; 10:466-71.

Drulis-Kawa Z, Majkowska-Skrobek G, Maciejewska B, Delattre A S, Lavigne R, 2012, Learning from bacteriophages—advantages and limitations of phage and phage-encoded protein applications; 13(8):699-722.

Weinbauer M G. Ecology of prokaryotic viruses. FEMS Microbiol Rev 2004; 28:127-81.

The invention claimed is:

1. An antibacterial composition comprising at least one bacteriophage having lytic activity against at least one *Staphylococcus aureus* (*S. aureus*) strain and a pharmaceutically acceptable excipient or carrier,
said at least one bacteriophage being selected from the bacteriophages having a genome comprising the nucleotide sequence of any one of SEQ ID NOs: 1 to 4 or a sequence having at least 95% identity thereto, and
said pharmaceutically acceptable excipient or carrier comprising a preservative in an amount effective to preserve the activity of the bacteriophage.

2. The composition of claim 1, which is a liquid, semi-liquid, solid or lyophilized formulation.

3. The composition of claim 1, comprising between $10^1$ and $10^{12}$ PFU/ml of each bacteriophage.

4. The composition of claim 1, wherein the at least one bacteriophage is selected from the bacteriophages having a genome comprising the nucleotide sequence of any one of SEQ ID NOs: 1 to 4 or a sequence having at least 99% identity thereto.

5. The composition of claim 1, wherein the at least one bacteriophage is selected from the group consisting of PN1137, PN1493, PN1815 and PN1957, said bacteriophage having a genome comprising the nucleotide sequence of any one of SEQ ID NOs: 1 to 4, respectively.

6. The composition of claim 1, wherein the pharmaceutically acceptable excipient or carrier is buffered physiological saline.

7. A method for preparing an antibacterial composition comprising producing at least one bacteriophage having lytic activity against at least one *Staphylococcus aureus* (*S. aureus*) strain, said at least one bacteriophage being selected from the bacteriophages having a genome comprising the nucleotide sequence of any one of SEQ ID NOs: 1 to 4 or a sequence having at least 95% identity thereto, and combining said bacteriophage with a pharmaceutically suitable carrier or excipient.

8. The method of claim 7, wherein the at least one bacteriophage is selected from the bacteriophages having a genome comprising the nucleotide sequence of any one of SEQ ID NOs: 1 to 4 or a sequence having at least 99% identity thereto.

9. The method of claim 7, wherein the at least one bacteriophage is selected from the group consisting of PN1137, PN1493, PN1815 and PN1957, said bacteriophage having a genome comprising the nucleotide sequence of any one of SEQ ID NOs: 1 to 4, respectively.

10. The method of claim 7, wherein the pharmaceutically acceptable excipient or carrier is buffered physiological saline.

11. The method of claim 7, wherein the pharmaceutically suitable carrier or excipient comprises a preservative in an amount effective to preserve the activity of the bacteriophage.

* * * * *

SEQUENCE LISTING

```
Sequence total quantity: 4
SEQ ID NO: 1              moltype = DNA  length = 17213
FEATURE                   Location/Qualifiers
misc_feature              1..17213
                          note = PN1137
source                    1..17213
                          mol_type = other DNA
                          organism = synthetic construct
SEQUENCE: 1
aacttctatt ccaacttatc taacctatta catattaatc aaatacattt attatacatc    60
tattgactttt tatcaaaatt tatgattgga acataaaatc taatttcttc tattaaatag   120
tagttttaaa ttatttaaac tttttaaga aaaactgttg acaaaacttt taaacgtttg    180
ctatactaat tatgtaatca aaacaaggag gtaacaaaaa tggttaatgt tgataatgca   240
ccagaagaaa aaggacaagc ctatactgaa atgttgcaac tattcaataa actgattcaa   300
tggaatccag cttatacatt tgacaatgca attaacttag tagcagcttg ccaacaacta   360
ttattaaact ataacagttc tgttgttcaa ttcttaaaag atgaactaaa caatgaaatt   420
aaaccagaat caatattatc ttacattgct ggtgatgacc ctatagaaca atggaacatg   480
cacaaaggat tttatgaaac gtataacatt tacgtttttt agaaaggaat gatataataa   540
tgaaagctga tgacattgtt gttttacgtg ttaaaggtta tatacttcat tacttagatg   600
atgataatga atacattgag gaatttgttc cacttcacga gtatcattta actaaaacgc   660
aagcaaaaga gttattacca gaatcatgta cactattatc cactacacgt acaacgaaaa   720
caattcatgt ttattacaat gatttactac aaatcgcaat tgcagaaagc aaataattta   780
aataagagga gaaattaaaa tgacaaacgt aaaagatatt ttatcaagac accaaaaaac   840
attagcgaga tttgaatttg aggaaaaaga aagagtattt atcaaactat cagaattagt   900
agaaaaatac ggtatgaaaa aagagtatat cgttagagca ttattcataa acacagaatc   960
ccaattcggt gaacagggtg ttattgtcac tgacgactat aatgtaaact taccgaacca  1020
cttaacagag ttaattaaag aaatgagagc agacgaggac attgttgaca ttatcaacgc  1080
tggtgaagtt caattcacaa tttatgaata tgaaaataaa aaaggtcaaa aaggttattc  1140
aatcaatttt ggtcaagtat catttttaata caatttcata gggggtattt atcccctatt  1200
tttatgaggt gctaaacaat ggaaaaatat acactgccgt attattatac aatgtatcaa  1260
ttaatgaaac atatgaacat gaaattgaac aattcgaaaa aataaataaa gttaaggtaa  1320
tatatagtta ttttgacgca aacttttaca aaaaaggtgc atataatctt tgtgtaaaat  1380
atattaagga gctataaaat gaaaattaca acaacattaa acacaaacaa attaattaat  1440
tacatttaa ctaatagaga gtgttttata aataaaataa caaaatttac atcactaagt  1500
gataaatgtg tcgttttgt tagatacggt gatatttcta ttgaatacta tgatagtact  1560
acaaaaaaca ataatgattt atttacttta gacattgacg ttgatattaa taaacatgtt  1620
tttaattgtc ttgtggtttt ttatcgagaa catttaaacc cactatataa aaaagaagtt  1680
ttcacgggat gtactattga tgatgtatta gaaaattttg agaaaccatt agaaagttat  1740
attactatta tataccaaaa aaaagtcata tacgataatg gggaagtgat tgaacatgaa  1800
taacctatta aacatagcca ttgtattcct tttagcgttt ttaattacac tgattatact  1860
tatgacactg catatacgcg tgtcatttgg tgtttattc actacattga ttatattcta  1920
cattatcttt ttagtggtta tatatgggtt atatggaggt cgttagcaat ggttagacat  1980
acgtccgaaa tggataaatg gaaaaaagaa agagacgcaa gaaaagagca ggaaaaagaa  2040
ttgttttttaa atgattttag tactgttaat tttaaatttg atgataaaga tttacaagag  2100
gcgtatatag acgcatggaa acatttcgca catttgccct attttccaaa agaaagaaac  2160
gtgtcatatg taaatgcggt atcattggta agaggtaaaa gacatgaaca attaaactat  2220
atacttgaaa tatataaccg taaagatgaa tctaataata aaaacgctaa aaaacataaa  2280
tatgcttat atgaattaca agctaaaaat aataattctt ctatgtataa atatataaag  2340
gaaattgaca ctttatacaa agaaattggt aaatcagaca gaccagtgac aactattgat  2400
gatgaagatg tgaggtataa tttttttatat tatgcaacat ttgaagacta attttaatac  2460
```

```
tgtaaacgac atcataaact attataagga gcaaaaaaat ggtaaaacaa aaccgtttag   2520
acatggtaag agattatcaa aatgctgtca atcatgtcag aaaaaaaata ccagataact   2580
ataatcaaat agaattagtt gatgaactca tgaatgatga tatagactat tacatatcta   2640
tttcaaaccg ctctgacgga aaatcgttca actatgtttc atttttatt tatttagcta   2700
ttaaacttga tataaaattt actttattat cacgtcatta tacattacgt gacgcttacc   2760
gtgattttat tgaggaaatc atagataaaa acccactatt caaatctaag cgtgtcacgt   2820
tcagaagtgc tagggactat ttagctatta tctatcaaga taaagaaatt ggtgtgatta   2880
cagatttgaa tagtgccact gatttaaaat atcattctaa ttttttaaaa cactacccta   2940
ttattatata tgatgaattt ttagcacttg aagatgacta ttaattgat gagtgggata    3000
agttaaaaac aatttatgaa tcaattgacc gtaaccatgg taatgttgat tatattggtt   3060
ttcctaaaat gttttactg gtaatgctg tcaacttttc aagtcctata ttatctaatt    3120
taaatatata caatttatta caaaagcata aatgaatac atcaagactt tacaaaaaca    3180
tttttttaga aatgagacga aacgattacg tcaatgaaaa acgtaataca cgtgcgttta   3240
attcaaatga agacgctatg acaactggtg aatttgaatt taacgaatat aatttggcgg   3300
atgataattt aagaaatcat attaaccaaa acggtgattt tttctatatt aaaactgacg   3360
ataaatatat aaaaattatg tataatgttg atacttttaa tgctaatatt attgttatac   3420
cttatacaaa acaaatgag ttttgtacta agatcaaaga tatagatgac aatgttattt     3480
atttaagaga agacatgttt tataaagaaa acatggagcg ttattattac aatccaagca    3540
atttacattt tgacaatgca tattcaaaaa attacgtggt tgataatgat agatatttat    3600
atttagatat gaataaaatt ataaaattttc atataaaaaa tgaaatgaag aaaaacatca    3660
acgaatttga aagaaaagaa aaaatatacg aagataacta tattgaaaat acaaagaagt    3720
atttaatgaa acaatacggc ttataaaagg tgtgtaagat tatgggatta cttgagtgta    3780
tgcaatatca taaacatgaa cgtaaaatga tattgtattg ggatattgaa acattatcat    3840
acaataaaat aaaacgacgt aataaccaa cgctatataa aaacgtaacg tattcagtag     3900
cgattggttg gttaatggt tacgaaattg atgttgaagt attccctagt tttgaagctt     3960
tttatgatga ttttttacaag tatgttaatc gccgtgatac aatcacaaaa tcaaaaacag    4020
atattatcat gattgcacat aactgtaata agtatgacaa ccatttttta cttaaagata    4080
ccatgcgtta ttttgataat atcacacgtg aaaatatata tttaaaatct gcagaagaaa    4140
acgaacacac actaaaaatg caagaggcta ctatttagc taaaaatcaa aatgtgattt     4200
tagaaaaacg tgtgaaatcg tctattaatt tagacttaac catgtttta aggattta       4260
aatttaatat tattgataac tttatgaaaa ccaatacatc aattgcaaca ttaggtaaaa    4320
agttgcttga cggtggttat ttaacagacg accaacttaa aacagatttt aattacacga    4380
tatttgataa agataacgat atgaatgata gtgaagcata cgactatgca gcgaaatgtt    4440
tttcaaaact cacacctgaa caacttatat acattcataa tgacgtgatt atattaggta    4500
tgtgccatat tcattatagt gatatatttc caaattttga ctataacaaa ttaacatttt    4560
cattgaatat tatggaatcg tatttaaata atcaaatgac acggtttcag ttactcaatc    4620
aatataaaga tattaaaata tcatatacac attatcattt ccatgatatg aattttatg    4680
actatatcaa atcattttat cgtggtggtt taaatatgta taacactaaa tacataaaca    4740
aacttattga tgagccttgt ttttctattg atatcaattc cagttatcct tatgtgatgt    4800
atcatgagaa aattccaaca tggttatact tttacgaaca ttattcagaa ccaacgttaa    4860
tccctacttt tttagatgat gacaattatt tttcattata taagattgat aaagatgtat    4920
ttaacaatga tttattaatt aaaatcaaat cacgtgtatt acgtcaaatg attgttaaat    4980
actataacaa tgataatgat tacgttaata tcaatacaaa tacattaaga aatgattcaag   5040
acattacggg tattgattgt atgcatatac gtgttaattc gtttgtgata tatgaatgtg    5100
aatatttttca tgctcgtgat attattttg aaaactattt tataaaaaca caaggtaaat    5160
taaaaaataa gattataatg acatcaccat atgattataa aattactgat gatatcaacg    5220
aacacccata ctcaaatgag gaggttatgt tatctaaagt tgttttaaat ggattatatg    5280
gcatacctgc attacgttca catttttaact tattccgttt agatgataac aatgaactat   5340
acaatatcat taacggttac aaaaaacactg aacgtaatat attattctct acatttgtca   5400
catcacgttc attgtataac ttattggttc cttccaata cttaacgaaa agtgaaattg     5460
acgacaattt tatttattgc gatactgata gtttgtatat gaaatccgtt gttaaaccgt    5520
tattgaaccc cgatttattc gacccgattg ccttaggtaa atgggatatt gaaaacgaac    5580
agatagataa gatgtttgta ctgaatcata agaaatatgc atatgaagtg aatggaaaga    5640
ttaaaatagc ttctgctggt ataccgaaaa acgcctttga tacaagcgtc gattttgaaa    5700
cctttgtacg tgaacaattc tttgacggtg ccattattga aaacaataaa agtatctata    5760
atgagcaagg tacaatatcg atatatcctt ctaaaactga aattgtatgt ggtaatgtat    5820
atgatgaata ttttactgat gaacttaata tgaaacgtga atttatatta aaagacgcta    5880
gagaaaattt cgaccatagt caatttaatg atattcttta tattgaaagt gacatcggtt    5940
cattttcact taacgactta tttccagttg aacgttcagt acataacaaa tctgatttgc    6000
atatattaaa acgtgaacat gatgaaataa aaaaaggcaa ctgttaaaat aacagttgcc    6060
ttttttttat tgagataaca tgaaaaatgt gtacgaaaat tgattatgtt ttgtattta     6120
tttactagca ttactagcat gtgttcatta tagcatacat ctttatgcaa tgccactaaa    6180
gaatacaata ttatcaccag cattatttgg tacaccatta atgagtgaat acaataccac    6240
acgtgacggt gcaacgtatg gtgggtacatt atagtttgct actaagaatg aaccatcgtc    6300
aaatactgcc actacaacac ctgtgtgacc aataccataa gctgttgctt gtaagtatgg    6360
tggtttactt gaaaaaccat aaccaacagt agggttgtgt gttgttttag cacctaactt    6420
tttataaaca taccacacac gttgaccgtt tgttattgt ccgtcgtcgg taggttgtct     6480
tttaccatgt agttgcgaca tataagccca tgttaattcc gtacactgtc ccgcattacc    6540
cgtttgagga aatatgttac cgggtttgta taagtattct tttttgaata aaggtacacc    6600
aattgctttt ttatattttt ctggtaactg tgcatacgtc cagttaccac caatgacgcg    6660
accactttta ccattaggtt tgactgattt accactaatt ggtttatgat ctccgtcatc    6720
atcagtaggg tttgaactac tacccccact atctacttgc acgctatcaa tcagtttttt   6780
taatgaatcg agtagcccaa tagtcatttt aatatgatat gtgttgttaa atgtttttg     6840
taataaaaa taatcattac taaaaaaattt gtcgctacct atactgtga catcccattg    6900
taatgcgtct tgtactttt taataattc ttgcatgtct tgttttgcta aagcgagtag     6960
tgaactacca ctgtcaccac tactaccact gtcagacgtg tcactaggtg aaccaccttt    7020
accgtcaat tttccacccc atgctagaat agcatttgca ccgtctaaaa atggattacc    7080
atagttttgt actttattat atgatgcttt caaacctggt ggtataatg ccgcccaagt     7140
agctgcagct gttaatggaa tatacgcacg tccaattgta ccctgctttca tattttagc    7200
```

-continued

```
aaaatctgca ttaccttttc tttgtacgtc ttgtggtaca aaatgcactg gattaccgta    7260
atcataccaa gacggttgcc cagcttgttt tgattgtgat actaattttc ttgctatgaa    7320
tttagcgtct gttaaataat caccacgtgc agacgtatga tttaaccaac ctaaaccagc    7380
actataaccc tcattttttt catatacggc aaaaagagta ggtgatacac ctatctcttt    7440
tactgcttt aatacttgtc tgattttact ttcattacca ccaagccata cattaaagcg     7500
cccatatcct tttactttag ggactaactg gtctatcgtt aaaccgaaat catcattaat    7560
atacgaatgc gtaaatttat ctatcttctc ttggttgttc attattatca ctcttttcag    7620
aatcattttt aattactctt aatttatctt taatttgttc tgggactaac acgtccattt    7680
ctgcacaatt ttctacgata gataaccct cattagcgat ataatagaaa atcgtaatca     7740
tgagtaagcc acctttaat tgtaaaatct ggtcaatgat gttagctaaa atgataatac     7800
agaatatcaa taatttttta gcaaaacctt tcattgattt tttagaccat aagttattat    7860
ttttaatagc tttagcaaaa cctgtgataa catcaataat cattaaaaca aataaaaagt    7920
atagtaattt taaatcccca gcatatataa acatgtgaaa cgcttctgag tctctaaatc    7980
tgaattttac ttcgttcata ttataccccc tctctaaatt tgttatttaa tggattttgt    8040
aacattggat tacctgaacc gtcattatgc caaaatctca caccagattc taaaattgct    8100
tttaattgtt ccattaacat ggggtcaatg tcacgtatgg tatacgtacc tgtacatttt    8160
aaatagttgc aaacagtcat actgttaatt ggttcaataa atgaattata gtcattcact    8220
tcaaaaccaa acaacatata atatttttgt aaaaatgtaa tttctttagg tgacggtaca    8280
ctaatttca tcgttaaacc gttaatactg tttgcaattt ggaatgcgtt gcccattcc      8340
gactctgtca ctgacggtgg ttgtaatgct aaatctttat attctgcttg ttgttgtttg    8400
tagaaattat attcttcatt aaacttacca aataaagcag tcggacttaa attacttgct    8460
acgctcactg cgtcataaaa acgtgatttt ggatcacttc catttaatac attatttata    8520
cgacttgtga ttaattgact ttctgcatta cgctgtctat tggcttgttg tgattgtcct    8580
aaaattccgt tattaattaa tataggtact tgcgcaaaac tattaaatgt tatatttgta    8640
tttaagaatg aacctgtatc aattaatata tctttatttt tagcaagtat cggtctatcg    8700
ttttcagcac tgttataatc tactggatat actcgcactt cattatgata accaatgatt    8760
gactttgtac gtaacttaac acctgttttt tgcgaaactt taccagcgtc tagtaacatt    8820
gtattaccgt tccagtcata aaattcaatc gtcatatact cattacgtat catatgttta    8880
aactcttctt ttttagacaa catcatttct tgaagctttg tgaacttaa tgataaatcg     8940
tttaaactcc attctttga ttttccacct tgttttaacg tctttaatcc agtaattttt    9000
tcacttgtct taacgtcctc taaatctttt gtattaataa agtctttagg taacatttga    9060
acctttgaa agtttgtgt aatccatgga tatgcactca ttttatccat aaaattgata    9120
aaatccccgt attccataac gtaaagttg actggtgatg tgatattgtc atatatcgta    9180
cctttagacg tatctaagtt tggctctttt ttcgtaccaa atttctttga taaatcagcg    9240
cttgactgga ataacactaa atttttctaaa tactgttgca tttggttata cacatagttt   9300
ttatttgata cttttaacac atcatcattg ttacgtaaca ttggtaacat atagttatac    9360
gtgcgttttg ataagtgttg acgttcaata ttaacgtttg agagttgctc taatacatta    9420
cctgtgtat acgtcataat agtacaatc acaaaatata ttttaccac aacatcattc        9480
acatattcga tttgattcac aaaagcataa taacgtctgt cctcaaaatc tgataaaaac     9540
gtcatatagt taatcccttg tgcgtcatgc cactgcatat caacattgat ttccattcta     9600
tcacgtataa aattatacgg ttgtttggaa tagtctaatg atttaaaatg acgaccattt     9660
aaaaaataat catcacgttc tttattacta ttaaaatgaa tcgtgttttg ataatctgta    9720
aacggtgtgt tatagaaaaa tttaaaattt gttaattttc tcatttttac ctccataaaa    9780
atagtcgtat aaaattattta tacgactatt ataacattt tattcaatga tttgtgtgtc    9840
tattgcaaaa cgtttatcac catttgttaa gtcactatcg ctataatttg atgtaacaaa    9900
atgtaagtta cccttaaagt ttaaatacat tcttgtattt atcattttat tatcaacagc    9960
acattgcgtg taatgatgtg ttgattttaa atttgcgtta atcgtaccta atttaatatc   10020
accgttttta ttaatccctt taaatacacc ttttaattgt attgtttta tgtcattgat    10080
tgtaacaatg cgatattta aaggtggata agcattacta ttataatctg ttgtaatacc    10140
actttctaat tgtatatttt gccaacctgt atcattaaat tcaactttta cactgttaat   10200
ttttgatta aaattgtt caattttctga tttggattgc gcaattttag tatcaattaa     10260
attaatttca tttgtattac gtcctacact atctttagta gcgtttaatg attgtgtaag   10320
tgtgttatat ttatcatcat actgtaacat tgattttca aattcattta attgtttttg    10380
atgttgttct aaactttcaa ttaatatgac atcttttct tttaatgcgt caatgttatt     10440
tttattacta tcaatcattg gttgtaattt tttttatcttc tctaaaaatg ttgatatttt   10500
ctctttgtta tcattaattg caatatcatg tttatctatt tgaccactat atttatcaat   10560
caatgttttt aaatcattat aaaacgttaa cttataataa cttgaatcag tacggacata   10620
aatatgtccg tctgatgtac taatcaagtc atttctttct gttaaaaaat ctgctaaacg   10680
ttctatatct tcgacacgtc ttaaacttct tacgattcta tcagccattg tttcacacctc  10740
ttatttatat cgtttccaac taaactcaaa gaaaaaacct aaaataccca ttatgagaac   10800
acccccaag gaataccaac actgtaacta ttacctgttt taccattcca ttgccttact    10860
ggtaaataat aacgtgtacc ttgccagttg taaccaatcc aaactaaccc atctgataaa   10920
catacttcgt catatggtgt atatccacca ggttgaaacc agtagcgtt aggttctgat    10980
aatttaggac taccaacatg tgcaaatatt ggtaaaaagc cacatgtaaa tgttgcattt   11040
tcatttctgt aatatgtacc gtattgattt tgtttccagt tgttagtttt ttgaatatttt  11100
tgttctaata ctttactatc actattgaa aattttggac gaataaaatg cgttacaccg    11160
tcataataat gggtgcgtat tgtcgctttt tcccaaccgt caaaaccgcc attcaaccag   11220
ttttgctcta aacatgtata ataatctaaa ttcccactta ttacacattg gatatgacca   11280
tattgagaat tagtataaac agcaacatca cctaattgag gtttaaagct cggtgtattt   11340
tcatacaccg ttgctaaacc tttaaagtta ttattaatag cgtctttggc gttaccccac   11400
atgcgaactt taccgtcggt aatgtaataa acataagcaa ctgctaagtc catacattga   11460
aaccatatg cgccatcaaa gtcaacgcca acacctcat gtttatatat ccaatctttc     11520
gcttgttgtt gtgatttcat ttatatcact cctatttttg atgttttggt acccaatcat    11580
attcacgatg tgtatttttt atcttacaa gactataaaa tctcttttatat gttgatgaat   11640
ttattaataa cgtttgtcta acttcacctg aaacgttacc acttgatact tgtaaccatg    11700
caccagcttc accaatatct ttaggttat ctttaaagtt attcatttgt gttgatgtaa    11760
tgtaatattc acctggtaat gtaatttag caatccaata accaaaattt ttagcctcta    11820
cgtattcttt tcagttgaa ttagtatcaa taacagacca gttaccaaat tcaaattttt    11880
gtgttttaa gttatatgtg aaacttctta ttagtttcat cattttctt aatcctgagt    11940
```

```
ttcttgttaa ttcttgatat ccacctaact gttgtgtttt tggtgataca aataaaaacc    12000
aaccggcatc attattgata tatgaaaaat catccataac tttagtatgt tctgtcatca    12060
tataataaaa tccagtttcg gtaatttggc ttaaacttgt tacaccatct cttattgata    12120
aagctctacc gtcatctttc gttagtttat agttttgccc acctttaac gttaatccta     12180
caaaacgctc atattcacca gtttgaaaga aaccatacaa taagttttgt cttttttccac   12240
caccagcagt tgtatatgca attaataaag attgttttt agttctagga ttaacgtata     12300
aatataatcc ctcaggttct ctaaaattat ctctaggatt ttcaacacca tgttcaaatg    12360
aaacatcgtt taaataataa tcgtatactt ttgattttgt tttaaaacta tatttttgaa    12420
ttaatgtttt actatctagt tctgaccaac cacttaacca gtataaatca tcaccataaa    12480
ctgcaatacc ttgcataggt ctgtctggtg tgttttcttt tacatcaatt tgtagttctt    12540
tttctacatt gtcaatgtga ttaattacat cttctcttga ccgtacttgt attaaaccac    12600
caccatatct aaatactaat ttgtcatttt cttcatccat aataggcgta aaatattcat    12660
gtgacgatgc tggcgtgaaa tcagttaatg cttctcgcatc atctactgtt aatgttgtat   12720
tatctctata agcgatttgc acaagttttg aaagtgcaac atgatacaac catattttta    12780
tctcaccgtt actttttctt tctaaagcaa tattagtacc atgaccaccc tctacaatat    12840
gcatactaga aattaaatca ccactaggcg taaatttgtt aatccaaaaa ccttcttttt    12900
cttgtgagtc ggattgtgta gagtacattt gatttgtttc tctatcaatt aatatacttt    12960
ggtttacagc gttacgaaca ccaccaaagc cagttacaaa ctttggttca agctcattta    13020
attcaaaccc attaacgaaa cggtcaatgt ctttaattaa gtctttcact tctgctttaa    13080
aatcattcat ttgtttcatt tctgcaactt taaataatgc aaacgccgat gttaatcctg    13140
cactatattt tttaaactcg tcatgaataa tgttatcaat cgtaccatcg tttaaccaac    13200
ctctaaataa gtctttcgct tggtctggga atgctttcat taagtcgtcc cagtttctaa    13260
aacgttttt taactcaccg tcatagtccc aaatacgacg tgctaatact tcaattagtt    13320
ttgataatct tgaaatataa tcataatacg attttgaatt tgtattataa tctgctctat    13380
catcgtaaaa cggtgtgtaa cgttctctag ttttatatat ttcgtctaaa aatggacgaa    13440
tgtcatcaaa atatttaaaa tcgttttcat tatatgccat aattttccac ctttaccaaa   13500
tttgtaaaaa acattttta tcaaattcat ttaaaatttt cttcttaaa tcgtatactt     13560
tatcaatatt atcaattaaa tactgctttg aaaattgtgt acctttcgca ttaccttttt    13620
gattttgatt acgttttgcg ttttgattac tttcgttact tgatttattc acagtttac    13680
cgttatcgat tgtattatta tcagcaaatc gtaacgttgt attatcaaca tcaatgttaa    13740
cctcactttg tggcagtgac acataagcat ttctgtttgc tgtcatccca gttgaattgt    13800
ctaaagatgt agcattttga ttcgatgttt catcagtatt gctgttgta tcttcattat     13860
gttctgtaaa accttgtgat tgtagatatt tttcaacttc tcttgatgaa taaaccacat    13920
tcaaataatc ctcatgtgtg atacatacag taatcacttg catgccaaaa gcttcaactg    13980
tttgtctgtt gatttctcta tctaaaaagt gtattgtaaa tgattttta aaaagtaagt     14040
cagataagtc atctttaagt ttaaaaacctt taaacactttt tcattaacg atggctaaaa   14100
cgtctttgtc aaacttcaac atttttgca tgaattgaaa ttcatcatca taaaacgtta    14160
atttatcatt atttacaaat tcattaaaac cttttttaat taattctgat ttaataaaat    14220
caaataaagt cattgtatat ctagccattg tattcactac tttcatcatt agacaatgta    14280
tctatcattg ttatttctga agtaacttca tcgtcgtaat acggtttaat atctaaacca    14340
taacgttttg ataagaatgt aatcggttca cgaccttta aataaatatt actatttgat     14400
gtggtaaaac ctcggttgct ttttgcctct tcgtccgaaa caccgctttc cttatccact    14460
gctagtgaat taatacctaa atagttactt aattcactaa ttttatttttg gtattcgcgt   14520
ttcatctcag ttagtgctgg aatcacacta ttactggtta aatctatgat atcatcatcg    14580
gcgttaaaca taggtgacat tttaacaaat ggtgcaccgt tatatatttc cgatacaagt    14640
tgattaactg actcatcatt aatgtctgat ttaaatattt tgctaaattt tgcttgcata    14700
attaatgaga atcgagataa aacaacctca gataattcat cagtataagt ttctatgatt    14760
tctatatcac tattatattg aattggttta ttttgcatga caacaaagtt accactcata    14820
cagttatcat atattttatg aatctgtaag cattcatctg gtattaaata ctctggtaca    14880
atgaaataaa tatcatctttt tgttaatcgt ttttgaaatt ggaaattaaa gtttgatgaa    14940
aaatttggtg cttgattaaa gtaagtgtta tttacataac caagaatcat aatttgttaa    15000
tttctagctt caccaaccac tacattgatg tttttgtctta aagctgattc taactgaata    15060
aaatctatac caaccgtatc acgattggta tagttgatga gtagcggtaa aaattccaaa    15120
taacgattaa acataagacg tttaaatctg ttgcgatgtt ctacaacacg tttattgatt    15180
tctttagata attcaacctg tacgccttta ttatgtttag tcatttatag caacctctatt  15240
attctgttct cggtgtaaca tcttggtcag taattaaaat tttattaaag aatgggctaa    15300
tggctttaaa tgaataataa tgaatccagt gtgtgacttc atcaaattca ccattataga    15360
atggttgttt taacatacct tttgtgtaac gtttatattt aattgaatta atatccaaaa    15420
taaacgcata taaatctgat tttggtttaa ttccttcaac gttagactta aattcagata    15480
aattttgaaac atcataagtg aatactgaac caactggaat tgtatcacct ttatgagttt    15540
gataatcacc gtaagcacgt aagaaattaa ctgattcgtc acttgatacg acaatatctt    15600
tagtaacttt aaatactcca cctaaatcat caaaactaat aacgtggtct gtaaagtcaa    15660
tccctgctac ttggaacgtg tgcgcaatct ttgtatctaa aagataagat tttaagctat    15720
cagtcgttaa aataacaata tcttttaatt tgaaactgt tgtatattgt ccaatagcac     15780
cacctgaagc acgatgaact tcattatatt tagcactcgt gttttgtaag ttgagaatag    15840
cttcaaaaac tttacttgct aaatcttctt tgatgttgc tttacgtaca tttgattcag     15900
ataattgatt caatgagtaa tcaactaaca ttgctcgcat ttctttttct tctaatacgt    15960
taatatcaga aattttcttt ttatagacac ctaatgcata attagttgcg tctgctaatg    16020
tttggaaatt gaaacgtgta tcattgttat ttaatgtaaa tttttgtttc ttcacaatac    16080
cactaccata taacttagta gccatacgtg gataattacg ttttagcatt aattcttcat    16140
ttttagataa atccatgtta ataggtacag tatccataat tacatattct tcactgtatt    16200
gtccgataaa gtcttgttct ttagctaacc aattaaaacg gttacctaat gcaatatcga    16260
ttaataacgt ttcattaatc ttagggaata aaaatttatt tacaaatgtt tcaaacattg    16320
tatttgagtt atcccactta tcgccaaacg tccatgtttt gaataagta tgattaaagt    16380
cttgtaatgc agatttagct gacttagcaa ctaatagtgc tgtttcgttt tttgtaatat    16440
tttctgccat gatttattat tcctcctcta catcgccagt aaatgactgt tttgaaagtg    16500
aatgaatttg tacaccataa ctatcttcac tttttgtttgt gtcaattgac atattttcat    16560
ttaattctgt tcgtttattt aatcttgaat cttcatatga tgtacccatc attgaacgca    16620
tattgttttcc ctcatacatg tttaaattcc tcctaatcta aatctaactt ttctattaat    16680
```

```
tcttcatctg aatagtcgtt atcttctttg tctgattctg ttacatctgg ttgtgtttgt    16740
tgtacttgtt gtggttgttg catttgtgaa gataaataag tagttacttg ttgttctaat    16800
gaagtaatac gctgctctaa tacaacaggg tcaaatttag aactatcttc atctgttgta    16860
gtaggttcta atttgttttc attttcttct tcgattgttt ctactgtttt atcttcagtt    16920
gattcttcag ttgattcttc agtagattct tcagttgatt cttcagttaa ttcttcagtt    16980
gattcttcag ttgattctga agtttcttct ttgtcgtctg gttttacgat ttcatcaaat    17040
tctgtcattt agacacctcc aaatatttta taactaatta tatcatagaa tatttaaata    17100
agtaaaataa ttttattata tgttcaaacc ataattttg ataaaagtca atagatacat     17160
aaattttgta tttgatgaat atgtaatagg ttagataagt tggaatagaa gtt           17213

SEQ ID NO: 2            moltype = DNA   length = 134876
FEATURE                 Location/Qualifiers
misc_feature            1..134876
                        note = PN1483
source                  1..134876
                        mol_type = other DNA
                        organism = synthetic construct
SEQUENCE: 2
aaaacctata gaacctgaaa aacctataga acctgaaaaa cctatagaac ctgaaaaacc    60
tatagaacct gaaaaaccta tagaacctga aaacctata gaacctgaaa aacctagctc     120
agatactacg atacctttag ttccattgga acctagcaca cctgtagatg aaagtaatga    180
tactaatgga gagggataac ctctcctttt tttgctatat taaaagagta ataaaataaa    240
cattatagtt ggtgattttt tgataggatt aaacgtactt acagctatat ccgtagtttt    300
tgcttgtgta agtctactag cactaatgat atttgcgtat attaaaactg aaaaaagtag    360
taagttggtt ctatacttga tatatgctat aatttctata ggttcttatg tagtattaac    420
aatgtttcaa gccacgtcaa tcattataaa aaatgatgtt atagactcta ttgagaatac    480
agagcagtat gtagggttta ataacccttt aattgttttt ggtataagtt tctttggagc    540
tgtaataggc agttttttggt ttttagttat gaagattgta aatactagga atttaaaaaa    600
taaaaaatta aaggattgaa gcatttgcta ttttcaaaag acgataaatg ggatgaagca    660
aaagacttta taaaaggtca aggattagca gataattgaa tagaagtagt ggattactat    720
agacagatag gtggtaaaca tgtagctatg tttattgcta ttgataaagt taaatatatg    780
gtactagaag ctacaaagga taataaagta atattggtag ataaggataa taatattgtg    840
ttagaggatt atgatattgt tatggaaagt aagaaaatgt tttactatat agaagaacca    900
ttcgaagtaa agataaatat tcctaaacat atccaagaca ttacctataa taacactgtt    960
atactaacta ctattcgagg aggtaaaata aaagttgcct gatttattta aaagtctaag    1020
gttaggtagt atgtataaag aagacactga gacctatg gttcctatag atgacggaat     1080
acaagctaac attagacaaa tagaacaaga tacaaaagag atgcaagaaa ttactaaatc    1140
tttgtatggt aaacagcaag cttatgcaga accattttta gaaatgatgg atacaaatcc    1200
tgattataga gataagaaga gttatatgag aaatgtcatt aattacatg aagtgttaaa     1260
gaaatttggt aataactcta tactaaatgc tataattatt acaagagcta atcaagtatc    1320
tacatactgt aaacctgcta ggtattcaga agaggagtg ggttttgaag ttaaattaaa     1380
agacttagac gctacacctg gtattaaaga aaaagaacga atgaaacgta ttgaagaatt    1440
tattcttaat acaggtacag ataaagatat agacagggat tcattccaag agttttgtaa    1500
aaaaatagta agagatactt acacgtacga ccaagttaac ttcgaaaaag tttttagtcc    1560
taaaaacaaa actaagatgg agaagtttat tgcagtagac cctagcacca tttttatgc    1620
tactgataaa aacggtaaga taattaaagg tggcaatcgc tttgtacagg tcatagataa    1680
gcaagtagta gctagttta caagtagaga acttgtcatg ggtattagga acctaggtc     1740
agacttaaat tctagtgggt acggattgtc agaagtagag attgcaatga aagaatttat    1800
agcttataat aatactgaaa gttttaacga taggttcttc agtcacgtg gaacaacaag     1860
aggtatctta cagattagag ctgaccaaca gcaatctcaa catgcgttag agaacttaa     1920
aagagaatgg aaatcagttt tttcaggtat aaacggtagc tggcaaattt gcctctataa    1980
aaagtaattt gtatagatga agggttaact gctaagaaca cctaaagctc aatacactac    2040
aaagtaaccc gaaagggtag gcttgaatgt tacgaaagta gaaaaagat attgagatac     2100
gttaaggtta aatcctaaga cgaagaacaa tggttgttta gcatcgaaag tcctaaagaa    2160
ctgaaaggtc tatggaatac gttcaacgac tatcccgtta caagacggga gtaaagctcc    2220
aagctattgg gagaagaaaa atccttaccc tacacaatgg gataacaaa tagtctagtc     2280
tcgtactgaa aggtagagca tgtgaaataa cacaggttta caagtagcg tttgtaaata     2340
aataaaacta aggtttataa aaaaaaatta ttcctttact agttgacaag taatcttttc    2400
tatgatatac ttaaaccata gaaaagaggt gaaagtcaat gaagaaacta aaattaagat    2460
tattaccaac tccagagcaa gaagacttaa tgtgggttca tgtaaatcat acacgtaatg    2520
ttaaaaaatat atttttagct aaatgttttg aactaaaaga aacaggagaa tttataagta    2580
aaaccacatc aaatactaa agattagaat taacggaaat gttgaaaaca gataaaatata    2640
gttatttaaa aagtgtatca agagatacac tagatagagc tgtaaatagt gtagttcaat    2700
cttatgttga ttggtgtaga ggtactcatg gtaaacctaa attcaaaaag aaaaataaat    2760
gtacaaaata ctttgatgtt agggaaaata gattaaaaag gtatggacat acttttcata    2820
tacctagtat aggaaaagtt aaagtatcta aaaatacttt aagaataat tttagtatta    2880
taaattctat agaagttta gataaattta gaaaacatc tattaagtat gatggtaagt     2940
attggattat gtttattact tatgatgaca caatagtaac ccctcgaaaa ccaagagaat    3000
tatctaatga aaccataggt atagacttag tgattaaaac attagccact tgttctaatg    3060
gtaaatctta taaaatatt aataaaagtt ctaaagttaa aaaactagaa aagaaattat    3120
ctagactaca aagacaagta agtagaaagt atgaaatgaa taagcaaggt aagaagttta    3180
ttaaaactaa taatattatt aagttagaaa agaaatataa actcttacat agaaaactta    3240
gtaatattag aaataatcat attcatacta tgactaaaga aatagtagaa caatatccta    3300
gtgaaatagt aatagaagac ttaaaggtaa gaaaatataa catttatctc a             3360
atagtatttc taaagctaat tggtatacaa ttagagaata ccttacttat aaatgtgaag    3420
atagaggaat attacttact attgctaata cttactatcc gtctagtcaa acatgttcta    3480
attgtggtaa tcgtttaact aaacaagata actatctttt atcacaaaga acatataaat    3540
gttcttgtgg aagtagtata gatagagatt taaacgctag tattaactta agaactata     3600
gatactccaa ttggtatcac aatcatgttt taactaaatc aaacagtaaa catgatatgt    3660
```

```
aggattccgt aaatccgaat taacgccttt ggagtatcac acaaacctga gtagagtata  3720
taaaagtagc tagtaatagt gaagatactc aaaaagggat acgttgaaaa aggaataaaa  3780
tttttttataa attttagatt acgaagtccc cgtgatgatg gctgatgatg ttaagtttgt  3840
taatatgaca ccaacagcaa atgatatgca atttgagaaa tggttaaaact tttttaatcaa  3900
tattatttct gctttgtatg gtatagaccc ttctgaaata ggattccta ataagaggagg  3960
aggagccaca gggtcaaaag gcggttctac attgaatgag tcagaccctg ctaagaagca  4020
acaacaatct atgaataaag gtttacaacc tctattaaga tttatagaag aattaattaa  4080
cagacacatt atatctgaat ttggtgataa gtatactttc caattcgttg gaggagatac  4140
taagtctgag ttagataagc ttagtatttt acaaaaagaa gtacaagtat ataaaactga  4200
aaatgaagca agagaagaac agggattgaa accaatagat ggtggagatg taattcttga  4260
ctcagcattt ttacaaagta cagcacaaga aatacaaaaa gaccaatacc tagatactaa  4320
acaaaaagaa agacttcaat tactatgag ttatacacaa ccacaaactg atgagcctac  4380
agatgatagt aaacaagaaa ctactaatca agaagtaggg acagataacc agttaaaagg  4440
tgatgataac gtatatagaa cacaaacatc aaataaagga caaggaagaa aaggtgagaa  4500
atcttccgac tttatgtaga taatattagc aacctaatta atacttaggt tgttattttt  4560
taatttggag ctacatttat actatgttat actatgtgtg tagtaatgaa taatgttgat  4620
gatatacttt ttgttatatt atgtatgtac atataaaata acaattaagt gaggtgtata  4680
atcactttgg aagaaatgaa atttagtgct tttgttccta tggacttaaa gaaatccata  4740
gatacggaag atgatacaaa taatatttct atcgtatctg gttgggcttc cacaccagct  4800
gttgatttgc agaatgacat tataaatcca aaggtattg atatagaata ctttaaaaaa  4860
aatggatata ttaactacga acatcaacaa gataatgtag taggtatacc tacagataac  4920
tgttatgttg atttagaaaa aggtttattt atagaagcta agctatggaa agatgatgaa  4980
aatgttataa aaatgttaga cctagctgag aaactagaaa agtcaggtag tggtagacgt  5040
ttagggtttt ctatagaagg cgctgttaag aaacgtaaca taaatgacaa tagaattgtt  5100
gatgaactta tgattacagg ggtagcacta gtaaaaaacc cagctaatcc tgaagctaca  5160
tgggagagtt ttgttaaatc attccttact ggaacggaaa caaccaccaga cacacaagta  5220
gatgcaggag ccttacgtaa agagtcatta gcaagctcta ttactaattt aacctatgta  5280
acaaaaatta aagatgttaa agagtataat gatatttgga ataatgtagt agaggactta  5340
actaaatcta ataatatggg ttatgaagaa tcagttatta cattcaatt agccaaagga  5400
ctatcaagaa aagtgctga gatagcagtt atgagtata ataaaaaaa tttagaatag  5460
gggattatat tatatgccta cggaattaca aaatattcta caagaatatg ataacttaga  5520
caaagaagaa gtatcaaaat ctgtagaaga gtctaaagaa gaagtaaaag aagataaaac  5580
agaagacact aaaacagaag acactaaaac agaagaaatt aaaaatgaag tagaagctac  5640
agaagagcaa gtagcagaag ctaaagaaga accacaagaa cctgcaaagg ttactgaaga  5700
agatgctaaa gaagcacatg aacaagaaga aaatctagaa gaagaagtat ctaagtcagc  5760
taaggagtcg aaagaccctg tagataaaaa agatactaaa acagaagaca aagacaacga  5820
gaaacgaaaa aataaaaaag acaaaaaaga agaaaaagat gaagaagagg aagaaaaaac  5880
atctaaatct atttctgata aagatattgt agatggtttc cgtactatct tgaaatcatt  5940
ccaagacatt aaaaaagaaa atgaacaata tgtgactaaa tcagatttag aaagaagtaac  6000
taaatctatt caagctttaa ctgataaaat taattctaat gaagaagttt ctaaatcagt  6060
tgagagcaac caagaagata agaagaagc agtagaaaaa tccgtaacga ctaataacac  6120
ttcgaatgaa caagatgtag ttggttatgt agctaaatca gtacaaacag aagaacaagc  6180
agaaactaca gaagataaag aagaacaaga agtagaagtt aaagaagaaa gtagagactt  6240
atctgtagaa gcccgtgaaa aattcatgag tacctataaa gaaaaatctc aaaacccaca  6300
tacgaatcgt tcagaagtat tgaatgctta tcaagcttac ttaaatatcc gcaacaatcc  6360
agagcaagca agtgaaaaag actttaatat tgtaaaagaa tttgctaatc tttaattaag  6420
aaacaaagtt gtgttatatt atagtgtgta aaataaaaca ataaaaaaaa gagcatatat  6480
gaaaggtgat atatataaat gaaccaaaat gaactttcaa aaaagcaaca tgcagttgct  6540
gatgaattac aagaaaaatt atcgaaatcc ttccaaactg gatatggtat cactcctgaa  6600
acacaagtgg atgcaggtgc tttacgtcgt gaaatttag acgaccaaat cactatgctt  6660
acatgggaa ataatgattt agtattttac cgtgatgttg cacgtagacc agctgaattca  6720
acagtaatta aatatgatgt tttcttacgt cacggtaaag taggtcattc tcgttttgta  6780
cgtgaaatcg gagtagcgtc agtttcagac cctaatatcc gtcaaaagac cgttacaatg  6840
aaatacattt ctgatactaa aaatatgtca ttggcatcta gtttagtaaa taacattgct  6900
gaccctggtc aaatcttgac tgaagatgct atctcagttg ttgctaaaac aattgaatgg  6960
gcttcattct atggtgatgc ttcattaact tctgaagttg gtggagaagg actagaatttt  7020
gatggactag ctaaattaat tgatgctgat aacgttatcg acgctaaagg tgctcactta  7080
gatgagaaat tattaaactt agcttcagtt aaaaataggta aaggttttgg tacagctaca  7140
gatgcttaca tgcctatcgg tgtacattct gactttgtta ctaatatttt aggtcgacaa  7200
atgcaattaa tgcaagacaa tagtggtaat gtaaatactg gtttcagtgt taacggattc  7260
tattcatctc gtggattcat tagattacat ggttctactg taatggaaaa tgaattaatc  7320
ctagatgaaa ctttaatccc acaaccaaat gcaccacaac cagctacagt aactgctact  7380
gtaaaaacag accaaaaagg taaatttact aaagaagaag accgtgcagg tttatcttat  7440
aaagtagttg ttcactctga tgaagctgaa tcagccacat cagaagcaca agttgctaca  7500
gtaacaaatg ctacgatgg agtagaatta aagattactg ttaactctat gtaccaacaa  7560
agcccacaat tcgtatctat ttaccgtcaa ggtaaagaaa caggtatgta ctacttaatt  7620
aaacgtgtag cacttaaaga tgcacaagaa gatggttctt tagtattcgt tgataaaaac  7680
gaaacattac ctgaaacagc agacgtattc gttggtaata gtgtcaccaca agtattacac  7740
ttgttcgagt tattaccaat gatgaaatta ccattagctc aaattaatgc tagtattaca  7800
tttgcagtat tatggtatgg tgctttagcg ttacgtgccc ctaaaaaatg ggctcgtatt  7860
aaaaacgtaa gttaccttgc attaaaatag taaatacaat taaaaattga atacaataga  7920
ataaggagta tacctaaggg ttgctccttt tttattacta cttatagtat acacgaaagg  7980
aatttaaaaa tcaatgttaa cttataaatt aaaaaatatt aaaatggcta ctgtacatgg  8040
tcaagtagaa gtagatgata aaggcgtagt taaggatta actgctaaac aagaaaaaga  8100
ttttgctaat ttaccaggtt ttacacatat ggaagacaag aaaacaacaa agaaagaagt  8160
aaaacctaag gaagaaaaag aagagaagag accaattaaa aaaacaacta aaaaagaaga  8220
taagtaggtt gatagaatgg taaacagtat gtttggtggt agtttagacc cttacgaaag  8280
ctctttatca tatgagtatc cttatcaccc atctggaaac ccaaaacata tagataaaag  8340
agaattagat agtattactc tagctgatta tggttggtca gcagatgctg tgaaagccta  8400
```

```
catgtttggt ataacagtac aaaaccccga tacaggacaa cctatgggtg atgatttttta  8460
taatcatata ttagaaagag ctataggtaa agcggaaaga gctttagata tatctatttt  8520
acctgactta caacatgaaa tgagagatta ctacgaaaca gaatttaata gttatatgtt  8580
tgtacacgca tataaaaaac ctatattaca ggtagaaaat ttacaactac aatttaatgg  8640
tagacctatg tatgattatc cagctaactg gtggaaagtg gagcatttag caggtcacgt  8700
acagttattc cctacagctt taatgcagac gggtcaatct atgtcttatg atgctgtatt  8760
cagtggatat cctcaattag caggaatgta cccaccaagt ggagcaactt ttgcacctca  8820
aatgattaca ttagattata ttagtggtat gttacctaga caaagagcag gtagaactaa  8880
accatgggaa gtaccaccag aattagagca attagttatt aaatatgcac taaaagaaat  8940
ttaccaaata tggggttacg atgatattac cctgtgtgta gcgtaagttg cacattttca  9000
aaggttaact gctaagaaat cctaaagcta actaaactac aaagtaagtc gaaagactaa  9060
gcttgaatgt tgagaaatca gaaaaaatta gttagatact ctaaggttaa atcctaaaga  9120
gaagagcaat ggaagtttag catcgaaagt cctaagtcaa tagataagga atacgttcaa  9180
cgactattct gtatagacga cagaagtaaa gctccaagtg attgggagaa gaaaaatctt  9240
taccctagtc ttagggataa caaatagtct gcacacgtct tgaaaaggag tgctaggaat  9300
tgacctagac ttatttagta gcgtaagtaa ggaaacaatg ttaattaaat gaaaacttcc  9360
tattgaaatt accccaagta tatgttatat tatagatata atatataagg tggtgaaagt  9420
aaatgaaaaa aacggaaaat acattttata gaggtataac actaaaagta aaccctaccc  9480
aagaacaaga agagttaatg tggaaacatg taaaccattc tagatttatt tataattata  9540
tgttagaaag atattggaaa gctctcgata acggtaaaata tatagaccat aaaaaatgaa  9600
tttctatatt aaaagaaata aagaatgatg ataagtatag tttcttaaat gaagtatcta  9660
gaaaaacctt agttggtaaa atagatgact taagagaaac attaataaaa tatcataatc  9720
atgaaattag aaaacctaaa tttaagtcta agaaagggaa atctaagagg tttcctatta  9780
gatatgaccg aatgcacttt aacaagaaaa acatgttaa agttgaaaaa ttaggttact  9840
taagaatttc taatggtaca tataaaaata ataatcagt actagagaat gaaagcatta  9900
aaccttttaaa ccctaaatgt tactatgatg gtaaaattg gtatatatct ttttcaattg  9960
aagtagataa tcaatacaag aaagaaaagg ataactacaa cgaagtcata ggtatagact 10020
taggtagtgg taaaaaacac gtaatttgtt ctaacagaaa aatatatggt aatattattt 10080
attccaagaa aatgaaaagg ttagaaaaaa aattatctga cctacagaaa agattaagta 10140
ataaatatga tattaatcac accaaaacaa ataaagtttt aaagctagaa ataagatag 10200
ctaaagtttta tagaaaaatg tcaaatatcc gtaaaaatca tgtacatgaa ataacaaaag 10260
aaattgttga aaagtatcct aaagagatta ttgtagagga tataagagtt cgtgatttaa 10320
taaaagacaa aggatataca ggacaaaaaa gaaacaaat acagttttct aatttctata 10380
tgattagaca gcaattacaa tataaatgtg aagatagagg tataaaattt acagtagcta 10440
gtacttatta tccatcatca caaatatgtc gtaattgcgg agaaagaaaa agaaatgctt 10500
taaaattaca gttaggtgat aaagtctttta aatgtaatgc ttgtgggatat gaagaagata 10560
gggatataaa tgcaagtatt aatttaaaaa attaccataa ttccccaatgg ttaaaagaac 10620
aaaaccaata atatgtttgc ttttagtagg gttccataac ccgaatgtat aatgcccttt 10680
atttttacaaa ggaagttaat ttaattaaca tatgtaatc tcattatcgg tgcaggaata 10740
gcaaacaaaa ctctagatgt agatggtatt acagaaacaa taggtactac acaatctgct 10800
atgtatggtg gagcaagtgc tcaaatacta caaattaatg aagatataaa agagctatta 10860
gctgggttaa aatcttactt tggctccaat atgataggca tatagtagga aggagatatt 10920
aaatgaaaaa acctttatg ataggtacta ataataatg ttctaatata attaataagt 10980
ctactatgta tacatctaca acacaagcag atgaacaaga acaaaagtta tctacagcta 11040
gactagagtt tgacactaag gatatgagaa gatttgtcaa tgatagaggt ataaaggtac 11100
tgtgggaaag agcttacttt tgtccttgcc ttaaccctga cacaggacat cctagagtag 11160
attgtcctag gtgtcacggt aaaggtattg cctatttacc tcctaaagag acaataatgg 11220
ctattcaatc tcaagaaaaa ggaactaaca atttagatat aggaatttta gatactggta 11280
cagctatagg aactacacaa ctagaaaaac gagtatctta tagagacagg tttactgttc 11340
ctgaagtatt gatgccacaa caactatat accatgttac taaagagcgt atacaaaaag 11400
gtattccttt gtattatgat gtcaaagaag taacttttat tacatctaac gatggtaagt 11460
tttatgaaga tgactataat atagagaaca atagattatt catgacgct aagtttgaaa 11520
acaaaactgt atccttaaat atttttaatgg tacttagata tgtagtatca gatatattaa 11580
aagaaagtcg atatcaatat actaaattta atcaacctaa tacaaagttt gaaaatttac 11640
ctcagaagct attattaaaa agggaacg ttattgtact acctgagcca tttaaagtta 11700
atgatggtat agaagaggac ttagagatac aggtagaaga ccctaaaaaa gaatctaaag 11760
ataatcattc aggtggtttc tttggaggaa tgctataatg cctataaaag caactagacc 11820
taagttattt agagacacga actataaaaa tataggtaag agaacagtag atgttatgcg 11880
ttctgatatt ttagatagat tacaagctac agcattacaa gtagtagtca aataaataaa 11940
acgcatgcct acttatctac aaataactga gaaaaagcta gagaagcaag gtgtaataga 12000
ccttaagaaa gcttttgctc attcacctaa aaagaaaagg actaaagatg gtggttggta 12060
tctaacggtg cctataagaa taaaacaag taagatgaat aataaaacat accaagactt 12120
aaggtctttta aaaatagaca gttcaagtaa ttcagtatct actcttactg attatttaga 12180
aggtagacga agtaatatta gtcaccccatc actaaagcct cagataaat caagtagaat 12240
tactaaagta agaaatggta aaaaatctag ttactttatg tttagaacag tatctagtaa 12300
atcccctgca agttcatgga tattaaatag agataaggtt aatgaaaaca acttctctaa 12360
aacaacatta aagtatgtta gaaatcttat gaactggaag attaagaatt taatgtgaaa 12420
aggttatgga agtaggatgg caataacatc agtagactca tatttactag agcaaataaa 12480
gcccagatta catacagtac taagtaattg ttatattata gatgaagttt taaaagactt 12540
tgattatcaa actagggaaa tgttcaaaga ggcttttttgc ggtaagaacg caaagcacga 12600
agtaacagta gggttcaatt tccctagctt taaaaacaac tacgaagctc attacctaat 12660
acaactagga caaggtcaag aggttaaaaa ctctttaggt agtatacaag ggtcttatct 12720
agaagcttcg ggtaacacat atagtgaaca atcagtagct aaaagagaag gtaatcgttt 12780
ttcatt gtatctaaac ctattctaaa tgtaataaga gtagaagcaa tagcgttttga 12840
ttcttacgat gatgttaaag tatcagataa cactgtatct tttaattata ctaacaatga 12900
gacttatgaa ggctacaacg caaatattgt atatgtagaa aaaacaaatg atagtaaagg 12960
gttagtaaaa ggtattacca tagaagaaca agtaacaatt gtgggtatgt cgtataatgt 13020
agatgttgct agatgtttag atgccgtatt aaaaatgata ttgatatcta tgagagacag 13080
tatagaagaa caacaaacat tccagctaca aaatcttgca tttgggagata tcgcacctat 13140
```

```
attccaagac ggtgagtcat ctatctttgg tagacctact ataattaaat acacaagttc   13200
attagattta gattatacaa taacacaaga tattaataag attactttca agaataaagg   13260
agcaaaaaga taatggctaa gaaaacacct aaaggtaaaa cctttacagg ttatgtacat   13320
atagatacat ttttaaaaac agcacagacc ttgtttaata tgaaagagtc acaggtagca   13380
ggttttaaag cctacatgga aggtaaacac tacctgttca atgaaaaaga ctttattcca   13440
tttttagaaa agtatttagg tagagaatta gaaatttaat atatagatag gagaattata   13500
catggcagtt gaaccgtttc cacgaagacc tgtcactcgt ccacatgcag tcattaatgt   13560
agacagtaca ggtatcggta aatcagctag ctccagtgaa aagatttat gtttaattgg     13620
acaagctgaa ggtggtaaac ctgataccgt atatgaatta agaaactacg cacaagctaa   13680
aagactattc cgctcaggtg aattacttga tgcaattgaa ttagcttggg gttctaatcc   13740
acaatacaca gcaggtaaga tttttgctat gcgtgtagag gatgctaaac cagctacagc   13800
tgaagtaggc ggattgaaag ttacttcaca gatttatggt aacgtagcta acaacattca   13860
agtaggatta gaaaaaaata caatcagtaa ttcattacgt ttacatttaa tcttccaaga   13920
tgatagattt aatgaaacat atgataaatc tggtaatatc ttcactatca aatataaagg   13980
tagtgaaagt acagctactt tttctgtaga gcacgataaa gagacacaaa aagcaaaaag   14040
attagtatta aaagctaata gcacagaagt taagtcttat gacttaacag gaggagctta   14100
cgctactact aatgccatca ttaacgatat taaccaatta cctgatttg aagctaagtt     14160
atcacctttt ggagataaga acttagagtc ttacttatta gacccctatg a cagatgttaa  14220
cattaaggat aaagctgagt atgtaaaagc agtatttggt gatttagaga aacaaacagc   14280
ctataacgga cttgtttcat ttgaacgatt agtatctgaa caagcaccta aaaacgtaga   14340
agtagacgca catgaagaat ctgctactgt aacagctgtg tccccaattc aagaaatcac   14400
acctttgaa ttaacaaaac tttctggcgg tacaaatggt gaaccaccag ctacatgggc     14460
agataaaatt gaaaaatttg cacatgaagg cggatactac atggtacctc tatcatctaa   14520
acaatctgtt catgcagaag tagcttcttt tgttaaagaa cgttctgatg caggtgaacc   14580
tatgcgtgct attctaggtg gaggatttaa tgaaacgaaa gaacagttgt ttggtcgtca   14640
atcatcatta tctagcccac cagttgcttt agtagctaac tcaggtatat tcacaatgga   14700
caatggtcgt aagttacatg taccagctta tatggtagct tctgctatcg gaggtttggt   14760
aagtggtttta gctataggtg agtcattac ctttaagcaa ctacgtatta ataatgtaga    14820
ccaattatat gaatcattag acttagatga gttaaatgaa aacggtatta tcaccgtaca   14880
atatgttcgt aatagagcta atacattctt tagattaaca gacgatgtta cgacatttaa   14940
tgataaaaat gaccctgtta agtcagaaat ggctgttggg gaagcaaatg acttcttatg   15000
ttctgagtta aaacttgagc ttgaaaataa ctttatttggt actcgtacta tcaatacaag   15060
tgcttcaatt atcaaagact ttgtacagtc attcttagga cgcaagaaac gagataacga   15120
aattcaagac ttcccacctg aagacgtaca agttattgtc gagggtaatg aagctagaat   15180
ttcaatggtt gtatacccta tcagaagctt caagaaaatt tctgttagct tggtataccca   15240
acaacaaaca ttaagagcct aaactaggac aaggagtacc tagtttaggt actcctatta   15300
aatttaatag gagagtgaat taatatggct tcagaggcta agcagtctgt ccatactggt   15360
aataccgtta tgctaatggt aaaagtaaa ccagttggaa gagcacaatc tgctaaaggt   15420
caacgtgaat acggaactac tggtgtatac gaaattggta gtattatgcc acaagagcat   15480
gtttacttaa aatatgctgg tacaattaca ctagaacgtt tacgtatgaa aaaagaaaac   15540
ttcgcagatt taggatatgc ttcacttggt gaagagattc ttaagaaaga tattattgat   15600
atcttagtag tagataactt aacgaaacaa gttattattt catatcatgg tttaattaaa   15660
cagaccccctt gtacagtgat gtgcattgaa taataccctta aattgctaga acaccgtaaa   15720
gctaactaaa ctcaaagta agtcgaaaga ctaagcttga atgttgagaa atcagaaaaa   15780
attagttaga tggtataagg ttaaatccta agtactacat aattggtaat tagcatccaa   15840
gctcctgtaa aatggagaag gttcaacgac tataataggt aagtcttagt tacatattaa   15900
gattatggca tagtctagtc ccttaaaata tcgaaaga tagggtataa acggttcagc      15960
aaacaactac aacgagactt ggcagacaaa tgaaattgta acagaagaaa ttgagtttag   16020
ctaccttta ctaatagagg ctatgtttgg tgacaagcat agaaaacact ttaaattgcg    16080
tgaaagtctt aaagactaga taactacaaa gtaacctgaa agggtaagct tgaatgttga   16140
gaaatcagaa aaaatatcta gtatagtata aggttaaacc ctaagtacag taaaatagat   16200
gatacgcagg caagcctacg agagtgggaa gcttcaacga ctataataag tgagtcttag   16260
ttacacatta agattatggt atagtctact cccttaaaaa tatcgaaaga gatagggtat   16320
agaggacagc atcagataag gctagaactt aaatttcgta ttaagaccta acaataaaag   16380
ttaggtcttt ttttatactt gttttattag aagtactgta ttataattaa aaataaaagg   16440
aggtgtacta aatgacaaac aggaaaacaa taggtaaagt aagtaattca agggcaacat   16500
ggaaaattaa accaacaaca agaattaaaa aagataaaac aaaatattct agaaaaaata   16560
agcataaagg tattgacaat tataaataac tgtaatacta tagttatata aggagatgat   16620
gaactgtgaa aactttttat tcaggtagaa gaacaacaag taaaaacagg caagtaaaga   16680
agcattataa acaaatgact aatcaagaaa taattatatg taggaactta ctaaaagagg   16740
cttataataa aaataattac tttaagttaa caaatcactt caaaggtaaa tgtaagaaac   16800
cagtaaattt taaagcgttt gttcattata tacataataa gaacttagat attatagaat   16860
ataatgaaac attatacaat aacaaaatac aacgtagggt agttgttaga caccccttatg   16920
tagtaaaagt taataataaa ttatcttacc aatatttagt tatagaagtt gaaacaggttg    16980
aagttgtaac tatgtactat aacagagtca cagataacca caaaacatta aatttaaatg    17040
attattatga taaaaatttta aaaataaagt attgacataa gtaaatacat aatatatact    17100
aaggttacat taataaagag gagaataaaa aatgacaaat aaattaagag ctatccatga    17160
agaaatgaaa attgagttac ataaattccc acagtaagta gatttaacaa gtaagacaac    17220
tgctattgca atcaatcaaa ttcttgacaa gtttaaaacc ttaacggaac aagcaggtaa    17280
aatcactaaa aagtattttg agggtcaaga gattttgacg attgattttg aatattatga    17340
ctcacttcaa gattactaca tttacttact taaaaatagt gaaacaattg aacaaaggtt    17400
acaagaaatt gaaaaagag tagctgaata tgttaagtaa tttggagtta taaccacatt     17460
atgttatact gtatgtgtat aaaaaacata agttagctgt tatattaatt atgagaaaat    17520
aataaaggat ggataaagaa ttggaaaag aacaaaaaga tattaaagat atgacacctg     17580
aagaaattga tgaattaaaa tatcagcaac aaaagataaa agagcgtgtt attaacaaag    17640
taattaaagg tgttaatgat gtatgggaga aagaatacaa ctttgaagaa ttagattttaa    17700
aattcaaagt aaaaattaga ttacctaatg ctagagaaca aggtaaatatc atggctttac    17760
gttctgcata cttaggtgga atggatgctt atcaatctga ccaagttatt aatgcttatc    17820
agatgttagc tactctacaa gaagtaggg tagaagtacc taaagaattt agagaccctg     17880
```

```
aagagattta taacctaact ccacttgcta ttatgtggga tgattggtta gactttatga   17940
cgtcctttcg ttactagtaa cgtaaagaag ttaaatgaag atatagaacg gttaggtgga   18000
cttttcacata tagctagaga gcctttatca agaaacttat gggctatcat gcgtgagttt   18060
aatgtgctac ctaccgaaca acgttttaaa gatttagatg actatcaaat agagtttatt   18120
atagctaaca tgaatttaga tacaaaagaa atgatggaag ctagagacgg taaaaactat   18180
gatatgaaag cggaagacgt agacacatca tggttcgaag cgccgacaga tgaatttgat   18240
gttgttcctg atttcttaga cttagatgat ttaaatacac aagtagataa aagtttaagt   18300
gagaaagaaa agatagaaag agatagacga gttgaagctg agttagaaga tgaaaccgag   18360
ggattaacaa ctcaacattt agctatgatg gaacacataa gacaaaaaca aaaagagctt   18420
gatgaaagtt taggtattga taacaaagaa acaacacaag aagatataaa caaagcaata   18480
gaagatgtag atgattggta catgtagggt aatggtataa caccaatacc cttattttt    18540
gattaggtgg tgaatactgt ttggcaatga atgacgatta taggttggtc ttgactggtg   18600
atagttctag cttagaacaa agtttaaaag ctatagagat gtacatggat gcgttagagt   18660
ctaaaaacat agatgcacca ttaacaaact tcttagagaa attaaaagta atagcaaaag   18720
aagtaaaatc tgtacaaaac attatggata aacaaagtga taagtcttta atatcaccaa   18780
aagctatgga tgaggctatt agttctacac agaatgtaac taagaatata aacgacctaa   18840
agaaagcttt aaatgacata caaacagata atattacaaa gggtatagct cctgaccctg   18900
aagtagagaa agtatatagt aaacttaata agacactaaa taatacacaa acagaactag   18960
agaaagtagc atctcaaaag attggttcag actcagatat aacaaacaga ataaaagaaa   19020
tgaaaacact gaaccaagtt acagaagagt ataataaatt agtaaaagat gccagttcag   19080
ctaaggagta cacaaagcaa ctaagagcta atcgtaatat ggtagaggt catatatcta    19140
ggtctgaagg ctctaataga atgtcctatg accaaggtgc tagtagtacgt tctgaattag   19200
gtaaagtaga cacttttgaa aagcaacgag aagctaacaa tagaagaata aaagaaaacc   19260
aagatagata tagaggttat agacaacaac aacaagattt agtaggcaaa agagctcgtg   19320
gtgaaataag ttctgaggat tataaaaaac aatcagcttc tattaaaatg atgattgatg   19380
aaagtgaaaa gctttctgaa gtttatagaa aaacaggtgc tgaattagac aagtcaatca   19440
actactataa aaatagtgct aaaaaacagt ttgctcagcg tgagatagaa cagcaacgag   19500
gaacaatggg taaattgttc caagatagat taccatctat tggtgcacat gctactatgg   19560
cagtaactgc tcttgcaggt ggtatgtata tgaaaggtgc ctccttatcc gaggcaaata   19620
gacctatggt aacatcatta ggacaaaatt cagataatat ggatatagac gcagtaagaa   19680
atacatatgg agatttgtca atagataata agcttggtta taattcaact gacatgctaa   19740
aaatggctac gtcatatgaa agttctatag gacataaaag cgatgcagat acgtataaag   19800
gagctaaaca gttagctgta ggtggtcgtt cattaggtat acaagaccaa gaagcttatc   19860
agcaatccat gtcacaactt atgcatacag gtggcgtaac ctcagataat atgaaagcta   19920
tgcaagatgc tttcttaggt ggtatacgtg aatctgatat ggttggtaga caagacgagc   19980
aattaagagc tttaagtact attgccgagc agtcaggaca aggtagaaca ttatctaaag   20040
gagaaatgtc taatcttact tctctacaag ctcaagtagc gggtacaggt agtaaaggtc   20100
tacaaggtgc acaaggagct caagccttaa gtagtattga ccaaggtatt aaaaatggta   20160
tgggtaattc ttatactaga ttagcaatgg gatgggtac taagtaccaa ggattagaag   20220
gtatgcatga cttacaagca caaatggata aaggtatatc agaccctaat aacttagtta   20280
atatatttga ccaagctaat aatataggaa gtacaacaaa agaaaacaa gccatagcta   20340
aaaaaggctt tgaaagcatg ggagctaact taacacaaga gcaaacagat gagttgtaca   20400
atctttacgc ctcaggtaaa ctatctaaag aagagttagc tagtaaagct aagagctagg   20460
aacaagaagg ctctaaagca ggagataaaa ataaggataa gtattccgag tctaaagcag   20520
gtagaaatga ccataacaaa gctaagacag atgataaagc tgaggatatt tatgacttag   20580
ctcaacctat tagagatgtt catagtgcta tggcaagctt gccagctcct ttatacctag   20640
cttcaggagc agtacttgcc tttgtagcat cttagctaa atctactgcc atgatggctg   20700
gtggttcttt attaggtaaa ggtcaaaaag gactaaaaga ttggtttaat aaccgtaaag   20760
gaggttcaac aggtaagact ggtggtagta acctggtgg taatcctaac ggtggtggac   20820
gctttggagg acttaaaaac ttagctgaca ctatactagg tgataaccct agaggtggag   20880
accgaccatt taaagaccaa gcaaaaggag caggacaagc tgctaaaggc atgggtaaga   20940
ccttgctttga tacctttgga aaaagagatt ttacttttgg tgaatatatg ggaagaacca   21000
aagacctagg taaaggtgca tggaacaaag gtaagggagc ttttggtaaa gctaaaggta   21060
aatttagcgg taaaggttct gacttaggtt ttatgtcaca agcacctact gctaacgcag   21120
gaggtcttgg taaactaggt ggtcttacaa gtaagctagg ttggattggt gcaggtctat   21180
cggcgtttga tataggtagt tctttaatac aaggagatac taaagaagct tcttctaaat   21240
ttggtaatac tataggaagt attatagacc cgttaaattt aggctatgga gatggcttaa   21300
gagattatgc tacgaaaaca gcggaaggtt ctatgacaag tgatggttgg aaattatggt   21360
ctaatggaaa taaagatggt aagaataaat tccaagacte tcctgtaggt aaactaggg   21420
gtggcataac agatttcttc acaccagata acccttctaa attgacgag acagtgaaaa   21480
ataaaaaagg taacataatt agttatatac taattgcctt gcttatagag caatctgtaa   21540
gtaccgagtg ttaactgcta tgaaactact aaagctaact aaactacaaa gtaacctgaa   21600
agggtaagct tgaatgttga gaaatcagaa aaaattagtt agatactcta aggttaaatc   21660
ctaaggagaa gtacaatggg tgtatagcat cgaaagtcct aaagacctga aaggtctacg   21720
gaacacgttc aacgactatt ccgtataggt gacggaagta aagccacaag tgattgctgg   21780
aagaaaaata ctcaccctat actaatagg ataacaaata gtctgcgcac gtaccgaaag   21840
gtagtgtcta gaaataacta gagaatatac agtagcgtgt atatttaaac attgttaaaa   21900
tatataaata attaaaattt gtattctact tctgcatata aaccttttctt attttgtaag   21960
gtaaacttgt tattaaataa atatacataa ctaatacgat aggttatata tgaaagtata   22020
ctattgttta tatgtttaa cttatgtgtat taatgataaa tcacaaagta aagacaggca   22080
aaaagcagaa gaaaaagag aaaagaataa tgattctaga gaaggaaatg taacagtata   22140
ctcacatttc ttagaccatt tagcagataa cctaacaaat aaaggtagta gttctaacga   22200
cagttcatca ggaggaacac ttgactacct tgatggtaaa aactttacgg ataaagacgt   22260
aactaagcat gacttaggta aactgctaa aggtgtaaac gccgaaatgt taaataatg    22320
gattgagtct caagcaccta gtaattctaa aatgcgcggt ttaggtgagc tttatatgaa   22380
agcaggtaaa gagtcaggac ttgacccaag gtatttagta gcacatagtg ctgttgagac   22440
aggctgggga acatcaaatc tttccaaagg aggagaccct aacaaggta actggttcgg    22500
tataggtgct tttgataaca atcctaataa tggttttaac tatggtttgg gtattgttgg   22560
tggtgctaaa tggattagag acaacttcta caacaaagga caaagaact tacacgatat    22620
```

```
gagacacaac aatggtgttc atgaatatgc aacagcaggt aattgggata ctatgattgc  22680
cagtattatg aaaggttcag acaagttcat aggtggcgga ggtggaggca gtgatgttat  22740
gcctagacat gctctaaaaa acgaccatca accaaagaat cttaaatata acatagaagt  22800
acctaaaagt aaaaaccct atgaaacagg gaaagcaata ggtagaaaat taaaacaatt  22860
attagaatct aattttaga atacaattat aatacttaca tattttaaca aatggtataa  22920
ataataaaaa acagaaaatg tctacagaac aactaagaga aaagaataat aaatcagaaa  22980
ctaaaaactt aaaaacttac agtaacctat tagatagagc acaacaaatt atagaagatg  23040
ctaaagcgct agactcagga ggttcagaca gtagttctga ctcagggggt tcagcttccg  23100
atgtagatgg agaaggtgcg ggtaagattt acaaattcct taaaggtaaa ggtttatccg  23160
ataaccaagt aggtgccgtt atgggtaacc ttaagcaaga atcggtgctt gaccctaatg  23220
caaagaacgc ctctagtggt gcttttggca ttgcacaatg gttaggtagt aggaaatcag  23280
accttgatac ctttgctaaa tctaaaggta agaagtctaa tgacttagac gcacagttag  23340
atttcttatg gaaagaaatg agttctggtc aaaatagtaa tatgcttaaa aatgcaggat  23400
ggagtaaaag tggtagttta gaaaaaaaata caaaagcttt tgcacaaggt tttgagcgta  23460
tgggtgctgg agaggctatg atgagtactc gagtaaataa cgctaaagt tatgtaagca  23520
aatacggtaa gtcaggtggc ggtggcggtg gagctatacc atcatcatat acgtccgtat  23580
taagaaaccc gatacttagt agtgcttcag gaagtactgc atctcaaaat aatgtatctg  23640
tgaatgttag cattacagga acaaatgaca aaagggatgc tgaagaaata ggtaaaggca  23700
ttaagtctac ttttggagat gacttagata ttttctcaaa cacatataaa cgtaattact  23760
agggtagtat tattaagtac tacccttat ataaagaaaa aggaagtaca agtatgtata  23820
gaattagacg tcctaagata cgaatagaaa tagtaacaga tgataataca tttcattaa  23880
agtttgaaga tactaaagat tacaacggca atcaatttgc ttcaaagtta cttagttttc  23940
aaactaagaa tgctatggaa gatgatagtg ctgtattcca aataactatg gcagggata  24000
cgtattggga taagctagta atggcaaatg atattattaa gatatatatt acgcctaata  24060
atgaccataa agataaagag ggaaaccaag agaaacttat acaagtaggt atggtatctc  24120
aagtatctaa agtaggtagt tatggtaatg accaagtaca atttagaata acaggtcaat  24180
catttgtaaa accttttatg aagtttggtt taggtgttat tcaagaggta caagctgtat  24240
taccaactgt tggttggtta gttgatggcg atggagagaa tcaggttaaa tttacaggta  24300
gttccgctaa agatgtaatg caaggtatta tacaacgatt tattccttac atgaagtaca  24360
attatacgga taaacatac aacacattag agagttactt agattatgat gatttatcta  24420
gttgggatga gtatgaaaag ttaactgaag tttccgcttt tactaacttc gatggtacat  24480
taaaacaact tatggactta gtaactgcta gaccttttaa tgagttattc tttagaaatt  24540
cagataaaca taaaggtaaa gcacagctag tattaagaaa aactccttt aatccaactg  24600
aatggaaagc actagaatac atagttgtac caactgatga ttttatagag gaggatgtag  24660
gtaagagtga tgtagaaacc tactctatct ttacagtaaa accagcaggt atgttaaaag  24720
aattaacagg ggatgtattc tctaaacctc aatttcacca agaattagta gatagatacg  24780
ggtattctaa atatgaaaca gaaaacctat acataggaac taagagtggt agtgctacag  24840
aagatagtga aactacaggt ggagataacg gtcatgaacg agtaactat gacagactac  24900
ttaaagattt aaataactat ggtagagagt ccatatctaa aggattagat aaaatactcta  24960
gtaagatatc atcaaagtac aacaatatta ctaaacctga agtaaagagt atttagagt  25020
cttacataaa aaaaggtaat ttaagtaaag aagattatga aaagataaca aagaataata  25080
cttcaagaga atcagtatct gatactagac caaagttaac aaaagaaaaaa ttaaagtcta  25140
tattagcgga aaagtttaat aaaaaagaaa cttttgatga taaagattta aataagaaaa  25200
caacaaagc tgtaatagat gatattacaa agaattataa atatggtaat cctgcacatg  25260
ctaagaaact actagaggat tacactagat ttaaaggcaa cccacctaca agtaccacag  25320
gtgatattta tgataagtat cttaaagccg tagaggagt agctaatgtt gctagagata  25380
caggttctga cgcaagtgat gacccttaa ttatatttca taaaatgtca tttaattggt  25440
atcactcaaa ccctaatttt tatgcaggta atattgttgt attaggtgac cctaagtatg  25500
acctaggtaa acggttattt ataaaagata acaacgagg ggatatatgg gagttttaca  25560
tagagtccat agaacataag tttgattata acaaggata ctttactaca ataggagtaa  25620
caagagact aaaaagatgct attataaaag atggtagga aagcaaacat aggttttaaag  25680
gactatggaa tcagtcatct gactttatg gtggtcttat gggtgaagag acatctaaag  25740
aattaaaaga aaaaggtgta gccgagaaga aaacaaaaag aaataaagat ggagattctg  25800
acggaggcgc acaagatgga ggtaccttag cttcactaga aaaatataat ggtaagttgc  25860
ctaacacga cccaaatttt gttcaaccag gaaacaggca ttacaaatat caatgtacat  25920
ggtatgctta taatagacgt ggtgagttga gtattcctgt tccgttatgg ggagacgcgg  25980
cggattggat tggcggtgct aaaagtgctg gttatagtgt aggtagaaca cctaaacaag  26040
gagcttgtgt tatatggcag agaggcgctc ctggcggaag ccctcagtat ggacatgttg  26100
cttttgtaga aaagtatta gacggtggcg ctagtatatt tatatcagaa cataattatg  26160
caactcctaa tggctatggt acaagaacaa tagacatgag ttcagcaata ggtaaaggtg  26220
ctcaatttat atatgataaa ggataattga tatggcaacg gataaacaag ttaaagatgt  26280
tatagataaa tttatagata atcttttcaa ttttgaagta ttaccaaag aaaaggttga  26340
agaaaaagat agagaagtta aaaagataac tacagagagc gtatacaata aagttgttga  26400
tattagacca tatgtaggtg ttatacaaag tataacacct acagcaggtaa catatgatag  26460
ttttactaat aatggtacag atatagaagc taaactcaca tttagaaaaa taagttatac  26520
tacagataat ctcacagtac ctactgatgc attatcaact tgtatggtgc atatggtaga  26580
aagaaatggt gtacttgtta tagattactt tgatgagtta cagaacatac tgtatggtag  26640
ctacatggag aatgagcata tatttgatga agatgttcca gttagtacat tagtaacatt  26700
agacttgaaa gagaaatttaa ataattaaa acatatacaa tatatgttta aagggaatac  26760
ggataaaaat cctttttgaaa gtaaggatat agtacctttta gatacataca acttattata  26820
ttggatgtat aaaagagaaa atgtagagct aaaaaatcca ttaacagtta actacttctt  26880
cacaggtaaa agcttctata ccatatttgg taaggacac aaatataaag ttggtattga  26940
caaattcaaa ataggtgata tactattctt tggacgtagt gatgataata tagggatata  27000
catgggagat aagaagttta tttctcttat ggtgtacatt cctaaagata acacctctat  27060
tagtacctat gagttagacg attattggga tgacttttaat ggtagggtta tgaggtttga  27120
tgaggatgat atagcatggt agtaagatta caatcttctt taggtagaag tttaaaaaaag  27180
atagactcag aagaacttaa tgttaaaggt ctattattag gtacagtaag caaaataaat  27240
tataagtacc aaactgtaga agttaaaata aatagttaaa cattaggaca taaccctagt  27300
gatgatggta agttagctgt tccttatcct aaagattatg taggaagaac acctgaaggt  27360
```

```
agtatgtatg gcagtaatac tttaataacg gaaggaacta ctgtactgtt aggatttatt  27420
aatgatgaca ttaattaccc tattatacta gctatctacg gtaatacaga agcaaaccaa  27480
ctcataaata cgaatccttt agagggtggt aaaatgagta atgatgatgt ttataaatat  27540
agtagtgctt tgtattctat attacctgac ctaacttata catataaaga tggtgaaggt  27600
acatctataa cattcaa tggtaaatct ttcttatcct ttacttcagg tgataaagaa  27660
aaacctttat cttcagactt ttatacaggt actgaatacc aagacttatt cccatcatac  27720
tatagtaaca aaaatttaat agaacctaga atacaaaagg cacctaacat gttatttaaa  27780
caccagggtc tatactttga tgatggttct gaagataatc atgttacaac tttatttatt  27840
tccgaaaaag gtgatgtaag agcttccgta ttagacaaag gcacacaaaa aagaacaaca  27900
caagagatgt ctcatgatgg ttcttataga gttataaagc aagtagatga cctattatta  27960
gactcagcgc aagtatgggt agagtttggt ataaatgata ataatgtgtt ttatataaaa  28020
aaccctaagc atatgtttga atttaatgat aaaggtatat attagatga taagccaatt  28080
ttagatacgt tagatgctag cattaccgag tctatagata ggcttaagga agtacagaaa  28140
gaattagatg acattaacta cttacttgag ggtgtaggta aggaaaactt agaggagtta  28200
atccaagaga ctaaaaatc tatagaagtt tctagtaaag caagtagtga tgttacgact  28260
atgaatctc aaatatctaa tgtaagtagt agagctgagg gcattattac acagtttcaa  28320
gagtttagag acaaaacatt taaggcttta tatgaagatg cttctactat gataaataaa  28380
tacaaccaag aaatacctga gttaaaagc agattgaata ctctaggtac aattacatta  28440
cctaacatta ataataccctt attagagaaa tcaagtaaga cctatgttaa taatagttct  28500
caaagtgtta gtagtaatta tctaggttca ttactgcaat tagatagtaa ccttactatt  28560
tatccgtaca cacctacacg tattatatgg aataagatag tttttaataa ttctgagttt  28620
gtaaataaga ctaaggatgc ttttgttatt ccgttaggta tatctaagt taaagttct  28680
attaatctta aatgggatat attacaagat aaagtaaaaa ctattgcagt caagaagaat  28740
agtaatacat acaaaactat aaccaatggt aatacacacg ataatataat tacaaatgtt  28800
atacctgtta aacaaggaga tacattcaca gtagaagtac aacaagataa tgatattaac  28860
cttacattac tacaagataa tacaatgttt agtatagaaa tattagaaac tactttagca  28920
cctactaaca ctgagttatt aggtacagta tccgaacaa cagataagca actacaaaca  28980
cttgtaaatt ctaatgttga tttattgagt ttgacaacac aagttactaa agataatcag  29040
ttagtctgtc ttaatgattc taaattagat actataacaa caggtaaagg taatgtgtct  29100
gattacactc tacaacaaat aaagtcattt tcttctaaga gtggagaag tatttatctt  29160
ttagaagaag tattaactaa atataaaaat tctgttagat acagtattaa tttaccaact  29220
actgcaaaca tagtagaact actgaaaaa tataatttaa ttggtataag agcacctagg  29280
aatcaagtgt atttgaaagt taagattta acaatcacac aagaaatatt aataatttt  29340
tctaacttac cagtattata taatacttcc tatctaacaa gtcacagatat taacaaaggt  29400
atatatacaa atatatacgg agtactacta ccatatacta gcatcactca agatacagta  29460
aatacagcac ataataataa cctatctata tatgctagtg gtgatatgac aagtgatatt  29520
ataaataagc ttattttata tggtatagat ggtgtagaaa caaataaaat attagagttt  29580
aaaaaagttt aaaagtccta ttaatagggc ttttttatat atgtcatgtt atattaaact  29640
tgagaaagta gttgtattta aatcctatat atgatataat acgatataga aagtggtaa  29700
gttatgcctc aatcagatgg aaagaataca ataagacgta ttgcattacg ttttccaaca  29760
gcaagcggta aatataatat gtaccgttc aaagtaaacc ctgaaagtta tgaatatagat  29820
gcaccacaaa gaacatctat aactaaaact aaatcagaca ttattgttga agactacggt  29880
aaagatatag agacaataac ttttctggt tactactggt ttagacctgt aaaagaagta  29940
gatggtacta aaacaggaaa acaaaaaata gaggaactac aagaacaagt agaagcatat  30000
gctaagcagg gtgagatgg tagcgtagca ggagcttata tagagttcta taactttact  30060
gatgataaat attacaaagt acatctagca ccgcaaggtt taaaaataac aaggtctaaa  30120
gatgaatcct tgttatatag tatgaaata acttttagttg tgataggtaa ccttgctgaa  30180
gcagatagag gttccgtaac atctgctgag tttggtaatg taaaaccta tgctaaacaa  30240
agagttgatg agggtgttaa tgatttagat agtaacgcac gaaaaacaag aaacaaaaat  30300
aatcaaatag tatcacaatt tgaaaataaa agcagtcaaa gctcttctaa ttctagtagt  30360
agcggttcac gatatggaac ggcaggaaca ttaagaggag gtagtggcat aagaacagt  30420
ggttctgagg gtaatagaga cggtatgagt aatataggta tatatacccc tagacagaat  30480
actaacggtc ttagtagtac tgttgatgat atggcactta aaataggata cggtgatgga  30540
ggtgtatcta ggtaatgaat aattatatac ctcaaccaca aggactatta aggttttaa  30600
atggattgga gttagacatg tcttacacac atatgaactt attagatgag gaagtaccctt  30660
ttgtttctaa attctataca ccacaaatac aactaagtga acttgcaaga ataaaattaa  30720
aagagattaa gtctactgat atcccctactt tagaaaaac atttaacaac aatacaaatag  30780
ttaataaagt agaacaaaca agtttaaagt tacaatcacc tagaatgtat ttaattatgc  30840
aatctatcgt aatggaagct tacgctattg taaactgctt tgtagaaagt cctgaatact  30900
taaaatattt aacagaaaaa gatgtatcta tagtaagaag taatgttaac tacgtagctg  30960
actacttaag tgattatgaa gaatacaata gtattgttct cgatttaaga gacttagact  31020
tatgtttgg ctcttggaa ttacaactac cactaattaa gagtgaggtg gtataatgag  31080
atttagaaag catgaagtcc aaccagaaga aacttacaa gctatatcac aaaggtatta  31140
tggtgatgtt agttactggt tagatttaat agaacataac aacttacaat atcctatat  31200
tgtagataca gatgaagaaa agaaaaagaa ccccgagcat ttaataacta aaggtgatat  31260
tattattata cctttagatg ctgagttaac agactcggtt tctaaagaaa taacatcaag  31320
agacaaagat gtattagtag aattagcttt aggtagagac ctaaatatga cggataataa  31380
agagtatata gacgctcatg gaacagatga tgaaatatta gccctatctt cagatggtag  31440
aggagacctt gatagatta aggcataga taatattaag gagctagact  31500
attgacacct aaaggttctt tattattaca tcctgaatat ggttctaaca ttcataattt  31560
attggtttta aatatacctg aacaagctac gttaattgaa gtagatgtat taagactct  31620
aacatcagat agtagagtta aatcatctaa cttaaaaggt tgggagataa aaggtaatga  31680
atactatggg tcatttaatg tagaaatcaa gtccgtagaa gaatctatag actttgtatt  31740
aggtcaagat gattcaggtg tcttttgcttt atttgactaa gaaaggaaat ttatatgaga  31800
acaagaaagt taacacagat attatctagg ttaatggata agacgataca aggtacaagc  31860
aaaaataacag actttacacc tggttcagct gtacgctctc ttttagaagc agtagcttta  31920
gaaatagaac agtattatat attaacaaga gaaaacatta ttgggggcat tcaagaaggg  31980
attattgaag cttttgattt tcaaaaaaga aaagctaagc gtgcttatgg taatgtaaac  32040
attcaatttt accaacctt agacatgaga atgtatatac ctgcaggtac tacattctca  32100
```

```
tctactaggc aagaataccc tcaacaattt gaaacactag ttgattacta tgctgaagaa    32160
ggaaccactg aaattacagt agaagtttat tgtaaagaag ttggtattgt aggtaatata    32220
cctgaagata tcattaatac aatagcctca ggctctagtt tagttcgtac aattacaaac    32280
ccgacttcct ttaatacagg aacaaaagaa gaatctcaag aggattttaa acgtaggttc    32340
catatgtttg tagaatcgag aggaagagct actaataact ctattagata tggtacatta    32400
caagtacctg atgttgatgg tgtttatgtt tatgaagaag taggtcatgt tactgtatat    32460
gcgcatgata aaaacggaaa tttatctgct actctaaaaa atgacataat aacggcatta    32520
gaagattaca gacctagtgg tataaaatta gatgttgtag gcgtagagaa agaggaaata    32580
gatgtgtctg cagtagtaac aatatctaat aaagctagga taggtgacac attacaaaga    32640
catattgaaa gtgttattag agggtatcta aatagtttga ctacttctga tgacttaatt    32700
attaacgatt taattcaagc tattatgaat atagatgata atttaattta tgatgtagca    32760
tttaagaatt tatctacaaa tatagaagta tcttcgaaag gtattattag agcaggagat    32820
attaaggtag aattaatata gggggtaaac aatggctaat tttttaagaa acttcacccc    32880
tttattaaga agaaataaga ataataaaga taaccaagac cctaactatg ctttaataac    32940
agcacttaat gatgagatga acaatataga gttagacacc attaaaagca aacttcaatc    33000
atcattaaaa actgccacag gagattactt agataagttt ggggattggt ttggtgtata    33060
cagaagaata aatgagaatg atgacagcta tagaaaaaga attataaaat acttattatt    33120
gaaaagaggt actaataatg ctatcattag tgctattaaa gactacttag ataatgagaa    33180
tataaatgtt agtgtatatg aaccttttaa aaatatattc tataccaata aatcaaaatt    33240
aaatggtgaa gattatttaa tgggttatta ttatagattt gctgtgataa atgtttctgt    33300
tgatggctac tttcctttag agattataga tgtaataaat gaatttaaac ccgcaggtgt    33360
taagttatat ttaacttatg atggtgctac taccataagg gtggatggtg ttgttaaatg    33420
gcttaaaaat ctacctaaga ttgaaacata tatggattta gatagattat taggttatga    33480
tgaaactttc tatggacatt taaacatggg tgaagcaaca gctgaacaat ctgataaaac    33540
aaggttcaga acaaataaga gtacattaaa tagtgaagat attctatcag gctcttctaa    33600
tattggacgt agatttataa attatgctta tgttacgaca tatgcatatg aacctactag    33660
tacatcagcc gtcacacata tagcttcttt aaatgataaa ggaaaagaac cacccttaga    33720
ttattactta tatacatcct taaagaatac taatgatata aatatatcaa tggaaacttc    33780
ttacggtgta tcttatttat acaataactt taatgtaggg gagtttatca gtagatacaa    33840
acctaatata gatataacta gagataatgc taaaaaacaa atatccgatt ttgtagggga    33900
actaacaatt gatttctttg caaaagcttt agtttcacct gatgaatcat tacctattaa    33960
gttacaaata tttgattttc gtactaatga atggttaact gtatcagaaa cagaactatc    34020
tttttacgag aaaaacatag gtgtaaacat aggttatata agagattact aaatgatga    34080
ccttaattta tttacaagat tagaggttaa tataggtaaa gatgagcaaa aagatataag    34140
tattaactac atggatttac atttttataa ttataaaaaa gatgtgtata ctatcaaacc    34200
ttttaaggca ctagttgaaa actacataga tttgactaaa gatacttata ttgaaggctt    34260
taaagtagcc tcattattaa atggagacat aattaataaa aatggatacc aacccataaa    34320
atatttaagg ttacatgcta cttatgattc aactaaacct attgtaagta ttacaggtaa    34380
aaacagcaat aatgaggtac aaaataacta acctatagat ttatataaaa atgcaactaa    34440
tagaaactta ttgcaatcat ataaaggtga tagtagtata ttcaaggatg ttgtaagcac    34500
aaaagagttt tatatctcat catgggctga caccttatat aactcaacgt atttatctaa    34560
agtactgaaa ccacaaaaat tatatacttt gtcattcgag atggaaatca cagatgctaa    34620
tatgacttta aaaacatatt ctgacaatca tggtatatat ttatatagta gtactaaagg    34680
tattgttgct aatggtgtta aaagcatgca aagaaagata ggtaataaga ttgatgtatc    34740
taccacattt acagcaccta caattacaga ccatagactt gttgtttaca caggtagata    34800
tacagcgagat ggtactgcct ctaaaacacc tattgcttct aatacggtaa aagtaacaaa    34860
ccttcaacta aaagaaggag ctactaagaa ggactacacg gtagcacctg aagatgtaac    34920
taatgttata gacaaagcta ttgtgtttga taacatatta acagatatac aaacaatagg    34980
aataaaataca caacaccctc ttagaaatat tgagctaagt tattcttact atggggataa    35040
ttggacaaac ctaaaaacaa taagtaattt aagtcaaggt gaaacaataa cacctaataa    35100
cctagtagat ttatatggct tagaaacaat agattattca agtattacca ctttctctag    35160
ggttatactt aaaactatat ggaatgctaa cctgaataat ttaacaaata aaaaaggtag    35220
tatttctaac atgagtaata actatttcaa tgctgtgtgg caagaggtag atatgatata    35280
taacactaca ttaagtagca tgagcatact tactgatagt gaaggtaatg tatttgatag    35340
ttcaacagga caggtaataa aattagcacc taagatatac caaggatata ctgatgtaga    35400
tagattgcta acgtctacta ctctatataa cgagaatatt acattaggtt caaatagatt    35460
tatttatgac ttacgggata tgttactatc aagtgtataca ttcacagtag ataataaaat    35520
taaagtaata gatacataca cagaagtaca gtaaagatat tgacaataaa gtattaatat    35580
gatatagtaa ggtatgcgta ttatagta ccttgttata ttaatacaga atactagaca    35640
tgaaaggaat aaaaaatatg gctatagcaa caaatgcttc acatgtgaaa ttagctaaat    35700
acattgtaag taaggctgac tctatttatt taacaattgg taaaagtaca gcgtggtcta    35760
atgaaacaag tccacctcaa cctgaagaaa cagcaacatc attacaagaa gttatcggat    35820
ataaaaaagc aactaaggta gcattagtta gacctgcaaa aacaacaggt gatgaaaata    35880
aaaaagaaat tacatatggt aataacgat gggtagaaat tgattcagct aatgcagttg    35940
ctgaaggtgc taagtgggtg tacttagaaa gtagtattgt tggggatgaa ttacccttag    36000
gtacatatag acaagtagga tttgttatgg atttgttagc taaagataat atttctaaat    36060
ttaacttact acctagtgaa gtgcaatcta caggaacctt attattttat gataataaac    36120
aattccaaaa tagaagtgaa caaacaactg taaaagagcg ctttatcatt gaagtttaaa    36180
aaggagaatt gaatatatat ggcaattaat tttaaaagtt ctccatactt agatagattt    36240
gaccctacaa aagatagaac aagagtacta tttaatccag atagaccact acaacaatca    36300
gaactaaatg aaatgcagtc tattgaacaa tattacttaa aaaatttagg ggattctatt    36360
tttaagatg gagataaaca atcaggatta ggttttcat taactaaaga taatgtacta    36420
caagtaatc caggttatgt gtatataaat ggtaagatac gttactatag tagtgaagac    36480
actgttagga ttacgggtgt aggtaaagaa acagtaggta ttaaactaac agaaagaatt    36540
attcacctg atgaagatag tagcttatta gaccaaacaa gcggagtccc tagttatttt    36600
tctaagggtg cagaccgttt agaagagaag ttatttttaa cagtcaatga ccctacttct    36660
gctactttt atacttttat ggatggagac ctctatatcc aatctactaa tgctgagatg    36720
gataaaatca acaaagtatt agcagagcgt acttatgatg agtcgggctc atataaagtt    36780
agtggatttg agctattttc agaaggaaac gccgaagatg ataatcatgt atctgttgtt    36840
```

```
gtagatgctg gtaaggcata tgtaaaaggt tataaagtag ataaaccagt ttctaccaga  36900
attagtgtag agaagtcaag ggaattaggt aaagcagaga atgaaagtac tgtatttaat  36960
aaatcatcaa ataatattac tttagctaat acccctgtaa aagatgttca acgtgtaaca  37020
gcacaagtat tagtagataa agagcgtgtt acaagaagtt caacaggaga ttctcaagac  37080
tatttatcta ataaaacagc ttttgaagta gttagagtat ggacagaaac aagtccaggt  37140
cagacaacaa aagaatacaa acaaggagaa gactatagac ttaccgatgg tcaaacaata  37200
gactggtctc cttcaggtca agaacctaat ggaggtacat cttattatgt ttcgtataag  37260
tacaatagaa agatgtgaagt aggtaaagac tatgaagtat ctacagtagg tgagggagta  37320
ggtaaacgtt ggtctattaa tttcacacct gttaatggta ctaagcctat tgaccaaagt  37380
gttgtacttg tagactatac ttactactta gctcgtaaag atgctgtttt tattaataag  37440
tttggtgaca ttgctattct taaaggtgaa cctaatatta tgagattagt aacaccacct  37500
ttaaatacag accctgagaa cttacaatta ggtactgtaa cagtattacc tgattctaac  37560
gaagcagtat gtatttcata tgctattact agattatcta tggaagactt acaaaaagta  37620
aaaactagag tagataattt agagtataat caagctgtta atgctttgga tgatggcgca  37680
atggaaaaac aaaacccatt aacattacgt tctgtattta gtgaaggttt tatatctta  37740
gataaagccg acattacaca ccctgactt ggtattgtat ttagttttga tgatgcggag  37800
gctactttag cctataagga agctgtgaac caacctaaga ttattcaagg agacactaca  37860
gctcatgtat ggggtcgatt aatttctgct ccatttacag aagaacgtac aatttaccaa  37920
gggcaagcat cagaaacctt aaatgtaaac ccatacaaca taccaaataa acaaggtgta  37980
ttaaaattaa ctcctagtga agataactgg atagatactc aaaatgtaac aatcacagaa  38040
cagaaaacta aaaagtaac aatgaaaaga ttctggagac ataatgaaag ttattatgga  38100
gaaacagaac attacttata ttctaactta cagttagata aaggacaaga gtggaaaggt  38160
aagtcatacg catatgatag agaacatggt agaacaggta ctctattaga ggctggagga  38220
cagcgtacac ttgaagaaat gattgaattt attcgtgttc gtgacgtatc tttcgaagtt  38280
aatggtttaa atcctaatga taataatttg tatatttat ttgatggtgt tcgttgtgct  38340
attacaccag caacaggtta tagaaaaggt tctgaagatg gtacaattat gtctgatgct  38400
aaaggcacag ctaaaggtac atttacaatt ccagcaggta ttcgttgcgg taatagaaa  38460
gtaacattga aaaatgctaa ctctacaagt gctacaacat atacagctca aggacgtaag  38520
aagactgtac aagatgttat tatcaaaaca cgtgttacag taaacttagt agacccatta  38580
gcacaatcat tccagtatga tgaaagtaga actattagtt ctttaggttt atactttagt  38640
agtaaaggag ataagtctag taatgtaact gtacaaattc gtggtatggg agatacaggt  38700
taccctaaca agacggtata cgctgaaaca gtaatcaact cagatgatat taaagtatct  38760
aataatgcta gtgctgaaac tagagtatac tttgatgacc ctatgatggc tgaagcaggt  38820
aaagagtatg ctattgtcat tattacagaa aatagtgatt atactatgtg ggtcggaaca  38880
agaacaaaac ctaagattta taaacctaat gaagttatta gtggtaatcc atatgtacaa  38940
ggcgttctat ttagttcatc taacgctagt acttggactc cacaccaaaa ttcagattta  39000
aaatttggtg tatatacttc taagtttaat gaaacagcta caattgaatt tgaacctatt  39060
aagaatgtat cagcggatag attagtttta atgtctacgt acttaactcc tgaaagaaca  39120
ggatgtactt gggaaattaa aatgattta gatgacatgg ctacatctac tacattgac  39180
caattaaaat gggaacctat tggtaactac caagatttag aggtattagg tttagctaaa  39240
caagttaaat taaaagctac atttgagtct aataaatata tttcacctt attaagttct  39300
aatgacttaa cgtttactac attcttaact gagttaaaag gttcctatat cggtagagct  39360
attgatatga cagaagctcc atataacaca ataagttta gttatgaagc attcttacct  39420
aagggcacta atgttattcc taaatattca gacgatgatg gtaaaacttg gaaaacattt  39480
actaagtctg ctcaagtagt taaggctaat agagactta atagatatgt tattgatgag  39540
aaagtaaacc aatctactaa gaataacaaa ttacaagtaa gattagactt atcaactgaa  39600
aatagttct taagacctcg tgtacgtaga cttatgggta caacaagaga tgagtaagtt  39660
taaagagggt ttcataccct cttttatttt aactaaggaa gtgatattat gcctacagaa  39720
tatagagacc cttactcaca agctaaactc tttattccta ctgtagaaga aaaagctata  39780
aaagaaatgt aacaaacata taagataaa ctacaagaag ttaatgagct tattgatgag  39840
cttaaaaaat tgaaaggtga ttcacacat gacgtttaac tacacacctc taacagaatc  39900
acaaagatta aaggatatgt accctaaagt aaatgaaatg ggtaaatact taaaagaaga  39960
agttaactta tctgatttaa aaacgattag ttatcctgac ttaaataatg ttctaaattt  40020
catacaagac tcaggtgact actttgtaac acaagccaga acacccccac aaggtgtaag  40080
tactacgggg ttttacact tagataaaaa gggtagtact tattataagt tatattatgc  40140
cccatctaac acaaataaat tgtttgtgaa aacttattat aatggtactg tctatgattg  40200
ggttagtttt aaactagatg aaggtacact atacgattca ggaaatacaa ttaatgtaaa  40260
agatttaaca gagtctacaa ctcaatttgc aacactcata aatcctccta aaagtaattt  40320
aaacacagga tggataaatt ataaggaaag taaaaatggt acctcagttt tagctgagtt  40380
taatcctatt aattctactt caacatttaa aatgattaca aagttccac gccaagacca  40440
acaacctaac ttgttaaggg atagtttatt cacattacca atgacggatg tagctaatat  40500
aagaacgtat tatatagata atacatcttt ttggggtttt actaataatg catctacctc  40560
aacagttaga tatatgggtg aaaatactat tcaattagat gatgggggg aatcatatcc  40620
tactgttata tctaaacgtt ttagattagg gaatgattta tatgtaggtg atacagttac  40680
aatgtctgta tacctaaaag taaatgacac tagtttatta aatggtaact tcccttactt  40740
tgaaatagcg ggttatgata atgtatctca aacaaataac ccttacacag gaggaaggag  40800
agaagttaat tactatgagt tatctacaga atggaaaaaa ttctcatta cttttacatt  40860
gcagtattat aaccaagagg ctagcagtga cactgttaat tatatatcga cattattaag  40920
atttaactgt tctaactcta aaaataatgg tgctattgtc taccaaaatt  40980
agaaaaatcg tactcggtaa ctccatttat tacaaatact tatgataaaa gaaaatgatga 41040
tgagatatgg agcaattgga tagagacaac aagcaaggat gaacttcaaa cacatagtgc 41100
tgtagatacg tacaacaatg actactacaa atatgtatgg aattatcaaa acgcaaacgg 41160
tagaagtttta caacaattag caatgtctgt acctcaaggt ttttatactt tttattgtga 41220
tcatatgta gttctata agtggaacac ctaacaataa aactatacaa aagtagcata 41280
taagaataat aatataaata ctacaaataa aataatacaa atgattta gtgaccctaa 41340
aggtaaaaga tattctttaa catataataa agatactaat ggttgcaag atatgaaaat 41400
tcaaatgtct agtaatagtc tttgggaagg tactcttgac ttagcttcag gtaatacagt 41460
aaacttatcc tcttcattag ataattatga ttttattgaa gtagtatact ggactagaag 41520
ttctggacat aatacaacta aaaggtaccc agcaagtaca tctagtattg taattagaga 41580
```

```
ttttaactta gtaaatgatg gttctaatgc tagtgtagac ttttttgaag ggtattgtga   41640
cattacagat agagtgaatg ttactgctaa aatgtcaaaa acaaatacaa tagatgggaa   41700
tagaaatact atgtctgttg ctcagtttaa tcaaactggt catattgaag tattaagagt   41760
tgtaggacta acgtatattt aataaggagt tttgtaaatg ataaaatatg atattagtaa   41820
agatgaaatt gtgttacatt tagaagatag taagtatatc atgggttaca ctatgttgg    41880
agggtatgat gagaacaacg gtgacgtaaa aatttctagg tcaattcttc ctgacgggtt   41940
ttttactgag tttgttagta ctaagtatgt atactataag aatactaacg aagtaatata   42000
taacaaaaat tttaaggata atgctaagag tattgaagat gctgattacc aaccacctaa   42060
agagtatgtt cctaaagaag attataaaaa gctagaaagt gaagtagaag aattaaaaag   42120
aatgctacaa gaattgttat ctaagaaggt ataaataata tggcactaaa ttttacacct   42180
attacagaaa atagtacaat agcagattta acaaaacaag ttaataatat aggtggtgta   42240
ctaactgagg acagaaatgt ctttgaagta acaacagact tacaagcaga tgtaagtaga   42300
acacagaaag ttaagttaac aacagataga gggttagcta aagatattga ttatactaat   42360
tacttaagag atattagaaa ggtaggtcta tattatatag gagctcgtac attagctact   42420
atgtatgata aacctgatat ggaaaacatg gatgtactac ttcaagtact aaccttagat   42480
actgaggata gagtagtaca gatattacat acattatcta ccgctgattc taaagtaaaa   42540
gtactatata ggtttgttaa caattatcaa acatcacaat ggcaagtagt acaaagtcta   42600
ccaaataata aatacacatc tcaaataggt ggaagtcctt ttgatattaa cacacaaggt   42660
atatattatg tgtctagtat gtcggatatg ccaaatggtg tatatgaagg ttttttacag   42720
gttattatag acaataatga aaatagaatg ttaagattaa cggatattag cacaggaaaa   42780
gaatatctta atgttaaaaa atcgtatggt agctggggca catggaaaac tgatttagat   42840
gtacaaaaaa taagtaatga tttattatct aatgtagatg gtgatgctga aagtaataac   42900
tactctttat ctgtatatac tacagacaac ataacatttc aacaggcaat agctaaacat   42960
attgaagaaa caagtaaaac tgtttttact ttttatatac aaggaggtgt tgtagggtct   43020
ccgtcctcgg ttagttgtag aggtgtattc atatcagatt caactaactt tactaatcta   43080
tatggtgttt atactgctat aggtactagt ggaagaacta ttaatggttc tgtaaatgat   43140
aatgtgtgga acacaacaaa aacactacca ggatttaaag agctgtggaa tggtgcacat   43200
aactttaaag atacaaataa aaaagaaacc atgtctgatt ctatatctaa ctaccagtat   43260
gtagaagtat acacaagata tagagctcta caaaatacaa aaggtactga taaaacaggt   43320
acactatgtc ataagttcta tatagacgga gacggtattt acacatgttc aggagcttat   43380
gtatcaggag actctaatat tggagtagag tattatagag taacactatc tattagtggt   43440
gatacttgga caattaaaga tagtgcagta aataataata aagaccaata tgttacacgt   43500
gttgtaggta tctcttttac catagactagg ataattccta gtcttttttt cttgactaac   43560
tttaataaat atggtaagat aataaaggac taaaaagaaa ggagaataa tgcagttaag   43620
acaacagaat atatatacat atgtagagattt tgacgaaagt gatgggtata ttaaagatat   43680
catacttaag cgtgttcata aaacattagg agctaaaaaa gatggttatc aacatagctt   43740
agcttttaaa cgaggtgtgt gggatggtta tgtagatttc tatgattatt ctgagaacaa   43800
attccccagt ggggttgttac ctaagatgat aacattaca ggtgagttac aatcaagaca   43860
taacttcaa tacgaaatta ttgataaaa atctgaaagc ttttagctg aagaagtat    43920
tgatgatgaa atacaactac tagataataa cgtaggtaag attacattac gtgactatca   43980
gtacgaagct gtatttaata gtctagtcaa ttataatggt atatgtaagc aagctactaa   44040
tgcaggtaaa ttttgcccct tatagtagaa atattataag tgtgactcct ttaattcatg   44100
ggaactctct catttgagac aatcatgagc caagcctata aataggaagg tgcaacgact   44160
attatgtaca tccaagtgga tggaaacggg gagaacctaa gtctcattag atatggttaa   44220
gatatagtct gaactttgta ggagactaca agaaggttag gagtaacgaa cctaaccgta   44280
acaaaattga aaacagaggt tgctagcgga atcatagacc aactattacc acaactagaa   44340
aaaggagagc gtgtagcttt cttttacaagc tctaccgaga ttttaatca atctgctgac   44400
cgtttaagtg aacgattgaa tataccagta ggtaaagtag gttctggtaa gtttgatgtt   44460
aaacaagtaa ctgtagttat gattcctact gttaactcta acttaaaaga ccctacagaa   44520
ggagtaaaag tatctgctaa agtaaactta agtaaaaaga tagctaaaga gatacttcct   44580
aaatttgaag gtggtaaaaa tcaaaaaagg ttacttaagt tattattaga aagtacaaca   44640
cctaaaacta aagtagagca gaatgtgctt gatatacttc aagatattta tcataattca   44700
aagacggatg ctgaagtatt aatggcatta acaatcata atgttatttt ccaaaaagaa   44760
gtaagaaaga aaaatcaaaa gagctatgat aaatatcata aaatgcgtga gttcctagac   44820
tctatagctg taatgatagt tgatgaagca catcacagta aatcagattc atggtataca   44880
agtttaatgt cctgtgagaa tgcactatac aggatagcac taacaggctc catgagacatg   44940
aaagatgagc tactatggat gcgtatgcaa gcattattcg gagatattat tgtaagaaca   45000
tctaatgagt ttttaatcga gaatggctat tcagctagac ctacaataaa tattatccct   45060
attgctaacc ctgatgatat agataatatt aaggattaca gggatgcata taataaaggt   45120
attgtacata acgagtttag aaatacactt attgcaaaac taacagctaa atggtttaat   45180
caagataaag ctacacttat tattattaac tttgttgaac atggtgagat actatccact   45240
atgttgaatg aaatgggtgt agagaatttc ttttacatg gtgaaataga gtcagatatg    45300
cgtaaacaaa agttagatga aatgcgtaat ggtaaactta agttatgat tgctacaagc   45360
cttattgatg agggtgttga tatcagtggt attcgttcat taatcctagg tgcaggtggt   45420
aaatctttac gacaaacact acaacgtgta ggtcgtgcgt tacgtaaaaa gaaagaagat   45480
aatacaacac agatatttga ttttaatgat atgcacacata agtttttata taacattct   45540
aatgagcgta gaaaaatata tgaagaagaa aaatttgaaa ttaagaatt aggaaagtag   45600
gtatgggtag tgactaagac agaaagaaga ttatatgatt acattgaaaa aaaatcaaaa   45660
aataatactt atcaaataac tactaaaaaa gagttagcag aagagctaga tgtctcagtc   45720
tctactttat ctaaaaacct taaagattaa gaacaggata acaaaattaa tgttgtttct   45780
aaaagaggaa ataaggtgg tattgttata tcactagtaa gagattatga tacagatagt   45840
ctcttacatt ttaatgctac agatgataat gttattactt ctaatctaga atacgctact   45900
gaattacgaa atagattttt tcctagttac gtatatgaaa gaaagaaaa taaacgtaga   45960
acaaaactga aaatggttca atataatgct attaaagata aacaggaa aataatatca   46020
aatatgaatt tttatagtag tagcttacct taccctacta aagatatttt taatatgtct   46080
tatgaccctg agggtttta taaagcttat atatttgta agttatatga ccaatatgct   46140
atagcacaca tgaatgctaa atatatacaa catttaacat tatcaatgg taatgaagac   46200
gtagatagac ataagcattt atctgagtac tacagaaaga aatgttaca gaatttatca   46260
cgagatagta tttgtaaaga cttctttggt agtaagacat ttaatacatt ctacaacttt   46320
```

```
tacttaaaga taaaagataa gaacattaat gttttaaat acatgcaaaa tgttttaag    46380
aataccacat ttgggtttga gaataaaaca caaccttacc ctatacctgc accaaatttt    46440
tttagttccg ataaatactt aactaattat gaaaattatg taaaaggtat taaacgaggt    46500
gtaaataaaa caaatagaca aattggggaa gtagagtctt taattaagtc atctgattac    46560
ttattaaatc ctgctgtagc acaattacat caactatata caacaccttt aaatgaagag    46620
atacatgata ttgatacaat gtttaaaaca gctttaaata tagaagatac tatttatggt    46680
atatttaatg gcatgaaaca tattatactt ttatcatata ataaatatat agaacatcta    46740
atagaaaaat tacctagtaa acataaaaac ttattaaata aatttattaa acaatgtatt    46800
gtaaatgagt attcacctac tacaatacct aacaatgcta gactatctat gtttttaatg    46860
caaaaagagt ataaagcaaa tatcgcagaa ttaaatggtg gtatagatag aagagactta    46920
ataggtataa gtttagtaaa cactacagac ttaagtaaac aagatattgt aaatatagaa    46980
caaacaacaa tgaattatct acatatgaga agatttactt caacatcata tattttacaa    47040
atgtatagta attacttagg ttatgaggtt aatttaaaag aagttaagtc tataattgaa    47100
aaatataatt taattgataa aataccattg acaaaagaag gtatgttgaa ctataataag    47160
gttattgata tagtaaagga tgacacatat gagtaaacga attaaggaga ttatcctaca    47220
taagtctatg aaggatatac attttgcaag agaagtacta gataagttac ctaaaagtct    47280
atttgctaca gaatcggaag acatgggtta cttattcaca gctataaaaa gaacagcaca    47340
cattgctgat aaaatgtcaa atgaatcttt agctattaaa gtagagcaat taatgggtag    47400
tgataaacaa gatgatgaaa aagtaacaca aacattaaaa tatttagata gcttatatac    47460
agtagacatg aataataaag acgattctgt aaactatgaa gtagaaaagt atattaaaac    47520
agaaatgtct aaagaagtat tagttaagtt catagctgag aataagcaag aggactcaga    47580
taacttacct gaactagtag agaaactaaa acaaatagaa gtcagtgaca ttaatggtac    47640
tgacggagaa tttattgact tttttgaaga cgtagataaa aagagagaac tattaagcaa    47700
cttaagtatt aataagtatt ctacaggttt ccattctata gaccagcaaa ttgaaggtgg    47760
tataggtaga ggggaagtag gattagttat tgcacctaca ggtagaggta agtctcttat    47820
ggcaagtaat ttaggtaaga actatgttaa acaaggttta aatgttttat atattgccct    47880
agaggaaaag atggatagaa tggtattaag agcggaacaa caaatggtag gtgtacaaaa    47940
gaatcaatta cttaatggtg acttatcttt aaacacagat gcttataata agatacaaga    48000
acactataaa aagaatagac aactgctagg taactttta atcgttaaac atatgcctgg    48060
tgaggtaaca ccaaaccaat tagaacaaat tataattaat acaacaatta agaaagataa    48120
acatatagat gttgttatta ttgattatcc taaacttatg cgtaaccctt accttaagta    48180
tcaaagtgaa tcagatgctg gtggtcgtat ctttgaagat attcgaaaat tatcacaaga    48240
atacaatttt gtttgttgga cattagcaca aacaaacaga acagcttacg gttcagaaat    48300
tattacaagt gagcatgttg agggaagcag aaagattgtc aatgctgtag aggttgcttt    48360
tgccgttaac caaaagatg aagaatttaa aaatgtttt ttaagattgt acttagacaa    48420
agtaagaaac agttcaaaca caggtgagag atttgttaat cttaaagtag agcctactaa    48480
aatggttgtt agagatgaaa caccagaaga ggcagaagaa cataagcaaa tactagcgga    48540
acttaatggt gaagataaaa gtagatttaa agaaaaacct aataagctg aagctattaa    48600
taattctttt ggagggttga gttttaatg gatgactta ctaagcttta taaaaaagta    48660
cgtagaacat ttcacgtaa taaagcagaa tgggattata caaatacagg attaagaacc    48720
ttccaattaa aaggaactaa tgtatgtgtt acattactag actctatagc aaggaataat    48780
acaacaggat ataagtacaa cgttatgtct aataaagtac ctgctatacc ttgcaataca    48840
catcaagaag taattaaagc aattgaatat aagttaaaaa attgagaaaa agccttgaca    48900
atgtatttgt taaggcttat acttttatta taaacaataa agaggtggta agatttgaac    48960
ttaaatgaag caaaagtaaa attaaaaaac tttaaagtca ttaataagca cggatttata    49020
gagactataa acacaaagta ctctgaaaag gagttagagg atgtctcaac cgatatattt    49080
aatacattag ataattacgt aattgtttaa tattaagcct    49140
aaaagaagta ttatagagtt agaattaaca aacaataaaa ttaaacactt aagaaagtag    49200
gatattaata tggaattaga attaaataaa atatataacg aagattgttt agaaggtatg    49260
aagaaaaatc ctgacaatag tatagactta atagtaaccg accctcctta tttaattaat    49320
tataaaacca accggagaaa aaataaagag catgatttg gaaaagttat tttaaatgat    49380
aataactaac aacttattat aaattatatt gaggagtgtt acaggatatt aaaaaacaat    49440
agcgctatgt atatgttctg ctcatcagag aaagtagatt ttttaaaca acaattagag    49500
aagaaattta aaataaaaaa tatgattata tgggtaaaaa acaatcatac agcaggagat    49560
ttaaaaggtt cttttggtag aaaatacgaa atctttattt tagtagtaaa gggcaaaaaa    49620
catttaatg ggagaagatt aactgatgta tgggaatttg ataggaagtg tggtaaaaaa    49680
caattacacc aaaatgaaaa accattagat ttaataaaac aatgtattat gaagcatagt    49740
aataaaggag atgtggtttt agatgggttt attggtagtg gcactactgc tattgcttgt    49800
atgagtacta accgcaatta cattggttta gaattagacg aagaatacta taatttagcc    49860
agtgaaagaa tagaaaaata taaggagata ctaaacaatg aaaatgacaa tacaggaact    49920
acaagataag actgaattt taagacacgt aaaggtatat acggaagaag caatggatat    49980
ccttgaagat atattaagag gagagcctta cacagatgag gtatgtgaat tgatacattt    50040
ttattcaagt aagctactaa atgagattaa tgacaatcat atgtttaaat tacaggagtt    50100
tgctaatcat gatgttatag aaattagtga agagggagta aaataatgat aaaattatta    50160
caggggatt gcttagagtt attagataca attgaagaga gtagtatcga tgctattgta    50220
acagaccctt catataacat ttcaaaagaa aacagattta caactatagg tagagctggt    50280
attgattttg gagagtggga taaaaatttt gaatctactt tatggattaa taaagctata    50340
ccaaaagtta aaaaggtgg taatatcgtt gtgttttgtg acatgagaca attcacaccg    50400
atcattaata ctatggaaga attggctgt gaatttaaag atgttattcg tctgaaaaaa    50460
tctatcccta tgcctcgtaa tagggataga cgatttattt ttgatactga atttgctctt    50520
tattttgtta aaaaaggaga taaatggact tttaaccgtt tagatgaaaa atatgaaaga    50580
ccttgtatta aaacaagtgt aacacctaga agtgaaagc agggcaaagg acacccaaca    50640
cagaaacctt tatatgctat ggaatggttg ttagagtgct taactaatga aggagacatt    50700
gttctagact gcttcatggg aagcggaaca acaggtgtcg catgtaaaaa gttaataag    50760
aattttattg gttgtgaatt atcagaagaa tacttcagta tggtacaaga tagattacta    50820
aataatacaa attaaaacaa aacccttgac aacatgtttg ttaagggtta tacttttatc    50880
ataacgtact aaaggaggac actaatgaaa tttatatttt ttacagatag ccattttcat    50940
atgtttcga attatagtaa acctgatgaa gaatatggta atgatagatt taagaacaa    51000
attgagacat tacaaaaagt attgattta gctagagaaa ataaagctaa agttatattt    51060
```

```
ggaggagatt tattccataa gagaaatgcg gtagatacta gagtatataa taaggtattt    51120
gaaacctttg ctaagaatca agatgttaaa gtctatatgg ttagaggaaa tcatgatgct    51180
gtgtctaatt ctttatatac ggaatctagt attgatatct ttgaaacatt acctaatgtg    51240
gaagtaacta aagatttacg tagtgactca ctttctagta aagtacaatt aactatgtgt    51300
gcttatggag atgaaacaga agaaattaag gagtatatta aaaaatatta ccaaaaagat    51360
aaagtaaata tattagtagc acatttaggc gtagagaata gtttaacagg taaaggctca    51420
cacagattag aaggtgcatt tggttaccaa gacctattac cagaaaaata tgatttattt    51480
cttcttggtc actatcatag aagacaatat ttaaacaata accctaatca tatgtatggt    51540
ggttctctaa tgcaacaatc cttttcagat gaacaagaag ctaatggtgt acatttaata    51600
gatacagata agctaacatc aacgttcatt ccattagata ctagaaggtt tattacagtg    51660
caaggtgaca atgtaccaga taacatgaat gatttagtaa accaaggtca ctttattagg    51720
tttattggta ctccagaaca agctaaagta attgaattag ataaaacaga gatgaatct     51780
aatgtacaag tacaaatgaa gaaagaatac acggtagaaa agagagtcga cgctgacgtg    51840
tctgacagcc ctataacgat tacttctagc tatgcagaca aatactatcc agaagcaaaa    51900
gatgagattc tagagtgttt aaaggcggtg ctgtagtatg atagatatta ttataaagaa    51960
tattaaacca agtatatata aatctaaacc tattttacag ttcttacata ataaaagaac    52020
atatgatgta tgtaatgtta aaaatattga tgatgcgatg taccttatta acaaagtatt    52080
agaggaagct aactatgctc attattatac gaggattatt gaacaagaag attgttatat    52140
tctagattat ggttcacatc aatgtttctt taaattgtta aaagaaggtg gtacaaatgg    52200
ttaagtttaa ttatgtagag atgaataact ttttagctat tgagcatatc aagctaaatc    52260
tggataagca aggtcttgta cttattgagg gtattaataa aacaaatgat agttttgaaa    52320
gtaatggaac aagtaaaacg agcatgatat cttctattac ctatgcactg tttggaaaaa    52380
ctgagaaagg tttaaaggca gatgatgtcg ttaataagta taagaagaaa gacacctacg    52440
ttaagctttc tttcaacata ggtaaagacg agtatttaat cgaaagatac cgtaaacata    52500
aagaacacaa gaacaaggtt aagctgttct gtaataacaa agagataaca ggctctacaa    52560
atgatgttac ggatactcaa atacaagagt tatttggtat tcctttttaat acatatgtaa    52620
atgctattat atatggtcaa ggagacattc caatgttttc acaagctacc gacaaaggta    52680
aaaaagaaat actagaatct attactaaga ctgatattta taagcaagcc caagaagtag    52740
ctaaagaaaa ggttaaagaa gtagaagaga aacaaagtaa agaacaacaa gaaatagaaa    52800
aactagaata taaaagaaac ctaaaacaag aacaatata taatgaagta aataaataa    52860
ataacttatt agagcgtaag aagcaagaag aggaacagtt taatcaaaag aaacaagagt    52920
acgagaataa attaaaagat ttagacaatc agattggtgt atgtaaaggt agtattccta    52980
aagttgaaga ctttgaattt gtatttagtg aaaattatac aaaagctaac caaggtattg    53040
aaaagattaa cacaaatatt aatgataaat tattgccatt attgagtcaa gaaacaacaa    53100
ataagaatac aactctaaat ataattaatc aattaaaaca atctattaat aaactagata    53160
caaatgacca ttgtcctgtt tgtggttctc ctatagataa tacacacaaa ataaaagaaa    53220
aagaaaactt agaattacaa attggaagaa gacaagctaa aatatctcag tacgaacata    53280
atgagcaggc tataattaat aagaaagaag agctactaca taaatctaag gaactacaac    53340
aatttataca gcaagaagat atagaaaaga aaaaacatga tgatgatatt caacggcaat    53400
atagagaaca gcaagaagta tatgatgaaa ttagccaatt agaaaacact aaagctaatt    53460
taaaagaacc aacattaaat gattactctt atatagaaga acctaatgaa gaattacaca    53520
ataaagaact aaaagatact gacaatacta ttgacaaaca taaggaaaat atagtacaat    53580
tagagagtaa gaaaacaaaa tataaacaag ctgtagatgc atttagtaat aaaggattac    53640
gttctgtaat attagacttt attacaccgt tcttaaatga gaaagctaat gagtatttac    53700
aaatattagc gggttcggat atcgaaattg aatttcaaac acaagtagaa aatgctaagg    53760
gagaacttaa agataagttc gatgttattg ttaagaataa caatggaggg gagtcttaca    53820
aatctaattc agcaggagag caaaaacgta ttgacctagc tattagtttt gctatccaag    53880
acttaattat gagtaaagaa gatatatcta caaatatagc cctttacgat gaatgctttg    53940
acggactaga cactattggt tgtgagaacg tagttaaact actaaaagat agactaaaaa    54000
cagtaggtac tattttgtt attactcata ataagagtct agcaccttta tttgagaata    54060
caattacggt agtaaaagaa aatggtgtag ctacactaag aaaggaatta aataatgaaa    54120
ctaaagatta aagataacca gtttgcatct ttaacagtaa attacacaaa caatgcaaag    54180
ttacatatag ataatattcc tgtttctact ttagtagact ggtacccttt aagtaatgca    54240
tacgagtata aagctagtaa tgactttgga tatattgaac taaagagatt acgtctagt     54300
ttacctatgt cttatggatt aacacaccga acttatata aaggtgaaac tgttaaatgt    54360
aaactaggat tatggtataa tgaaaaaata aaggaagata atgagaaaat tattgagaaa    54420
gctaagttgt acggtttacc tactatagat gaacccttca caagtaaaga tgtaaagcaa    54480
ggatttagtg acttaggtgt tattttccaa acactaaaaa caatcagtac aaacgagtac    54540
ttaaaagata aaacaattga agagattaac atctttagta agaaatcaga ggattatcaa    54600
ttaaatgaag tactcaagta cagtacaaca ctggtagatg atacttatag tgacttaagt    54660
caaatctata atatgttact attaatgaag aaaattgttt ctatataggaa agtgactgaa    54720
aatgaggttt gaagactttt taagtcaaga gattggaaca cccaaagaga atactgtagg    54780
agaattacga tattgttgtc cttttgtgg ggaacagaaa tacaagtttt atgttaaaca    54840
gtctttagac gctactaatg gtatgtatca ttgtaagaag tgtgggaac atggtaaccc    54900
tattactttt atgaagtctt attatagtat tacaggtaga caagcttttg agttactaga    54960
aacaaagaat attgatatac aattctcacc aacattagaa atatataaca cagatttaac    55020
tgaaagtgag aaattattac taaggcttaa tggatataca aagataata gtagtataaa    55080
atcaaaagca cctgaactac ctataggggtt taaattgatt aaagataact taaataataa    55140
agaagtagta ccgtatttaa gatatcttaa gaatagaggt attacactac agcaaatcct    55200
agattacaac ataggttata ttacagatgg ttattgttat tcttatggta ttaatatgta    55260 
gaaaagaaa atagtactta gaaatagtgt tatatttttt acttatgaca atgaaggtaa    55320
gtatatatac tggaatacaa gaagtattga acaaatcca tatattaaat ctataaatgc    55380
accttctaaa cctaatgagt atggtaaaag cgatgttata tttaatttaa atatagctag    55440
taaacaaaag tttgttgtta taactgaggg tgtttttgag gccttacat tgataagta    55500
cggtatagct acgtttggta aacaagtttc aaagatacaa gttaataacc tcatttcaag    55560
tattcctaaa gaaacaccta tatatattat gttagacaca gacgctacag acttagtat    55620
taatttagct aataagctta tctcacattt caatgtagtg tatttagtac cacatggtaa    55680
tgaagatgct aatgatatgg gtatggaaaa agctttagt actttgaaac acaatagatt    55740
tttagttaca cctgaaagta ttcaaagtta caagttacaa caaaagttaa aactttaatc    55800
```

-continued

```
ttgcattata atgtatagta tgttacaata catatataaa aataaaggaa gtgttatttt    55860
ggaagagaaa gatattctac attttgtaga tgagtatgtt acagcattac gtgtaggtaa    55920
tgaacagcgt atgcaccaat tagaagagtt aggtaaagaa caaacagcaa ctttaacaga    55980
tgttatgaaa gctattacta acttattgtt aggtgttaat aaacaaatgg ttgacctaga    56040
gcaaaataca gagttaaact taaacattct aattgatgct ttatacaaag ctgagttagt    56100
taacgatgac gtattaaaat atattgagga agcaattgaa gaatcaaaag aaaaggatga    56160
agaataatgg aaaaaaatat tagtacacat acaaaaggta tttcacaaaa agatatggac    56220
atgtggttag aagctattac acaaggaaca gtagaaggca aggaattaac tgaggacact    56280
gctaagcaat tacatcgtat tggagcacgt agtgtatcgt tagatgaggc tactagaatt    56340
gcacgagcaa ttaatgccgt tacagttcaa gagtatgcat ctgcctttaa tgatgctttt    56400
aatgctattg atttgttaat gattgttatg gaagataact tagatgtaac tactgagcaa    56460
gtagagaagg cgcaacttaa attaaaagaa aaacgtgaaa agtatttaga agaaaaacaa    56520
gaagaagtaa gaaaaaaaca agaagagcat aaagcaaaag aagtaaatga aaaagtagtg    56580
cagttgaaga aacatgacaa atagtaaaaa aaaaggtagt gtattcgaaa gaaagattgc    56640
caaagaactt tctgattggt ggggttatcc ttttagtagg tctccacagt caggaggtgc    56700
ttcatggggg gctaataata atgctgtcgg tgacattgta gcacctttag agtctaattt    56760
tccattagtt gtagagtgca aacatagaga aaattggatt atggacaatg tttacttaa    56820
taataaagaa cctcatacat ggtgggaaca agttatagga gatagcttac aagttaataa    56880
aactccttgt ttaatattta caagaaatag agcacagtca tatgtagcat taccttatat    56940
agaagatgta tatgtaaagt taagagatga agaatacct attatgagaa cggatttat    57000
tgtagaaaat gttagaaaag ataaacattt ttatgatgtt cttataacta cgatagatgg    57060
gttgactaac ttaacacctt cttatattat atcttgctac aacaaaaaag agattaaacc    57120
atatagagtt gtcaagtcta aaatatctaa agttagtaaa aaagaagata agttgattga    57180
tgatttactt gatggtatat aaggaaggga tactagttga ttacacaaat aaaaaaacgt    57240
gatggttccg ttgtagatta tgatttaagt aaagttacta atgctatttt aagagccaac    57300
tcagaaacag aagaatatat tgaagatgat attgattctc ttgtagatga tgtagatct    57360
ttactagaag aacaagacac tatcattact gtagaattaa tacaagatat agtagaagaa    57420
gttttatttta gtagtatgta taaagatact gctaaagctt ttattttata tagggataaa    57480
aagaaaagag agcgtaaaag agacttattc aaaccaagaa aagaattaaa acctatgaa    57540
tacctgaat tattagaata taaagatgct atacgccaaa gttactgggt acacactgag    57600
tttaactata catcagatat tcaagactat aagaataacg ttaaatacaa tgagcaaatg    57660
accattaaaa aagctatgtt agcaattgct caagtagaag tagcagtaaa gactttctgg    57720
ggtgacctat atcatagaat gcctaaatgg gaaacaggag ctgtaggtgc aacttttagt    57780
gagagtgaag cacgtcatgc agacgcttat tcacatttat tagagatttt aggtttgaat    57840
gaagagttta aaacaattga cgatattcct gctcttaaag aacgtgttga tgagttagcg    57900
atgcatgtaa aactaagtaa gagtgaggat gatagagatt acgtactatc tgttttata    57960
ttttctatat ttattgaaca tgtatcttta tttagtcaat ttttaattat gatgagtttt    58020
aataaatata aaaacttatt tagaggttta tcaaatgcta ttgaagctac atctaaagaa    58080
gagcaaatcc atggattatt tggaacagaa atcattaata ttcttagaga agaagacct    58140
gagtggttca acaaagaaat ggaagatgca gtttacacag cctgtaaaaa atcttatgaa    58200
tcagaaacac ggttacttga ttggatgtat gaagatgggg aactagagtt cttacctaag    58260
aaagtagtac aagaatttat taaaaataga cttaataact ctctagtagc tgttgggtat    58320
aataaacttt ttgatgttga tgaagagtta ctaagtgaag tgtcatgtt tgatgatgaa    58380
gttattagta ctaagttaac ggacttttta tctaaacgtt ctgtaaacta tacaaaattt    58440
agtaattctg taacggaaga tactattttt tcaacggaat ctgatttga aaatactggt    58500
aaacgagtta ctaaagataa agtaaacgct attttaagac taaaaatgat ataaaggcag    58560
tgtatataga tgagtaattt tgaatggtta aataatgatt ctagagtt tctagaacgt    58620
ggttatttaa gtgatggtga aacaccagaa caaagaatta agatatatgc agattatgct    58680
gaagatattt taggtattga tgggtttttct gacaagtttt atgattatat gagtaaaggt    58740
tattattcct tatccagtcc tatatggtct aatttcggga aagatagagg atttagtatt    58800
agttgttttg gtagttgggt agatgatact ataccatcga tacttaatac tgctagtaa    58860
gtaggtatga tgagtaaata cggtggtggt acaagtggtt acttcggtaa catcagacct    58920
agaggctcag aaatcactga taatggactg acaagtggtt ccgttcatt tatgaagcta    58980
tttgagcaaa tgcagatac gataagccaa ggatgttatg atgataaaac tgaaatactc    59040
acagagagtg ggtatgaatt attatctaat gtagttagta gaaaagatgg aacaaaagtt    59100
gcacaggtaa cagataatga tgaaatagag tttgtagagc ctacaggtta tatgaatttt    59160
gtacctgaag ataatgaatt agttcatttt aaagatagta aaaatattga cttattagtg    59220
actaagaacc ataatatggt ttttaaatac agaactaaaa ggactaataa agaaacagga    59280
aaaagagaaa gtgttttagt acctgagtat agaaatagat tagcagaaga tatgccatta    59340
catagagacg tttatttagc acattcttca tttgctaaag aaggcagagg actcacattt    59400
aaagaacgtc ttttggtagc cttgcaagca gatggtagta ttattaaaaa ataccctaaa    59460
tctttgaagt ttagatttag taagaacgt aaaaagata gactattatg gatattagat    59520
ggtctaggag ttgaatacac atataatgta gacaaagaca ataatcataa tatttatgtt    59580
aatatgggtg aagaattacc taacaaattt agtaaatggg taaattaca aaatgtcaca    59640
caacaatggg cttatgattt tattgatgag ttgtctcatt gggatgctag tagaagaacg    59700
gataaatcat ttatctacat gagtgtgtt gaacataatg tagacattgt tcaagccata    59760
gcttctatgg taggttataa atctcgtaaa tcagttgatt taagggaaag agaacctaat    59820
aaagccacta tgtataaaat atatctatct gaagtcaat tatttggagg ctcaaatgtt    59880
actgtggaaa cggtacaata taaaggtaaa gtatattgtg ttgaagtacc tactcataaa    59940
cttgttgtaa gaaggaaagg gcatacatta gtttgtggta attctacacg tagagggcgt    60000
tttagtcctt atttacctat agaacatgag gatattgatg agttttaga gattggtacc    60060
gaaggtaatc caattcaaaa cttaacacat gcagtaacag ttactgatga ctggttatta    60120
gacatgatta atggggataa agaaaaaaga aaaacatgag ctaaagtat aacaagaaga    60180
acacaaatag gatacccta tatcttcttt catgataatg taacaagtaa tacagtagat    60240
gtatataaag acaaagggtt aactattaat aactcaaatt tgtgtaaaaa tttgcacctt    60300
tagtaagtaa ttactatcga aaaatccatc taaacggtga atatctaagt taaaatatat    60360
gacaacaccg tgctaaatca gattataaat ctgtaaatgc ctaacgacta tctgtaacct    60420
attcacataa gtgaagggat aaggttagag ccaagtggta taagtattga gtaataatca    60480
agtaaatctt atttaaatcg aaatggtgga cttccttatt aaggaagatg atatagtctg    60540
```

```
ctctatatgg aaacatatag aagttcatat taacaataat aattaagagg gtcgaaaatg   60600
gagtaccata tttataaaat tacaaacaaa aacaataata aaatatacat cggaattaca   60660
tcaaaaacag ttcaacatag atttaaaaat catattagaa aagctaagat aggctcaaca   60720
actaatttta accaatcaat gatgaaacat ggtgaagaga atttttatgt agaagaatta   60780
tacactttta gtacagagga taaaaagttt gcttacatgt tagagcaaat ttttatagac   60840
atgtacgaat ctgtaaaaaa aggttataat atggagatag gttttgggtg gaatataatg   60900
gatagacgag gaaaaaacaa tccgatgtat ggtaaagaaa gcgctaatgc taaaaaagtt   60960
attgttgatg gcgtagttta taaaaatatg ggtatatgct ctgaagagct aggaataaac   61020
agaaatacat taaccagaag atgtaattct gaaaaattcc ctaactataa atattgttaa   61080
ttagagaact ggtagtgatt aacgaccact attgaacatg taggagtgaa ataatgttac   61140
ctaataaaga agattggtca tttgtatgtg acctatctag tatgaacctt gttaagtatg   61200
atgaatggaa acacacggat gctgtagaga cacttgttta cttttagat gctgttatgt    61260
ctgagtttat tagagactta gaatatctaa gagactcaga tgaaaaagat aaacaagaag   61320
catttaaatt tatggagaga gcttataact tttctgttga gaacagagcc ttaggaatag   61380
gcgttcttgg ttaccattca tacctacaat caaaactcat acctttgaa agtattaaag    61440
ccagtcaaat taatgaagag atatttaaat tattaaaaga aaaacttat aaagctagtg    61500
agcagttagc taaactttat ggagagcctt ctatttaaa aggttatggt agaagaaatt    61560
catgtttgat ggcggtagct cctacgactt cgagctcatt tatcctaggt caagtttcta   61620
aatcaattga accttttatg agtaattatt acgttgtaga cactgctaaa gtaaagaaaa   61680
ctatgattaa tccttacctt aaaagactat taaaagaaaa aggaaggac aataaaaaag    61740
ttattgagag tatcagagat aatgatggtt ccgttcaaca cctaactttc ttaagtgatt   61800
atgaaaagga agtatttaaa acatatggtg aaattaatca atataataa ttagaccaag    61860
cttctacaag acaaaaatat attgaccaag gacaatctat aaacattatg attaacccta   61920
aacatgttac agcagaggag ttaaatgaac tttatctctt tgcatggtct aatggtatta   61980
agtcattgta ttatcaacat ggtacaaatg catcacaaca attcaattta tctaaaattt   62040
gtattaaattg tgaagcctaa agaggtgact aaatgaataa aaagaagcg tttggattac    62100
taagtagaac tgaagatata ttcaaatcaa atgatatttt ctcacaagta gtaatgtac    62160
aagaccctat taagatgttt aataggaag atgatactaa agcagatagt aaatcaagta    62220
aatttcagct agagtttatt tataatacat atgtgtacat tcttatatat gaaggtacat   62280
taaagctatt taaagctgat ggtacggaac agttaacaca tgtagctgat attgaaacat   62340
ttaaagatat tattgacaca ttagaaaagg atgatacaga aaatggaaaa agtgaatagt   62400
ttattagagt taaatacaac aatcagacaa aaacaggatg ttattgtcat ggttacacaa   62460
gatgagtgtg ctaaatgtga aattttaaaa agtgtgattc ctcttttcga agcagaagga   62520
gatattacta aacctgttta tgttattaac ttagatgata aagatgtaga tagagaaaaa   62580
gcggtcaagt tatttgacat tatgagtaca cctgtactta ttggttataa agatggagaa   62640
cttgctaaga agttcgaaga ccaagtaaca cctaaaaact taatgaatt agatttactt    62700
taatttgtaa ttacctacta cttatgctat acttatatta gtaaaaggta gtaggttttt   62760
tcatgaaagg atgaatagtt atcgcaaaaa ataaaacatt aactatatat aatagtgata   62820
gatattttaa tatacatgta aaaaacaaag atgaattatc taaagctatt aaagttacaa   62880
ctttaaatga agatgagata gaaaaagata tggacaactt agctaataaa tcaactaggt   62940
atatactaag agatgataaa cattcacatgc tatttaatga gaagtataac aatgataagt   63000
tgattgaaaa aatatgcaag cacggtggac aagtaacata ctataccgat tcgtaattc    63060
cttactatgt gcttaaagat ttatcagctc acctaaactc atcagttgta tatagaatgc   63120
gtagtaagtt tagtaacaaa gagatgggata atatagcttt gagtttcatg ggaacaaaag   63180
tcattattga tatttcagtt gtatttcctt acgtcaatcc ttacgatatt attagaagtt   63240
tatacgatgt taaaacgaat gtagacgagg ttcatctatc attccctcgt attagttcta   63300
tagacgctaa acaaggtaag tactacacgt atgataaaga agcttataaa ctaaaaccta   63360
ggtatacgct tgactttgca gacaaattaa gggtttcttt gtccgtgtgg aaaatgtata   63420
tctatattct tgctagtaaa gaaaataaag attatgaaac aatagaagac ctacttactg   63480
aattaaaaag acaagaaaag attaagattt aggtgatttt gtgagtacag caaatagaag   63540
agatatgca agaaagtat ctgagagtac aggtattat atccaagacg tagaagagat     63600
actagaagca gaaacaaaag ctatttctga attactactt gaagattacg ataaggtaaa   63660
gaatcataag tactttcaaa tagaagtagt agagcgtaag ggtaaaaaag catgggatgg   63720
actaaataaa acatacttca ctttacctaa tagaaaggca ctaaagttta aacctttgtc   63780
tgaattagat aaagttatag atgattaaa caaagaggaa gaaaacagtt aaatatttta   63840
tatagcataa gatttagtat ctactcttca tgtatttagt tggtagtata tgttttgcta   63900
ttatatacta tttattaac agagattgag tcaagtttat acttgactct ttttttatg    63960
ttatgttata gtttaactat aaggagctga ttgaatatga aatgaaaga tttagataac   64020
ttacatattg ttgtagtatg tattaagaat gatacattac ctgatgtagg gtatatggtc   64080
ttagaaaata taaaaagaa gtaaaagaaa atagtgacat acaatgaaat catataaaac   64140
agaagtaaaa ccaaataaac aacaataat tgagattaat aaaacaatta atgcttgtag    64200
aagtgtttat aataaattta ttgaagtaaa taaatttcgt tatgataacg ggttgaaatt   64260
tttaaaccat agaaagttta gtgtttggta taataatgat tttattccta ataataaga    64320
taaaaaatgg actaaggaag taaatactaa agcaactaaa caagctatgg caatgctgta   64380
ggatgcatat aaaagattct ttaataatat atcaggtttt cctaagttta agaagacaca   64440
aagtaacggt tcttactatt taataggtac tatacatgta gaacgtcata gaatacgact   64500
acctaattta aaatgggtta agttaaaaaa aaaggatat ataccggaaa acaatataaa    64560
atcagctact attattaaag aaaatgatag atattatgtg tcagtgttag tagatgaaga   64620
acctaagact atactttaaa aaaccacatac tgaaggtatt ggtatagcc taggattaaa   64680
agatacacta tttacacctt caggcgttaa gattacagat ttaaggaaaa ataaaaaatt   64740
agttaaatta cataagtctt taaaacgaca acaaagaaaa ttatcacgaa aacaaagaa    64800
gtccaataac tggtctaaac aattattaaa agtacaaaga ttatatcgta aaataagcaa   64860
cattaagaag gatattaaac aaaagaaaat actagaaata gtacaggaaa acccacaatc   64920
tatcacaatt gaaaatttaa atattaaagg tagatgaaaa aataaagat tgtcctaatag    64980
tttccaacaa ataggattag gctacattat tgaatggctc aaatggaaat gttatcaata   65040
tgatatagaa ctaagacaag tagatagatt ttacccttca agtcaaatat gcaatcaatg   65100
tggaaataga caaaaaatgc ctttaaataa aagaatttac gaatgtgata attgtgatat   65160
gatagaagat aaagatataa acgcaagtat taacttaaaa caagcaaaag aatatacaat   65220
actagtataa aagaaaaaga gaagttactg agaactagta tcttacttaa agtctaaaca   65280
```

```
aatacggtag gctatatcgg aattaacgct ctgggagagg tttttagacc tgattgttaa  65340
tacaatcaac ctcgttgaat ggagaaactt tctaaatata catttaagta tgttttagt   65400
agcaggatta agttcctctt tttttttattg actactatga ttagatatgc tatactgtat 65460
ttaagttaaa gaagggattg gtaataacat gaaagttta atttatacg actatatcag    65520
agaggaacac ttttcagtta gtaatgatgg tagtgttaag aatgtactat taaatacacc  65580
taatggtaga gtactaaaac aactattgtc taatatttct ggtattaata gagataggag  65640
cacaaaggat tatgacattg atttttata tcctaaagta cctacaccta ttaagaataa   65700
ctatggtaaa acaattaagt accaagacgt taagttatct gaagttaaac cttactatga  65760
aagaatgagt caaataatca taaacaataa gtacgatatt attattcctt taggtaagct  65820
aggggttaaa tatttattaa atgtatcagc tatcggtaaa gttagaggtg tacctaataa  65880
agtaactatt actagtgaag ataaaaaaca tgatgtttgg gtattaccta cttatagcat  65940
agagtacaca aacgttaata agaatagtga gcgtcatgta gtagctgacc ttaagttatt  66000
aggtaagttt gtagaacaag gtgaagatgt atttaaacct aaagaagtta agtatgaact  66060
tgttacaagt attgagcgtg taagagaaat atttaataaa gaagtaaaga atgataatca  66120
tgacggtgta gacattaccg catgggattt agaaactaac tcacttagtc ctgatagaga  66180
aggaagtaaa cccttagtat tatcaatgag ttgggagaat ggtcaaggtg ttacaatacc  66240
tttatataaa tcagacttta cttgggagaa tggacagcaa gatattgatg aaattctttc  66300
cttattaaaa gaatgggtag ctagcaaaga agacattaag gtactacata atgctactta  66360
tgatataaat ttccttatgg caacgcaagg tttcacaaaa tttgaaaata atcaagacac  66420
taaggtaggt tggtatttag ctgtaacaca agaacaagca gagtctctaa gattatcaga  66480
ccttgcttac gaagtaacag atgtaggagg atatgacaaa ccccttgaag attttaaaga  66540
gtggtatgta ttgaagctac taagattctt atcagataaa ctaaaagata ttaaaaaaga  66600
aaataaaaaa gttgctaaga aagaatataa cataaaagca aatgagtatg atacttggtt  66660
gaaaaataaa ctcgataaca ttgatatagaa actaacagat gaagataagt attatggtat   66720
cacagaagag caaaaaagat atttagagtt aaaactaaca cctgaggtta ttacaaagaa  66780
tatgcttatg gattctgaat ttaaagaagt agccgaatca tcacctgagt atatgagttt  66840
atctaacaaa gctaaagatt atgtattagg tacatctatt aatttaatta acacgtataa  66900
agacaatact aaagttatta atgaggtaga tggaggtgac tttaattatg attggattcc  66960
attagagctt atgcatcctt atgccagtgg tgacaccgat gtctgtagaa gaatatactg  67020
tgatgttatt gaaaagttaa aagaacaaaa tagacctaaa gcattggact taatgtcaat  67080
aagttacccct agattaatta gaacattagc tagaatacaa tcaaatggtt tacattgtga  67140
cctagaatac atgcataaaa atgatgaatt ttatattaat gagatggaaa aaacccacca  67200
agaaattaga gaacattggg ctatccaaga atttgaggag actaggtata atttatacca  67260
attagcctta gcagaacatg agaagaaacc atctgataga aataaagaaa tacatgagta  67320
tagagctaaa tttaaagatg aaggttggaa gtttaaacca agctcaggtg accataaagg  67380
tgaagtattg tatagcattt taggtataca gttaccttat agtaaagaga cagttaagga  67440
taaacctttc agtaatggta ctaaagaaga tgagttatca tggaaagatt acaaaacaga  67500
tactaagtct ataaagatgg cattatcttt ggttgagaat gaagataata aaaagctact  67560
agacttactt atttatttatg cctctttgca aactaaaaga aattcttta ctaagaaatt  67620
acctaaaaga gtaaataaga atacacataa tttacatggt aactataata gtacaggaac  67680
tgcatgtatt acaggtgatt ctttagttat tactgataaa ggtataaaaa aatagaaga   67740
cttatcaaat aatagaaaag aaaaagtatt tagtagtatt gatgtaggta ttgttaatag  67800
acagggaaat ttagaaaaag cttcacactt ttattatagt ggtgtaagaa atggattaaa  67860
gattactttta gaagatggta ctacattaac tactactttta aaccaccct tattacgaaa   67920
taattattat agtaatactg gtagggttct aaataaaaca aaacaaacaa ctaagcattt  67980
actagataat gattgggttg tagctgaaga tttaaaaata ggtgattata taaaaatgtc  68040
ttataattct aatcttttata ataatagtta tattgattta gatactaaag atttatata   68100
tagtaaagaa aaaagtatta caaacacaaa aagctataca ctaccctaatt atgtatctga  68160
agattttgct gaatggtacg gtatgtatac agctgatggg tctttttcta caaataacgg  68220
ttcattcagt ataagattaa ctaatagtaa tcttgaagtt aggaatagat tctttaacct  68280
aactaaagat ttatttgata ttacaccata ctacattagt aataaagata gaagtgattc  68340
tattgaattt tcttcaattg gtttaggtag atggttagaa catatttta atatgcaaag  68400
taaagcatta aataaagaaa tcccacaaca aatattagat agccctaaaa gtgtacaaca  68460
agcatttctt aagggtttaa gtttagatac tgcaacagaa aagaaaaagt atcctagttt  68520
gtactataat actgtatcta ataaaatgtc tttaaaata agaacaatgc taatgaatat  68580
gggtatctat tgtaggtatt ctataggtaa agtttataaa aataataata gaaaagtaca  68640
aaatgaatgc tattctatac aaataactta tgatgcatta gataaaatttt acgatgaaat  68700
aggggtttatt gaaagtatta agcgtgatag agtaaagtat aaatcagaaa atctaaaggc  68760
attaggcaga agaaacggta ttcttttata tgataatgtt ttattaggta aaataaagaa  68820
aattgaaaaa ataaaagata tggaattttt tgatttacat gttcctagta gccattcatt  68880
tgtagctaat aatattgtaa atcataatac tagcaggctt tctagtaaca accctaaacct  68940
tcagaatctt cctgctcata catctgatgt aaataagttt gattatcacc accctattaa  69000
acgttctttt atctctagat ttaaagatgg tgtaatttta caagccgatt acagtgcctt  69060
agagatgcgt attacggcac tatatacaga tgataaaag atgtttttaac tgttttaaac  69120
aggacaagat attcataaaa atacggcaag tattatgtat ggtaaaagta tgaaggacgt  69180
aacagcagaa gaaagacaag ccagtaaagc tgtagccttt ggtttaatttt atggtgaatc  69240
ggaattttcg tttgcaggta aaaataatat gacagttgat gaagctactg aaatatttaa  69300
taagttttat tctaataaac ctgctattaa gaagtctata gatgaaactc atgagtttgt  69360
tcaaaaacat ggatatgtag aacaatgaa tggacacaga agatatatac actcagcaca  69420
atctagagat aaaaagatta aaaatgaggg tcttagacag tccctttaaca cgattattca  69480
aggtacaggt ggttaccttta ctaacatggc tattacttat attgacgact ttattcaaaa  69540
taagaatatg aaatcgaagt tagtagctac tgttcatgat agtattgtag tagactcacc  69600
tcctgaagaa gttaatatta tggctaaagt tattgtccat gtaatggaga accttcctta  69660
tgatttccta gttaataaaa ttaatggtga gttaaggcag tatcctatag atgctgatat  69720
agaaataggg ctaacatata atgatatggt agaatacaac gaagagttaa taaataaatt  69780
taattcatat aaaggatata ttaaaatata actagcctta cagcaaatta aggactacta  69840
tgaatcaggt aaactaactg aagagcagta caaacaaaaa acggaatata ttaaaaataa  69900
tattgacagt ttcaaagtta tatagtatag taacctatat cataataaaa tagaggatgg  69960
tattatggag atacatttag atacattaga tttcaatgag ttaaccttaa aagataacaa  70020
```

```
tggaaacaca cagacgttta atattcatga tgaactaaaa cttagtgagt atacaattca    70080
agacgaaatg taccaacagt cgtctaaatt tgcatggtgg gcttccttaa aagaacgtgt    70140
gagtaattat gccgaagcag agcaacgtaa gttagaaaaa ataggagctc aacttaatct    70200
acaaattaga gctcagtacg aacaacaggg aaagaaacct acaaaagacc aagtagagtc    70260
tgctgtattt ctttctgatg aatatcaaca gcaagcaagg gttgtagaag catggaatta    70320
tagagaaaaa caattacatt atatcgtaaa agcttttgaa acacgtacaa ctatgttagt    70380
acagattagt gcggaactaa gacaaacaaa taaaaatggt ggtgttacta acccatttac    70440
acattaggta ttgacaaaca aaagaaaaca tgttatacta attaagtaat ttttaaaata    70500
aaaggagaaa agatattatg gattttaatc aatttattaa tcagcaatca gaaaagctac    70560
aatcaagtgg ttttgacaat gaggtagaga cgtacaaacc aaagaatccg gttttgcgat    70620
taggaaagat taaggacgtt aacaataatc aaattaataa agagtctgca cttgtacgtg    70680
tactaccgcc tgtagcaggt tctaatgagt tctttaagga atttagaaca ttaggtatta    70740
actatgttaa aaaagatggg gcacaaaagt tctctatgct tactttaccc gagaaagtta    70800
actcatctgt tgtagaccct tatgtaaata catggttaaa gcaaggtgta caatttagta    70860
acttccctaa taaacctgca cgacgagcat atattcatgt gattgaatac tttaatcaaa    70920
acggacaatt agttcctaac acagatgaac aaggtaatgt tgttattcaa cctatggagc    70980
tatctaatac gggtctgtct caattgattg accgattaaa agataaaatg ttatcaccat    71040
cacctactgc tacacacagc tttatttcag ccgatgatgc attccctatt aatattgcta    71100
aagctaaaaa aggtgaaaaa tcatggaatg taactgttta tcctacagta aaattaggtg    71160
ccttacctca aggttgggaa cagcagttat cggatttaga taagttagct acaccaacag    71220
aagaaaataa ccctaacttt gtaaactggt tgattaacaa tgttaataac acagaagttt    71280
ctcatgataa ttttaaattc agtagagaaa caaacacatt aggtgaagaa tcatcaacac    71340
aagagcaaac acaagctcct acgcaacaaa gtgtagagca acaattacct agtaatttag    71400
gtggacaaaa taacacacaa ccaaacttta ataatgtaca acaaccaaca ccacaagttc    71460
ccccacaaca aaatacacag tttggtcaag gaacacctgt gcaacaagca ccacagcaac    71520
agcatcaca gcaaccaaca caacaagaac aaagtaatcc atttgagaac tttgatgcta    71580
ataacattga cgattctcaa atcccattca acacaaatga atcaacacca gaaccaccta    71640
aacaaaatca acctaagagt gtagatgatg tattagcagg tttagattta taataacttt    71700
atagagtgct atcttagcac tcttttattt aaatttcata taaaaggatg atataatggc    71760
tagacaaaa aaaggtaaag aagtagatac tacaaattta aatactattg acttaggtaa    71820
agaattaggt ttaactttac tatcagatag taatagagca gatattaaga atatcattcc    71880
tactatgatt ccacaatatg atagaatttt aggtggaggt attcctctag aaagacttac    71940
agaagtttac ggattaactg gctcgggtaa atcgaccttt gcagtacact tatctagagt    72000
agcaacacaa ttaggagtta ttacagtttg gattgatatt gagggaacag ctgataatca    72060
acgtatggag cagttaggcg tagatgtatc taaattattc tcagtacaat caggtgaagg    72120
aagacttaaa aacgttactg aattatcagt agaaactgtg ggtaaagagt tagagtactg    72180
gattgataca tttaatgaga aagcaccagg tattcctatt ttatttattt gggattcact    72240
cggagctaca cgtacacaag atgaaatcga tgcaggagta gaccataaaa aacttggaac    72300
aaaagcgaca tctactcaaa aagtagttaa tgctatttca cctaagctta atgatacaaa    72360
tacaggatta attgttatta accaagcacg tgataactta aatatgagta acccttatga    72420
tgaccctatt aagtctacag gcggaagagc ctttgagcac ggtgctagtt tacgtattaa    72480
agtatctaaa ggaaaagaat cggaattaaa gcaaaatgat tctatgacag gtaaacctac    72540
gtataaagga catgttatgc gtattgaaac taagaagtct aagttatcta gacctggaca    72600
aaaagcagaa gttgatttat tatcaggtta tgaagtaggt tctgaggaag acactgttca    72660
attaaatggt gttgacccttt atcatactat ctataaagaa gctgttgaac gtggtttaat    72720
tacaaagggt acatggcgta attatgttac gttaaatggt gaagaaatta aaaagtacga    72780
taaagactgg gtaccaacat taatggataa tcatgaacta tatttagaat tatttaatag    72840
agtttatcat gaaaacttcc ctaataagta tgtacccttta agcaatacaa aagtagacat    72900
tacccaacta gaagagttta aagcattaca agattactac gaagagctta gctctactaa    72960
taaagagact aaggaagatg taaatgaata atctaataga tagaaatatt aatagtgtta    73020
aagaagcatt aggcagggct aatacaaatg acgtattgcc cttaccttat attgaaatag    73080
cagaacgttt taaaaagct agagatacta aggaagctat tattgtagaa gaagcaggct    73140
ttccttacac tgattctaca gttatgtata ttgagcatgt agagtcaagg tgggcagggg    73200
gttactcttt agtacgttat aatggttctg aagttaaagt acctaaaaca atacactatt    73260
ctgatatcta tgtatcaaat gatgtacaca ggattaagat tgtatttgag ggagcacatc    73320
cttatgaaga aagttaataa tgggaataga tatattatag acttagatgg tattcctact    73380
gactttggta gagacttaga catgctttta aagagatata aaaacttag atggtcatta    73440
tttcataggt actctagagg tatgagtcat gactttgaaa acaagagtt acgggaatac    73500
atagatgac agtttattaa gttagttaag gagtatgata tacaaagtaa agtagattt    73560
ccagggtata ttaaaacgaa actaacacta cgagtacaga acagttatgt taagaagaac    73620
aataagtata aacgtactga acttgtaggt aaaacagatt atacagtaga gtccttaaca    73680
caggagttaa atgtgggatt agaagaaaat gaattactta attatgtctt tgatgataca    73740
caatttactg aagtacaaag tgaactgcta aaagaactcc ttattaatac agataaagaa    73800
gacaacgcat ttattgttt aactgtagct aataggttag aggtagagctg ttcagaaata    73860
actaaggagc ttacagaact aaagattat gttaaattta aaataaatgc ttaccacgaa    73920
caaaacagta aagatacat tagagacaac aaaatagata cacaaaatca tgtatgggaa    73980
taacacaaat aagccttcct tttgttatat tattaatgaa aataataaca tagggaggtt    74040
ttttctatgt tataatgtaa aaaataatga ttgggagctta attattatgg ctaagaaaaa    74100
tattaatgaa gtattaaaac aagctaccgc tactgtagca gataagtatt tacaagttca    74160
agtagagcaa gatggttata cacgtacaca ccgtggtcag tataactaca aagtagtaga    74220
taataaggga gaattattct tatcccgat tgaaacagat ggtagaggaa atattaaaat    74280
tatgaaaaag gctcctgttg cttatacaga tggagaccaa attcattttg tagttaatac    74340
tgttaaagac ccttacaacc atgctttttat tagaactgaa aatattaaag gtaaagataa    74400
aggtaaacaa ttaattcaag cgttttttagс attcgtttga gaccgtttca gcttttggat    74460
atacaatgta ttccttgcta ataacaagaa ggatgtttttt gctttagttg atgctgaaag    74520
taaagatgct aaaaaagtag tagatagtaa tgagaaacct catgaagacg tgagcgctga    74580
gtttcctgct agtccgctac gtaaagacgt taaggagta gactcaggag aaggtcaagg    74640
agatacttca gaacctcag tacctaaaaa tgtaacagta accgctaaag aaacaacagc    74700
tgatattaca gctgaataaa catataaagg atgacttagt ttggataaat taaatttata    74760
```

```
caaaggtgac cagctattaa aaagtgaaga gaaacaagca ggtaaaacat caattacaat   74820
tgataactta actgctaaca cagactaccc acaaggtaca tataaagtat ctttctctaa   74880
tgaatcagga gaatcagaaa aagtagatgt tcctgcgttt aagactaaag atattaaagt   74940
agtatctgtt actttagatg ttgaaagttt agatttaaaa gtaggagaaa cacataattt   75000
agtagctacg attgaaccta gtaacgcaac aaaagctact tatacattta cttcagaaca   75060
tgatgatatt gctagtgtat caagtaaagg tttagtagaa gctaaagcaa aaggtcaaac   75120
tacaatcact gttactactg atgatggtaa tcatacagat actgtaactg tagttgttaa   75180
agataaagta cctgaagctc ctacagatgt aactgtagac cctaaagaaa caacagctga   75240
tattacagca taatcggagg taaaaataaa tggaaaaaac attaaaagta tataaagatg   75300
gtgaagtagt aggtactaag actgctgaac aaacaggtaa aacaactatt tctattagtg   75360
gtttaacagc agatactacg tatcctaaag gaacttataa agtagcatac tctaatgagt   75420
ctggtgaatc agaaaaggta gatgtacctg aatttaagac atcaccacat agtgagctat   75480
aataaattaa agtccaactt aattgttggg cttttttta ttgacttata tttatttata   75540
tgctatagtt aaacaagaat taataaagga ggtactatat ggatattaaa acagtatact   75600
taacttcaga taacgaccat ttgaaagtta aaaaattaat ggaaagtaag gaaaagtata   75660
ttgcagttac gtatgataat aaatcagtaa gtaaggtcaa tgtcgttatg gttattaatg   75720
ttattaaaga cctagtgcat atgtataggt ataaaattgt tgagtatggg ttatctaata   75780
atgataagga taaggaaatg gtagggtatt tattagaaag gattgaggat tgatgttatt   75840
tattttaaat gaagtagctt cacacacaga acatttatcc gaaggtatag atatgttcga   75900
cgttgaaagt gtagtatctt ttgactcggc attacattta gctagtgata atacgtatga   75960
ttctgttatt tttttaggtt ttatatacaa taatgaggat tacttaaagt ataaagaatt   76020
attaaaggat acaaaattat actttgtttc taatataaac ttacctgaca ataaggagtt   76080
tattacagta ggtgatgact taaagtacct atccttatta gagcaacttg tagtattaga   76140
agataaagac ctagacatta actttagtca gtatactaaa gacacggctt ctaagtacac   76200
tgagttgttt agctttaaat ctacttatga ggaggcaaaa gaaatgggtc tagtaggtta   76260
ccccgcagat atagtattac tctattatgac tgacaagttt actgtcggac atgatttgta   76320
tgtactatac gaagtagcac ctgagtataa attcccttta gcatatgaat gccttaagga   76380
taaagaaaaa ggtattgttg ttataggttc acaaacaaga ggtactagtg atatccttac   76440
tttctatgta aaaggttatg atgttaatag tgttgctaaa acattcggag catcttataa   76500
tgaaaattct aatatattca gtatatttat tgatagtcat atccatgtgt taggtgagaa   76560
tatgaataag tatttaataa cggaaggaag tatttatgag taattataaa acagtagaaa   76620
agttacaagc agttattgta ggtgtgtttc ttaaagatga aggtaaagta gttacctcta   76680
aatttaataa agtattagca agtttgtta ttgatagagt aaatcgcaat gaattaaaag   76740
atattgtaga taatattagg aaagacacat acttaaatga cttgaaaaat aaagcagtta   76800
aaggtgaagt gttattagag gacttaagag atgtagaaga taaacaagta tttgagggta   76860
atgattatca tgaagaagta tcatcttatg tagtagcaca tgaaaaagaa ctatctagac   76920
taagggaatt acgaaagatt aatagacaaa ctgcataccc tactattttg tttgatgaat   76980
taaagcgtac tatggttaat gagctaaaag ggaataagtt actagaccat aaagtaagta   77040
agtatacttc tactgaggaa gaagaagagc tggttatctt actgtcggac ttccatgtag   77100
gttgtgcttt tcaagattta actaatgagt ataactttga ggtactaaaa agaagattaa   77160
atcagctact acaggaaact attaaggata ttagtaaacg tggtattagt aatgttacag   77220
tatactttgt aggtgattta atagagcata ttaatatgag agatgttaac caagcttttg   77280
atactgagtt cactatggca gagcaggtag caaaaggaac tagactatta attgacttct   77340
taacagaatt atctccatat gtatgggta atttacgttt cggtatgata gcaggtaacc   77400
acgaccgtgt acagggtaat aagaaccaaa aagtatacaa tgatagtgta gcttatattg   77460
tattggattc tttactgctg ttaaaagaaa acggtgtatt agaaggtatt gagattatcg   77520
acaatagaaa aatgtatat actattaaag acacagtatg taacttaaat attattataa   77580
accatggaga tggacttaaa ggtaaaggta agcatattcc taaatttatt gagaacactc   77640
acattgactt attaattaca ggtcatgtac atcacttttc agtaacacaa gaagattaca   77700
atagaatgca tattgtagca agtagtccta tgggatataa caactatgct aaagaactac   77760
acttatctag aacgaagcct tcacaacaac tactattttt aaataaaaaa aataaagaca   77820
ttgacattaa aactgtattc ttagattagg gagagataat atggacattc tatcaattat   77880
agccttaaca ttgcttatca ttattattgt taataccaca atgaactttg taggtatgtt   77940
acgtggtgag cgtgatttag taaaaaaagg aggtaaccct ctacccaatt ggcagtacta   78000
taatgtgtta ttacctaatt tatgtggtat tatcctctta ggtattgttg tttattttgg   78060
agattcgatt tataaaatta caacaaggtt agaggttctt tttgctatta ttgcgcttat   78120
tgtaatagat gtattgttaa cagcgttagt attattagta ttgagtttcg taacaaaaaa   78180
taaagaatag taaagaaggg agtctggttt atacttgact cccttttgtta tttatggtat   78240
attagatatg aggtgattt tgttgcaatt aaattttggt aaatttgata atgaaattat   78300
taagacaaaa gtaagtgaag gtgtttactc ttttagaagt gttccttatt actacataga   78360
acatgtccaa gatgaaactt ctgagtatgt attagtatat aacatacata gtgttgatga   78420
tgaagtacca caaagagaaat ataaaataga aacagtaagt aaaactatta gaggcggtac   78480
gatattaagt aatacaatta agtcaatgct acctaataat aagaagtata aaaaagtata   78540
tgaacctcct atcttttag ctaatattat acctttaggt acagatacaa ctacagttgc   78600
tgtaggtaaa gggttttttcg aaagagaaaa agatagagta actattacac aaaaagaagg   78660
cactaaagtt atacatggtg aatatacagg agtatttata tgtttatcta atattaaatg   78720
gattaagtcc tatactcctt tagacagtat attacaatat tatcaacgta ttaaagggga   78780
tagaataaat gtctgagata actaaaattct atgagcagga cattaaagat ttaattagaa   78840
ctaagacaca tatgtttaaa gatgatgaga taacaagtaa tatacaagat attagaatat   78900
ttaatgaaaa agctatttgt caaggtaaat gtagaactga ctgtttaatt cttgatagaa   78960
acggtactgt tatgggtata gagataaaaa cagaacgaga ctctacacaa agacttaata   79020
aacagttata ctattatagt ctagtatgta agtatgttta tgtgatgtgt catgataagc   79080
atgtacctaa agtagagcaa ataccaaaaa ggtataaaca ccatcatgta ggtattatga   79140
gctatattaa cttttaaaggc agtccagtag taggaagta taaggaagct acgccttcac   79200
cactaagaag tccttatcat acactaaata ttttatggaa gcaacattta atgactatac   79260
ttaaacagtt aagagattat aatacatacc taactggata taactatagg agcacggta   79320
aaaatactaa caatgaaggc agttatatag aaggaacaca acgtatgaga atgaaaaagt   79380
cagctattat taaccaagtt attcattatt taggtgtaga gaactcttat aagatattta   79440
ctagaggtgt tatctatggt tatagtaata gatggcagat attagaagat gatttctta    79500
```

```
aagttataca gaacggagtg agggtattat atggcaaaga ggaaacctga tgcatttaaa   79560
cctaaatcta acggatataa acatcaacct gttaactttg ctcctacagg taacttatca   79620
ggtagaagta cttcttttt taataaaaaa agaaaagata tatcagatga aagtattgtt    79680
gttaaataca aaccttgtt tgttaaaagg tttgataatg ttactgctac cgacattaaa    79740
atacaaaaga aatatgcgtt agacttaatt agtgaagctg tgaatataaa gaagaaatat   79800
cttgtaatga agcaaaaagg taaattaaca caaactatt tacatacgga tagagtttat    79860
tatgttata gaggtaagaa attaataggt aaatgtagca ttcgtgaaca acgtacattt    79920
agaggtacac atttaatcta catttttagt actagacata gaatatctat acgcaaaaat   79980
agtagattag ataagaaaag aacaccaaag aaaatgatat ataaaggtgg taaataatgg   80040
ttaaatattt aagaacaaaa gctaaaaaa caaatataag tactttattt aagaaactac    80100
aaagtaaaga tattcacta ttaggagtgt cctatgatag tgattattc cctagcggtg     80160
taacaataat accttattta gaggacatat cacaagtaga agatggtata gaatttacga   80220
ataaagtaat agttactgag aacttaaaac ctgctattgt aggtatgaat aatatgataa   80280
gtgattcagg actaggttat gttaaaacag agcagttaaa taaaagatta gaaaatactg   80340
gattaatgac agatttatta tctaaaggaa cagaattaac ttcaacaaag aaagtagaca   80400
ttgtatcaac ttttattgaa cctactatta tgtaccaaga tactactatt aataaagaat   80460
taaaacttag attatacact atcgaagatg tatccccttt aaatgattac acacatgttg   80520
tatacttact agtaactaat aagcaatatg acggtcaatc attcataggt acattatgta   80580
accaaggtac attaaacaaa ttagatactc taaaagttct tacattcttc aagggtaata   80640
atttaatcaa tagaagtgtg ttttctgtta agttagatac gaataaaatat cattatagtt   80700
tatataatac acatgagacc ggtatttct ttttagtga tgataaagac ttaattattg     80760
cttgtggtca atcctatgta aaagttaggt ataaagatat tgttagtagt aaaatagaga   80820
aagttagtga taataactat aaaatgattg ttaatcttgt tggtaatgat gagctaacaa   80880
ttctcttata gtataatact cccttaaata tgtatactaa ggtataaata tacgtatcta   80940
agggattttt tatacgtatt tttttcaagt agttagttaa ttttttaaaag gtattattct   81000
tattttaaaa ttatatttat aaaacattaa aatatctttt aggtataggg ttttagaaaa   81060
aagatttata ttgcttaaaa tagttacact atagtgtaaa aaattagaat atcctttatg   81120
aaaataaaat agatgcagaa attgtgatat attatatagt gtaaagtata aaacagttga   81180
tttgataagg ttatgtgaat acacatactc cttattttag ttcacacata tgtaaagaca   81240
cttgagacaa gaagggaata tataatggct agaaaaaaga atttaagaaa taaaaatct    81300
gatataaagg tagttccaga taggaaaagt attctatcta aactatataa taataaacta   81360
ttaaggtcta aagtggataa tgctatagat gaagatgtta gttatgatga tattatagac   81420
ctatgtaaag agtatgactt agagttatcc aaatctgcca ttacaagata taagagtaaa   81480
cgtaaagaag ctattgaaaa tggatgggat ttaggagaac ttattgataa aagaagaaaa   81540
gttagcgcta ctcaaataca gaaaaagaa aaccctatga aagaattaga tagtgagaat   81600
tatacacctt ttgaactggc tacacagaat gtacaaacaa tatatgatga tattcaaata   81660
ctagatatga ttattcaaaa aggtgctaaa ggtttaaact ttgtagaaac attagaccct   81720
gctttaatga ttaagctat ggaaacaaaa gatagaatta cgggtaacca actaaaaggt    81780
atgtcattca taggactaag agactaatg attaaacaac aagcacaaga tactgctatg   81840
acagaagtta tgcttgagtt tattcctgaa gataaacatg aagaagttct tcaaagaatg   81900
gagcaattac aagaagagtt ctataaaaac ttagatttag atgaagaagg aagaagtta    81960
aaagatacat tagatagagt aggctataca atatagataa tgaggtaata catatgacag   82020
aagaaattag tttaattcca ataaaagatg ttaaaccact tacagatata gtagatatta   82080
taacacacct acataaaggt gatgtactta gagttaaaca agagaaccaa ggagatatat   82140
tacttagact aagtactgga aaacataagt ttactgaagt gtcaagagac ttagataaag   82200
aaaccatgtt ctataaaagg tattgggtac tgtataatga atcctattaat tctttactaa   82260
cttttgatt ttatttagaa gacgattatg tagaatctac aaaagttaag ttccctaaga   82320
acacaattgt agaatatgta agagataatc aagaatcaga tgtagccaag gttaaagata   82380
ttttagtaga tagtaaaggt aattatttct atgcactttc aggagaaaca tcttatata    82440
atgaagataa acttaataaa attaaaaatt aatgattgac acactcatat gggtgtgtta   82500
ttcttttat acaaacaata aaaggagcaa ttgattatga ttattcatt aaatgaagaa    82560
gagaaagcat tattgaaaaa taaaagcaac tatacgccat taagtaagaa taaagagttc   82620
aatacaccaa aagaagaata tattgttaca agttataata aaggtgtacc tgtgactgat   82680
attgctaagg aagctaaagt aagtatgggt ttgatttata cagtgttaaa cttctataaa   82740
gtaccaaaga aacataagaa atctagagta gcaaaacgtg taaagcatat tactaatgat   82800
aagaataaag tacaagcctt aattaaagat tatcaatata tagacttaca aagtatttat   82860
aaaaagtata acattcataa gaatggttta tattatattt tagatttgta taatattgaa   82920
agaaaatcag atttaaaaga gaaagcctta gaagatacta tcgaggtaga ataagaggtg   82980
tcatatgcgc aaagaacgaa ttgtagatta cttgtataat gtaaagaaca ttgataataa   83040
tttaactata caaggaatag aaaatagttt atttaacaaa gaatctttac aagacttaat   83100
acctgatttt gatacttcta gtaaagagat taatgaaagt aatttatacc tatgtacaat   83160
accagaagat tataactccg accacgtaga aagtggtcag tatataggta tagatgttgg   83220
gtatgtatct gaagaccctg cttttgacca tttaataggt caagttccta gaagtgtata   83280
tgagaaagcg catgttatgc aaccactaat taagatagaa aatactgata tagattatac   83340
tcaggctgat atgattaatg acattaaagt aggtacaagt attagtgatg taaagattaa   83400
agataaatta agtttaatgt caaataatct tattacacat ttagaaattg ttgataagca   83460
ctactttgat agtagtatgg aagaagcact actaaagtat tatgagttaa aaaatcctga   83520
ctattattta aaacattttc ttaaactaaa agaacttgtc ggagacaata gaatgatata   83580
ttgtccttta ctgttaaaat gtattaaagt tagactaa gttattatat tataagtagt    83640
aaaggatggt gcgctatgag taaaaaagca ataattgctt atgtaattat cttagttatg   83700
ttagccttat ctatatctac ttattacgta tcctcatact tatatcatga aaaaaccaaa    83760
tcacaagtta cagaccaatt aacacatcac ggtaaactaa aaaagataa aatgtagag     83820
tacgtaggag attacacgct taagaaagta gtagacaaca aagcatactt tatggaaaaa   83880
ctacctacct atttaccagg aagaacaagt gataaaagta ttgatatgag atattataag   83940
actagtaaat ttagagaagg tgtaaacttt aaacttattc gtgtgtatac ggaggataat   84000
gacaataatc cagtacataa gtataggttt gaagcagtac taaataaaaa gtaaaggtat   84060
gatagtctat gacagtagta attatactag tatgttttgc tattatatac tatttattta   84120
acaaggattg agtcaaggtt atgcttgact ctttttttat gctatgttat aatttaaata   84180
taaggagatg ataaatgatg aaaaaagtg atttagataa tttgtatatt gtggtcgtaa    84240
```

```
gtattaagaa tggtgttta cctgatgagc gtataattcc aattggttta gatgtactaa      84300
gtaaagtatt agagggtaaa actatatgga cagttaagaa agaaattaaa catacatttg      84360
gtaaagatga attaaaaata tttaaagata attacaagtt cttgcaacat aaaattgtag      84420
accttgctac aaaaggatat aggtaggtga tataaatgga tatagtagat aaactcatgt      84480
taggttttat tttattgttt tatgtaggtg tatttatttg gtacttatgg gaagtctgaa      84540
aattaacttc tttaatatct gatatagtta ttaagtatta tgttcgtaag gagtgggtta      84600
aaggtttatt accttatttg attcatcaag ttattattac gttagtttgg gctactctag      84660
tattagtacc ttttatactt agctatataa tgataaaata tttgatagga ggttactaaa      84720
tggaaatagt atatgaagat gaatgtagag gatattatat ttgtgtcata gataatgaag      84780
gtaagtatga agtatcatct tttaaaaaat cagtaaacaa gtatacccct gaaattacag      84840
ggtatactac agaaaagtta ctcttggaat taaaaatacc atgtacatat gtaaatgcta      84900
gtgaagtaga aagttttatg caagaattaa aagtagcacg tattgcgctt gacaagttta      84960
ctaaagattt atataataaa ggcataacaa atattatatt ctaaagggtg gttagtatgt      85020
atacagaaaa atatagaaat ttaatccata ttacatatag tatcttggtt agtattcaag      85080
aattagcaag taatttatta aataaagaag taaaactagt tacaaaagaa aataagtact      85140
tatgtgttgt agatggtatt attatgttaa ttgttgagga aggattagta tacacctatt      85200
ttgataaggt aggttttaaaa gtgcctgaac gtattgcact tggtcattta gcaaaaagtt      85260
tacagtttac aatatcggaa tcaaataaag atttagaaaa tcaaaaataa gtgttgacac      85320
ctttaacatg ttgctttata ctaagagtaa caaaacgtta gaggtgattt tttatgtgta      85380
aagaaaaagt tcatagacag ctatctaatg ctatagaaat attagcaact acaaagagt       85440
ggtggtcttt tccaaaagaa ttaagtccca cagaaacatt taagattatt aactggaaag      85500
aagatacatt agtaatttga gttagagata acggtaatta tataggtagt tagtgtag       85560
caactcctat tattgacttt cattatgata gaattaaaaa aacgacagca caatacatga      85620
taaattattt tgctaaacta gtatgtaaag atatgtatac gtattataaa ttacagagag      85680
gacagtaaaa atgaaaaatt taaataaaca aaaacgcttg acgttggaat tgattagtga      85740
taatctaaat acacaacata acttaaatac atcggttagt cttgtagatt atagtataa       85800
agactttaca aatagaaaag tgtatgtaag aactaaaaaa ggtttagaac ttactaatat      85860
gaaaagttta aaaagtactg agtcattaga tttattattt aagtatctag aattaatttt      85920
aaaaggagat gtataacatg ctaacaccag aacaaagaac acaattaaaa gagtatcaaa      85980
ataaaatgac aaaaaagaaa aaataaatgt tgacttacta ataacaagt tgtataatta      86040
acttaacaaa gaaaaaggag attgataaat atgaaaaact tatataaaat tttaacagga      86100
gtattcttta gcactacact attattagga ggttgtgctt actactcaca agcagataca      86160
ccgacacaca attataagga agacaagaaa gaaaataaga aaaatgattc atctaaagta      86220
gaagaacaag aaaataaaca aattcaagaa gacaacactg ttcaaaataa ccaacaagat      86280
aaccaagtac aagtaaacca agcacaacag aacgaacaaa tgcaagaggc aagcagaagt      86340
gaacataatg gactatctaa tgctgagtat gcggacaaat acaatcagta taagaagct       86400
caacaagcac aagcagaatt agaaaacaga actgaagcag ataaagctag tggcggtgga      86460
ggcggaggag cctcatggaa ttatgcaggt gctaatgaga gctttgagca atggttacaa      86520
cgctcgcaac aagaaaaggc tgaggctgga gtacaagcaa attaataaaa ggtataggag      86580
aataacaatg aaaacaataa caaagaagaa actacataaa gttttagaag agcataaatt      86640
atggttagat agtaatagtg aagaaggagc taaagcagat ttaagttata ctattttaag      86700
aaatgctaat ttagtagatg ctgacttaag gagtgctaat ttaagaggtg ctgtcttaag      86760
gtatgctgat ttagaggata ctaatttaag aggtgctacc taaaaggtg cggatttaac      86820
aagagctaac ttaacatgtg ctaacttaag ctgtgttgat ttagatgatg ctaacttaga      86880
aggttctgtt ttatatgaa ctgatttata ttatgctgat ttaagaaaag ctaatttaac       86940
agattccaga ttaaatgagg ctaatttaga atatgcagac ttaacaaata ccaatttaac      87000
agatgctaaa ttatcccaag caagtactca aaatatcaaa ggactaaaag tatactctat      87060
agataatatt ggaacttta atggtaaagt gacttatatt cctagcttag atagagtata      87120
cgcagggtgt tggataggta gtttagaagc gtttttagaa aagggattag agatgaatga      87180
aggaaataat agtaaacttg aggaaataag agatgcttac tgctttttta gtaaacgtaa      87240
atagatataa ggatgattaa ttatgaacat tgtagaacaa cgaaaaccca taaagagtaa      87300
gcatattaac ctaactaaac atgcgtatga acgttatact ttaagagtta gtaacgatag      87360
taaagaacgt gcttgtcagt ggtttgctag tgctttaatg caagctactt ttgaacatac      87420
acaaaaaggc ggtaatgaag tatatgtatt taaaaattat agaattgtta ttgataagca      87480
tctaactatt attacagtta tagatactga agatgataat tgggaaggta taaaagaagc      87540
aagagaacaa atagatacgt atattaaagg taagctaaaa agaactgtta cacctctatt      87600
tactaaatta gatagaatag atattagtat ccatgaagca catatcagca tgattaaaac      87660
aagaaaccct aagacaaaag atataattaa caaaaatatt gttgaacttg aaagaaataa      87720
atcttacta ttaaatagta tagaaggtgt aaagaaaaca gcacataagt ttaatatgaga      87780
attaaaagac attcataaaa gattaaagga ctgataataa tgtgtttaaa agatttaatt      87840
gaagattata taaatcaaga taagaaata attataacag ttacaagtac taaagtaatt       87900
attgaagcag actatgatgt tatttgttta cctaaaagta aaattgatat tgacgattta      87960
aaagcttatg tatatggatt taatagattt aatatagagc aaattgtatt aaaggacgtg      88020
gaataatgca agacttaaaa aggataacac aacctgaatt agatttattg ataagaaggc      88080
atgaacaatg gctagctaca aatgaaaagg aaggagaaaa gctcttttta cagtgtgtag      88140
atttaagaaa tcttgacttt cattccgctg accttcaata ttcaactatt gtaatgtcta      88200
gtttaagtga tgctaaccta agttattgtg atttaagtta ttctgattta agttacagtg      88260
agtgtatatc tacgagattt acacatgcta gaatgagaga tactgagttg cctcatacta      88320
acttagaagg ggctaattta ataaagcca acttagaaa tgcctgctta gctgaagcta       88380
atgtaagtga agcagacgct aggtgggcta atatgaaaaa tgctaactta agtatggcta      88440
atttaaaagg tgcagatttc ggtggtacaa acctaactaa tacaacatta tattatgcta      88500
atactcttga cgtatttgga ataagtatat atactataag taatgtactt gattttgatg      88560
agcatgtaac ttatttacct gattatgata gaattattag taattataat gaatatccc       88620
ttgaaggtt tggtaaacta gaacctacac ttgagtacga agaagataga ataaagaag        88680
tctcaaagaa aatagaataa aagaagtctc aaagaaaatt aaattatctt acgatttctt      88740
taaaggagtg aaagaattg ataaatttta attcagacga acataaacat atacttaatg       88800
ttatggatag attaccatat acttgctggt tagatactgt agatggtgag tcaggtgctg      88860
acttttatg tgtattaaat aggacacact atgaacttac tgaactaggt ataatgattt       88920
atagttatga tagttggtat atgataccat atgacaaaga agatttaatt gaatatgcaa      88980
```

```
taaaaagaga tatagaggag gaagggaat  ggtaggtatg gtgattacat ttttaattgt 89040
tttaggtatt atattgctaa gtgtactaat tattgttata ccagatttaa gcaaagcaaa 89100
aaaacgtaaa gaagacgcag atattaacta tagccaatat actaaagaca tggcttctga 89160
gtactatgaa aagtatataa cacctactga acacattatt caaactaaag tagaagaggt 89220
aattgaaaac ataaagaaag agtatactgt ctctactgta attattgact cttctagtaa 89280
tgaagacaaa attatcttac atgttaacga taagtactta aaaaaggtag tgtataaaga 89340
tacgtatgaa tacatctacg attctaatac aaaataccaa tacattatta ataatgtaac 89400
atatgagtcg agtatcttat taaaacaaga tgaagtaaat aaattaaaag atatacttaa 89460
taaagtacct gtcacagcta agcatacatt taaaaatgag ttgcttaatc gtaggaatga 89520
atatgtgtta ggttatatta caatatatat ttatgatgat ttaactgcta aaattacaaa 89580
gaatggttat gtacaagact ttagtacact agaagatttt tgtgataagt atgaagctta 89640
ctgtagattt gttagaattg atttatatga ctgggtaaaa gaagtaagaa ctattaatgg 89700
gtataaatta aaggtagata ttaaaccttta ttttaaaatt actgctacta aaacaagtaa 89760
atacgaattt gtagtaagtg atgatgtatc taatgttaag gtatatagag atgatatgct 89820
actaacaaac aggtatgtgc aaaaagcaat tgatatacag gaaatagtag aggaaacatt 89880
gaataataat actgtggtat tttaaaaaag gaagaagtag ggaaattccc tacttttttc 89940
atatataagt gttgacatga ataagtgtaa ggtttataat aagtatataa gttaaataat 90000
tatagaggag acattaatca tgaaaaaaat attaagttta gttttatccg tactaattgt 90060
actaacaata atcaatgtgt tgaaaaacca agagcaagta gaacaaagta accaagaatc 90120
tcaaaataat gaagatgcag atgaccatac ttcatacgta cctgagaata atggagaaca 90180
caaagatgtt agtggagaac acaaagatgt tagtgaagaa cgtaaaagat tatggggtac 90240
agagtatcaa gaaggtgaaa cacataaccc aaatgctaaa gtgtttaatc aagatacgag 90300
agaacaggtt caataaagag taagaggagc acttattatg gaatactgga agaacaagaa 90360
catatatttat tcaaaaacaa aacaaggtgt taaagctat atagacttat cttccttgct 90420
ctaaacaatg ttcaacatta ccaagaagtc agtggataca tgaaccacca gaaaacaaaa 90480
ttatcagaca tagaaaagag agaatattgt aaagaaaata gtatacaata tatatagaga 90540
ttgatgctag aaagtctacc tttaaacata tattaagtaa cctacaaaga acatttaaat 90600
actctaaatat agatagtaaa gaagtaatta aaagatatag acatgtatat aggtaagtgt 90660
agaagagtaa acaaccaaac agacaaacaa ataggtatag agattgatgt aggtagaagt 90720
tatataagta agtaataggt aaaagaaaac aatatatata agtagataaa gaaatcagat 90780
aagtaacaca taagaaaaca actgatatta taagtaccta tatatcaagg aaataagtaa 90840
tagataaaaa aacaataatt gatagcacat agataagcag taggtagtat ataagtaata 90900
gctaaataga taagtaaata aatactgtat aacagtttga agatatgaat aagaagaaag 90960
aattattaag taacttaagt attaatagat attctaatag taagtaagtag atattaagta 91020
gtaggtaagt aactaaaaga aagtagctaa aagaaagtag ctaccactat cacttaggtt 91080
aggtaagaac agttacctag taatttcttt acatcttcta gatagataaa taagtagata 91140
ctaagtaata gctagtaagt aattaaaaga aaacaggtac atggtatacc tatatactaa 91200
gtagcaagta gcaagtagca gtagcaagt agcaagtagc aagtagcaag tagcaagtaa 91260
gaacaggtac atgggaattt ctctgcttcc ctccttcata gtgtatatat agttaggtgt 91320
ctaactatta gatatctaac tatttatttt tatatagttt taactactgt gaactatgtt 91380
tatgtagtat taaactatgc tgattatatg ctaaactatt ctaatgtata gttaaactaa 91440
gctgaagtag tatttactgt gtataaaggt atatttagta ttagatattg tgtatatggt 91500
atactataat tctgaacatt acttatttaa tatatatata tttgttttct gtggtagtat 91560
tgacttaatt ttccctagag taaaagttta atatatttag taatttccga acaataaaga 91620
aattttaact attttacaca tatgtgttga cagtatatta cttatggttt atactaagta 91680
tataaagtta aaggagatga tttattatga agattaaaag agaagtttcg tttatagaat 91740
taatgtatat gtattataaa ggtgatataa aaaaaggtcg acactattct actgatagtc 91800
agtttattgt tgtttaaact gttgatgata tatcgttttat taatgcattg tatcctaata 91860
aatctattac tattactata cctaatgaca ctaagttttat tgtagaagcg gttatagatg 91920
cttctactga gttaagtagt atagtagtta cttataagca aggtaacagt gtattaaact 91980
cagtatggta tagaagtagt attaatgaag ttattgacta ctatgtcgaa ggtaaaaata 92040
catggttatt gtctgttagt actgttgtag ataatgagtt agttactata tggaaagatg 92100
gtaacgtatt gtgatttggt atatagtaat attcagtata cttatatatg tacagcactt 92160
gtattattat gtgtagtact agtatataga ggggttaaat aaccgcttca ataaaaaggg 92220
ggattagttt atgagtatat ttataagtat cgttgctata ttttttagcta ctattagtat 92280
tgtactaagt ataaggtttg gtaagaagta ttataagcat gtactcgata attatgatag 92340
tgttagtgat ttagaatcag cttgtgtgtt tggtttatta tttatgagta tttgtattgg 92400
tactatttct attgttttga gtttaggtta tctaatagtt aatttgttac attgttaggt 92460
gtatttaggt atatagagta gggcatatta agtaagggta tttttagatg ttaattttaa 92520
gttggtttat tatcggcata tatcttgctt gtttagttac tattcacttt ttttctatta 92580
aagatagggta tattattcct gctacactag gtattgtagc tcttattata gttattattc 92640
ttatatctac caaagtgtta aatatgtagc ttaagtgaga ttaagtaagg aggattataa 92700
atgttaagtt ttattttgtt atgtgttgct ctaggtattc cagaacttt cttacttact 92760
attttaggtg ttatcttagt gatatctatt aaagatagga atatagtctc agctatattt 92820
gctattgtag ttttttattat aatgagtata cttatatccg cttcagtact acgtatgtta 92880
ggtatgtaat ttaaaaagga ttaaataagg aggggttagag atggaaaac tacaagtatt 92940
aaataaggta ttagaaaaca ggttaggcat aaaagcgttt acgtattctc attatagtaa 93000
gcataacagt aacggatata tttacagttt tcatatgaaa aagaatctt ttacttgtca 93060
tattgttgta tatgtatgtta gttgtgaagg tttagatca tatagagtaa aagtactaga 93120
caaggatgat aagtaaatg tttcaacttt tatatacttta atagaaagta tgtatgatat 93180
actactatat gaatatgata agtacctaaa agacaaagaa catcaaaatg aaatttactc 93240
tatgtttgat aaacaattag atactattta agaagaggtt tttctctagg gaaagtagt 93300
caaaggtaaa aatagggctt gaaccgcat tctatggttg acatttaggt aaaattagat 93360
aggtttccc tagaagaaaa gttttaaaagg taaaaaggtg ttggttact atgtcaaaat 93420
tagctaagtt ttgtaggaag tatgagaag ttactggcat aatggagaat attacagatt 93480
atgagatgta cttaggtagg ggttataaag taaggtgtag agtaggtaat agccttattt 93540
atgttcttgt atataaagac aaccatatca ttgctaggtt tgaggaagcg gataatatag 93600
tatttccttt gagtgatacg cttgaggtgg ggacaattaa agacttagag gagctagaag 93660
agttgtataa taatatctat acattattag ggtatttata tacagaatat gaaaataaag 93720
```

```
ttatgtatga gtatgggagg ttagaataat ggatattacg gtaagtgagt tatttgagta   93780
tatattaggt cattatacct ttagtagtgg ggattggtat acttatgact taggtgaagg   93840
ttactgtatt aaatttaatg atgggtattg taggagcatg cattttatca aaggtactag   93900
agtagtaaaa gaggttctta tcgatgataa acagctcttt aaagggttta gtagtattta   93960
tgattttatt gattactgtg aggaagcttt agatgaaaag tgcagaaaag aaaaagagcg   94020
cctaaaggaa attcgtacgt tcttaggtaa gtagagtatt atttattatg tataaccgct   94080
tctatatgaa actttatacc tatagttatt ataccatag ttattatacc tatagttatt   94140
atacctatag ttattatacc tatagttatt ataactacag gtatttttt atatttctta   94200
cataaatgtg ttgattttat gtgtgttaag gtttatctt aatatataat taaaggagtg   94260
aagttaatat ggatatgaat aaagaagtat tagaacgttt agatagttta ggtgtaagt   94320
tagagcaagc aggtacacat ggttatgaat ccttaattaa atacacagtt actcaaggta   94380
ttatagattt atgttcaata agtatattat tatctataac agctatctta tgggtggctt   94440
tgtataagtc agataaaaag tctaatgaag gtcatagtac cttattattt gagtttgttt   94500
gtaagaatga aaaagagctt tctgctgcag gatgcatagt aattatattt gctgttacta   94560
tgtctattat ttcttttta gtgctattaa taggcttgcc tattgctatt caagagattt   94620
ttaatccaga aggatatttg attaagagta cgatagataa tttaaaataa ttgtaaaaat   94680
aaggaggaaa atataatgtt agaacaagct aaggtataa ctacagatta tattatggaa   94740
tttattgatg aacatgagca ttattcctat gaagacttac acaagttagc agggagtta   94800
gtgttaaaag atacacatga cacaaacct attgttatta atgatggaga tggttactca   94860
ggtactatta tatctaaatt taaatcaaag gtagagggtg ttccagatat cactgttagt   94920
gattttacg gttcatgttc tttctgtgat actttatcta atatctatga aggtagtgat   94980
gaacttgaa taattagaga tttagctact atggtactac atcaattca atctatgaa   95040
gagcaagtag aataatgtat aagggagtgg tatagtgttt agtaagaaa agaaattaa   95100
agagtataag aaacaaggtt actcctgttga gtatataagga agtatttag gtttatttgg   95160
tattggcgat gttttatact atgtagaaac taataagaaa tacttaaagt caattagcgt   95220
aggtaaagat gacaaccaat atgtatatga cttttaatggt tgaatact atcaagaca   95280
taagttaaat atcaaagaag aagaactaat gtctaaagct attgctcagt taagtatcaa   95340
aggtttaaag aattttaatg gagttaagca taaatgggat gtaggtttct tagagcaatc   95400
ttttaatgta catcgtaaag ctattgatat ggttaaact aaactaagtt ttgatgaagc   95460
gggtaaccta tattatgaat tagaattagg ttggattaat atttataaag agtatacagg   95520
tgtaaaagac tttcttaata cagtagataa ctatctcaac ttcttctata aagatatagt   95580
cactagtggt cttgaattaa aacaagtact atataatact tttattggag gagattatga   95640
gtttgtagta tctccatata aggttgaagt atatagagaa gctgagttaa ttgatgtaag   95700
agattttaat tatagcttct gggaatatgg gtacggcact aatgtacata aaccttaca   95760
aacaattaag tattatctgg aatacctat gaatgaagt gacattaatt aagtataggt   95820
gtatgataga tatataaaga ttaaggaga atagataatg agtagtaaca aaaaatagca   95880
gaaagagtta ttgagaaatt tttagatgag actaataaaag gtgtagattt tactaatcaa   95940
gatgaattta accgcttctt agataataca gaagacttgt atgaagtatc tgaaactcaa   96000
agagataaga ttattaaatg ttacaaaac attgtagtta ctgtattat ggataaggat   96060
aaataatag gagaaatac aatgaaaaca ataaaaagaa aaatagtaca agaaggtatg   96120
aacaaagaag aaactatgag ggaagacgat tctgttgtaa tcaaaaaat tcaaaaaata   96180
acaggtgggg ctattcttcc tttatccaat ggcaaggaat atgtagtagt gtttagtaaa   96240
gtagaccata ctaaattaat tgtatttaat gtggaaaata atcaaatcta tttaagtgac   96300
tctggttcg atagtgaact gtcttatgta gacagtaaaa gcaaccctat taccttagaa   96360
acagttaggt taatcactaa tttattgtaa ttattatttt gaagcgggta acagtccgct   96420
tctttttta aataagtagt tgacaagtat attagtatgg tttatactta gtatataaag   96480
attaaaggag ttggttatta tgaaaacaat tacacaagaa tattagata aagtattaaa   96540
agaacataaa ttatggctga acagtgatgg cgtagaagga actagagcaa atttaagtta   96600
cactatgttg agacatgtta atctaagagg cgctgattta agaagagcta ttctccgtaa   96660
agctgactta agtcatgctt acttaacagg ggctatctta agagaagttg atttggatgg   96720
tgctatttta agtcatattg atttaagtaa cgcggaataa acacacgcca gcttaaaata   96780
tgttgatttta agatacgctg atttaagcta tgctatttta tcagctacag attttaagtag   96840
tgctgatttg agatttttctt atttagataa tgctatttta aagttactaa atctaagccg   96900
agcaagtata acaggagtta taggactgaa tatttactct atagataata ttggaacttt   96960
taatgttaag gtaacttata ttcctagttt agacactgta tttgcaggat gttggaatgg   97020
aaatttagaa gcgtttttag aaaaaggttt agaaatgaat gaaggaaaag aagcggacaa   97080
gattaaaaaa gcatatgaat ttttaaagt gtgtacagat taaagattat taggctttta   97140
aagattaagt tattttatag gataaatact actagaaaat gattaccgtt taatacagaa   97200
tttaacgta cctagtttag aggtcttaaa tataaaggag ggtattagaa tggctaaagt   97260
tgtaagtaga ggatatagtt ttgaagaaca agaagtaagt atgaattata accaagggca   97320
atggattatt tacgcaagta ggaaacctta tattaccgat attatgaaaa aatatccgga   97380
taaggtagaa gtactagagc aactagataa tggtacaccct gtactcgtta agttatatt   97440
agatgaggat ttaattacgt taagaaaacc tgtaagtaac gagcgtaaag aacaaatgaa   97500
aaagattgct aaagaaagat ttggtaaata attaaatata ctagtgaaga agaatctgac   97560
attaataaac accaacgtga taccgtaaca cttgtaggaa ctagactaat gttacaagat   97620
atctagtatg gttatggtct tattgagaat gagtatgctt taactaaact agttaaagaa   97680
gataaacagt atttacaata tcatatcgaa gaagtagaag cggtattaaa ccgcttcttt   97740
tttatacatt atttcacttc tgagtaaata tactgtattt aatcttggct aataattgta   97800
tatcaatttg agcatagtat gcccgtttca acatagttaa tctaataatt tataattta   97860
tctgttagtt atgtataaat atttgttatt acttattat atatttgtat ttcgtactaa   97920
ccgtacgact tatctttta aaagataag aacaaaacag cgtataccc gttgttttac   97980
gctacgctac aacaaggtaa cgcctgtaat aagttattcg tattaaaata ctaacaacta   98040
attacttgtt gtttagatta taacatatgt ttatgagaat tagatgagaa tttagttaca   98100
acatattatta aatatatta cagttatgtt acaagttgca agtatgttt tgttactaca   98160
atatattgaa tatgaaaact ttagaccttt tctgcagaca agtaattatt acaggtatgt   98220
atgataaaag gtaagtatca gggattaaat taaggttgga ttaatgaagc ggataagtta   98280
gatactgatt aaaataaaat actttacatt acctaaaact tatgatacac ttaggatagg   98340
ataaaggagg aatatcaatg aatattcaag aagcaaagga taaattatac gatgaattac   98400
tttatacagt aagtctttgt gagggaacag aagaagattt actagaactt attgagaatt   98460
```

```
tattttatat ttacaatgac gagcctgcat ttttaagtaa agacggtatg caatatacta    98520
ttaaagagtt tatggagaga agaaaaacat tagaacctat cttaactgaa ttaggtatag    98580
ggtacgcaat gatagaatat aacacacata cagaatacga gttagttact cattcagtac    98640
ttaaagttat acagtatgat gtagataact atactgtaat tattgatact aatagtgata    98700
agaatattaa gttatcagat ttaacattag aagctgttaa ggacattttg aatcaaatta    98760
agtagctagg gttgttttta ccctagcttt tttatatgct tgtattgcct atttaactac    98820
attatataag caagtaagta ttataggata aatactacct aaaaagtatt accgttgaat    98880
atagacctat aagattaagg ctctcttact gttataaaca tcataagtat aaatctatga    98940
ttttcctaag tagcaggcgc tgttttttact aaaaaatgta aatatcgtaa gtatcaggcg    99000
ctgttttccc tttatattaa ccgcttcaaa caacataaaa aaagattagg ttaatagcct    99060
aatctataac tctttatat aattcttgta attcttttc taactttttt attgtttcta       99120
tatcattatt tcttttaata gactgacata taaatgcaat acctttaatc aaatttaaatg   99180
gttagtttta cactgcattg tatacaatta aatcgattga ttataataat taatttaagc    99240
tgtactttct agtttcttct atataatggt aagaaaacat ttatttaaaa aactttcgta    99300
taacctattg acattaaata caagatactg taatataata agcgtagtaa acaaaccgaa    99360
aggaattgat aggatatgaa cgtaaataaa attggggata tacttgtaga acttttagac    99420
atggacggtt acaaaagcaa taactactat agaaatgact taaaatactc tacacattat    99480
caagttaaat atttagctta cattgatgat agctatgaaa cattagaact atttaaagaa    99540
acgaaagtct ttagcgtatc acattcaaat aggttaccaa ttaacattaa tattaaggta    99600
gtaaacaaac acttatttat agagctagat aatacgttat acctagtgaa cgagaatgca    99660
gaaattatta agaaaaaaa gttaaaataa tagttgacac tagaattaat atagtgtaat      99720
ataataggtg taatacaaat aaactaaaag gattgattaa ctatgaaaac attaattact    99780
aatagtaagc cgtataagaa ctacggctat gaaatggaac aattcgagag agaaaacaac    99840
gttattatca cacgagcata ccacgaacca acaaaacaag gctatgacct tgtagtacat    99900
tatacgagg ttaaataata tgaaatacgt agactacatt agaggcacgt acaacagaat      99960
taaagcacaa ggatatatta cgaataattg tagtttgtgg tctgatatgg atgaatgta    100020
cgacttatat tactatatca ataaagcttg ttttaactta tacggtcaag gcgtacaagc   100080
aataacaaca acgccaaaat gtgttaaaat gatacttaat gacggtcaaa caaagtttgt   100140
taaaaaaggt taaaataatg tttaacatta cacttaagat actgtaatat aatagatgta   100200
gtaaaaaac aaatcaaaaa gggattgata cacatgatta aatttaaata taacggcaag     100260
aaataccgtt caacacaaaa gacagatgct attgtaacta ttataggtgg tacagcagta   100320
atcacattga tagactggtt tattagatta caagataata ttaatatatt tattaaataa   100380
gggttaacca cccttatttt tttttgtgct tatataaccg cttcacatta gtgtaaaact   100440
tccttatttt ctttgctaaa atactttaca aatatgagct tatactgtaa tatataaagt   100500
gtagtaaaga acacgacaga gaacactaaa aaaacttaaa aaagtttaa aaaagtgttg      100560
acactaacat taatatagtg taatataata gatgtagtaa acaaaaacaa acagaaaagg   100620
aattgattaa ttatgaaaaa tacagtaaaa gaaatggcaa acggaaacac taaacttgaa   100680
agattattag ttttagcaat tgaggaagcg gttatgacag agcttgttga atatgatgca   100740
ttagataaat acaaccactt agaacagcag ttattaaaca atgaaacatt aacacaagca   100800
gaacgtaaac catctaacat tgactatagc acttacgagg gggctatatt agcacaagac   100860
aaaagcagaac actttactaa cgttatctta aaccacatga acaagaaca atttgaacaa    100920
atgattatgg atattgaaac actagaattt aatgcagaac aaatgctatt ctaaggagac   100980
attacacatg aacttatctg agaaagaact tatagatata attggacaacg ttaatagctt   101040
cactggtatt gatgaagcta ttaacgaaat ggaaaacaaa caacaacta aaggcagtga     101100
caaagacgca ggagcaatta agaaatataa tagtttagat gagttaagac aagactatga   101160
cataacaaca ttagcaccag atgtaataaa agaattactg aataatcatt agtgtaaaac   101220
ttcccaaaat aattaactaa aactattgca attaactgta gatttgatat aatgtaatta   101280
aggaaaaaca aataaaagaa aaaggattga taaactatga aattacttaa ccaaatgaaa   101340
caaacagcag aacttgaagg aattgaattt gacttattat taacagctat ctatgaaaca   101400
atagaggtag aagctgttga acatgattta ctatgtaaat acattcatat tgtaaaccaa   101460
ttaaaagaga ataaagacat aacaccatta gaatatatc cttctaacct agactttaca    101520
gacaatacaa caataagact agttgataat aaagtgtttg agttagcaga ttatataatt   101580
gaacatatga gtgttaaaga gtttagtaaa cacattaaag actatgaaca aattaaagca   101640
aaagctatag aaatgatgta aaacaaattg aaagggaata aactcccttt cttttttta     101700
ttattaatta ggattgtata caataggtta atataaatat attatacggg ggcaggggta   101760
aaatgccact aaagtgggtg ggtcttacag ggctataggg ctacctaagg aacctaatta   101820
gtgagtaata ttatataact tattattaaa agtcaacatt aaccattact ttattaaact   101880
atgtcaacat tactaataac taattgtatt cattttacaa taaagttagt aatatgtttc   101940
cttactctct tacacttaat tagagtatta gtatattacg acatataagt agttagtat    102000
ataggagcct ttccttatat atagtttct atggtattct atggtattct ttagtatacc     102060
atttttaataa ctatttatgt aagataccat cagttagtat gggatattac ataacttatt  102120
attaaaagtc aacattataa agtacagtgt actaaaaagt caacatagta ttattactat   102180
taaagtcaac ataataggat ttccattatt gttcttattg tcctacctat ccctattgaa   102240
ttactagcag tagtgttact ctattttctta caatataaaa aacacctata gtaattaata   102300
ggtgtttaat gtgaggtatc atatccatac tcaaacaatt ctttatctac ttgttcgaaa   102360
ccttttcttt tatcttttat aatatagtta ccgcgtacaa ctttctcaat acctgaaggt   102420
gttttaataa acaggctatt gtctccttgt ttatctactg ctctaaatgt ttgaccttct   102480
gtccactgat taataacatg cttattatat cctgtatatt gaatatactc tactacgtct   102540
tccatatcga ttaagactt tagcatatac tctcttactt tagcataatc atctgtagtg     102600
gtatctaagt ctaatggttt taattttgct atattgctta tattacgttc tcttacaggt   102660
gttttttgaat attctaccat taaatctagt aattcttcac ttgcacctaa actcctaaaa   102720
gaatattgtt cgttgagaaa cacccaagca ataggttgtt ggttttcttt tttaataagt   102780
attttttctt ttctcttggt agtattttta tttgctaagg taacagtata ttctaactgt   102840
tttacattaa caataaattc atttgtatac ataggtggta cttcctttgt ttaattatta   102900
tccactatgt ctatttcatg gattgtaatc atgtcatctc tatactcatc tatatgctta   102960
aggtaactga cgccatcatg ttttctagac attccttgta attctctata tccttcggct   103020
ttaatatctt taacaagctg ttcctttgtta gtgtatactt tatcttctct atgagtag      103080
ctatcctcat aaggctcaca atagtcatgt tctacttgat atagtttcat attattttta   103140
ctcctttta attttatctt ctaattctgg taatacattt tttgaaatat atttatttaa    103200
```

```
gtcatttatt gttttaactc tataagtacg catgtttctg ttactaatat ataaattata   103260
taaatcctct accttacttt caatataata gaaaggatag cttatacaac tcattaatag   103320
agatatacta tacagtatat tttcaggtaa ttctctagta aattttttaa ttttatttac   103380
cctttttctt cttcttaatt ttttatatag cttttcttagg ttgtgctcat gttttttaat   103440
tacaagtagt tgattttggt taagtaagct atcgtcgttt ttgtttatat agtttaatat   103500
tcctttatat aaagttagta attctctatc atccatatta atattatctc cttatgttct   103560
acatttaacc agactaaagt ataaatgact tgaggctcta tatctcattt attctatgtc   103620
cttcttttac tgattggttc catgatttta gttttttcaaa gaacttggag tctactttac   103680
cttctaatttt ttggttagta taatcatcat agaaactaaa tgttccgcct ttaaaaaagc   103740
aataatacgt gtctgtcgta tagttaatat taatgtactc tatatagtct tttgttactt   103800
ctggtttgtc ataacgtaag actggtattt cttgacgtaa caatttatt ccttctttac    103860
ttaaacctgt atatctttt agcttgaaac cgaacctcaa ccaaaagtct atttcattga    103920
ggttaaaagg ttcatttact tttttaccta aaatactatg cataaatagc atataaacaa    103980
gttctatata ctctatacat gttgttaaaa aatgttgttt gtcttcaaag tgatggtaag    104040
ccaacaaata caaaaacgta aaagggaaaa gaacaatgga cattaaaaaa tataaaaatg    104100
attttaatct tgtgttcatt actcagacac cttctctaca tcatatagta ttgggtatag    104160
attgaagata tgaactctat atccaatagt tttaactttt actttatctc ctactttaa    104220
tctagcttgt atgtctgcgc tatcaaactt tcttttgaag aataagtctg agttttcaat    104280
gacttgtttg ttgtcaaata caatatagaa cttgtcttct ttatcttgtc ttttgttata    104340
tttatctgta attgttcctt ggtgcgtttc tttgtgttga tagctagcca ctgtatagat    104400
aggtaaagtg ataacaagta gcaatacggt tataccgaat aatgacagta ttccaaaaat    104460
aaagatatcg aaccaattca tatttttaag tttttaatc attgttacag caatctccca    104520
tcttcccaaa ttagtcttaa cttacttttga tgcataatat agaagcgctc agatttacta    104580
gatttaactt catttattga catattatga tgagtgagta tattttcgtt atctagatac    104640
tcgtatagct tagtaaatac catgtcttcg gtatagtcaa taactgatag ctctttgatt    104700
aaaacatggt cttccttata atcatttata ttttttgaat acccatatcc ccttactgca    104760
tcccatacct ttttcgtaccc ttggtctaaa agtgagttta ctacttgttc tttatcccta   104820
tagacttttg tttctgtata tgtttcttga tattcacgag gttacaatt atcatgttct    104880
agttgataca gtttcatagc taccccatcc tttccaataa gtatggattt tcatatatat   104940
ttcctttaac ttgtaactct aaagtatctg tgtatggttt tatggagaaa tcactaagta   105000
aagtaagttt acaccctgca tacctcacta tagaaaaa tccccttaccc ttcttaatta     105060
aacctaggtc actataatta cctttggtat ttagtatttc tataatatct ccttcatata   105120
tatcattacc gtttacatct ttaacttctg tgctttgcat aatttcaagg ttttctccta   105180
aataaccttc acaagcaaat agatgtgaat atactgtgta atctgcaaaa tcaaatctat   105240
caatattaaa cattctttgt gattcttcat cccatgctct aaatttcaac atcatactac   105300
ctccactttt tcgatttcta tgcttacagt tttgaatagg gcttttttac gagtcagttt   105360
taatgccata ttcttagctt cttcctcatt tatactttgc acaaaataat gctttttat    105420
tttgtaatca catttagata ctaagaactt gatacaaaga cttactttat aggtttgcat   105480
cattctacca actccccatc tttccaaatc aatgtcatcg tcatgtcatc gtttaagata   105540
tagaatgctt tggtagggaa agacgcgttc tctaaacgtt cttttgatact ggtattgtgt   105600
gcagcgctga catataggct ctttctcgaa actcatatac ttcaaacaac ctatcaaact   105660
tagtatcttc tgtgatttcc tcttcaactt tgacttcgaa aagagtatcg atagaaataa   105720
aacctcctag agtaaaaact ttatttgtat cttttttgaaa acataccgct tcataacttt   105780
cacctgttgt acaatatttt ttgccttgtg atagctctgg attttctcta gcccatttaa   105840
ttaactcgtc taatggcatt tctttttttag ttttgatttt catttccata tctcctaatt   105900
atttaattttt tctatcattt tcacaatctt ttttgattct ctaatgtcag ctttctcaca   105960
gttttttaat atgaaattaa ttttgttttt tacaacatta acgtaatgt ccacttcttt    106020
ttctgttggc tcgtaggga aaagcaaccc tacaactatc tgaatttgat tttatttag    106080
tgagtaaaca ctaatgttac atttctcatt aaagtcaata tgtggttac ttgaattaaa    106140
tacctcatct acaattgtat ttaattcttg gataggttta aaataatgtt gttttctttg   106200
tatcattacc tgtgacatta gtttatatag tttctgttct ttatcaagca tttctttttat   106260
aagtcttttta acttcccccta tctttatagt attacctcgt gcatcataat tattttttaat   106320
atactcagct tcttctatgt tagtagtata tccctattact tctgaggtgg ttcctcatc    106380
gtagtaacag tcctcttcta catatatagc atatatctta ttcatatcta tcaaaccttt   106440
cttaagtta aattaactat aacatataag cattagggtg tcaactacta atatacactt    106500
tttacagtaa acaaaaaaaa gaacctttt acaggttctt tactaggtta ttaatttttt    106560
aaatcttgat ttccttttat tagcttctta tcatcaatag gatgaccatt gtataaaatat   106620
tttacttcca tatatacatg attatccgta gccgtaaggg catctaggat atccggattt   106680
gtgttaattg catttgtatc aggaaacgaa aattttcttt tatcagactg gattgtatct   106740
acatgaaatt tttcttgttt tggtaaagag taattaaggt cttctaaatt ttgtaggaat   106800
ttagtaagag aaaagggttt gaactttcct tgtaaattat tatctatata atcatttaat   106860
agtcttgtca tttcctcttt atttaagtc attgtttcat aatcgttaac atcataaaaa    106920
acaacaatat taggttgctc aatacttgta tctccatctt tgtacttagc aatgtaaatag   106980
cctatttcac cttcatgagc taaataatct tctttctagca tattaaatac ttctctagca   107040
ataggttttg tatatagttc ttcccattca tttgtttctg ttgtaaaa atgtggtaat    107100
aagtttgcca ttatagtttta tccttttctta ttccgattta agccatattt tgttagtgtc   107160
ttaggtggt tcattgctga ttgtgtaccc gtcggtaccc atatctaatg tgttaacaat    107220
gacaggctga gctacagctt cttttttcact ctctaatgtt ttgaaactag gcacatcgtt   107280
tttattagat tcttgtccat cgactaacca agagacttta agtcacctt tattataagt    107340
agtattaggt tttaaaatctg ttaatgttac ttttactgtg ctacctgtaa cttcatcaga   107400
agttaaaata agctgttcct cttttgttgta gacctttaat ttttagtca taatgttatc   107460
ccttctgtt gtgtaataca ctaataatat agcatataaa aaacaggtaa gggctttcaa    107520
aacctttacc tgcttattct ttactgataa tcataccaat caagaaaatc atctgaacag   107580
cttaactcta tagttatatc attttataagt tcagtagctt catctttact taatgactct   107640
atatcaaaag taaactcatc atataaacaa tctatatgct tataaataaa atattttgt    107700
ttttccgtag ctttgtttaa ctcattgctt tttttactta taaattgact aaagtttatca   107760
ctcatttaaa tcttcctctt taataaaggt accattaact gttttttcctt tacgaccttt   107820
aatttcaccg taagcaaact ctaaacactc ttgtaatgac atgtcgtgtt gctgagctaa   107880
aataattaaa gtaactacag tgtcccccaat accatctta agagcttcta ggttaccacg    107940
```

```
tgataatgcc gatgctactt cacctgcttc ttcgtagaat ttaagagctt gtctatcagg    108000
gttgttattg ttcaatcctt tatctttact ccattcctct acttgactaa ttaaaccttc    108060
tagcgtgcgg tcttctgttt caccttcatt aaagttaggt ttttcatcat ttggtacatg    108120
ttcttcttgt tctctatcct ctattgtaat aaataaagtg tctatttctt tttcgtactt    108180
atttctctgc atataattat actgcccata ctcaggataa ggtacatata cagtatcgtc    108240
tgtaccatcc tcataattca aacaaacaca aacaatatct ttgccactta atctatcata    108300
taatgtcatg ttgtagggct catctaagaa accatgaaac tcttcaaagt attcatcctt    108360
cataccactt acctcaatag aaacttttt tgctgactta cttgtatcta cttcactatt     108420
tccatatatc atagttttt cttcactaat accttctagt atcaactcta cattttctgg     108480
ttctaacacc gcactatcta agttttcaaa aacaatttca atattttaa ttttttagt      108540
cattaataat cattccttt tttagtata tagtaaatat aacacataag taaatagaag      108600
tcaataaaaa aaaacaccta ctttaaaaat aggtaggtgt aagatatttt agtaggtatc    108660
ttgtggaaaa aaatcctgag cagggactcg aaccctcga ctaggtagct acaactagcc     108720
aatgccatta ctcaggattg ctagtaacgc taaatagggt cataacgtta ccgtagacct    108780
tttctacgat ggtagatagg tagaatataa tgatttcaca gtacccatat ggttaggctg    108840
ttactctcat tataaggtta aaaaatgcta actgtgtttc gcattgttaa gaggcgttag    108900
ttaactacta taataatata gcatatattt tattgtttgt caagttcttt attccattta    108960
ctttttctt ttagtaatcc ttttttaatt aattcttcac taatattt atactcttta       109020
ttttctttgt agaacacttt agctaaatat ctaccaaaag aatcatcttt gtatgtttga    109080
attaaaacat cttttccttc taacatagtt gttgtaaatt ctttagcttc ttggtaatta    109140
ttttgtttct tttctggtgt gtcgacacct agtaatctta ttctttgttc agaatatgtt    109200
ctcattccgt ggtcaatagt tacatgtata gtatccccat ccactacttt gtccacgtgt    109260
gctttaaata aatataaatt gtcttctatc atcattaaat cccctttta ctaatttaaa     109320
attatccaat cagtattgct tgatgtacct ttagctacat atacagatga gcctattata    109380
gcaatttgac ctttgtataa aggtatatta ctaatgcttt cagttacacc tatttggctt    109440
atgacttcaa aattagcttt tgtggatata aattcccaca gtatagagcc atctgatata    109500
acaccgttat tatgagtagg ttgtgttcca ccacttgtac ctgaagctac tgctttatat    109560
acataattcc cattataaac aatttgaccct tgtgtataat ccgtattaga tgtccacttc   109620
atattagtag caactccatc gctagtacat ctccatttct caggactacc tgatgttagg    109680
gttctactag tattaacaac aatatctccc aatctccaac ttcctgtagt tggtattgca    109740
gtaccgttca gtactttagg taaattataa gctatattat ccttacttat aacattaaat    109800
gcattactag aaatacttaa gttttattc atattgttat ttaatacgaa tagattacta    109860
caagaacctt gaacacttaa tgaatcatta cctttatctg tttttatatc attattagta    109920
attgtactat ccataacaaa atttaagaac atagctttat ccaaagcagt atttgtactt    109980
cttaatgtat tatttttaaa gttaatttct gacacaggtt tactagttgt tcctgaaaca    110040
taaataatac ttgtttttaa acttgttgta tcttgtttta atacattatt ttgtatatct    110100
atgttattaa ctcctggata aaggtacaac tcgtaaccct cattacctga tacattattg    110160
ttactaataa ttccttact acctcctgta atagcaatac cattagatgg tttattactt    110220
aactctcctt tattactatt accataaatt acgttattag taattgtata attagtacct    110280
gatatactca gtcctgagta cttattgttt gtatgtatgt tattacttat aataacatttt   110340
tctgttcctg attcaaaacc gcttgaacca ttccctgtag atacattatt aacatagtaa    110400
ccatttttag tgccacccat aaagttaaaa ccattctcta aacattgtgt agctgagcaa    110460
ctatctatag taatgttgtc tgagtaatca taaacaccat ctaccgcttg catagtgtta    110520
actgcattta caacgttacc cataatatta taaccatga cattatatgc tttacagtttt    110580
ctacttcctt taaatgctat tccaatagaa cgaggtgacg catatctaaa ttcaccttta    110640
ccatcccatt ccccttaa tgttaatcct tctacaagaa tgttatcaca gttgataaat      110700
gagaatcctg taaacatatc tctaccacta gaagaaacat catctataga gtctagatag    110760
tttttagtga ttcctgacat aataaatgta ggattacctt caccttaat gtatatatta     110820
cttcctgtta cttttacacg tgatgggttt tgtacagtag gtgttttagt tttgaataaa    110880
tagtcctctg ttccttagg tactataaga gttccaccct tagtacttat taaataatct     110940
aaagctcttt ggaatctagg gtaatcatta tcttcatcat taattcttgg gtaatcttt     111000
atattaatta ttactttact cttagaatta gtatctttac ctagttcttt ccaatcatta    111060
cctttagta cccaaccata tgcttgtgtt gtaccattgt tgtataccttt tcatcatat     111120
ttaaaatctt caacactaga aggtttaaca tgagaataaa aaacatcagt tttattctta    111180
ctactatcgt ttgaagactt aataatatta gatggattag ttgaagctac aagtaaacct    111240
tgcatagttc cagatattaa aataacgata gacttaacat cttcactatt aacagtaaaa    111300
gtatcttttt gggtgttatt gaaagtgaac gctttatatt tatcgttata ataaccatcc    111360
agtaatattg tatcataatt attagatatt ttgtctaata tattaccgtc tttatcaaaa    111420
catttaataa atataccact agaattacct ataaatgata acttgttaat aattaactcg    111480
tcaccaacac taacattatt aacatataaa gccataggt acgagccgt aaaggtaagt      111540
aatcctttat tatctactaa actaggtgta gtactgtagt cataagatac ttcatctgtt    111600
agagaagttg actgtaatgg ttttctaaat acattttga ctgtgtgata gttacctcct     111660
aatcttctat agtctttgct aaaatcatta ttttataca ataatgttgt tttgtattcg     111720
tctactattt tagcaatact ccttctaggt attttagcag tataatt tgtaaacgtt       111780
agttatgtc cattacctaa aacaaattca ggaataaact taatatcttt actatgtgtt     111840
acataagatt ttgtcatatc ttgagttct aaatcaacaa ccgcaaaagt agctttgtta    111900
ttaaattcaa atctgtaatt cttaaatata atcctactg ctttcttaag ataaaccata    111960
acataattt cagatgttgt ggaagcagtt tcaaatttaa gtgaatcgaa tacattgcta    112020
tttcctccat aggtattacc attttgtaga gtttgtttga tgttatatga tgtgttaggg   112080
tgtttattaa actcagtgcc actatatgaa aaagctgatt tatagaagta attactattc    112140
atccaagatt gctcaccatt agaatctata ccatctgtat ttaattctat atgtgtttca    112200
ttattaataa agaaattaat aatagtatta ttaaaccaat gacctctacc accagtagct    112260
ttatgtttat tacctactgt aaaaccaata atttcattaa tattagtatt aacatttcta    112320
cagttaacta attctagtcc tatatagttt tgactcttaa aaccatga gcctccacca     112380
taagttggat aagaactatc atcataaata cctttaattg taacattaga atatgataaa    112440
ctatctagtt taatagctgg tttatcctta ctaccattat aaacaatctt agcatcagat    112500
acaatattaa tattcttatc tattatcaaa gtatcatcta ttttaatagg tgattcacta    112560
gaaggaatgt gtagggtatt accttcactt gtatcttaa tagcacgtct taaccttga     112620
acatccgaag tatcatcttt ttgctttata tactcgttag agtatacata aggactttta    112680
```

```
cctgttttaa gccaatctgt agctgaacct gtaaaaccgt tatttacagc tacttcataa   112740
gcacttaaac cttgcttacc ttgttcccct ttctcccctt tttctcctttt aatagactta  112800
acccattctt cttcagaacc gacaaaacca ttatctactg ctacatcata agcagattta   112860
gcatttacaa gtatatgatc tttaaaatat aatgttattt ctttgaatga tgattctagg   112920
gttgtaaaac caggaactac tacttttatcg gtttcatatt tttcagcttc ccatgataca  112980
tagaactcac cttgagggta atgtgtgtga ggagctaagt taggtatgat tacagaccct  113040
acttcttcat gtaactctac attgtaacct attgccaata tattaccgta tttatcatat   113100
gcttttaaat gaggcattga aaatctcctt tgctattagt caatgttaat atatcataaa   113160
acacaaaaaa gggcaaattg cccctttagtt acagatatca tttagatgaa tatggtcttg  113220
tactgaatag tctacaatga catgtgtatg ctttttctt tttgttaaca ctttatatgt    113280
gataaagaat gatacaatag ttaaacatat atttaatttt ttcataaaat ttctcctta    113340
aagaaagtat ttaccatctc agtagttaat tctttgcttt taaagataca agattctgta   113400
ttgttattca atatttctaa catatttgc atactacttg cttttgtaa atccgttaag     113460
tctataacaa ctgttattc tgcgttatct attagaatat tacctatgta ataatttta    113520
actccgttct ccgtagcatg agaggtgaca ttatgattta aaacaactat accttttgat   113580
ggtaagtaat ctgaaaagta taggtaacaa aagtatttat gtatcttttt tttattctct   113640
tccattacta ttaccatatt ctatgaagtt taacaacctt tcggtatagg ttttaatttt   113700
ctctacttct tttctttcat cgtctttttct tcctaatctt gttgtatatt taacaatatt  113760
aaatagcatg cagtctataa agccaataat gtagaaaatat tcttctaaaa atgatataac  113820
atctttttg cctttataat ggtttggtgt attagtggta gaattgacat tatagtataa    113880
ctctagtgt tctacatttc tcataagctt tttagcataa tataatgtgt catctaaaga    113940
atgtgtcaca tctaaagatg attcaataat gtttatcttt agttctttta attctgttgc   114000
ctctttgtta cttccaattt gtgagtcaat aaattctcta gtatccatat tggtgtcctt   114060
tcgtatctaa aataaaaacc ctatctgaaa tatagatagg gaaaaggaaa gatattatgg   114120
aagtgtacta taaagtacac atataatata acagttcctt tgccttttaa tctatatcat   114180
ttattttaac ttcttgtact ttaacataat ctgataaact attaacgacg atattatctt   114240
ctactaattc gtttctatta tttgtaacat catatgagtc tctataaggt gtttgtacta   114300
atgctctaac tgtaatgtct atatctacat attcttact ataccttttcc attactcaac   114360
gtagtttcct ttagcaagct gatacttttt gtgtaattct tcatataatt tctccatatc   114420
tttatatttt cgtacatctt cttcaaaatg acttaaatac tctattaatg tcttaacttc   114480
tttaggttca aaagttataa ctggttttac cattacgcaa catcctcact aaattgttta   114540
tttatatttt taatatcttt tattaattcg tcttttaatt ctttaggtaa ctcatgactt    114600
tttaaagatt gttgttgacc taacgtatat ccatattttg ttatccttac ttctacagta   114660
taccatgatt tttctaaatc gtcaactttt ctagctagta atattaaaca tctgtcattt   114720
ataatattcg aagcataact gccgacacaa tgagatagct gttcaccttc tctttttaat   114780
ttttcagtag tatccgcagg taaaaattta acttttagagc catcgtttaa cttatattct  114840
ttatttgtga tattatttaa tttattatca tattttttgtt gtaactttaa gtcatcgact   114900
tcatctcttaa ctgttaaata ctcatcagta acaaatatcag gctctagttt taaagaatat  114960
ggttttaagt taatactttc tttagttcta tatccaagaa gtactaggtc tgaagcaaag   115020
tctatataat ctctatataa attattaaca gcgtatgaat gtatacgttg tctgtttctg   115080
acatcatagt ttatataatt caccattttt ctaaagtcag aaaatgaaaa gttaagaact   115140
tctttcgtag tacccttaaa agataaagca tttcctattg aatatgaatt agtcaccatt   115200
ataaagtcgt catcgaatag tttgtgtaag ttagactcat tatataaact aggaaattta   115260
tttatgataa ctcgaagtat attaaggtaa ttttcttgct cttctttact aagagtaata   115320
aacttattat atgtttgttt acttaaattt aaagcttcat gtaatttcca tttatttttg   115380
tttggtatta ctagaaactc tttgtgttct ttaaatatat cacaatcttc gttgttataa   115440
acttatcaa tattagacac aactaattt aacagattgt ttaaattatc agtagcattt    115500
tcacctttac taactgtgcg ataaccatca ggtctatcta tcatagagta tacatcaaag   115560
tttttttcat taagtctact tagatttaag taataatcat tattcttag tgtttggatt    115620
attatgttaa aagctaaatt ttcctttcca tatttactta aaataatatt taaaaggaca   115680
ggtaaagtaa tgttatttttt taatttatcc ttattaaaat catcttcata catattaaat  115740
ttaaattctt tatgttgtag tgtatttgat aggtgtaggt atacatttcc attttttatta  115800
ttaaagtcac cgtttactat actccaatct gttgttacta tacttatgtc tttttaaataa  115860
caagtcttaa ttaaaaacgg agtattatta tcttttatag gtgttaattt gttaagcccct  115920
atttttatat ttttttaaaac ttcattgtag tattcgtagt tattatcata agatttacca  115980
aatgcataag ggtcaatatt aataccaaat atactatagt cacccattaa taatacatca   116040
agtatatcat tagttgtagt atttatttgt ctttttaaat ctcttattt ttttgtaagg    116100
tagttattac tgctcttatt ttgcatactg tcaaattgtt ttaattcatt ttcatagttt   116160
gcacggcagt atatcttatt acgatagtgt cttttgttat ataaaggaaa ttcagaccta   116220
tcgtcacttt ctatatactc actatataca gtatttacat ctgtaactgt tttacttaac   116280
tcttgtactt ttttatatgg gtctccctta aacgtagtaa gttttttatt cccacataat   116340
gctataaata aaagcaaatt taaagcacta gaataacaaa aggtattatt aatatctctt   116400
aataattctt tagagccaat atctacaata ttttttattt ttattttaa atatactctt    116460
tcttcaccta taaatatact atttctattt acttttagata atttaagaat ttcttcttca   116520
gttaatcctg tttctttata ttctactgac atgtgtcatc acctcattta ttattatata   116580
agtatggtaa catagttaaa cttaatagtc aacaaaaaag aagaactttt ttacagttct   116640
tctagataag tttcatattt aatttttta gttcttctta cgggtacaat atcgggatta    116700
ctcattaagt cttttgtactt cttagaattt ttaaagttaa tagtattagg cattgctaat   116760
acttcctcta actcatcctgt gtacatagta acttttagata ttatatctat gtcactaatg  116820
tataaattt tagatttact tttaaaaata atctcatcgg tactagttac ttctttatta    116880
tctattaaat ccatatagaa gtcctttcta gtctacataa acaagtatac aatctttgtc   116940
tgataaagac accgaggtca tatcattaag ttcttgtagt tgtttaatag acacatcata   117000
tttcttactt atagtccata aggtatcacc attttctaacc ttaataaga atttattacc   117060
tttttgtatt aagtctttca ttgttatcta cgcctttata ttcataataa gatgcctgta   117120
ggtaacatat cgtaataaga ataaagttag ctacttctgt atatattaca tgtggtgtcg   117180
tatttgttat taacatacta ataattaaac aagctaatgc aatacctata ataagaaata   117240
aatatttgct agttccattt gtactttag ttttataaaa tttatttatt tgggataaat    117300
aagctacgat aatactaata gtagccatta tctgtccata ttcaacactg tagttagcta   117360
ctgaatagcc gatataaata acaattataa acataaccat ttctaaaaga ctaacttctg   117420
```

```
ttgttctaaa taagtatata ataaaacaaa taatccctag taataaaacta atacttactg    117480
atataatttg aaatagggggt gcatgtgtta caaataagct tgttaagcta atacttactg   117540
taacaacaat ataaaaccaa aaatagctat ctacacctt aacattctta tcttttatca    117600
aacctactaa agcaggtata tatcctacag taactaaat agcatatagg atgcttaata    117660
tatgagctaa attagacatt agatgcacct aacttttcta attcccctaa aacttcttcc   117720
catgaaataa caccttttacc gtctgttaaa gataaagcta ctccgtatac gtaagcgtta   117780
aaggaatatg gaactctatc catatcatca tgcatatctg ttgtgttcca tctgatgtca   117840
ctagagtaaa ttaaaacagg tttatttagt attttctcgt taatttcaag ctctttatct   117900
aaaactgttg ctacatctgt taattcacca tttacatcaa ggtaataaat atcatataag   117960
tcgtttagcc tgtcaatagt aatttgtgct tgtcttttca tttgaaaaat ttgacctaac   118020
tcggtgatgg ttcctaaacc tccattaccg ctaataggca aatcaataac ataaatatca   118080
gattcctcaa tagcacacgt gtcgttttct acaattcgtt ctgccaactt atgtgagtct   118140
gtattctttt tatcgttaaa tgattgtgag ctagggtcaa aaactttaat accaacaata   118200
cttttccatct cttcttttg tttgattcta tattctttta acccttgcat caacatatcc   118260
gatgcatgat acacctgaag ttctttcatt aaatttgtca ttctactct ccttttcttt    118320
ttcaaactca tctttttagtg tgatgatatc tttattcagt tcttctgagt cttttcatttt  118380
agcccaataa taaaaatctc taagttcagg gtttcttgtt aaaatatatt gcttaggtct   118440
tacatctctt ctttgtgata aggagtaagc tatatctctc atatattcc agtctttgta    118500
atagtcagac ttatatttaa acataaatcc tttcaaatct tcaaatacat acccttcatg   118560
caatatatta taagagccat tattatcctt ataccattta taaaattctt cccaactagc   118620
aaactccaac tctttttcttt ttagttgtaa tcctacttca tcagcaacat atttcaaata   118680
atcataatct ttcttttca tatttaaagt atttgaaata atatcaagta agaatatatc   118740
gcttttttcta tattttatga tatgtggggtc ttcttcaata tcaactacct cgaacactag   118800
ggtaaaacta tcgtcagcaa tataaatagtt ttcaaggaat gttgctagta tttgtatttg   118860
tctttttggtt aaagttttt ctactaactc tttaaatagt agtgcatatt tatttccatg   118920
tccacttaaa tggggttttag atttacttgc atatataatt ccttcaaacg ggtcatagaa   118980
cattagtcct aaaaatccat tttctttctt atatccagtt aaagggaatt ggatagtgtc   119040
tggcatattc tctaatttgg tttcttctac ttcattgata ttaaagaact tattatatcc   119100
tcttcctagt actgtgtttc tatcttcatc aatataaaga cctctagaac tcactgttaa   119160
ttggttccat ttcttttag aaaaagctct tttgtaaag ttaactgaga acacatctct    119220
atattgttga ttggttttga tggttttatt ttctttctg gctatatcta ggtattgatt   119280
aggagtgagg tctttgtcaa tactatcgtt ccgtctgttt gataaaagga atttagggtc   119340
gtaaatagtg tttttactt catgcttctc aatactgttg tttttattta tcgttatagc   119400
tcttaagcaa ccaccttttt ctacacgacc ttctaaatta actgaattt tagtagtatc   119460
taaaggctct ctatataaat tcctatgtcc atgtatttgt attgtattag aatgttccca   119520
ttggtcatca acattaaaat catatccccc gattccatta ataagctgac ttgttgaaat   119580
cttatttaaa ttatcaagaa cttcaggaag gactccgcca tgattaacaa tgtagtcttg   119640
accttttaaaa ctaaagtaag ccacctgctg taactttcta agaatagact ttactctatt   119700
tgagttatt ccgttctcta tgaaggattt caaggtaggt ataaatcctc ttgcatgaaa   119760
tatttttaaa gcttgtttat aaaaatcttt ttcactaata tctacccaac tataggctaa   119820
acaaatatta tcatagtctt ctttttctaa ctgagtatat ctgcgaaggt gtctttcatg   119880
atttccttct aatagaatga cgttttttaa tttataaata atctcaagat actcaaacat   119940
ttgcttcgat tctaatcctc tatcaaaata atctccgaca aatatgaaga gttcattttg   120000
attatctata atgtaatcag tagggaaaag agaatgaagg gctgtaaaac aagaatggac   120060
atctccaatt acatgaattt tctcatatga atcagtattc atgagatttt tgtcccactt   120120
aatagtattt aacaaatcat ttttatctac ttcttttgca aaacttggga tattctcatg   120180
ttttaaacgc tcatagatat tttcaataac atccacagga acttccttta gttcttgtct   120240
attattatta cgttcaaaaa gagtgtctag ctctgcttct atgttaacca catatactct   120300
atatccgtat tttttttgata acttctcata tttttttaatt agtttagccg tagaatgtgt   120360
agcatctatt acagtaaaact ctccattttc catacgcttt tctaatatgt taaataataa   120420
atcccatacc ttgttgtctt cttcttgtga tattctaagg tttcctttg tatcatatac   120480
aggtgcgctg tattgcgttc taaggatatc agggctaaga gaatatccct ctaatccatt   120540
ttcttttata tacgttgttt tacctgagcc tggagcacct ctcattagta ttagtgtct   120600
catatttcat tctccttgag tgattttata tgttattgct tatacatcat ttttcctttt   120660
cttttatata ctatagcagg acaaaacaaa tcctctccta tcctatataa aaagtctcct   120720
tcttaatatt ccttttcctt attttaatta tcaagtactc ttaagtcact tttaagaaca   120780
tccatgctag aggtatgtct attttatacca tctagatttc catctttaa cttattatct   120840
ttcatgattt ctttttaat ttgttttct gttttttat ttgtcatagt gttttcaata   120900
tcaaaagaca tctcttcaat aataagtgtt ttaataaaat caataaattc cttaattgta   120960
tatctactaa aataatcttt atcctcaaag tacgtagcac aaaaacttt acgtcttgtt   121020
agtacaccta ttgacttatt ggaagtagca atataaacat gatatgtttt tccttttact   121080
tttatttaa atcttgtatt atcaacaaa tggttatagt ctttaaataa gtaattgttc   121140
aaaattagcc ctccttttgcg ttaacccaaa tttatagtat ttattgtag ttttctctcc   121200
gctgtagtaa aggtgtcatt attccaacca ccatcatgat taataaactc taaatcacct   121260
gtcacagtac ataagacatc aaaactaata ttttcttttc tacctttttga aatacctgtg   121320
taaactattt taggtataca actaagggtc tgtaatccta aaccatctat atattctcta   121380
aaagatacat gaggtaataa ataagcactt aattcactac tgatacttct actaaaaataa   121440
atgataatgt ctccaacagg tagttcatcg ttatatagat ctacaatatc atcttcttca   121500
atagtccatg ttgtatgttc tatatctgca ggtgctacat gaacaagttg tttaacttca   121560
ccatgtataa tggactcctt ataggaacct acagcgtttg ctttctctaa atactgtgca   121620
ataaaagtac cgtcatcact aattaaatat ggcgttctat tttgaaaatc tatagattgt   121680
tccatatcta gtttttcgta ggtatccttt aagtactccc taattttatt aacatctttt   121740
gttttaactt tatttgttcc tacccttaact tttaattctg tcattctttt agtctcctta   121800
taagtacttc ctaactgtt ccgagtaatc attaatatc ttactcttg gatactttaa    121860
aatactaaaa gcaataatac ctagagctac aataggtgct aataaaaacca agccccagaa   121920
tgttaatact gtttgtaaga aaaacattac actatctact aaaaaccatg tagctactac   121980
tagtaatgtt gtaactgtaa ataaaaataa cttttcccaa aatccacctt tttgaaactt   122040
ttttgataat ttttttcatca taatatttct ccttatattc caattgcttt ttttgctaat   122100
acatctacat attcattcca tttgttatta tcatgagcct ttacttttat aaaatttata   122160
```

```
tctataaact ttgagtattc ccttagcata ttaatatatg tttttacttaa attgttttta    122220
gttttccacg aaccttcata ccattgaata agtcctatat aatctacatg aataatagcc    122280
tgcttataac ctagttttat agcctcttca ataccataac aacaagctag tatttcacct    122340
gcaacatatt tatacttaat taaactacta ttttcaatag gttactgat ttcttttaca    122400
atgttctcat ttttatctaa aataatagct cctgctccaa caagacctt attataagat    122460
gagctaccat ctgtatatat taatgcagtc ttatgcatat ttatgccctt ctacaaagca    122520
agggaacatc tcacttgtat aaatctcttt gtagtcttgt aatttatag tagagaaatc    122580
aaaaaactta taacaatgtt cttctgcttc gatatagtca tctgcaataa cattaacttc    122640
aaaaccatca actaaaataa cgaacaattt cttaaacatt taaaaaaccc ctttataatt    122700
taataaggta cttaattaaa tcaatttcag tgtacttttc tgagtgttct agctcttcta    122760
atttttcttt tacttcttca agtctgtatg actcttctaa aagttcaaac tgctctaata    122820
atgtgatact atcaaattca ctactattaa tgatgttgtg tatatattct agatgtgtgt    122880
ctttaataat gtttgttaag tcatcaccag tataataatc ctcgatatac gataggtctc    122940
ctaataactc agccgtactt ctaataatac tatatttaga tatattaggg taagattgat    123000
ataaacaatt atctaattta ttacttaaat gctctactac tttttgcatt gtattacctt    123060
tttcttcagt actatatgaa attctaatat tagggttttt agaatcataa tcaactaaag    123120
aactcctatt agtgtttaat aacttatcta aagaagttaa aataatagct ctatcttcta    123180
tattatctaa ggttaagata atatctataa tagtataaaa tgctttgtct cctattgctt    123240
tattaacatc ttgaagttca aaaatattaa tcatatcctc aatctcatga cgctcaacaa    123300
agttaataat agattttgta aatttattca tcaacatcaa cctctcttaaa taattctaca    123360
ctattagtat ttaaagcttt ttctaatttc ataagattag cactcttagg ttttcttta    123420
ccactctccc aataagaaat aagtgagtag tgaactccaa tctccttgtgc taacttcta    123480
actgtatgac cttttttcttc tcttacttttt tttaaattta atactttagt ctcttccata    123540
ataaaccact acctatcttt cttcaatttt taaaatacta tagttatttt tattataagc    123600
atacttattt aaaacgtcaa gcgttttttc tttagcctct actttacctt tagctttcat    123660
attaacatag aaaacattac ttttatttga acgtgtgtgc ttaatatata ctttgtactg    123720
cgtaacctca cttttttaata cattacgttt aaaccatttc ttttaattttt ccatttatta    123780
taaccacctt taaaacttat atatgtattg tagcatatga taaatacatt gtcaacttaa    123840
aaataaaaaa atactaggga aaattcccta gtacattatt tccagttaat acgaccccaa    123900
tactcctctt ttagcatacg ttcccacttg tcagtgatt tacatactgc catatagaag    123960
ttaccagctg acgggtttgt aggatattta aacctaatcc accagtagcc gtctgcttta    124020
ataacttggt caaagtttac atattgacca ctataaataa atgattcagc acctactatt    124080
gaaccccttta aacctggtgt gcgtcttacc ttaatcgttc tatcagcagt aaatttacct    124140
ccccaattcc aagttgtttg tacctcgtct ttgaaattag gttctataaa ccacataggga    124200
aagtcgtaac catgggctct aacggtagct ttctccagc caccgcctcc ttgagcatct    124260
cccaagtcc aacctccacc taaccaatta ttttcaatta ctataatttg gttttggttt    124320
gcacttagta cccatgcgac atgaccataa ccgcacccgt atgaattat aaagataacc    124380
atagtgcctg gtttaggaat gtaggatagt gtattttcta ctactctagc tttatcttt    124440
aacatagctt tattatccca tggaatgtta catgcacttg ctccacctaa agaataacct    124500
gggaagagct tgttaaatcc atagttagct aagtcgtaac attgctgacc ataccaacca    124560
tcaaagtcta ttgctttgcc ttctagactt tttaaaaatc gaacaaattc acttctagtc    124620
atcgatgctt tcaaaagttt tcactcctta tttccaatct attttccaa aatatttttc    124680
tttcttaata cgctcttgtt tatctgttat ctcacataca gcacaataga aataattttt    124740
actagagcct ggttttggat atttaaatcg aatccaccag tagccgtctg ctttaataac    124800
ttggtcaaac tcaacccaat catccttatc gtatagccat gaatctctat ttactaatagt    124860
gcctttaagt cctggagatt ttctaacttt aatagctcta tctggataaa aagtacccttt    124920
ccagctccac atagtttag tagattgtgt ttttactcta ggctcagcat tacctgattt    124980
ctttacatct actgacttaa taactttctt gtaatactta gctacttcct tatctaagtt    125040
actagtgttt ctacctaatc cacatgcttc taataagtta cctgggtctt gtttgtcgtt    125100
ttggatgtct tggtgacctg gcatatttgt tttgtaatca acaccccagt attcagctaa    125160
ataagctaag acacgagctc cattgtctaa tgattttta gaacgttctt tatcactaaa    125220
gtaacaaatt tctacaccaa tagcaccatc attagcgtta attccgtacc ataggtcatc    125280
cataggagcg ttatacaaca catgccaagc ttttctgta gtaggaacac atatgatagc    125340
ttcttttatca tctacaaaga tatgtgcgga tgcagtagaa gcccaatcaa tgttatatgt    125400
attttttgtaa taatctacat tattttgagc tgtagtatta atattccctg tatcatgagc    125460
tacaataaaa acgggttttt taaccgccat agcttgacct gtgcgtcttg ttccaatagg    125520
tagtaaatca taccaacac ttacaccttt ccaaattct atcattactg ttcacctact    125580
tcttttgggt tatcttcttt atctaattca gacactaagt cttttctac tttaccatgt    125640
tctaatggtt ctgcattgct tgtatctatg tcttcattat taactcctc aggagccatc    125700
ggcatctttg taggaggtaa ctctgaggta ctattcattg cttcactctt gtatgttaaa    125760
gctttatctg ggtcattata atctctaggt ttgttaaagt cctgtacaat agggctatcc    125820
gctataccct tagtgtcatg acttacaaga acacctaaac cagtcaagaa actaataact    125880
acacctgcaa ttgcagtgcc ttggtttaca atatcttctg cacctttgat tcctaataaa    125940
ctacatacac tgacaataaa cgtagctaaa acaggtacaa aacctgtcca aaatgtagcg    126000
cttttttgctt ttgcagtaat attgttacct gctattaata atggttttttt atctttttt    126060
gacataaaaa aaataccatc ctttctgtta ttgtaaagct aataataata taacaaaaag    126120
aatggtttta gttattaaat tttaagttat tgttcttta tttgagaaag tgttttgatt    126180
acttctgaca tttgttttatt atctaagtct tctaacttag tgtgtggaag taaatctaat    126240
ttatcccaaa tatctttttt agttgtgaat ttttcattaa taattgctct accgattaaa    126300
ctttcggtat aataaaattg ttttgcagat gccatattag tatctaccct tctatagtat    126360
aattaaacat acatacataa accgtctcac tggtaagtaa catactagac ctattgttaa    126420
gttaatcact acgcttgact ctattaggta gctaacctaa gtccatctca cgtaacctat    126480
taaagcagta caaccgtagg gttgattctg tttaatattg taatgtgata ctaacatatt    126540
aattagtaac tttcacatgg tatgaagaat tttagcgtct ttctataatt tgaccaatta    126600
ttattttgca ggtttatgct acttgtacta gtatcgtatg ttatcaaaca ttttttcaatg    126660
ctccaactgc atatacttgt taaggtgtat ttgtaaagga ttccaccaag accctttaca    126720
aaaattaagc ccatcagata ctatacttta taaacctaat atgttactgc tgagtattcc    126780
gattgtaata agcattacta ttgacgaatt atctcaccga tataaaccga caagttttaa    126840
ttcgttcgac aatctcacgc cttacaggta ccaccctgtt taaatcagcc attatgtatg    126900
```

```
tatgtttaat aatactactt ttaaagtata acatatattt attcggttgt caagaaaaat  126960
ttataacttt ttatagtttt tttatactag ggtaaaaaag ttttaaagaa cctagtttcg  127020
acaaataaaa ataaggagga ataacacttc aatttgacaa caaattaatc tctatgcaat  127080
cttaactata atataacata atattctaag tttgtcaagt tctttttttct ttttatcttg  127140
ataattcttc ttgtatttta tcccaatatt tttctgtatt tgttctatta tcctcaatgt  127200
gagcagttgt acatttacac ctgatacaat gtaaatgttt tatgtgtcct tcttctcttc  127260
tttgagctct tttttcttggt actgtaaaag tattaccaca ttctgaacaa actaaattac  127320
tgtggaacat tttctgtctt tttttcatga ttatcaatcc ttttaaaatt ttttgtatag  127380
ctagtatatc atataattat tttgatgtca atacaaatac tgttgttttg ataaaagctt  127440
attactagtt atatttaact attctgaata tttagatact ttacctattt ggaaaataag  127500
gaggattcct tatatatata ataaataatt ataaatacta aaataataat actagttata  127560
ataattaata atatatatag gaaagtcaac aaagagtaat aaaaaaaagt gacttactta  127620
aaagtcacta attttcaaat actaacttaa atgattctat gaataaaggg ttaatgaata  127680
ctgtatcaga attaataatcc tcagagactc taactctaac tgatgcttgt ccatgtcctc  127740
taattgttcc atttatctct ctttgtgtat actcaatact atcgtcagag attaaataat  127800
atttttttcc actaatcatt gttacctcag catgttttac catatcaaaa ctcctaacta  127860
aatttattga aaatgaaagt tataatgaaa cctaacacta gtagtagtac tttctcggta  127920
gtatccttct ttcttgtgtc cttaacaact gtattgttag tgagttcttt tatcttttcg  127980
tctaatctat ctagctgtat ttagatagac gattgtttct cactattaac agctacttct  128040
ttgtctaaac taactaccat ttttcttagt tcatcaactt cattttctaa ttccttatac  128100
gtattttat caatatagct accatcttgt attttatctt ttatcttatc tacttgtccg  128160
acaaggttttt ttagttcttc attcaactaa agtcaccttct taatgtctaa cttttcagat  128220
tctgaatgga cgtcatagtt ttcgaaaaag tcattaataa tttgcatata atcctcagta  128280
actatctcac catatgacgt tttagtattt atttcaaacc taagcttacc aaactcatgg  128340
aggtctattt ctttaataac ggtattagga ttatcagatg gtatgtaata ataatcaaaa  128400
tatataatag agccgttgat aagcaaccta tcaatcctat agacgtggga gaattttcta  128460
tctcgtctaa agtgagctaa ggcatcttta aactctaatt ttaatatatc tttatactta  128520
gtcaaatcaa cttaccccct tataattaat tttgagctac actagttttg tgttataata  128580
gttattgtag tagcagatat gagtattacg tttaataaaa ttagcaacca ccaactacct  128640
gtacttatta accataatga aaaacaagat aatatataaa caaccaccaa gtagcctata  128700
tatttcatag tgttttttaca ctcttttaat actactacgt atgctagtga tttagataag  128760
ctaaacagaa agtaaaaata aaaaataaaa agaggtatag ctataatgct tgctagtata  128820
atcactaatt acacctaatt tcttttagct agataataaa atcttatata atacaacttt  128880
aataataacat tgaaacctgt ttataaatca acaatgttac attaatagtg tacggtatat  128940
tttaaattag gaggactgaa ctaataggggt gaataataac atagctgtat ttatatttaa  129000
aactctaata attattattt ttattttgtt tattttgtct attattaact cactgtcatt  129060
aatatactct attcgaccta gtacagttat gacttacttt atatttggtg ggatagtttc  129120
taatgtggca ttaacaataa ctgataaatt attattcac aaagaagacc ccttacccga  129180
ttatattcta aaagaagtag agctaaataa caatgaatta caagtattaa agaaaattgt  129240
agagtcacaa actaatgttt ctgctgagga agtaagagta agagcaaaag cacaacgtcg  129300
agtactaaaa gataaaaaga gagatgctgt caatgaaaac gaagaaggac attaaggaac  129360
aacgtaaaga gctgaaagat aatgcaaccg ctgtttcctt aacaaaaaga ggagataaac  129420
gtattgcaag tcctagtagg gtgtgttgtt tgtgtggtca gtcctttca ggaatgaatt  129480
atactaaagg taaagctata gctaaagtta atcatttttca tttacagtac actaagtact  129540
tatatttgaa catgtgcgca gatattaata actgttacaa gaatttaaag aaagtaggtg  129600
aattgataga gtgagcgctg aaagtttaag agatatgtta tctaagaaga aaattgaaga  129660
cgaagataaa cgtaaaatata tagctgatgg attttatgtg ggtattacta aacttatgta  129720
tgactttaat aaaaagattg acagagggga aatagaagta aaagacccta atgatttgta  129780
taaagtgttt gttatcttcc aacaaatgca aaacttaatt acagatggtt ctgatggtgg  129840
cggtgctata ccgcaattat caagaccaca acaagagctc tttgatgaaa taacaaatga  129900
gaatagtaaa ggtgagaaag aagtagattt agagaagtta tctcaactat ctgctgataa  129960
tattactgct atgattattg ataaagaaaa ggttatgaac gaagagaact caaatacatt  130020
ctaaagaaag gtgtatatga atggatggta aagaattatt aaaaataaca caagaaacat  130080
tcggtacaca aaatgttacg caagaacaag ttgaccatat tatcaacatg ttaaacccta  130140
gtactattat gctaaaatat catacgttac gaggtcaccc gataacttttt agtattccaa  130200
acagggacag aagtaaagca caagctcata gaccataaac tagtgctgtg gtctttaaac  130260
tctgttaaac ggtcatagga aaataaagaa tatcctggta agaaaagcta agtcctaatg  130320
gatagagctg ataccgtagt aaagaatcta caacatgtag aggaaaaact ctaacgacta  130380
aatttctagg tagttatcta aatggagata gtgagaacta gataagaaaa ctcttttatag  130440
agaagtaaag cagagaaccc ttaaccaaaa ctaagggcta taatatagtc taaaccctta  130500
ataaatatcg ggaaaccgag ggtagtagtg ggcaagttaa gattgtcaac gatagtcacc  130560
ctaataaagc ggtaattaag agtagacaat taggactcag tgagatgtca gtaatggaaa  130620
tggtacactt tgctgacatg tatagttaca gaaatgtaaa gtgcctctat acgttccctc  130680
gattaaacag tgtgggggaa ttaaaacctt gttaaacggg catagtaaaa taatgtatag  130740
aaaaaacaat atactggtaa gaaaccctaa atctgactat acacagacag tgggaaccaa  130800
ccgtgctaac tgttgacttt atatgtagtg tatgttatac tgtatttata aagttagcta  130860
aaagcctaac gactaaactt actaataact atataaacgg atatagtgaa aatagtataa  130920
gaaaatttta actaaacatg taagaaagaa aaggtatatt gtaatgacta aaagaaaac  130980
acataaagag tttgttcaag atgtgtataa tctagtaggt gacgagtata ctgtttatata  131040
tgccaaagat aacaacatat cattgatacg aatacccttac tattataaca tggatgaaat  131100
agacaatata ctttcgtatt tagttaaaaa agtaaagcaa ggagctacta accaaaatta  131160
gtagctatga tatagtctaa tcccctaata aatatcggga aaccaagggt aaaaaatgac  131220
acaagagcag ttaagaaaat ttgtacagtc acgtcttaat cctgtattag ataaaactc  131280
ttttagagat attgtgaatt gggataaaga ctccttagtc tataaacaaa ttagaaactc  131340
aagtttgttt tttagaacta gtagtaaacc aggttcagtt gagggtgttg acatagactt  131400
cctcgcaatg gacgaaatttg agagggtgaa ctcactagcc gaaagttcgg ctttagagtc  131460
tatgtcaagt tcaccttta aagtagtaag aagattctca actccgtcag cacctggggt  131520
aggtatacac aaattatatc aacaatctga ccaatggtac tatgctcatg tgtgtcaaca  131580
ttgtcaatat gaaaacgaaa tgaaatatgc tgattatgac cctaatgact taaataagag  131640
```

```
tggtaatctt ttacttttaa acccagatgg tattgatgaa caagctaaaa cagtacaaga    131700
aggtacatat caatacgttt gtcagaaatg tggaaaaccc ctagaccgtt ggtataatgg    131760
catttggaaa gtaaggtatc cagaaagaac aaaaaataat tcaggtatta gaggttacta    131820
catttcacag atgaatgctg tatggataag tgcaagccaa ttagtagaga aagaaatgaa    131880
tacagattct aagcaagcat tttataacta ttctttgggt atgccttatg aagatgttaa    131940
aatgcgtgtt ttaccagaag acatctttga caataagtca gaaattgcaa aaacacagtt    132000
atttaataga gataaataca aatttatttc agtaggtata gactggggta acttccactg    132060
ggtaactgta catggtatga ctgaggaggg taaagtagat ttaatacgtt tattctctat    132120
taagaaaaac agtagaccag atatggtaga agcagattta gaagctataa tattagagat    132180
atctaaatat gaccctgata ttattgttgc agataatggt gattcgggta acaacgtact    132240
taaattaatt aatttctttg gtaaggataa agtatttggt tgtacttata agtctagccc    132300
acgctcatca ggtcaattat atgcacaatt taatgaaaac agtaatacag taactgtaga    132360
taaattaatg cataataaac gatatataca agatttaaaa gctaaacgta taagaatgta    132420
ccaacaggta gatgatgaat taaaaactta tcttaagcac tggcaaaatg tcctaatcat    132480
ggacgaagaa gatgaaaaaa caggagaact ttatcaagtt attaaacgta aaggcgacga    132540
ccattattct cagtctgcct gtattggtta catcggtctt actcgtctaa aagaattata    132600
tgacaaaggc aacggtacat cttttcacatc cacttttata tcaacggatt acaatactac    132660
acaaaacaac tcgtctaatg agttctattt tgatgactaa gaaaggactg agacttgac    132720
aagtatatta aattatgata caatacaaga agatgatata agtaaagaga catttaattt    132780
attaattgaa gaacctttaa ctttatctta tgtttctaaa catagtgatt ctttagatag    132840
taaatatgac tacatatata aatcactagg ctttgataac ttcatggact gttatttata    132900
cgtaacaaga gaaccagaac gtatatacaa aggtgggaagt aaagatataa gctcattgaa    132960
taaagtaaaa agaactgtag tacgtaatgg gaaagaaatt gaaatgacag tctatgaaga    133020
taataaaaat gatgataaac ctaaagagaa aaatggtgaa gaaccaaaag aacctaaaac    133080
tgctaaaggt tcaaaggttc ttactcatgg tgatgctgag aaacctaacc ctaaaaagat    133140
tgccagttct ctttctactc taaagaataa gggtgtgaac actgaccaca tagatggcaa    133200
cgcatcaatg tataaagaat ttgtagatga tagtaataac acaataggac tagcttcctt    133260
taaagaaact gattacgata tcatattaca tggatatgta tcagacctcg aaactaatgg    133320
ggtaggtgct aggtctattc tagagttaat ttctttagca ataagaaaga acaagaacgc    133380
tgttgtttat gatatagaat tatctcaagc catagagttc ttaaagtctt tagggtttat    133440
taaacgtaaa gatgagtatg tgttgaaaaa acaagatata aagttatttt taggtagtga    133500
cagtgagctt atttagcact gtactcattt atacgattat atatgtaagt attattatat    133560
tagtagttgt aaatgtaata gtaaaagaaa aaagattgaa taatactaag cagttactta    133620
tacaagtaaa aaaggatatt ataaataact taaaaaggg agatatgaat gattaaagat    133680
aataatacaa aaacattgga agagttaatt acacctattt ctacaaaaga aaaagaaaat    133740
aaagttaaag aatttagtaa aacattatgt gaaatgatta gtaagttata tgagtcttat    133800
aatgtgttaa gacaagaccc tattgatgaa acacaaagat tagatggttc tctaatggtg    133860
tttcaaagta gattagatga tacattaaca ggtgaggaac accaaaaact tttcaagtta    133920
gcctttgatt ataacattaa tatctttgaa gctaacaaac aatttaaaaa agatgtgcaa    133980
aatggaaatt ctattaagtt aggtgatgtt gttgtaaccg acacagcttt aagtaatgtt    134040
ttatctagta atgagcttaa tgttagtatt acatttatgt taagcaaaga ctatgaagaa    134100
aagaaacgta ttgaagaaga agaaaaggaa aaactagata agttataata gatattatga    134160
gaccttatg gataggtagg aataaataat atgaaacgta agttagtag taatgagatt    134220
actataacac ttataactat tgtagttgct ctatttatag tattaattac agtagcattt    134280
aacaagtacc aaattgctaa agaagataag gacagatatc aaaagctagt agaaatttat    134340
caaaaagcag atgatgatga cggtaaaaact aaaaaaaggt atgttgagaa gttaaatagg    134400
gctgaggaag aacttaaaaa ggttaaagaa gaaactaatt ataaaggtta taatgataaa    134460
acagaaaaag aaagagataa agaggataag agtgtaagaa aacgtattta tggtaatgat    134520
aaggataaag atttagtatt agtaaataat aaggttgttg taagtaatga agttactaga    134580
cctaagataa tagaagataa tggtgtcagt acagttgtag tacctcctgt tgtaagtcct    134640
gttgagccac caagtgaacc tagtatacct tctcctacta tacctaaacc tattattcct    134700
aatcctatta acctaatcc tattctacct aaacctaaca tccctaccec taacccacta    134760
ccccctatag aacctgaaaa acctatagaa cctgaaaaac ctatagaacc tgaaaaacct    134820
atagaacctg aaaaacctat agaacctgaa aaacctatag aacctgaaaa acctat    134876

SEQ ID NO: 3           moltype = DNA   length = 136156
FEATURE                Location/Qualifiers
misc_feature           1..136156
                       note = PN1815
source                 1..136156
                       mol_type = other DNA
                       organism = synthetic construct
SEQUENCE: 3
ttgagctagg ttttcaggt tctataggtt tttcaggttc tataggtttt tcaggttcta    60
taggtttttc aggttctata ggttttttcag gttctatagg tttttcaggt tctatagggg    120
gtagtgggtt aggggtaggg atgttaggtt taggtagaat aggattaggg ttaataggat    180
taggaataat aggtttaggt atagtaggag aaggtatact aggttcactt ggtggctcaa    240
caggacttac aacaggaggt actacaactg tactggcacc attatcttct attatcttag    300
gtctagtaac ttcattactt acaacaacct tattatttac taatactaaa tcttttatcct    360
tatcattacc ataaatacgt tctcttacac tcttatcctc tttatttctt tctttttctg    420
ttttatcatt ataaccttta taattagttt ctctttaaac ctttttaagt tcttcctcag    480
ctctatttaa cttttcaaca tacctttttt tagttttacc gtcatcatca tctgcttttt    540
gataaatttc tactagcttt tgatatctgt ccttatcttc tttagcaatt tgatacttgt    600
taaatactac tgtaattaat aatataaata gagcaactaa aatagttata agtgttataa    660
taatctcatt actactaaac ttacgtttca tgttatttat tcctaccctat ccataaaggt    720
ctcataatat ctattataac tttataactt atctaacttt tcctttttctt ctgcttcaat    780
acgtttcttc tcttcgtagt ctttactcaa cataaatgta atactaacgt taagctcatt    840
actagataaa acattactta aagctgtgtc agttacaaca acatcaccta acttgataga    900
cttcccattt tgtacatctt ttttaaattg cttgttagct tcaaagatat taatgtttata    960
```

```
atcaaaggct aacttgaaaa gttttggtg tgcaacacct gttaatatat catctagtct   1020
actttgaaat accattagag aaccatctaa tctttgtgtt tcatcaatag ggtcttgtct   1080
taacacatta taagactcat ataacttact aatcatttca cacaatgttt tgctgaactc   1140
tttaatttta tcctctttt cttctgtaga aataggtgta attaattctt ccaatgtttt   1200
tgtattatta tctttaatca ttcatatctt cttccttttt taagttattt ataatatcct   1260
tttttacttg tataagtaac tgcttagtat tattcaatct ttttctttt actattacat   1320
ttacaactac taatataata atacttacat atataatcgt ataaatgagt acagtgctaa   1380
ataagctcac tgtactcacc taaaaataac tttatatctt gttttttaa tacatagtaa   1440
tctttatttt taataaaccc taaagatttt aagaactcta tggcttgagg taattctata   1500
tcataaacta cagcgttctt gttcttcttt attgctaaag aaattaactc tagaatagac   1560
ctagcaccta ctccattagt ttcgaggtcc gatacatatc catgtaatat gatatcgtaa   1620
tcagtttctt taaaggaagc tagtcctatt gtgttattac tatcatctac aaattcttta   1680
tataatgatg cgttgccatc tatgtggtca gtgttcacac ccttattctt tagagtagaa   1740
agagaactgg caatcttttt agggttaggt ttctcagcat caccatgagt aagaacccct   1800
gaacctttag cagttttagg ttcttttggt tcttcaccat tgttctcttt aggtttatca   1860
tcattttat tatcttcata gactgtcatt tcaattctt tcccgttacg tactacagtt   1920
cttttactt tattcaatga gcctatatct ttagctccac ctttatatat acgttccggt   1980
tctcttgtta tatataaata acagtccatg aagttatcaa agcctaagga tttatatatg   2040
taatcatatt tactatctaa aaaatcacta tgtttagaaa cataggataa agttaaaggt   2100
tcttcaatta ataaattaaa tgtctcttta cttatatcat cttcttgtat tgtatcataa   2160
tttaatatac ttgtcaagtc gtcagtcctt tcttattcat caaaatagaa ctcattagac   2220
gagttgtttt gtgtattatt ataatccgtt ggtataaaag tagatgtgaa tgctgtacca   2280
tttcctttgt catataattc ttttaaacga gtaagaccaa tgtaaccaat tactgaagac   2340
tgtgcgtaat gcattcata ccctcggttt ccgatatttt attaggggat tagactatat   2400
cttagttatc taaattgata actcagtgct ttacgaataa aataatttat tgtttaacaa   2460
tttctctata cttttgtaat ccttagttgt atagaatatc tcaaaaagct cataaccgtt   2520
atcttttgca taagaacttt ttatactatc tatctttttt tgtagcttaa attgttcttc   2580
tcctccaaaa tgcttgacag gtttaacgtg ttgttcacct tgatattcga taagtaagtt   2640
atattcaggc aaataaaaat catatgtaaa gttatttatt aactttaagc cttcaaaagt   2700
tttttgtttt ttatatgtta tacctttttg tctctagataa ctttctacta atttctcacc   2760
tatggaattt ctacagtgtg agcatccttct acctttctta aaatttgcca tagttccccg   2820
atatgttttt ccgcactcat tatgcttatt ttctatgggg gtgtgtgcat ttttataatg   2880
atttgaaact acttcatagt ttcctttcgt ttctttacgt acttcaaatt taatatcttc   2940
caatgtccta ttaaatctcc tgttacatct cgaacattgt ttatacttta aaatatctct   3000
tgcagtaata gtaaagtac tatcacaaaa gaaacagtgt aaagttatct tcttaaaatgc   3060
accttcatat tttgttatag ccattatacc ttcaggtaat tccttttggt attcttcatg   3120
tgttttctt tgcttactat ggactctttt tgagaacat gtattacaac ctgtcttacg   3180
tttactcata aatgttgatg gtgttataag tattttgtta ccacattttt tatgaatagc   3240
tcttagtttt gtgtactgat taacatagtc atctaaaaat tcatattctt catagtcctc   3300
tggtctaaca tctttaattc tattaataaa ccactcgtta tcataaacca cttaactacc   3360
ctcctttta gtatactcaa taaattattt taatctctta cgttaatagt aacgaattta   3420
gtcgttaggc ttttatctta atttaataat aacattaaaa aatataatgt taatatttaa   3480
attaagaatt tagcacggtt ggtccccact gtctgtgtat agtcagattt agggttttctt   3540
accagtatat tgtttttcta tacattattt tactatgccc gttaacact gtttatagac   3600
gaccatatta caaaatcgtc tcctctgcgt ttaataactt ggtacatttc acctgtctta   3660
tcatcttcct catccatgat aataaacattt tgccaatgtt taagataagt ttttaactct   3720
tcatctactt gttgatatac actaatacgt ttagctttta aatcttgtat ataacgtttg   3780
ttatgcataa gtttatccac agttactgta ttgttatttt cattgaactg tgcatataat   3840
tgacctgatg aacgtggact agatttataa gtacacccaa aatctttatc tcttccaaag   3900
aaattaatca atttaagaat attattacca gagtcaccat tatctgcaac gataaatcg   3960
gggtctgtact tagagaactc caatataatt ttttctgagtt ctgcttctac catatcaggt   4020
ctactattct tcttaacaga aaataaacgt attaaatcta catgaccgtc ttctgtcata   4080
ccgtgtacac agcaccagtg gaaattaccc cagtcaacac tgcaagaaat aaatttgtat   4140
ttgtctctat taaataattg tgttttttgca atttctgatt tattattgaa tacatcttct   4200
tctgttactt tcattttac gtcgtcaaaa ggggctccga tgatgtagtt ataaaagctt   4260
tgtttagatt ctgtattcat ttcttttct ttaatctcat cacagcttat ccacgttgcg   4320
tttaattgac ttatataata tcctctgata ccttttattat tttctgttct ttcagcatgc   4380
ttgcaatccc aacgaccagc gtaccaccta tcaagaggct ttccacattt ttgacaaaca   4440
tattggtaag taccacttg gacagtttta gctatctcat ctatcccatc tggatttact   4500
agtaatacat taccactatt ttccaagtca tcaggtttat aatcagcata cttcattca   4560
ttaaaatgac cgcagtgttc acaatcataa ccataaaacc attggtctga ttgtttatac   4620
agtttatcta taccataatc tcttacagtt ggtgtagacc accttcttac tattttaaaa   4680
ggtgaacttg acatagattc taaagctgag ctctcagcta aattatttac acggtcgtac   4740
tcatcaagtg aaagatagtc aatcaatttg taccccctagt ttcctagtac tttaacactc   4800
acttaagagt aggtttagac tatatcataa ccttttctatt aggtgaaagg ttctctgctt   4860
tacttccgcc aagcggtttt cttatctagt tctcactata ccctttttgta tagctaccta   4920
gaaattagt cgttaggcat ttagctaacc ttataaatac attatatcat attcttttta   4980
taaagtcaac atttagcacg gaattgcccct cgtctttacg ttaggggttt cccgttttaa   5040
cagagtttaa tgtggacttg ttacctatcc acacctcga cagtactagc tttactacta   5100
gttctgaaaa ataaactaga atttcttatt tgtttataac ctaatgagtc cttatcccag   5160
ttaacaatat ctctgaaata aggttttct aatactggat taagtcttga ttgtacgaat   5220
ttcttcatct gttcattcgt cggaaaggta tacaaacatt ttcacttgc ataactatgc   5280
atgtcagcaa aatgtaccat ttccattaca ccctcatcac ttacaattac taccgttagt   5340
ttcctaatac tttaacactt atttaaaagt cggttttgaca tatatcttca atatataaat   5400
aataatttat aattacggat tatatattgc cttgctttac ttctattaac gaaaattttt   5460
tatctaagta agatttcata cttgaatatg tgttatttt gtaggtaggc tcctataaaa   5520
caaagtcatt atctttagca aatttatttt taatattatc gttaacttgt gtttttttaa   5580
accttttctt tgctaactct ttagatatac cttcaaattt cttctgttct tcgtacctaa   5640
tgttatcttc ctttaagtat gtttcaatat attcctctcc acgagacttt ttacagtaag   5700
```

```
ggcaacctga atggtgttga ataatatctg tatatctaac cttaaatgtc ttattacaat   5760
ctttatgtaa taattttact ttattaccag caccattata ttctgatact aacttataac   5820
ttgaccctaa atgttctttt atattactat ctatttcctg aggtgttaat ctttgacttt   5880
gatagtaaca agctatacat ctagaatgat acaaaaagtt accaggtgat actttatact   5940
ctctaccaca cttgttatgt ctcataagta taggtgttgc tctattaata taatcttcaa   6000
gtaccgtata ttcatcacct acaagggtat agacttcttg aataaattct ttatgcgtct   6060
tctttctcat attaaacctc ttatttacgt taatagtttt cttatctagt tctctttatc   6120
tccattcaga taaataccta gaaatttagt cgttaggcat ttatattaat tcaataataa   6180
cataagtatt ttatactgtc aactattaaa ttaagaattt agcaacggat tgtcatatgc   6240
ttctttaagc acttagagtt tcccgtttta acaaggtttt acttgaacaa agtttatcca   6300
agctgtctac ttttaattac tacttttattt gggtgtgtgt catttactat catttactac   6360
cctcggtttc ccgatattta ttaggggact agactatctc atacatgtac cttttggtgt   6420
acatgccctc tttctttacg ggtttttatcc ctcttatact gttctaccta atcccttttg   6480
attagttacc agtaagttta gtcgttaggc atttacgtaa ctaaggtata tatcctagtt   6540
cgatttagca attgattgcc ctcgtcttta cgttaggggt ttccaattttt agaaaaggtt   6600
tatagtccgc atagtatgtt tacggacttg ccaaggtcta tgagcttgtg ctttacttct   6660
gtccctgttt ggaatactaa aagttatcgg gtgacctctt aacgtatgat attttagcat   6720
ataagtacta ggatttaaca tattgataat atggtcaact tgttcttgcg taacattttg   6780
tgtaccgaat gtttcttgtg ttattttttaa taattcttta ccgtccattc atatacacct   6840
ttctttagaa tgtatttgag ttctcttcgt tcataacctt tctttatca ataatcatag   6900
cagtaatgtc atcagcagat agttgagata acttctctaa atctacttct ttctcacctt   6960
tactattcgtc atttgttatt tcatcaaaga gctcttgttg tggtcttgat aattgcggta   7020
tagcaccacc accatcagaa ccatctgtaa ttaagttttg catttgttgg aagataacaa   7080
acactttata caaatcatta gggtctttta cttctatttc ccctctatca atctttttat   7140
taaagtcata cataagttta gtaatacctg acataaatcc atcagctata tatttacgtt   7200
tatcttcgtc ttcaattttc ttcttagata acatatctct taaactttca gcgctcactc   7260
tatcaattca cctactttct ttaaattctt gtaacagtta ttaatatctg cgcatatgtc   7320
aaaatataag tacttagagt actgtaaatg aaaatgatta actttagcta tagctttacc   7380
tttagtataa ttcattcctg aaagagactg accacataaa caacacaccc tactaggact   7440
tgcaatacgt ttatctcctc ttttttgttaa ggaaacagcg gttgcattat cttttagctc   7500
tttacgttgt tccttaatgt ccttcttcgt tttcatcgac agcatctctc tttttatctt   7560
ttagtactcg acgttgtgct tttgctctta ctcttacttc ctcagcagaa acattagttt   7620
gtgactctac aattttcttt aatacttgta attcattgtt atttagctct acttctttta   7680
gaatataatc gggtaagggg tcttctttgt gtaataataa tttatcagtt attgttaatg   7740
ccacattaga aactatccca ccaaatataa agtaagtcat aactgtacta ggtcgaatac   7800
agtatattaa tgacagtgag ttaataatag acaaaataaa caaaataaaa ataataatta   7860
ttagagttttt aaaatataaat acagctatgt tattattcac cctattagtt cagtcctcct   7920
aatttaaaat ataccgtaca ctattaatgt aacattgttg atttataaac aggtttcaat   7980
gttatattaa agttgtatta taaagattt tattatctag ctaaaagaaa ttaggtgtaa   8040
ttagtggtta tactagcaag cattatagct atacctcttt ttatttttta ttttttactttt   8100
ctgtttagct tatctaaatc actagcatac gtagtagtat taaaagagtg taaaaacact   8160
atgaaatata taggatactt ggtggttgtt tatatattat cttgttttttc attatggtta   8220
ataagtacag gtagttggtg gttgctaatt ttattaaacg taatactcat atctgctact   8280
acaataacta ttataacaca aaactagtgt agctcaaaat taattataag ggggtaagtt   8340
gatttgacta agtataaaga tatattaaaa ttagagtttta aagatgcctt agctcacttt   8400
agacgagata gaaaattctt ccacgtctat aggattgata ggttgcttat caacggctct   8460
attatatatt ttgattaatc tacatacca tctgataatc ctaataccgt tattaaagaa   8520
atagacctcc atgagtttgg taagcttagg tttgaaataa atactaaaac gtcatatggt   8580
gagatagtta ctgaggatta tatgcaaatt attaatgact ttttcgaaaa ctatgacgtc   8640
cattcagaat ctgaaaagtt agacattaag aggtgacttt agttgaatga agaactaaaa   8700
aaccttgtcg gacaagtaga taagataaaa gataaaatac aagatggtag ctatattgat   8760
aaaaatacgt ataaggaatt agaaaatgaa gttgatgaac taagaaaaat ggtagttagt   8820
ttagacaaag aagtagctgt taatagtgag aaacaatcgt ctatctacat acagctagat   8880
agattagacg aaaagataaa agaactcact aacaatacag ttgttaagga cacaagaaag   8940
aaggatacta ccgagaaagt actactacta gtgttaggtt ctattataac tttcattttc   9000
aataaattta gttaggagtt ttgatatggt aaaacatgct gaggtaacaa tgattagtga   9060
aaaaaaatat tatttaatct ctgatgatag tattgagtat acacaaagag aaataaatgg   9120
aacaattaga ggacatggac aagcatcagt tagagttaaa gtatctgagg atattaattc   9180
tgatacagta ttcattaatc ctttattttat agaatcattt aaattagtat ttgaaaatta   9240
gtgactttta agtaagtcac ttttttatta ctctttgttg actttcctat atatatatta   9300
ttaattatta taactagtat tattattttta gtatttataa ttatttatta tatatataag   9360
gaatcctcct tattttccaa ataggtaaag tatctaaata ttcagaataa ttaaatataa   9420
ctagtaataa gcttttatca aaacaacagt atttgtattg acatcaaaat aattatatga   9480
tatactagct atacaaaaaa tttttaaaagg atggtaatgt atgaaaaaaa gacagaaaat   9540
gttccacagt aatttagttt gttcagaatg tggtaatact tttacagtac caagaaaaag   9600
agctcaaaga agagaagaag gacacataaa acatttacat tgtatcaggt gtaaatgtac   9660
aactgctcac attgaggata atagaacaga atcagaaaaa tattgggata aaatacaaga   9720
agaattatca agataaaaag aaaaaagaac ttgacaaacc tagaatatta tgttatatta   9780
tagttaagct tgcatagaga ttaatttgtt gtcaaattga agtgttattc ctccttattt   9840
ttatttgtcg aaactaggtc ttttaaaact ttttttaccct agtataaaaa aactataaaa   9900
agttataaat ttttccttgac aaccgaataa atatatgtta tactttaaaa gtagtattat   9960
taaacataca tacataatgg ctgatttaaa cagggtggta cctgtaaggc gtgagattgt  10020
cgaacgaatt aaaacttgtc ggtttatatc ggtgagataa ttcgtcaata gtaatgctta  10080
ttacaatcga tactactcagc agtaacatat taggtttata ataatatgta tctgatggtt  10140
ttaatttttg taagggtct tggtggaatc ctttacaaat acaccttaac aagtatatgc  10200
agttggagca ttgaaaaatg tttgataaca tacgatacta gtacaagtag cataaacctg  10260
caaaataata attggtcaaa ttatagaata ccgctaaaat tcttcatacc atgtgaaagt  10320
tactaattaa tatgttagta tcacattaca atattaaaca gaatcaaccc tacgttgta  10380
ctgctttaat aggttacgtg agatggactt aggttagcta cctaatagag tcaagcgtag  10440
```

```
tgattaactt aacaataggt ctagtatgtt acttaccagt gagacggttt atgtatgtat    10500
gtttaattat actatagaag ggtgatagact aatatggcat ctgcaaaaca aatttattat    10560
accgaaagtt taatcggtag agcaattatt aatgaaaaat tcacaactaa aaagatatt     10620
tgggataaat tagattact tccacacact aagttagaag acttagataa taaacaaatg    10680
tcagaagtaa tcaaaacact ttctcaaatt aacgaacaat aacttaaaat ttaataacta    10740
aaaccattct ttttgttata ttattattag ctttcaaata acagaaagga tggtattttt    10800
ttatgtcaaa aaaagataaa aaaccattat taatagcagg taacaatatt actgcaaaag    10860
caaaagtgc tacattttgg acaggttttg tacctgtttt agctacgttt attgttagtg    10920
tatgtagttt actaggaatc aaaggtgcag aagatattgt aaaccaaggc actgcaattg    10980
caggtgtagt tattagttc ttgactggtt taggtgttct tgtaagtcat gacactaaag     11040
gtatagcgga tagccctat gtacaggact ttaacaaacc tagagattat aatgacccag    11100
ataaagcttt aacatacaag agtgaagcaa tgaatagtac ctcagagtta cctcctacaa    11160
agatgccgat ggctcctgaa ggtgtcaata atgaggatat agatacaagc catgcagaac    11220
cattagaaca tggtaaagta gaaaaagact tagtgtctga attagataaa gaagataacc    11280
caaaagaagt aggtgaacag taatgataga aatttggaaa ggtgtaagtg ttagatatga    11340
tttactgcct attggaacaa gacgcacagg tcaagctatg gcggttaaaa aacccgtttt    11400
tattgtagct catgatacag ggaatattaa tactacagct caaaataatg tagattatta    11460
caaaaataca tataacattg attgggcttc tactgcatcc gcacatatct ttgtagatga    11520
taaagaagct atcatatgtg ttcctactac agaaaaagct tggcatgtgt tgtataacgc    11580
tcctatggat gacctatggt acggaattaa cgctaatgat ggtgctattg gtgtagagat    11640
ttgttacttt agtgataaag aacgctctaa aaaatcatta gataatggag ctcgtgtctt    11700
agcttattta gctgaatact gggtgttga ttacaaaaca aatatgccag gtcaccaaga    11760
catccaaaac gacaaacaag acccaggtaa cttattagaa gcatgtggat taggtagaaa    11820
cactagtaac ttagataagg aagtagctaa gtattacaag aaagttatta agtcagtaga    11880
tgtaaagaaa tcaggtaatg ctgagcctag agtaaaaaca caatctacta aaactatgtg    11940
gagctgaaca ggtactttt atccagatag agctattaaa gttagaaaaat ctccaggact    12000
taaaggcact atagtaaata gagattcatg gctatacgat aaggatgatt gggttgagtt    12060
tgaccaagtt attaaagcaa atggctattg gtggattcga tttaaatatc caaaccagg    12120
ctctagtaaa aattatttct attgtgctgt atgtgagata acagataaac aagagcgtat    12180
taagaaagaa aaatttttg gaaaaataga ttggaaataa ggagtgaaaa cttttgaaag    12240
catcgatgac tagaagtgaa tttgttcgat ttttaaaaag tctagaaggc aaagcaatag    12300
actttgatgg ttggtatggt cagcaatgtt acgacttagc taactatgga tttaacaagc    12360
tcttcccagg ttattcttta ggtggagcaa gtgcatgtaa cattccatgg gataataaag    12420
ctatgttaaa agataaagct agagtagtag aaaatacact atcctacatt cctaaaccag    12480
gcactatggt tatctttaat aattcatacg gaggcggtca tggtcatgtc gcatgggtac    12540
taagtgcaaa ccaaaaccaa attatagtaa ttgaaaataa ttggttaggt ggaggttgga    12600
cttggggaga tgctcaagga ggcggtggct gggagaaagc taccgttaga gcccatggtt    12660
acgactttcc tatgtggttt atagaaccta attcaaaaa cgaggtacaa acaacttgga    12720
attggggagg taaatttact gctgatagaa cgattaaggt aagacgcaca ccaggtttaa    12780
ggggttcaat agtaggtgct gaatcattta tttatagtgg tcaatatgta aactttgacc    12840
aagttattaa agcagacggc tactggtgga ttaggtttaa atatcctaca aacccgtcag    12900
ctggtaactt ctatatggca gtatgtaaaa tcactgacaa gtgggaacgt atgctaaaag    12960
agaagtattg gggtcgtatt aactggaaat aatgtactag ggaattttcc ctagtatttt    13020
tttatttta agttgacaat gtatttatca tatgctacaa tacatatata agttttaaag    13080
gtggttataa taaatggaaa aattaaagaa atggtttaaa cgtaatgtat taaaagtga    13140
gattacgcag tacaaagtat atattaagca tacacgttca aataaaagta atgttttcta    13200
tgttaatatg aaagctaaag gtaaagtaga ggctaaagaa aaaacgcttg acgttttaaa    13260
taagtatgct tataataaaa ataactatag tatttttaaa attgaagaaa gataggtagt    13320
ggtttattat ggaagagaat aaagtattaa atttaaaaaa agtaagagaa gaaaaaggtc    13380
atacagttag aagtttagca caagagattg gagttcacta ctcacttatt tcttattggg    13440
agagtggtaa aagaaaacct aagagtgcta atcttataaa attagaaaaa gctttaaata    13500
ctaatagtgt agaattattt aaagaggttg atgttgatga ataaatttac aaaatctatt    13560
attaactttg ttgagcgtca tgagattgag gatatgatta atattttgtga acttcaagat    13620
gttaataaag caagttgatt atgattctaa aaacccctaat attagaattt catatagtac    13680
tgaagaaaaa ggtaatacaa tgcaaaaagt agtagagcat ttaagtaata aattagataa    13740
ttgtttatat caatcttacc ctaatatatc taaatatagt attattgaa gtacggctga    13800
gttattagga gacctatcgt atatcgagga ttattatact ggtgatgact taacaaacat    13860
tattaaagac acacatctag aatatataca caacattatt aatagtagtg aatttgatag    13920
tatcacatta ttagagcagt ttgaacttt agaaagagtca tacagacttg aagaagtaaa    13980
agaaaaatta gaagagctag aacactcaga aaagtacact gaaattgatt taattaagta    14040
ccttattaaa ttataaaggg gtttttttaaa tgtttaagaa atttgttcgt attttagttg    14100
atggttttga agttaatgtt attgcagatg actatatcga agcagaagaa cattgttata    14160
agttttttga tttctctact ataaaattac aagactacaa agagatttat acaagtgaga    14220
tgttcccttg ctttgtagaa gggcataaat atgcatagga ctgcattaat atatacagat    14280
ggtagctcat cttataataa aggtcttgtt ggagcaggag ctattatttt agataaaaat    14340
gagaacattg taaagaaat cagtaaacct attgaaaata gtagtttaat taagtataat    14400
aatgttgcag gtgaaatact agcttgttgt tacggtattg aagaggctat aaaactaggt    14460
tataagcagg ctattattca tgtagattat ataggactta ttcaatggta tgaaggttcg    14520
tggaaaacta aaaacaattt aagtaaaaca tatattaata tgctaaggga atactcaaag    14580
tttatagata taaatttat aaaaataaag gctcatgata ataacaaatg gaatgaatat    14640
gtagatgcat tagcaaaaaa agcaattgga atataaggag aaatatattg atgaaaaaat    14700
tatcaaaaaa gtttcaaaaa ggtggatttt gggaaaagtt atttttattt acagttacaa    14760
cattactagt agtagctaca tggttttag tagatagtgt aatgttttc ttacaaacag    14820
tattaacatt ctgggggctg gttttattag caccttattgt agctctaggt attattgctt    14880
ttagtatttt aaagtatcca agagtaaagg atattaatga ttactcggaa ccagttagaa    14940
agtacttata aggagactaa aataatgaca gaattaaaag ttaagatagg aacaaataaa    15000
gttaaaacaa aagatgttaa taaaattagt gagtacttaa aggatacct tgaaaaacta    15060
gatatggaac aatctataga ctttcaaaat agaacaccgt atttaattag tgatgatggt    15120
acttttattg catagtattt agaaaaagca aatgctgtag gttttttataa ggagtctatt    15180
```

```
atacaaggaa aagttaaaca acttgttcat gtaacacctg cagatataga acatataacg    15240
tggactattg aagaagatga tattgtagac ttatataacg atgaattgcc tgttggagat    15300
attattatta tttatcataa cgagaagtac agtagtgaat tagatgcata tctattacct    15360
catgtatctt ttagggacta catagatggt ttagggataa tggatagcat ttccctatct    15420
agagtagttt acacaggtat ttcaaaaggt agaaaagaaa atattagttt tgatgtactg    15480
tgacaggtga tttagagttt attaatcgtg atggtggttg gaataatgac acctttatta    15540
cagcggagag aaaactacaa taaaatacta taaatttggg ttaacgcaaa ggagggctaa    15600
ttttgaacaa ttacttattt aaagaatata accatttgtt agataataca agatttaaaa    15660
taaaagtaaa aggaaaaaca tatcatgttt atattgctac ttccaataag tcaataggtg    15720
tactaacaag acgtaaaagt ttttgtgcta cgtactttga ggataaagat tattttagta    15780
gatatacaat taaggaattt attgatttta ttaaaacact tattattgaa gagatgtctt    15840
ttgatattga aaacactatg acaaataaaa aaacagaaaa acaaattaaa aaagaaatca    15900
tgaaagataa taagttaaaa gatggaaatc tagatggtat aaatagacat acctgctagca   15960
tggatgttct taaaagtgat ttaaagtac ttgataatta aaataaagga aaggaaagga    16020
aaggaaaata aaagaaagga aaataaagga aaggaatatt aaggaggaga ctttttatat    16080
aggataagat aagatttgtt ttgtcctgct ataatatata aagaaaagg aaatatgatg    16140
tataagcaat aacatataaa atcctcaagg agaatgaaat atgagacaac taatactaat    16200
gagaggtgct ccaggctcag gtaaaacaac gtatataaaa gaaaatggat tagagggata    16260
ttctcttagc cctgatgtcc ttagaacaca atatagctca cctgtatacg acacggaagg    16320
aaaccttaga atatcacaag aagaagacaa caaggtatgg gatttattat ttagcatatt    16380
agaaaagcgt atggaaaatg gggaatttac tgtaatagat gctacacatt ccacagctaa    16440
actaattaaa aaatatgaga agttatcaaa aaaatacaga tatagagtat atgtggttaa    16500
catagaagca gagctagata ctcttcttga acgtaatgat aacagacaag aattgaagaa    16560
agttcctgtt aatgttattg aaaatatata tgagcgttta aaacacgaga atatcccaag    16620
ttttgccaaa gtagtagata aaaagagttt attaaacact attaaatggg ataaaaatct    16680
tatgaatact gattcatatg agaaaattca tgtaattgga gatgtccatt cctgttttac    16740
agccctctat tctctttttcc ccgctgatta cattatcgat aatcaaaatg aactcttcat    16800
atttgtcgga gattatttg ataggatt agaatcgaaa cagatgtttg agtatcttga    16860
gattatttat aaattaaaaa atgtcattct attagaagga aatcatgaaa gacaccttcg    16920
cagatatact cggttagaaa gagaagacta tgataatctt tgtttgcct ataattcatt    16980
agataataac aaaagaagatt tttataaaca agctttaaag atatttcatg caagaggatt    17040
tttacctacc ttaatatctt ttataggaaa cggaataact caaaacaggg ttaaagctat    17100
tcttagaaaa ctacaacagg ttgtttattt taactttaaa ggacaagact acattattag    17160
tcatggcgga gtccttcctg aagttcttga taatttaaat aagatttcaa caagtcagct    17220
tattaatgga atcggggat atgattttaa tgttgatgac caatgggaat attctaatac    17280
aatacaaata catggacata ggaatttata tagagaacct ttagatacta ctaaaaattc    17340
agttaattta gaagggcgtg tagaaaaagg tggttgctta agagctataa cgataaataa    17400
aaacaacaac attgagaaac atgaaataaa aaacactatc tacgaccta aatttctttt    17460
atcaaacaga cggaacgata atattgacaa agacctaacc cctaatcaat acctagatat    17520
agctagaaaa gaaaataaaa ccatcaaaac cagtcaacaa tatagagatg tattctcggt    17580
taactttaca aaaagagctt tttctaaaaa gaaatggaat caattaacag tgagctctag    17640
aggtctttat attgatgaag gtagaaatac agtattagga agaggatata ataagttctt    17700
taatatcaat gaagtagaag aaaccaaatt ggagaatagg ccagacacta tccaattccc    17760
tttaactgga tataaaaaag aaaatggatt tttaggacta atgttctatg acccgttaga    17820
aggaattgta tatgcaagta atctaaaac ccatttaagt ggacatggaa ataaatatgc    17880
gctactattt aaagagttag tagaaaaaac tttaaccaaa agacaaatac aaatactagc    17940
aacattcctt gaaaaccatt atattgctga cgatagtttt accctagtgt tcgaggtagt    18000
tgatattgaa gaagacccac atatcataaa gtatgaagaa agtagtattt tcctactcga    18060
tattatttcg aacacactaa atatggaaaa gaaagactat gattatttga gatatgttgc    18120
tgatgaagtg ggattacaat taaaagaaaa agagttagag tttgctagct gggaagaatt    18180
ttataaatgt tataaggata ataatggctc ttataatata ttgcatgaag gatatgtatt    18240
tgaggatttg aaaggatta tgtttaaata taagtctgac tattacaaag actggaaata    18300
tatgagagat atagcttatt ccttatcaca aagaagagat gtaagaccta agcaatatat    18360
tttagcaaga aaccctgaac ttagagattt ttattattgg gctaaaatga aagattcaga    18420
tgaacttgat aaagatatta tcacactaag agatgagttt gaaaaagaaa aggagaggta    18480
gaatggcaaa tctattaaaa gaattacaaa tctataatgg gggacatata ttgaacgatg    18540
caatggtaaa atatagaaac aaacaggcag accaaatcaa tggaatcatt ggtgttaaat    18600
gttataatgt attagatgat aaatcaatca atgacaaagc taacgcagaa caggttgggt    18660
tagctgaacg tatcttgaat aatgacttta aggctatgca agagtcagat atatttgtat    18720
tcgatgtatt gaatgaggga ttaggtacaa tagcagagat tagtattctt ttgggtatga    18780
aacaccaagc tcaacaaatt atcaacaaat atgaagatgt agattttaga gagttagata    18840
aaaacacaca agatgatata ttagaagcgt atcatgtcgt caataaacct gttttaattt    18900
attgctctga tattcgtcaa gggcacggga accatacac tgacccagac agagcagagt    18960
tttcaacgaa ccagtttgtc tatggcatgg ttttatcatt aaccaacgc aaaggcttta    19020
tttcatggga agaagttta ggggaattag aaaagttagg tgcatctaat gtctaattta    19080
gctcatatat taagcatctt atatgctata ttagttactg taggatatat acctgcttta    19140
gtaggtttga taagagataa gaatgttaaa ggtgtagata gctatttttg gttttatatt    19200
gttgttacag taagtattag cttaacaagc ttatttgtaa cacatgcacc cctatttcaa    19260
attatatcag taagtattaa tttattacta ggtattattt gttttattat atacttattt    19320
agaacaacag aagttagtct tttagaaatg gttatgttta taattgttat ttatattggc    19380
tattcagtag ctaactatag tgttgaatac ggacaaataa tggctactat tagtattatc    19440
gtagcttatt tatcccaaat aaataaattt tataaaacta aagtacaaa tggaactagc    19500
aaatatttat ttcttattat aggtattgca ttagcttgtt taattattag tatgttaata    19560
acaaatacga caccacatgt aatatataca gaagtagcta acttttattct tattatgata    19620
tgttacctac aggcatctta ttatgaatat aaaggcgtag ataacaatga aagacttaat    19680
acaaaaaggt aataaatttt attataaggt tagaaatggt gataccttat ggactataag    19740
taagaaatat gatgtgtcta ttaaacaact acaagaactt aatgatatga cctcggtgtc    19800
tttatcgac aaagattgta tacttgttta tgtagactag aaaggacttc tatatggatt    19860
taatagctaa taaagaagta actagtaccg atgagattat ttttaaaagt aaatctaaaa    19920
```

```
atttatatat tagtgatata gatataaatt ctaaagttac tatgtacaca gatgagttag   19980
aggaagtttt agcaatgcct aatactatta actttaaaaa ttctaagaag tacaaagact   20040
taatgagtaa tcccgatatt gtacccgtaa gaagaactaa aaaaattaaa tatgaaactt   20100
atctagaaga actgtaaaaa agttcttctt ttttgttgac tattaaattt aactatgtta   20160
tcatacttat ataataataa atgaggtgat gacacatgtc agtagaatat aaagaaacag   20220
gattaacgga agaagaaatt cttaaattac ctaaagtaaa tagaaatagt atatttatag   20280
gtgaagaaag agtatattta aaaataaata ataaaaatat tgtagatatt ggctctaaag   20340
aattattaag agatattaat aataccttt t gttattctag cgctttaaat ttactttat   20400
ttatagcatt atgtggaaat aaaaaactta ctacgtttaa gggagaccca tataaaaaag   20460
tacaagagtt aagtaaaaca gttacagatg taaatactgt atatagtgag tatatagaaa   20520
gtgacgatag gtctgaattt cctttatata acaaaagaca ctatcgtaat aatatatact   20580
gccgtgcaaa ctatgaaaat gaactaaaac agtttgacaa tacgcaaaat aagaatagta   20640
ataattacct tacaaaaaaa ataagagact taaaaagaca aataaatact acaactaatg   20700
atatacttga tgtattatta atgggtgact atagtatatt tggtattaat attgacccctt   20760
atgcatttgg taaatcttat gataataact acgaatacta caatgaagtt ttaaaaaata   20820
taaaaatagg gcttaacaaa ttaacaccta taaaagataa taatactccg tttttaatta   20880
agacttgtta ttttaaaagac ataagtatag taacaacaga ttggagtata gtaaacggtg   20940
actttaataa taaaaatgga aatgtatacc tacacctatc aaatacacta caacataaag   21000
aatttaaatt taatatgtat gaagatgatt ttaataagga taaattaaaa aataacatta   21060
ctttacctgt cctttaaat attattttaa gtaaatatgg aaaggaaaat ttagcttta   21120
acataataat ccaaacacta aagaataatg attattactt aaatctaagt agacttaatg   21180
taaaaaactt tgatgtatac tctatgatag atagacctga tggttatcgc acagttagta   21240
aaggtgaaaa tactactgat aatttaaaca atctgttaaa attagttgtg tctaatattg   21300
ataaagttta taacaacgaa gattgtgata tatttaaaga acacaaagag ttttagtaa   21360
taccaaacaa aaatataatgg aaattacatg aagctttaaa tttaagtaaa caaacatata   21420
ataagtttat tactcttaat aaagaagagc aagaaaatta cctaatata cttcgagtta   21480
tcataaaataa attcctagtt ttatataatg agtctaactt acacaaacta ttcgatgacg   21540
actttataat ggtgactaat tcatattcaa taggaaatgc tttatctttt aaaggtacta   21600
cgaaagaagt tcttaacttt tcattttctg acttagaaa aatggtgaat tatataaact   21660
atgatgtcag aaacagacaa cgtatacatt catacgctgt taataattta tatagagatt   21720
atatagactt tgcttcagac ctagtacttc ttggatatag aactaaagaa agtattaact   21780
taacaccata ttcttttaaaa ctagagcatg atatttgttac tgatgagtat ttaacagtta   21840
aagatgaagt cgatgactta aagttacaac aaaaaatga taataaatta aataatatca   21900
caaataaaga ataaagttaa acgatggct ctaaagttaa attttacct gcggatacta   21960
ctgaaaaatt aaaaagagaa ggtgaacagc tatctcattg tgtcggcagt tatgcttcga   22020
atattataaa tgacagatgt ttaatattac tagctagaaa agttgacgat ttagaaaaat   22080
catggtatac tgtagaagta aggataacaa aatatggata tacgttaggt caacaacaat   22140
ctttaaaaag tcatgagtta cctaaagaat taaaagacga attaataaaa gatattaaaa   22200
atataaataa acaatttagt gaggatgttg cgtaatggta aaaccagtta taactttaga   22260
acctaaagaa gttaagacat taatagagta tttaagtcat tttgaagaag atgtacgaaa   22320
atataaagat atggagaaat tatatgaaga attacacaaa aagtatcagc ttgctaaagg   22380
aaactacgtt gagtaatgga aaggtatagt aaagaatatg tagatataga cattacagtt   22440
agagcattag tacaaacacc ttatagagac ttatatgatg ttacaaataa tagaaacgaa   22500
ttagtagaag ataatatcgt cgttaatagt ttatcagatt atgttaaagt acaagaagtt   22560
aaaatataatg atatagatta aaaggcaaag gaactgttat attatatgtg tactttatag   22620
tacacttcca taatatcttt cctttcccct atctatattc tagatagggt ttttattta   22680
gatacgaaag gacaccaata tggatactag agaatttatt gactcacaaa ttggaagtaa   22740
caaagaggca acagaattaa aagaactaaa gataaacatt attgaagcat ctttagatgt   22800
gacacattct ttagatgaca cattatatta tgctaaaaag cttatgaaaa atgtagaaca   22860
actggagtta tactataatg tcaactctac cactaataca ccgaaccatt ataaaggtaa   22920
aaaagatgt ttatcatttt tagaagaata tttctacatt attggcttta tagactgcat   22980
gctatttaat attgttaaat atacaacaag attaggaaga aaagacgatg aaagaaaga   23040
agtagagaaa attaaaaccct ataccgaaag gctgttaaac ttcatagaat atggtaatag   23100
taatggaaga gaataaaaaa aagatacaca aatactttg ttacttatac ttctcagatt   23160
acttaccatc aaaaggtata gttgttttaa atcataaagtt tacctctcat gctacggaga   23220
acggagttaa aaattattac ataggtaata ttctaatga taacgcagaa ataacagttg   23280
ttatagactt aacggattta caaaaagcaa gtagtatgca aaatatgtta gaaatattga   23340
ataaaaatac agaatcttgt atatttaaaa gcaaagaatt aactactaag atggtaaata   23400
ccttctttaa aggagaaatt ttatgaaaaa attaaatata tgtttaacta ttatatcatt   23460
ctttatcaca tataaagtgt taacaaaaaa gaaaaagcat acacatgtca ttgtagactt   23520
ttcaatacaa gaccatgaac atttaaataa tatttgtaaa taaagggcaa tttgcccttt   23580
tttgtgtttt atgatatatt aacattgact aatagtaaag gagattttca atgcctcatt   23640
taaaagcata tgataaatac ggtaatatat tggcaatagg ttacaatgta gagttacatg   23700
aagaagtagg gtctgtaatc atacctaact tagctcctca cacacactac cctcaaggtg   23760
agttctatgt atcatgggaa gctgaaaaat atgaaaccga taagtagta gttcctggtt   23820
ttacaaccct agaatcatca ttcaaagaaa taacattata ttttaaagac catatacttg   23880
taaatgctaa atctgcttat gatgtagcag tagataatgg ttttgtcggt tctgaagaag   23940
aatgggttaa gtctattaaa ggagaaaaag gggagaaagg ggaacaaggt aagcaaggtt   24000
taagtgctta tgaagtagct gtaagtaacg gttttacagg ttcagctaca gattggctta   24060
aaacaggtaa aagtccttat gtatactcta atgagtatat aaagcaaaaa gatgatactt   24120
cggatgttca aaggttaaga cgtgctatta aagtacaag tgaaggtaat accctacaca   24180
ttccttctag tgaatcacct attaaaatag atgatacttt gataatagat aagaatatta   24240
atattgtatc tgatgctaag attgtttata atggtagtaa ggataaacca gctattaaac   24300
tagatatttt atcatattct aatgttacaa ttaaaggtat ttatgatgat agttcttatc   24360
caacttatgg tggaggctat catggttta agagtcaaaa ctatataggga ctagaattag   24420
ttaactgtag aaatgttaat actaatatta atgaaattat tggttttaca gtcggtaata   24480
aacataaagc tactggtggt aaaggtcatt ggttaataa tactattatt aatttcttta   24540
ttaataatga aacacatata gaattaaata cagatgtat aggttctaat ggtgagcaat   24600
cttggatgaa tagtaattac ttctataaat cagcttttc atatagtggc actgagttta   24660
```

```
ataaacaccc taacacatac tataacatca aacaaactct aacaaatgct aatacctatg   24720
gaggaaatag caatgtattc gattcactta aatttgaaac tgcttccaca acatctgaaa   24780
attatgttat ggtgtatctt aaaaaagcag taggatttat atttaagaat tacagatttg   24840
aatttaataa caaagctacc tttgctatta tagatttaga aacacaagac atgacaaaat   24900
cttatgtaac acatagtaaa gatattaagt ttattcctga atttgtttta ggtaatggac   24960
ataaactaac gtttacaaat attaatactg ctaaaatacc tagaagtagt attgctaaaa   25020
tagtagacga atacaaaaca acgttattgt ataaaaataa tgattttagc aaagactata   25080
gaagattagg aggtaactat cacacagtca aaaatgtatt tagaaaacca ttacagtcaa   25140
cttctctgac agatgaagta tcttatgact ataatactac acctagttta gtagatgata   25200
aaggactact tacctttaca ggctcgtacc ctatggcttt atatgttaat aatgttagtg   25260
ttggtgacga gctaattatt aacaagttat catttatagg taattctagt ggtatattta   25320
ttaaatgttt tgataaagac ggtaatatat tagacaaagt atctaataat tatgatacaa   25380
tattactaga tggttattat aatgataaat ataaagcgtt cactttcaat aacgcccaaa   25440
aagatacttt tactgttaat agtgaagatg ttaagtctat cgttatttta atatctggaa   25500
ctatgcaagg tttacttgta gattcaacta atccatccaa tattattaag tcttcaaacg   25560
atagtagcaa gaataaaact gatgtttttt attctcatgt taaaccttct agtgttgaag   25620
atttttaaata tgatgaaaaa gtatacaaca atggtacaac acaagtatat ggttgggtac   25680
taaaaggtaa tgattggaaa gaactaggta aagcactaa ttctaaggt aaagtaataag   25740
ttaatatagaa agattaccca agaattaatg atgaagataa tgactatcct agattccaaa   25800
gagcttttaga ttatttaaca agtactaagg gaggtaacta aacagttgca atagaaatat   25860
aaaaatatat aaatactttt gtattttatt aaataaaact gtttgccttg cttatagagc   25920
aatctgtaag taccaaaggt taaatgctaa gaaatcctaa agactcaata actaaaacag   25980
aatctgaaaa gataaatggt atagttacga aagtagaaaa aatattgagt atggtataag   26040
gttaaatcct aagtactgtt acaatggaag tttagcaggg aaagttctaa gggattatta   26100
atcctatgaa agaccctcaa cgactattcc gtataggtga cggaagtaaa gccacaagct   26160
attggtggaa gaaaaatctt taccctataa taatagggat aacaaatagt ctccgcccgt   26220
actgaaaggt agggcttgga aataaccaag aacatagaag tagcgttcta ttgttaaaga   26280
aagttaaaac ttataaataa tttaaatttt attctaaata actgttgaca ataattctac   26340
cttatggtat attatatact ataaggaggt gggaataatg tcagaagaaa aatataaacg   26400
tattaatatt agactattac caacaaaaga acaagaagaa ttaatgtgga aacatgttaa   26460
tcattcgaga ttcattaaaa attattttat tcagtattgt attgataaaa gagaaaatga   26520
aagtatttat tatagagata ctattaaaca tttatcagaa ttaaagaaac atttaactca   26580
actcaaaaag caaaaatatt ttaaatggtt aaaagaaaca agtagacact ctaaaaatga   26640
agctattaaa gatgtactag tttctttga aaaacttttac actaatcaat ctaaatcagt   26700
aaggtttaaa aagaaaggta agtatctaa tacttattct atcagaaatg atttattgcc   26760
tagtggttta tgtaggttta gaagagtaga gaatactttt cagatagaaa agttaggtag   26820
agttaaattt tctcaaaaac agtataaaaa gaataaacat atttttgatg aaatagaaag   26880
taaactaaag tttataaacc ctattattac tcatgatggt aaatactggt acgtatctat   26940
gctatataga gatgatttag taagcaaaaa ccaagttact gagttaacta acgaaaccat   27000
aggtatagac ttaggtatta aaacattagc cacttgttct aatggtaaat cttataaaaa   27060
tattaataaa agttctaaag ttaaaaaact agagaaacgt ttaaaacgat tacaaagaca   27120
agtaagtaga aagtatgaaa tgaataagca aggtaagaag tttattaaaa ctaataatat   27180
tattaagtta gaaaaagaaa taaaactctt acatagaaata cttagtaata ttagaaataa   27240
tcatattcat actatgacta agaaaatagt agaacaatat cctagtgaaa tagtaataga   27300
agacttaaag gtaagtaact taagaaaaaa taaacattta tctaatagta tttctaaagc   27360
taattggtat acaattagag aatacctac ttataaatgt gaagatagag gaatattact   27420
tactattgct aatacttact atccgtctag tcaaacatgt tctaattgtg gtaatcgttt   27480
aactaaacaa gataaactat ctttatcaca aagaacatat aaatgttctt gtggaagtag   27540
tatagataga gatttaaacg ctagtattaa cttaaagaac tatagatact ccaaatggta   27600
taacaatcat gttttaacta aatcaaacag taaacatgat atgtaggatt ccgtaaatcc   27660
gaattaacgc ctttggagta tcacacaaac ctgagtagag tatataaaag taactagtaa   27720
tagtgaaggt actcaaaaag ggatacgttg aaaaaggaat aaaatttata attatttata   27780
agttttaact tacggcactc ttatagtacc taaaggaaca gaggactatt tattcaaaac   27840
taagacacct actgtacaaa acccatcacg tgtaaaagta acaggaagta atatacacat   27900
taaaggtgaa ggtaatccta catttattat gtcaggaatc actaaaaact atttagactc   27960
tatagatgat atttcttcta gtggtagaga tatgtttaca ggattctcat ttatcaactg   28020
tgataacatt cttgtagaag gattaacatt taaaggggaa tgggatagta aaggtgaatt   28080
tagatatgcg tcacctcgtt ctattggagt agcgtttaaa ggaagtagaa actgtaaagc   28140
atataatgta catggctata atatcatggg taatgttgta aatgcagtaa acactatgca   28200
agcagtagat ggtgtttatg gttactact caacattact atagatagtt gctcagctac   28260
acaatgttta gagaatggtt ttaactttat gggtggtact aaaaatggat attatgttaa   28320
taatatatct acaggaaatg gttcaagtgg atttgaatca ggaacagaaa atgttattat   28380
aagtaataat atacacacaa ataataagta ctcaggtttta agtatatctg gcactaatta   28440
cacaatcact aataacgtaa tttatggtaa tagtaataaa ggagttaa gtaatacc     28500
atctaatggt attgctatta caggaggtag taaggaatt attagtaaca ataatgtatc   28560
aggtaatgag ggttacgagt tgtaccttta tccaggagtt aataacatag atatacaaaa   28620
taatgtatta aaacaagata caacaagttt aaaaacaagt attatttatg cctcaggaac   28680
aactagtaaa cctgtgtcag aaattaactt taaaaataat acattaagaa gtacaaatac   28740
tgcttttggat aaagctatgt tcttaaattt tgttatgat agtacaatta ctaataatga   28800
tataaaaaca gataaaggta atgattcatt aagtgttcaa ggttcttgta gtaatctatt   28860
cgtattaagt aacaatatga ataaaaactt agtatttct agtaatgcat taaatgttat    28920
aagtaaggat aacatagctt ataatttacc taaagtactg aacggtactg caataccaac   28980
tacagggagt tggagattgg gagatattgt tgttaatact agtagaaccc taacatcagg   29040
tagtcctgag aaatggagat gctactagcg a tgggattgct actaatatga gtggacatc    29100
taatacggat tatacacaag gtcaaattgt ttataatggg aattatgtat ataaagcagt   29160
agcttcaggt acaagtggtg gaacacaacc tactcataat aacggtgtta tcagatgg     29220
ctctatactg tgggaattta tatccacaaa agctaatttt gaagtcataa gccaaatagg   29280
tgtaactgaa agcattagta atatacctt atacaaaggt caaattgcta ataggttc      29340
atctgtatat gtagctaaag gtacatcaag caatactgat tggataattt taaattagta   29400
```

```
aaaagggat ttaatgatga cagaagacaa tttatattta tttaaagcac acgtggacaa   29460
aatagtggat ggggatacta tacatgtaac tattgaccac ggaatgagaa catactctga   29520
gcaaagaata agattactag gtgtcgacac accagaaaag aaacaaaata attaccaaga   29580
agctaaggaa tttacaacaa ctatgttaga aggaaaagat gttttaattc aaacatacaa   29640
agatgattct tttggtagat atttagctaa agtgttctac aaagaaaata aagagtataa   29700
aaatattagt gaagaattaa ttaaaaaagg attactaaaa gaaaaagta aatggaataa    29760
agaacttgac aaacaataaa atatatgcta tattattata gtagttaact aacgcctctt   29820
aacaatgcga aacacagtta gcatttttta accttataat gagagtaaca gcctaaccat   29880
atgggtactg tgaaatcatt atattctacc tatctaccat cgtagaaaag gtctacggta   29940
acgttatgac cctatttagc gttactagca atcctgagta atggcattgg ctagttgtag   30000
ctacctagtc gaggggttcg agtccctgct caggattttt ttttccacaag atacctacta   30060
aaatatctta cacctactta tttttaaagt aggtgttttt tttattgact tctatttact   30120
tatgtgttat atttactata tactaaaaaa aggaatgatt attaatgact aaaaaaatta   30180
aaaatattga aattgttttt gaaaacttag atagtgcggt gttagaacca gaaaatgtag   30240
agttgatact agaaggtatt agtgaagaaa aaactatgat atatggaaat agtgaagtag   30300
atacaagtaa gtcagcaaaa aaagtttcta ttgaggtaag tggtatgaag gatgaatact   30360
ttgaagagtt tcatggtttc ttagatgagc cctacaacat ggcattatat gatagattaa   30420
gtggcaaaga tattgtttgt gtttgtttga attatgagga tggtacagac gatactgtat   30480
atgtaccttta tcctgagtat gggcagtata attatatgca gagaaataag tacgaaaaag   30540
aaatagacac tttatttatt acaatagagg atagagaaca agaagaacat gtaccaaatg   30600
atgaaaaacc taacttttaat gaaggtgaaa cagaagaccg cacgctagaa ggtttaatta   30660
gtcaagtaga ggaatggagt aaagataaag gattgaacaa taacaacct agatagacaag   30720
cccttaaatt ctacgaagaa gcaggtgaag tagcatcggc attatcacgt ggtaacctag   30780
aagctcttaa agatggtatt ggggacactg tagttacttt aattattta gctcagcaac    30840
acgacatgtc attacaagag tgtttagagt ttgcttacgg tgaaattaaa ggtcgtaaag   30900
gaaaaacagt taatggtacc tttattaaag aggaagattt aaatgagtga taacttttagt   30960
caatttataa gtaaaaaaag caatgaatta aacaaagcta cagaaaaaca aaaagatttt   31020
atctataatc atatagattg tttatatgat gagtttactt ttgatataga gtcattaagt   31080
aaagatgaag ctactgaact tataaatgat ataactatag agttaagctg ttcagatgat   31140
tttcttgatt ggtatgacta tcagtaaaga ataagcaggt aaaggttttg aaagccctta   31200
cctgtttttt atatgctata ttattaatgt atcatacaac agaaagggat aacattatgt   31260
ctaaaaaatt aaaggtctac aacaaagatg aacagctaat tttaacttct gatgaagtta   31320
caggtagttc tgtaaaagta acattaacag atttaaaacc taatactact tataataaag   31380
gtgactttaa agtctcttgg ttagtcgatg gacaagaatc taataaaaca gatgtgccta   31440
gtttcaaaac attagagagt gaaaaagaag ctgtagctca gcctgtcatt gtaaacacat   31500
tagatatggg taccgacggg tacacaatca gcaatgaacc acctaaagac actaacaaaa   31560
tatgccttaa atcggaataa gaaaggataa actataatgg caaacttatt accacatttt   31620
tacaacacag aaacaaataa atgggaagaa ctatatacaa aacctattgc tagagaagta   31680
tttaatatca tgaaagaaga ttatttagct cacaaaggtg aaataggcta ttacattgct   31740
aagtacaaag atggagacac aagtattgag caacctaatg ttgttgtttt ttatgatgtt   31800
aacgattatg aaacaatgac tttaaataaa gaggaaatga caagactatt aaatgattat   31860
atagataata atttacaagg aaagtttaaa ccctttttctc ttactaaatt cttacaaaat   31920
ttagaagacc taaattacgc tttaccaaaa caagaaaat ttcatgtaga tacaatccag   31980
tcggataaaa gaaaatttct atttcctgat acaaatgcaa ttaacacaaa ccctgatatc   32040
ttagatgccc ttacggctac agataatcat gtatatatgg aagtaaaata tttatataat   32100
ggtcatccta ttgatgataa aaaattaata aaaggaaacc aagatttaaa aaattaataa   32160
cccagtaaag aacctgtaaa aaggttcttt tttttgctt actgaaaaaa gtgtatagta   32220
ttagttgaca ctatattgat tatatgttat agttaactta acttaaagaa aggttttgata   32280
gatatgaata agatatatgt tatatatgca gaagaagatt cctattatga tgaagaacct   32340
accttagaag taataggta cactactaat atagaagaag ctaagtatat taaaaataat   32400
tacgatgcat ggtgtcgtat tataagagta ggggaagttg aaagacttac aaaagaaata   32460
cttgataaaa aacagaaact atataaacta atgtcaacgg cagtgataca aagagagcaa   32520
cattatttta aacccataca agaattaaat acaattgtag atgaggtatt taattcaagt   32580
aaaccagata ttgactttaa tgagaaatgt gaaattatcg tttattcatt aaataaaaat   32640
caaattcagg tagatatagg tttacttttc cctactgagc caacagaaaa gaagtagac    32700
agtatcgtta atgatgtaaa aaacaaaatt aacttcatat taaaaaactg tgaaaatgct   32760
gacattagag aatcaaaaaa gattatgaaa atgatagaaa aattaaataa ttaggagata   32820
taaaaatgaa aataaaaact aaaaaagtaa tgacgctagc cgaacttatg gaatgggctt   32880
gggaatatcc tgatttaaca aaaggaaaga gatttttacac agaaaatcaa gataatgaga   32940
actttgttta tttttcttcg gaagacggaa gaaaatgtct tgccagtgaa tttatatcag   33000
ctgacgacac ttttgaagtt gaagtcgaag ttgaagagga aatcacagaa gagactaagg   33060
ttgataggtt gattgaatta ttcgagattc aagaaggaga ctataactct acactatatg   33120
agaacactag tataaaagaa tgtttatatg gcagatgtgt gcctaccaaa gcattctaca   33180
tcttaaacga tgacctaact atgacgttaa tctggaaatg ggagttg gtagaatgat     33240
gcaaacctat aaagtaagtc tttgtatcaa gttcttagcg tctaaatgta attataaatt   33300
aaaaaagcat tattttgtgc aaagtacgaa tgaggaagaa gccacgaata cggtattaaa   33360
actgactcgt aaaaagctcc cgttccaaac tgcaagcata gaagtagaaa aagtggaggt   33420
agtagaatga tgcctaaata tcgagtgtgg gacgaatata caggaagaat acacgatgtt   33480
gtaggattcg acttcatcga gaatgaagtt cactatgaaa atactacgcg aagcagaagct   33540
ttaatacacg caagagattt caaagatgta gaacttatgc aaagtacagg acttaaagac   33600
aaaaacaaca acgagaatata tgcgggagat atagttgagt ttgaagatga aatattagag   33660
atgccagacg atgaatctgt aataggaaca attaatagag cagtaatatc tattgatgtt   33720
gtaaatggta ttcaattaaa agatttatg tttgagagcg caatctccga aaatgattac    33780
tttagtata cagacaaaaa atcttccttt atgtacgat gtgaggttaa aggcaacgta     33840
tttgaatcat ctcatttatt ggaggtaata gaatgatacc gaaatttaga gcatgggata   33900
aagaatcaca aagaatgttt aatattgcta gatttgactt tgcagaccat acaatatatt   33960
cacacctatt tgcttgtgat ggttacttag gagaaaaacct tgtaattatg caatctacag   34020
gacttgaaga taagaatggt actgaaatat ttgaaggtga tatacttaga tattgggggg   34080
attgtagacc tgtaatattt aaagaagctt cttttggatg ggttgaaggg ggagattaca   34140
```

```
taccattctc tatgatgtgc atttcagaga ttggtaatac tgaagttgta ggaaatatct   34200
atgaaaaaag gagtaaaaaa gaatgaaata ttaccaagta gagcatgata attgtgagct   34260
atacgaagac agctactctt atagagaaga taaaatatat actagtaaag aacagcttat   34320
taaagacatt aaatctgaag gatacaaaga agtacaaggc atgtctagaa atcatgatgg   34380
tattgcttac cttaaacata tagatgaatt tagagatgat atgattacaa ttcatgaaat   34440
agaaattata gataataaat aaaggggtat tatttatgta tactaatgaa tttattgaaa   34500
atgtaaaaca gttaggctat actgttacca tagcaaataa gaatactacc aaaaggaaag   34560
aaaaaatact tattaaaaaa gaaaaccaac aacctattgc ttgggtattt ctaaatgaac   34620
catattcttt tcgaagctta ggcacagata gtgagttatt tgatttaatg gtagaatatg   34680
caaaaacacc tgtaaaagaa cgtagtataa gcaaatatgc aaaagtaaaa cctttagact   34740
tagataccct tacagatgac tatgctaaag taagagagtt tatgctaaaa ttcataatag   34800
acatggaaga catagtagaa tacattcaat atacaggata taataagaat gttattaatc   34860
attggacaga aggtcaaacg tttagagcag tagataagca aggagacaat aacctattta   34920
ttaatacacc taatggaatt gaaaaagttt taaaagataa ttatatcata aaaggtaaag   34980
agcaaggttt cgaacaagta gatagagaac tgtttgaata tagatatgat atttcacatt   35040
aaacacctat gaactattgt aggtgttttt aatattataa gaaagatatg taactactac   35100
tactataaat tcaacaggga taggtaggac aataagaaca ataatggaaa tcttattatg   35160
ttgacttttt attatattgt acttttataat gttgacttt aataataaag tataataa      35220
tactaactac taatagtaca tagtataact agttattaaa atagtatact aaagaccact   35280
atagcaacct catatataaa aaaaggctcc tatatactaa actacttata tgctgtaata   35340
tactaatact ctaattaagt gtaagggaag aaggggatat actactaact ttattgtaaa   35400
atgaatacca ttagttatta gtaatgttga catagattaa agagtaatgg ttaatgttga   35460
cttttaataa taagttatat aatattactc actaattagg ttccttaggt agccccatag   35520
ccctgtcaga cccacccacc tatattaaaa taaaggaacc tttaatttag gctccttata   35580
tttttttaaat actcgtccct ttcttttttc attcttgata gtttttcttc tacttgctta   35640
atattatggt caaaaggtat atagtctaca agaccaagac tatgtgcttt tttaatcta    35700
tccgtaatta ctgaagtaga agtacttaat tctttactaa ttttttttaat accataacct   35760
ttactgtata aatctataat ttcttgaata aatccgtttt ccatatattt atatacttct   35820
ttccaatcta tacattcggt aggtaaatca ctgcttataa tactttgttt aatatagtca   35880
aagctgtgtt ctcttacatc tatttctatg tattttagtc cgtggggaaag tgcttgactt   35940
ttcttccatt catcgttttt cttattttct tctaacgtta agtgaaacct ttgaccctct   36000
ttttgctcta gataatgctg tacaccatga acttctataa cacaatcgta ctcaggtaaa   36060
taaaaatcat aacgtttacg attagaccaa tcaaatgatt tttcagcagt ataaataata   36120
ttttgttgtt ttagtacctg ctctaccatg gactctcctc tacttctgtg tttattaagt   36180
tccttaaggg atttcttcat agaagaacag tccgcacaat aatccctaga gtaattattt   36240
atgtgacttg ttttttatttt ctttatcata ccacattcat tacattctac tataataaaa   36300
cgtgttgttt ctatcttacc atctttagct atctttttcct ccgttatatt ttcctttaca   36360
gtgaatttc ctaaagtact acctacatca taagggtaaa cataagggtc agcaactcgt   36420
tgtaaattac ctataataac attaagagca ttatacaaga aagtatcccc attactattt   36480
tctaatctaa catattcaat aaccttacct ttgttatttt gtttagaaaa agcatctata   36540
attttaagtt ctccttttatt atcttcaaaa cgatatgtaa aagaaagacc tatactattt   36600
ttaaaatcta tatcataaga taccttacca taatactttt cttatcaag tttaggtagg     36660
ttatttaagt ccacagaacg tttaccatta aatctttaa taaaccttt tcttttacgt     36720
tcactgtatg ttacttttatc taatgctact ctattaagag aacttatagt tattgttcct   36780
ttttcatttt tgtacacata atcataagtt acctcaggag tttagactt taaagttaaa    36840
tacatcttat cctctaaacc tttataacta aaaggaactt ctatatttt cattttttct    36900
ataagactgt aattacttt tgtatactta gtcttttta aaggtaggtt agttaagtct     36960
acccacacct cgtgattact cttattaact tttataatat ttttgtccat attttaata    37020
cctcgttttt tactatctac ttataatata acacatataa aggtgataca agaggtataa   37080
aaaaaatcgt tgacttatat taaaataatc attcttttat ttattgtttt gttgactttt   37140
gtattactac tatgtagcta taccatttac atagtacctg gacagaccga tataggtata   37200
taaaggtgt ggtattagtg gtattttacc cctgccccg tataatatat ttatattaac     37260
ctattgtata caatcctaat aaataataaa aaaaagaaa gggagtttat tccctttcaa    37320
tttgttttac atcatttcta tagcttctgc tttaatttgt tcgtagtctt taatccatt    37380
attagattct tcaacactca tatgttctaa catataatca gctagttcaa acactttgtt   37440
accaactaat cttgttgttg tatcgtctgt aaagtctagt ttagaaggta tatgttctaa   37500
tgctgtgata gctttattct cttttagttg gttaacaata tggatatatt tacctaatgc   37560
gtcgtgttca ataacgtcta tgtctattgt ttcatagaaa gctgttaata gtaagtcaag   37620
ttcgattcct tcaagttttg ctgttttgtt cccttttggtta ttaatttca taatttatca   37680
atccttttcg tttattgtgt tttctttata tttatatatt accatgtatc ttagtaagtg   37740
tcaacacttt tctttaactt tttttaagaa gttttacact attataagtt aagtaattct   37800
tttataacgc ttggtgctag tgttgttata tcatagtctt gcttagttc gtctaagctg    37860
ttgtaatgct taatagttcc agcgtctttg tcactgctttt ttgttgtaat ttttttgtta   37920
atagccttgt ctatatcctc aaggctatta acgttgtcta ttaggtttat taaatcagtt   37980
tcagttaagt tcatgtgtat tgtctcctta gaataacatt tggtagcgt taaactctag    38040
tgtatcaaca tccataatca tttgctcaaa ttgttcttg ctcatatgat ttaaaataat    38100
gttagtaaag tgttctgctt tgtcttgtgc taatgtagca ccctcgtaag tgctaaagtc   38160
aatgttttgat ggttttacgtt ctgcttgtgt taattcttcg ttgtttaata ttgttgttc   38220
taagtgttcg aatttgtcta gtgcgtcgta ttcaagtatt tctgtcataa ccgcttcttg   38280
aattgctaca actaataatc tttctaattt aatgtttcca tttgcctttt ctttaattgt   38340
gttttttcata atttatcaat ccttttcgtt tattgtgttt tctttataat tatatattac  38400
catgtatctt agtaagtgtc aacactttc tttaactttt ttaagaagtt ttttaatgtg    38460
ttgctgttcc ttcatctatt tatattacat gataatctag tatatgtaaa gtgttttagt   38520
aaaataa tagcaatttt acactagctt gaagcggttt aaaaagcataa aaaataaggg      38580
ctaataaccc ttatttaata aagatattaa tattgtcttg taacctgata aaccaatcaa   38640
ttaatgtaat tattgtcgta ccgcctaata tagttacaat agcgtcagtc ttttctgttg   38700
aacggtagtt cttaccttg tatttaaatt taatcattat agttagccct ctttataatc    38760
ttcctgtatt aataaataac tctaattgtt tgttaactc gtccatgata aagttatcaa    38820
gttcatgagc agtaatgttg tattttttgt ttcctgttgt cattgaaact acattgtaca   38880
```

```
cgttgtcaaa tttattaaag taaatgccgt actgtagtaa accccaatca ttgacataga    38940
tatcagtaac atctaaatca ttatgtttgc ttgaagcttc gttatatgtt ctaacaactg    39000
tgtaatcttg gtttaattcc tctaaagttt tataagtttt cataatttat caatcctttt    39060
cgtttgtttt attacatcta ttatattaca gtatcttagt gataaagtca agtgtttgtt    39120
taatattttt taataaattt tgttttgtta ttatcaagtg ttagcttaac acatttgtct    39180
gttactgtaa tttctttttac acctttatta taaagactat gacaagcctt attaatatga    39240
tagtataagt catcacattc atcaatatct gaccatagtc tatagtcatt tgatattgtg    39300
ccttgtgttt taattctgtt gtaagtacct ttaatgtatt ctaaatatct gttcatttct    39360
catcaatcct tttcatatta tttattacgt ctattatatt acagaagttt ctatataaag    39420
tcaataggtt attttaaatt tttttcttta attacattag cgttgttatc cactaagtat    39480
aacatgttat tcatttctat aaataagtgt tcattaactg ctttaacgtt tatattaata    39540
ggtagcttgt ttgaatgtga tacgctaaag actttcgttt ctttaaatag ttctaatgtt    39600
tcatagctat catcaatata gctaaaatat ttaacttgat aatgtgtaga gtattttaag    39660
tcatttctat agtagttatt gcttttgtaa ccatctatat ctaataattc cattagtata    39720
tctccaattt tatttacgtt catatcctat caattccttt cggtttgttt actacgctta    39780
ttacattaca gtatcttgta tttaatgtca ataggttata cgaaagtttt ttaaataaat    39840
gttttcttac cattatatag aagaaactag aaagtacagc ttaaattaat tattataatc    39900
aatcgattta attgtataca atgcagtgta aaactaacca tttaatttga ttaaaggtat    39960
tgcatttata tatcagtctg ctataatagt atttgtaaga taaataaaag aaaagggatt    40020
gattacctat gaaagaaaca cacggatata aatttgataa aagaaaaagc atgctacaaa    40080
atgcaaaaga aaaaggcatt aaaaaacatt aaataaaaac agtgacatta taagaataaa    40140
agaaagtaga ttaaaaatag ccaaaataaa taatgatata gaaacaatta aaaaattaga    40200
aaaagaatta caagaattat ataaaagagt tatagattag gttaatagcc taatcttttt    40260
ttatgttgtt tgaagcggtt aatataaagg gaaacagcg gctgctactt aggaaaatca    40320
tagatttata cttatgatgt ttataacagt aagagagcct taatcttata ggtctatatt    40380
caacggtaat actttttagg tagtatttat cctataactt tacttgctt atataatgta    40440
gttaaatagg caatacaagc atataaaaaa tctagggtaa aaacaaccct agctacttaa    40500
tttgattcaa aatatcctta acagcttcta atgttaaatc tgataactta atattcttat    40560
cactattagt atcaataatt acagtatagt tatctacatc atactgtata actttaagta    40620
ctgaataagt aactaactcg tattctgtat gtgtgtaata ttctatcatt gcgtaccta    40680
tacctaattc agttaagata ggttctaatg ttttttcttt ctccataaac tcttaatag    40740
tatattgcat accgtcttta cttaaaaatg caggctcgtc attgtaaata taaaataaat    40800
tctcaataag ttctagtaaa tcttcttctg ttccctcaca aagacttact gtataaagta    40860
attcatcgta taatttatcc tttgcttctt gaatattcat tgatattcct ccttatcct    40920
atcctaagtg tatcataagt tttaggtaat gtaaagtatt ttatttttaat cagtatctaa    40980
cttatccgct tcattaatcc aaccttaatt taatccctga tacttacctt ttatcataca    41040
tacctgtaat aattacttgt ctgcagaaaa ggtctaaagc tttcatattc aatatatttgt    41100
agtaacaaaa catacttagc aacttgtaac ataactgtaaa tattattata atgctgttgt    41160
aactaaattc tcatctaatt ctcataaaca tatgttataa tctaaacaac aagtaattaga    41220
ttgttagtat tttaatacga ataacttatt acaggcgtta ccttgttgta gcgtagcgta    41280
aaacaacaag gtatacgctg ttttgttctt atctttttaa aaagataagt cgtacggtta    41340
gtacgaaata caaatatata aataagtaat aacaaatatt tatacataac taacagataa    41400
attattagat taactatgtt gaaacgggca tactatgctc aaattgatat acaattatta    41460
gccaagatta aatacagtat atttactcag aatgtaaata atgtataaaa aagaagcggt    41520
ttaataccgc ttctacttct tcgatatgat attgtaaata ctgtttatct tcttaaacta    41580
gtttagttaa agcatactca ttctcaataa gaccataacc atactagata tcttgtaaca    41640
ttagtctagt tcctacaagt gttacggtat cacgttggtg ttttattaatg tcagattctt    41700
cttcactagt atatttaaatt atttaccaaa tctttctttta gcaatcttt tcatttgttc    41760
tttacgctcg ttacttacag gttttcttaa cgtaattaaaa tcctcatcta atataacttt    41820
aacgagtaca ggtgtaccat tatctcagttg ctctagtact tctaccttat ccggatattt    41880
tttcataata tcggtaatat aaggttttcct acttgcgtaa aaatccatt gcccttgtt    41940
ataattcata cttacttctt gttcttcaaa actatatcct ctacttacaa ctttagccat    42000
tctaataccc tcctttatat ttaagacctc taaactaggt acgttaaaat tctgtattaa    42060
acggtaatca ttttctagta gtatttatcc tataaaataa cttaatcttt aaaagcctaa    42120
taatcttttaa tctgtacaca ctttaaaaaa ttcatatgct ttttaatct tgtccgcttc    42180
ttttccttca ttcatttcta aacctttttc taaaaacgct tctaaatttc cattccaaca    42240
tcctgcaaat acagtgtcta aactaggaat ataagttacc ttaccattaa aagttccaat    42300
attatctata gagtaaatat tcagtcctat aactcctgtt atacttgctc ggcttagatt    42360
agtaaacttt aaaaatgcat tatctaaata agaaaatcac aaatcagcac tacttaaatc    42420
tgtagctgat aaaaatagcat agcttaaatc agcgtatctt aaatcaacat attttaagct    42480
ggcgtgtgtt aaatccgcgt tacttaaatc aatatgactt aaaatagcac catccaaatc    42540
aacttctctt aagatagccc ctgttaagta agcatgactt aagtcagctt tacggagaat    42600
agctcttctt aaatcagcgc ctcttagatt aacacttctc aacatagtgc aacttaaatt    42660
tgctctagtc ccttctacgc catcactgtt caaccataat tatgttctt ttaatcttt    42720
atctaattct tcttgtgtaa ttgttttcat aataaccaac tccttaatc tttatatact    42780
aagtataaac catgctcata tacttgtcaa ctacttattt taaaaaaga gcgggcaat    42840
agtccacttc taatagtatt tataatataat tagtgattaa cctaactgtt tctaaggtaa    42900
tagggttgct tttactgtct acataagaca gttcactatc gaaaccagag ccacttaaat    42960
agatttgatt actttccaca ttaaatacaa ttaatttagt agggtctact ttactaaaca    43020
ctactacata ttccttgtca ttggctaaag gaagaataga tccgcctgtt acttttttgaa    43080
ttttttgat tacaacagaa tcgtcttcca tcatagtttc ttctttgttc ataccttctt    43140
gtactatttt tcttttatt gttttcattg ttatttcccc ttatccataa atacagtaac    43200
tacaatgttt tgtaaacact taataatctt atctctttga gtaccagata cttcatcaa    43260
tcttctgta ttatctaaga agcggttaaa ttcatcttga ttagtaaaat ctacaccttt    43320
attagtctca tctaaaaatt tctcaataac tcttttctgct atttttttat tactactcat    43380
tatctattct cctttattt tttagtaact gtataatact cgtcatcagt aagtttacta    43440
atatctatat cttgttcaga aaaatataaa ttttattatt ctttacttaa ttgttctaat    43500
acactatcaa tgtatatagg tagtaccttc ccatcattaa aagtcacatc aacactatct    43560
cttaagtata tatgtttctc actcataatt gtataaatat tatagtcttc caataccta    43620
```

```
ctcccaatta acgctacttt tccgttactc atattaagca ctccttttat ataatatttg   43680
aagtggttat acttcattca tagggtattc cagataatac ttaattgttt gtaaaggttt   43740
atgtacatta gtgccataac cataggaata aattccataa gtatcagagt aaaatttctt   43800
tatatcaatt aactcaactt ccctatatac ttcaaccttta tatggagata ctacaaactc   43860
ataatctcct cccataaaag tattatatag tacttgtttt aattcaagac cactagtgac   43920
tatatcttta tagaagaagt tgagataatt atctactgta ttaagaaagt cttttacacc   43980
tgtatactct ttataaatat taatccaacc taattctaat tcataatata ggttaccctc   44040
ttcatcaaaa cttagtttaa gtttaaccgt atcaatatct ttacgatgta tattaaaaga   44100
ttgctctaag aaacctacat cccatttatg cttaacaagg aaatactata ttatccgctt   44160
cctcaaacct agcaatgata tgactgtctt tatatacaag aatataaata aggctattac   44220
ctactctaca ccttacttta taaccccctac ctaagtacat ctcataatct gtaatactct   44280
ccattatgcc agtaacttct ccatacttcc tacaaaactt agctaatttt gacatagtaa   44340
ccaactcctt tttttacctt taaacttttc ttctagggaa aacctatcta attttaccta   44400
aatgtcaacc atagaatgcg ggttcaagcc ctattttttac ctttgactac ttttcctag   44460
agaaaaatct cttcttaaat agtatctaat tgtttatcaa acatagagta aatttcattt   44520
tgatgttctt tgtcttttag gtacttatca tattcatata gtagtatatc atacatactt   44580
tctattaaag tatctaaagt tgaaacatgt accttatcat ccttgtctag tacttttact   44640
ctatatgtat ctaaaccttc caactaaca tcatatacaa caatatgaca agtaaaagat   44700
tcttttttca tatgaaaact gtaaatatat ccgttactgg catgcttact ataatgagaa   44760
tacgtaaacg cttttatgcc taacctgttt tctaatacct tatttaatac ttgtagtttt   44820
tccatctata accctcctta tttaatcctt ctataaccct ccttatttaa tccttttttaa   44880
attacatacc taacatacgt agtactgaag cggatataag ttactcatt ataataaaaa   44940
ctacaatagc aaatatagct gagactatat ccctatcttt aatagatatc actaagataa   45000
cacctaaaat agtaagtaag aaaagttctg aaataccctag agcaacacat accaaaataa   45060
aacttaacat ttataatcct ccttacttaa tctcacttaa gctacatatt taacactttg   45120
gtagatataa gaataataac tataataaga gctacataca ctagtgtagt tgagactata   45180
tccctatctt taatagaaaa aagtgtaata gtaactaaac aagcaagata tatgccgata   45240
ataaaccaac ttaaaattaa catctaaaaa ctcccttact taatatgccc tactctatat   45300
acctaaatac acctaacaat gtaacaaatt aactattaga taacctaaac tcaaacaat   45360
agaaatagta ccaatacaaa tactcataaa taataaacca aacacacaag ctgattctaa   45420
atcactaaca ctatcataat tatcaagtac atgcttataa tacttcttac caaacccttat   45480
acttagtaca ataccaatag tagctaaaaa tatagcaacg atacttataa atatactcat   45540
aaaactaatc cctcctttta ttgaagcggt ttttatttcc attacttacc tcacaaaaac   45600
cgcttcctaa ataccaaata aagctaatat acttgatacc agtccaaccg tcataactgt   45660
aaatgatacg atattagtcc acttatcaaa cctatcatac ttaattgact gaaccattc   45720
tactagcata aaggtataca taaacaaaac cattacagct actattgtaa gtaatattgt   45780
tagtcctatc atatttatct ctccttccta tcagacatat gatataagac agagagtata   45840
aaagcaagta caaaagtaat tacaaaacca ggttcaaaag gagctaaaca tgtaatagga   45900
attacctctt cccctatgat taaattccct acccacatac ctaaaattac ctctgctaaa   45960
caaaatatat aacgtaaaat aaactccaat gctttactca acttacttcc tcctttataa   46020
ttattctcaa gtaaacttta acaaaatact actttaataa cctttgttta aagaatctta   46080
ctacgtcttc accataataat acagataaaa atacattatc ccctgtaacc ctaaaaccac   46140
tatctataca tctattttcg atgtagtagt cattaacttt taatgtactt atatctccta   46200
aaacttctat gttatatcct aactgattta aatgtacata aatatctgat aaactcataa   46260
tacaactcct cgttactaag tctttattga agcggttatt taacccctct atatactagt   46320
actacacata ataatacaag tgctgtacat ataagtat actgaatatt actatatacc   46380
aaatcacaat acgttaccat cttttccatat agtaactaac tcattatcta caacagtact   46440
aacagacaat aaccatgtat ttttaccttc gacatagtag tcaataactt cattaatact   46500
acttctatac catactgagt ttaatacact gttaccttgc ttataagtaa ctactatact   46560
acttaactca gtagaagcat ctataaccac ttctacaata aacttagtgt cattaggtat   46620
agtaatagta atagattat taggatacaa tgcattataa aacgatatat catcaacagt   46680
tataacaaca ataaactgac tatcagtaga ataagttcga ccttttttta tatcaccttt   46740
ataatacata tacattaatt ctataaacga aacttctctt taatcttca taataaatca   46800
tctccttttaa ctttatatac ttagtataaa ccataagtaa tatactgtca acacatatgt   46860
gtaaaatagt taaaatttct ttattgttcg gaaattacta aatatattaa actttttactc   46920
tagggaaaat taagtcaata ctaccacaga aacaaactat atatatatat taaataagta   46980
atgttcagaa ttatagtata tcatatacac aatatctaat actaaatata cctttataca   47040
cagtaaaatac tacttcagct tagtttaact acacattaga atagtttagc ataataatcag   47100
catagtttaa tactacataa gcatagttca caatagttaa aactatataa aaatatatag   47160
ttaggtatct aatagttaga cacctaacta tatacacact atgaaggagg gaagcagaga   47220
aattcccatg tacctgttct tacttactac ttactactta ctacttacta cttactactt   47280
actacttagt atataggtat accatgtacc tgttttcttt taattactta ctagctatta   47340
cttatttatc tatctagaag atgtaaagaa attactaggt aactgttttt acctaagtga   47400
tagtggtaac tattttcttt tagctactta cctactatt atttactatt acttactatt   47460
agaatatttta ttaatactta agttacttaa taattctttc ttcttattca tatcttcaaa   47520
ctgttataca gtatttattt acttatctat ttagctatta cttatatact acctactacc   47580
tactacctac tgcttatcta tgtgctatca attattgttt ttttatctat tacttatttc   47640
cttgatatat aggtacttat aataccagtt gtttcttttac gtgttactta tctgatttct   47700
ttatctactt atatatattg ttttctttta cctattataa atttatatcct tctcaccta   47760
catcaatctc tataacctatt tgtttgtctg tttggttgtt tggttgttta ctcttctaca   47820
cttacctata tacatgtcta tatctttttaa ttacttctttt actatctata ttagagtatt   47880
taaatgttct ttgtaggtta cttaatatat gtttaaaggt agactttcta gcatcaatct   47940
ctatatattg tatactatttt tctttacaat attctctctt ttctatgtct gataaattttg   48000
ttttggtggtg gttcatgtat ccactgactt cttggtaatg ttgaacattg tttagagcaa   48060
ggaagataag tctatatagc ttataacacc ttgttttgt tttgaataat atatgtcttg   48120
ttcttttccag tattccataa taagtgctcc tcttactctt tattgaacct gttcctccgt   48180
atcttgatta aacactttag catttgggtt atgtgtttca ccttcttgat actctgtacc   48240
ccataatctt ttacgttctt cactaacatc tttgtgttct ccattattct caggtacgta   48300
tgaagtatgg tcatctgcat cttcattatt ttgagattct tggttacttt gttctacttg   48360
```

```
ctcttggttt ttcaacacat tgattattgt tagtacaatt agtacggata aaactaaact  48420
taatatttt  ttcatgatta atgtctcctc tataattatt taacttatat acttattata  48480
aaccttacac ttattcatgt caacacttat atatgaaaaa agtagggaat ttccctactt  48540
cttccttttt taaaatacca cagtattatt attcaatgtt tcctctacta tttcctttat  48600
atcaattgct ttttgcacat acctgttagt tagtagcata tcatctctat ataccttaac  48660
attagataca tcatcactta ctacaaattc gtatttactt gttttagtag cagtaatttt  48720
aaaataaggt ttaatatcta cctttaattt atacccatta atagttctta cttcttttac  48780
ccagtcatat aaatcaattc taacaaatct acagtaagct tcatacttat cacaaaaatc  48840
ttctagtgta ctaaagtctt gtacataacc attctttagt attttagcag ttaaatcatc  48900
ataaatatat attgtagtat aacctaacac atattcattc ctacgattaa gcaactcatt  48960
tttaaatgta tgcttagctg tgacaggtac tttattaagt atatctttta atttatttac  49020
ttcatccttgt tttaataaga tactcgactc atatgttaca ttattaataa tgtattggta  49080
ttttgtatta gaatcgtaga tgtattcata catatcttta tacactacct ttttaagta   49140
cttatcgtta acatgtaaga taatttttgtc ttcattacta gaagagtcaa taattacagt  49200
agagacagta tactctttct ttatgttttc aattaccttct tctactttag tttgaataat  49260
gtgttcagta ggtgttatat acttttcata gtactcagaa gccatgtctt tagtatattg  49320
actatagtta atatctgcgt cttcttttacg tttttttgct tttcttaaat ctggtataac  49380
aataattagt acacttagca aaataatacc taaacaaatt aaaaatgtaa tcaccatacc  49440
taccattacc cttcctcctc tatatctctt tttattgcat attcaattaa atcttctttg  49500
tcataaggta tcatgtacca actaccatag ctataaatca ttatacctag ttcagtaagt  49560
tcgtagtgtg ttctatgcga tacgcataaa aagtcagcac ctgactcacc atctacagta  49620
tctaaccagc aagtatatgg taatctatcc ataacattaa gtatatgttt atgttcgtct  49680
gaattaaatt ttatcaattt ctttcactcc tttaaagaaa tcgtaagcta atttaatttt  49740
ctttgagact tctttttattc tatcttcttc gtactcaagt gtaggttcta gtttaccaaa  49800
ctcttcaagg gtatattcat tataattact aataattcta tcataatcag gtaaataagt  49860
tacatgctca tcaaaatcaa gtacattact tatagtatat atacttattc caaatacgtc  49920
aagagtatta gcataatata atgttgtatt agtaggttct gtaccaccga aatctgcacc  49980
ttttaaatta gccatactta agttagcatt tttcatatta gcccacctag cgtctgcttc  50040
acttacatta gcttcagcta agcaggcatt ttctaagttt gcttttacta aattagccca  50100
ctctaagtta gtatgatgca atcaatatc cttcattcta gcatgtgtaa atatcgtaga  50160
tatacactca ttgtaactta agtcacaata acttaaatca caataactta ggttagcacc  50220
acttaaacta gacattacaa tagttgaata ttgaaggtca gcggaatgaa agtcaagatt  50280
tcttaaatct acacactgta aaaaaagctt ttctccttcc ttttcatttg tagctagcca  50340
ttgttcatgc ttttctatca atgaatctaa ttcaggttgt gttaccattt ttagttcttc  50400
cattactcca catcctttaa tgtaatttgc tctatattaa atctattaaa tccatataca  50460
taagcttttta aatcgtcaat atcaatttta cttttaggta aacaaataac atcatagtct  50520
gcttcaataa ttactttagt acttgtaact gttataatta tttctttatc ttgattttata  50580
taatcttcaa ttaaatcttt taaacacatt attacagtc ctttaatctt ttatgaatgt  50640
cttttaattc tacataatac ttatgtgctg ttttctttac accttctata ctatttaata  50700
gtaaagattt atttctttca agttcaacaa tattttgtt aattatatct tttgtcttag  50760
ggtttcttgt tttaatcatg ctgatatgtg cttcatggat actaatatct attctatcta  50820
atttagtaaa tagaggtgta acagttcttt ttagcttacc tttaatatac gtatctatttt 50880
gttctcttgc ttcttttata ccttcccaat tctcatcttc agtatctata actgtaataa  50940
tagttagatg cttatcaata acaattctat aattttaaa tacatatact tcattaccgc  51000
cttttttgtgt atgttcaaaa gtagcttgca ttaaagcact agcaaccac tgacaagcac  51060
gttctttact atcgttacta actcttaaag tataacgttc atacgcatgt ttagttaggt  51120
taatatgctt actctttatg ggttttcgtt gttctacaat gctcataatt aatcatccttt 51180
atatctatttt acgttcattc atctctaatc ccttttctaa aaacgcttct aaatttccat  51240
tccaacatcc tgcaaataca gtgtctaaac taggaatata agttaccttta ccattaaaag  51300
ttccaatatt atctatagag tatacttttta gtcctttgat attttgagta cttgcttggg  51360
ataatttaaac atctgttaaa tcggtatttg ttaagtctgc atattctaaa ttagcctaga  51420
ttaagttagc atctgttaaa ttagcataat ataaattagc ataatataaa tcagctcttg  51480
ttaagtccgc acctttaag ttagcacctc ttaaattagc atcttactaa gaagaatatt  51540
ttaagctagc acctttaag ttagcgctca ttaacttagc atttattaat tctaatccat  51600
ttaagtctgt ataacttaag tctgctctct taccttcttg actattacta tctaaccata  51660
gcttatgttc tgctagaatt ttatttagtt cttcttgtgt tattgttttc atacttattc  51720
tcctgtatct tttattaatt ttattgtaat cctgcctcgg ctctttcttg ttgtgaacgt  51780
tgtaaccatt gttcaaaact ttcattagct cctgcatagt tccatgaggc tcctccgccc  51840
ccaccaccgc tagctttatc ctcctcagtt ctattctcta attctgcttg tgctcgttga  51900
gcttccctat attgattata cttgtctgca tattcagcat tagataaacc attatgttca  51960
cttctacttg cttcttgcat ttgttcgttc tgctgtgctt ggttaccttg tgtttggtta  52020
tcttgttggt tattttgaac agtgttgtct tctttaattt gttttatttc ttgttcttct  52080
actttagatg aatcatcttt cttatttttct ttcttgtctt ccttataatt gtgcgtcggt  52140
gtatcttctt gtgagtagta agcacaacct cctaataata gtgtaggtgct aaagaatact  52200
cctgttaaaa ttttatataa gttttttcata tttatcaatc tccttttttct ttgttaagtt  52260
aattatacaa cttgttattt agtaagtcaa catttatttt ttctttttttg tcatttttatt  52320
ttgatactct tttaattgtg ttcttttgttc tggcgttagc atgttataca tctccttta   52380
aaattaattc tagatactta aataataaat ctaatgactc agtactttt aaactttcca  52440
tattagtaag ttctaaacct ttttagttc ttacatacac ttttctatt gtaaagtctt  52500
ttatactata atctacaaga ctaaccgatg tatttaagtt atgttgtgta tttagattat  52560
cactaatcaa ttccaacgtc aagcgttttt gtttatttaa atttttcatt tttactgtcc  52620
tctctgtaat ttataatacg tatacatatc tttcatact agtttagcaa ataatttat   52680
catgtattgt gctgtcgttt ttttaattct atcataatga aagtcaataa taggagttgc  52740
tacactaaac ctacctatat aattaccgtt atctctaact tcaaatacta atgtatcttc  52800
tttacacata aaaaatcacc tctaacgttt tgttacccctt agtataaagc aacatgttaa  52860
aggtgtcaac acttatttttt gatttttctaa atctttattt gattccgata ttgtaaactg  52920
taaacttttt gctaaatgac caagtgcaat acgttcaggc actttaaaac ctaccttatc  52980
aaaataggt tatactaacc cttcttcaac aattaacata ataataccat ctacaacaca  53040
taagtactta ttttctttg taactagttt tacttcttta tttaataaat tacttgctaa  53100
```

```
ttcttgaata ctaaccaaga tactatgtgt aatatggatt aaatttctat attttttctgt   53160
atacatacta accacccttt agaatataat atttgttatg cctttattat ataaatcttt   53220
agtaaacttg tcaagagcaa tacgtgctac ttttaattct tgcataaaac tttctacttc   53280
actagaattt acatatgtac atggtatttt taattccaag agtaacttt  ctgtagtata   53340
ccctataatt tcagggtat  acttgtttac tgattttta  aaagatgata cttcatactt   53400
accttcatta tctatgacac aaatataata tcctctgcat tcattctcat atactacttc   53460
catttagtaa ccccctatca aatatttat  cattatataa ctaagtataa aaggtactaa   53520
tactagagta gcccaaacta acgtaataat aacttgatga atcaaataag gtaataaacc   53580
tttaacccac tccttacgaa cataatactt aataactata tcagatatta aagaagttaa   53640
tttccagact tcccataagt accaaataaa tacacctaca taaaacaata aaataaaacc   53700
taacatgagt ttatctacta tatccatta  tatcacctac ctatatcctt ttgtagcaag   53760
gtctacaatt ttatgttgca agaacttgta attatcttta aatattttta attcatcttt   53820
accaaatgta tgtttaattt cttcttaac tgtccatata gttttaccct ctaatacttt    53880
acttagtaca tctaaaccaa ttggaattat acgctcatca ggtaaaacac cattcttaat   53940
acttacgacc acaatatgca aattatctaa atcactttt  ttcatcattt atcatctcct   54000
tatatttaaa ttataacata gcataaaaaa agagtcaagc ataaccttga ctcaatcctt   54060
gttaaataaa tagtatataa tagcaaaaca tactagtata attactactg tcatagacta   54120
tcatacctt  acttttatt  tagtactgct tcaaacctat acttatgtac tggattattg   54180
tcattatcct ccgtatacac acgaataagt ttaaagttta cacccttctct aaatttacta   54240
gtcctataat atctcatatc aatactttta tcacttgttc ttcctggtaa ataggtaggt   54300
agtttttcca taaagtatgc tttgttgtct attactttct taagcgtgta gtctcctaca   54360
tactctacat ttttatcttt ttttaattta ccgtggtgtg ttaattggtc tgtaacttgt   54420
gatttggttt tttcatgata taaatatgag gacacgtaat aagtagagat agataaagct   54480
aacataacta agataattac ataagcaatt attgcttttt tactcatagc gcaccatcct   54540
ttactactta taatataata acttagtcta taactttaat acatttttaac agtagaggac   54600
agtatatcat tctattgtct ccgacaagtt cttttagttt aagaaaaatgt tttaaataat   54660
agtcaggatt ctttaactca taatacttta ataatgtttc ttctatacta ctatcaaagt   54720
aatacttatc aacaatttct aaatgtgtaa taagattatt tgacattaaa cttaatttat   54780
ctttaatctt tacatcacta atacttgtac ctactttaat atcattaatc atatcagcct   54840
gggtataatc tattcagta  tttttatct  taattagtgg ttgcataaca tgcgcttttct   54900
catatacact tctaggaact tgacctatta aatggtcaaa agcagggtct tcagatacat   54960
acccaacatc tataccctata tactgaccac tttctacgtg gtcggagtta taatcttctg   55020
gtattgtaca taggtataaa ttactttcat taatctctct actagaagta tcaaaatcag   55080
gtactaagtc ttgtaaagat tctttgttaa ataaactatt ttctattcct tgtatagtta   55140
aattattatc aatgctcttt acattataca agtaatctac aattcgttct ttgcgcatat   55200
gacacctctt attctacctc gatagtatct tctaaggctt tctctttta  atctgattt     55260
ctttcaatat tatacaaatc taaaatataa tataaaccat tcttatgaat gttatacttt   55320
ttatagatac tttgtaaatc catatattga taatcttta  ttaaggcttg tacttattc     55380
ttatcattag taatatgttt tacacgtttt gctactctag atttcttatg tttcttaggt   55440
actttataga agtttaacac tgtataaaatc aaacccatac ttactttagc ttccttagca   55500
atatcagtca caggtacacc tttattataa cttgtaacaa tatattcttc ttttggtgta   55560
ttgaactctt tattcttact taatggcgta tagttgcttt tattttctaa taatgctttc   55620
tcttcttcat ttaatgtaat aatcataatc aattgctcct tttattgttt gtaataaaag   55680
aataacacac ccatatgagt gtgtcaatca ttaatttta  attttattaa gtttatcttc   55740
attatataaa gatgtttctc ctgaaaagtgc ataagaaataa ttaccttac tatctactaa   55800
aatatcttta accttagcta catctgattc ttgattatct cttacatatt ctacaattgt   55860
gttcttaggg aacttaactt ttgtagattc tacataactg tcttctaaat aaacagcaaa   55920
agttagtaaa gaattaatag atacattata cagtacccaa tacctttat  agaacatggt    55980
ttctttatct aagtctcttg acacttcagt aaacttatgt tttccagtac ttagtctaag   56040
taatatatct ccttggttct cttgtttaac tctaagtaca tcacctttat gtaggtgtgt   56100
tataatatct actatatctg taagtggttt aacatctttt attggaatta aactaatttc   56160
ttctgtcata tgtattacct cattatctat attgtatagc ctactctatc taatgtatct   56220
tttaactttc ttccttcttc atctaaatct aagttttat  agaactcttc ttgtaattgc    56280
tccattcttt gaagaacttc ttcatgttta tcttcaggaa taaactcaag cataacttct   56340
gtcatagcag tatctgtgc  tgttgttta  atcattagtt ctcttagtcc tatgaatgac   56400
ataccttta  gttggttacc cgtaattcta tcttttgttt ccatagcttt aatcattaaa    56460
gcagggtcta atgtttctac aaagtttaaa cctttagcac cttttgaat  aatcatatct    56520
agtatttgaa tatcatcata tattgttgt  acattctgtg tagccagttc aaaaggtgta    56580
taattctcac tatctaattc tttcataggg ttttcttttt tctgtatttg agtagcgcta   56640
actttctttc ttttatcaat aagttctcct aaatcccatc cattttcaat agcttcttta   56700
cgttactct  tatatcttgt aatggcagat ttggataact ctaagtcata ctctttacat    56760
aggtctataa tatcatcata actaacatct tcatctatag cattatccac tttagacctt   56820
aatagtttat tattatatag tttagataga atactttcct tatctggaac tacctttata   56880
tcagattttt tatttcttaa attcttttt  ctagccatta tatattccct tcttgtctca    56940
agtgtcttta catatgtgtg aactaaaata aggagtatgt gtattcacat aaccttatca   57000
aatcaactgt tttatacttt acactatata atatatcaca atttctgcat ctatttttatt   57060
ttcataaagg atattctaat ttttacact  atagtgtaac tattttaagc aatataaatc    57120
ttttttctaa aaccctatac ctaaaaggta tttaatgtt  ttaaaatat aattttaaaa     57180
taagaataat accttttaaa aattaactaa ctacttgaaa aaaatatgta taaaaaatcc   57240
cttatatacg tatattttata ccttagtata catatttaag ggagtattat actataagag   57300
aattgttagc tcatcattac caacaagatt aacaatcatt ttatagttat tatcactaac   57360
tttctctact ttactactaa caatatcttt atatctaact tttacatagg attgaccaca   57420
agcaataatt aagtctttat catcatctaa aaagaaaata ccggtctcat gtgtattata   57480
ttaaa ctataa tgatatttat ttgtatctag cttaacagag aacacacttc tattgattaa   57540
tttattccct ttgaataatg taagaacttt tagggtatct aatttgttta atgtaccttg   57600
gttacataat gtacctatga atgattgacc gtcatattgc ttatcagtta ctagtaagta   57660
tacaacatgt gtgtaatcat ttaaaggaga tacatcttcg atagtgtata atctaagttt   57720
taattcttta ttaatagtag tatcttggta cataatagta ggtcaataa  aagttgatac    57780
aatgtctact ttctttgttg aagttaattc tgttccttta gataataagt ctgtcattaa   57840
```

```
tccagtatttt tctaaccttt tatttaactg ttctgtttta acgtaaccta accctgattc  57900
acttatcata ttattcatac ctacaatggc aggttttaag ttctcagtaa cgattacttt  57960
attcgtaaat tctataccat cttctacttg tgatatgtcc tctaaataag gtactattgt  58020
tacaccacta gggaaataat cactatcata ggacactcct aatagtgtaa tatctttact  58080
ttgtagtttc ttaaataaag tacttacatt tgttttgttc gcttttgttc ttaagtattt  58140
aaccattatt taccacctttatatatcatt ttctttggtg ttctttttctt atctaatcta  58200
ctattttttgc gtacagatat tctatgtctg gtactaaaaa tatagattaa atgtgtacct  58260
ctaaatgtac gttgttcacg aatactacat ttacctatta atttcttacc tctataaaca  58320
taataaactc tatccgtatg taaaatagtt tgtgttaatt taccttttg cttcattaca  58380
agatacttct tctttatatt cacagcttca ctaattaagt ctaacgcata cttcttttgt  58440
attttaatgt ctgtagcagt aacattatta aatcttttaa caaacaaagg tttgtattta  58500
acaacaatac tttcatctgg tatatctttt cttttttat taaaaaaga agtacttcta  58560
cctgataagt tacccgtagg agcaaagtta acaggttgat gtttatatac gttactta  58620
ggtttaaatg tatcaggttt cctctttgcc atataatacc ctcactccgt tctgtataac  58680
tttaaagaaa tcatcttcta atatctgcca tctattactg taaccataga taacacctct  58740
agtaaatatt ttataagagt tctctacacc taaataatga ataacttggt taataatagc  58800
tgactttttc attctcatac gttgtgttcc ttctgtataa ctaccctcat tattattatt  58860
tttaccgtgc tccctatagt tatatccagt taggtaagta ttataatctc ttaactgttt  58920
aagtatagtc attaaatgtt gcttccataa aatatttaat gtatgataag gacttcttag  58980
tggtgatggt gtagcttctt tatacttacc tactacagga ctaccttga agttaatata  59040
gctcataata cctacatgat ggtgttata tcttttagt atttgctcta ctttaggtac  59100
atgcttatca tgacacatca cataaacata cttacatact agactataat agtataactg  59160
tttattaagt ctttgtgtag agtctcgttc tgtctttatc tctataccca taacagtacc  59220
atttctatca agaattaaac agtcagttct acatttacct tgacaaatag cttttttcatt  59280
aaatattcta atatcttgta tattacttgt tatctcatca tctttaaaca tgtgtctctt  59340
cgttctaatc aaatctttaa tatcctgctc atagaattta gttatctcag acatttattc  59400
tatcccctttt aatacgttga taatattgta atatactatc taaaggtgta taagacttaa  59460
tccatttaac attagataaa catataaata ctcctgtata ctcaccatgt ataactttag  59520
tgccttcttt ttgtgtaata gttactctat cttttttctct ttcgaaaaac cctttaccta  59580
cagcacctgt agttgtatct gtacctaaag gtataatatt agctaaaaag ataggaggtt  59640
catataccttt tttatacttc ttattattag gtagcattga cttaattgta ttacttaata  59700
tcgtaccacc tctaatagtt ttacttactg tttctatttt atatttcttt tgtggtacct  59760
catcatcaac actatgtatg ttatatacta atacatactc agaagtttca tcttggacat  59820
gttctatgta gtaataagga acacctctaa aagagtaaac aaccttcactt acttttgtct  59880
taataatttc attatcaaat ttaccaaaat ttaattgcaa caaaaatcac ctcatatcta  59940
atataccaca aataataaaa ggagtcaagt ataaactgga ctcccttctt tactattctt  60000
tatttttgt tacgaaactc aatactaata atactacgc tgttaacaat acatctatta  60060
caataagcgc aataatagca aaaagaactt ctatccttgt tgtaattta taaatcgaat  60120
ccccaaaata aacaacaata cctaagagga taataccaca taaattaggt aatagcacat  60180
tatagtactg ccaattgggt agagggttac ctccttttt tactaaaatca cgctcaccac  60240
gtaacatacc tacaaagttc attgtggtat taacaataat aatgataagc aatgttaagg  60300
ctataattga tagaatgtcc atattatctc tcccctaatct aagaatacag ttttaatgtc  60360
aatgtcttta ttttttttat ttaaaaatag tagttgtgt gaaggcttcg ttctagataa  60420
gtgtagttct ttagcatagt tgttatatcc cataggacta cttgctacaa tatgcattct  60480
attgtaatct tcttgtgtta ctgaaaagtg atgtacatga cctgtaatta ataagtcaat  60540
atgtgtgttc tcaataaact taggtatatg cttacctttta cctttaagtc catctccatg  60600
gtttataata atatttaagt tacatactgt atctttaata gtgtatacat cttttctatt  60660
atcgataatc tcaatacctt ctaatacacc attttctttt aacaacagta aagaatctaa  60720
tacaatataa gctacactat cattgtatac tttttggttc ttattacctt gtacacggtc  60780
gtggttacct gctatcatac caaaacgtaa gttaccccat acatatggag ataattcggt  60840
taagaaatca attaatagtc tagttccttt tgctacttgc tcagccatag tgaactcagt  60900
atcaaaagct tggttaacat ctctccatgtt aatatgttct attaagtcac ctacaaagta  60960
tactgtaaca ttactaatac cacgtttact aatatctta atagtttcct gtaatagctg  61020
atttaatctt ctttttagta cttcaaagtt atattcatta gttaaatctt ggaaggaaca  61080
tcctacgtga aaatctgata gtaagacaac caactcttct tcttcctcgg tagaagcata  61140
cctacttact ttatggtcta ataacttatc tcctttaagc tcattaacca tagtacgctt  61200
taattcatca aacaaaattg tagggtaggc agtttgtctg ttaatcttac gtagttctct  61260
tagcctagat agttctttt cgtgtgctac tacataagat gacacctctt gatgatagtc  61320
attaccctca aatacttgtt tatcttctac atctcttaag tcttctaata acacttcacc  61380
tttaacagct ttattcttta gttggttaag gtactcatca cttcaatat tttctacaat  61440
gtcttttaac tcattacggt ttactctatc aataccaaaa cttgttagaa tcttattaaa  61500
tttagatgta actaccttac cttcatcttt aaataaaata cctacaataa ttgcttgtaa  61560
ctcttctatt gttttataat tacccataaa tacatccttc cgttattaaa tacttgttca  61620
tattctcacc taatacacta atatgactat caataaagat actaaaatata ttagaattt  61680
cattatagga tgctccaaac gttttagcaa cactactgac atcataacct tttacataga  61740
aagtaaggat atcactagta cctctgtttt gtgaacctat aacaacaata cctttttctt  61800
tatccttaag acattcataa gctaaaggca atttatactc aggcgctact tcatatagta  61860
catacaaatc atttacgttg taaaacttgt cagtcataat aggtaatact atatctgcag  61920
ggtaacctac tagacccatt tctttttgctt cctcataagt agatttaaag ctaaacaact  61980
cagtatactt gtgagcaatg tcttttgtat aactactgaa attaatatttt aaacctttgt  62040
catctagaac cacaagttgc tctaataagg ataggtactt taaatcatca cctactgtaa  62100
taaaatcttt gttatcaggt aagtttatat tagaaacaaa gtataatttt gtacctttta  62160
ataattcttt atatttttaag taatcctcat cattgtatat aaaacctaaa aaaataacag  62220
aatcatacgt attatcacta gctaaatgta atgccgaatc aaagatact acactttcaa  62280
cgtcgaacat atctatacct tcggataaat gttctgtgtg tgaagtact tcatttaaaa  62340
taaaataacat caatcctcaa tccttttctaa taaatacct accattcctt tatccttatc  62400
attattagat aacccatact caacaatttt ataccctatac atatgcacta ggtctttaat  62460
aacactaata accataacga cattgacctt acttactgat ttattatcat acgtaactgc  62520
aatatacttt tccttacttt ccattaattt ttttaacttc aaatggtcgt tatctgaagt  62580
```

```
taagtatact gttttaatat ccatatagta cctcctttat taattcttgt ttaactatag   62640
catataaata aatataagtc aataaaaaaa agcccaacaa ttaagttgga ctttaattta   62700
ttatagctca ctatgtggtg ctgtcttaaa ttcaggtaca tctaccttt  ctgattcacc   62760
agactcatta gagtatgcta ctttataagt tcctttagga tacgtagtat ctgctgttaa   62820
accactaata gaaatagttg ttttacctgt ttgttcagca gtcttagtac ctactacttc   62880
accatcttta tatactttta atgttttttc catttatttt tacctccgat tatgctgtaa   62940
tatcagctgt tgtttcttta gggtctacag ttacatttgt aggagcttca ggtactttat   63000
ctttaacaac tacagttaca gtatctgtat gattaccatc atcagttgta acagtgattg   63060
tagtctgacc ttttgcttta gcttctacta aaccttact tgatacactg gcaatatcat    63120
catgttctga agtaaatgta taagtagctt ttgttgcgtt actaggttca atcgtagcta   63180
ctaaattatg tgtttctcct acttttaagt ctagtgtttc tacatctaaa gtaacggata   63240
ctactttaat atctttagtc ttaaacgcag gaacatctac tttttctgat tctcctgatt   63300
cattagagaa agatacttta tatgtaccTT gtggatagtc tgtgttagca gttaagttat   63360
caattgtaat tgatgtttta cctgcttgtt tctcttcact ttttaatagc tggtcacctt   63420
tgtataaatt taatttatcc aaactaagtc atccttata  tgtttattca gctgtaaatt   63480
cagctgttgt ttctttagcg gttactgtta catttttagg tactgaaggt tctgaagtat   63540
ctccttgacc ttctcctgag tctactcctt taacgtcttt acgtagcgga ctagcaggaa   63600
actcagcgct cacgtcttca tgaggtttct cattactatc tactactttt ttagcatctt   63660
tactttcagc atcaactaaa gcaaaaacat ccttcttgtt attagcaagg aatacattgt   63720
atactccaaa gctgaaacgg tcttcaacga atgctaaaaa cgcttgaatt aattgtttac   63780
ctttatcttt accttttaata ttttcagttc taataaaagc atggttgtaa gggtcttta   63840
cagtataac tacaaaatga atttggtctc catctgtata agcaacagga gccttttca    63900
taattttaat atttcctcta ccatctgttt caatcgggta taagaataat tctcccttat   63960
tatctactac tttgtagtta tactgaccac ggtgtgtacg tgtataacca tcttgctcta   64020
cttgaacttg taaatactta tctgctacag tagcggtagc ttgttttaat acttcattaa   64080
tattttctt  agccataata attaagctcc aatcattatt ttttacatta taacatagaa   64140
aaaacctccc tatgttatta ttttttttcac taataatata acaaaaggga ggcttattca   64200
ggttattccc acatatgatt ttgcttatct actttattat ctttgatata ccttttggca   64260
ttttgttcat gataagcatt aattttaaat ttaacataat ctttaagttc tgtaagctcc   64320
ttagctactt ctgaacgctc tacctccaac ctattagcta cagttgaaac aataaatgcg   64380
ttgtcttctt tatctgtatt aataaggagt tcttttagca gttcactttg tacttcagta   64440
aattgtgtat catcaaagac ataattaagt aattcatttt cttctaatcc cacatttaac   64500
tcctgtgtta aggactctac tgtataatct gttttaccta caagttcagt acgtttatat   64560
ttattgttct tcttaacata actgttctgt actcgtagtg ttagtttagt tttaatatac   64620
cctggaaaat ctactttact ttgtatatca tactccttaa ctaacttaat aaactgctca   64680
tctatgtatt cccgtagctc ttgtttctca aagtcatgac tcatacctct agagtatcta   64740
tgaaataatg accatctaag gttcttatac cttttttaaaa gcatatctaa gtctctacca   64800
aagtcagtag gaataccatc taagtctata atatatctat tcccattatt aactttcttc   64860
ataaggatgt gctccctcaa atacaatctt aatcctgtgt acatcatttg atacatagat   64920
atctgagtaa tgtattgttt taggtacttt gacttcagaa ccattataac gtactaaaga   64980
gtaacctcct gcccatcttg actctacatg ctcaatatac ataactgtag aatcagtgta   65040
aggaaagccc gactcttcta caatgatagg ctccttatta tctctagctt ttttaaaacg   65100
ttctgctatt tcaatataag gtaagggcaa tacatcattt gtattagccc tacctaatgc   65160
ttctttaaca ctattaatat ttctatctat tagattattc atttacatct tccttagtct   65220
ctttattagt agagctaagc tcttcgtagt aatcttgtaa tgcttaaaac tcttctaatt   65280
gagtagtgtc tactttgta  ttgtttaaag gtgcatactt atgagggaaa ttctcgtggt   65340
aaactctact aaataaattct aagtgttgtc cattaatgtc ggtacccaat                65400
ctttatcata ttttttaatt tcttcaccat ttaacgtaac ataattacgc catgttcctt   65460
tagtaattaa accacgctca acggcttctt tatagatagt atgataaggg tcaacaccgt   65520
ttaattgaat agtatcttca tcagaaccta cttcataacc tgataataaa tcaacttccg   65580
ctttttgacc aggtctagat agcttagact tcttagtttc aatacgcata acatgacctt   65640
tatacgtagg tttacctgtc atagcatcat tctgttttaa ttctgattct ttaccttag    65700
atactttaat acgtaaacta gcaccatgtt caaaagctct tcctcctgta gacttaatag   65760
ggtcatcata aggattactc atatttaaat tatcacgtgc ttggttaata acaattaatc   65820
ctgtatttgt atcattaagc ttaggtgaaa tagcatttac tacttttttgt gtacttgtcg   65880
ctttcgttcc aagttttttta tggtctactc ctgcatcaat ttcatcttgt gtacgtgtag   65940
ctcctaggga atcccaaatg aacaaaatag gtacgcctgg tgctttctca ttaaatgtat   66000
caatccagta ttctaactct ttacctacgg tttctactga tagttcagta acatttttaa   66060
gtctaccttc acctgattgt actgagaata gtttagaaac atctacacct agttgttcca   66120
tacgttgatt atcagctgtt ccctcaatat caatccaaac tgtaataact cctaattgtg   66180
ttgctactct agataagtgt actgcaaagg tcgatttacc cgagccagtt aatccgtaaa   66240
cttctgtaag tcttcctaga ggaatacctc cacctaaaat tctatcatat tgtggaatca   66300
tagtaggaat gatattctta atatctgctc tattactatc tgatagtaaa gttaaaccta   66360
attctttacc taggtcaata gtatttaaat ttgtagtatc tacttcttta ccttttctta   66420
ctctagccat tgtatcatcc ttttatataa aatttaaata aaagagtgct aagatagcac   66480
tctataaagt tattataaat ctaaacctgc taatacatca tctacactct taggttgatt   66540
ttgtttagga ggttctggtg ttgattcatt tgtgttgaac ggaatttgag aatcatcgat   66600
gttgtttgca tcaaagttct caaatggatt actttgtgtt tgtggttctt gttgtgtcgg   66660
ttgttggggt gtctgttgta caggtgtgcc ttgaccaaac tgtgtattt  gttgtggggg   66720
aacttgtggt gttggttgtt gtacattatt aaagtttggt tgtgtgttat tttgtccacc   66780
taaattacta ggtaattgtt gctctacact ttgttgcgta ggagcttgtg tttgctcttg   66840
tgttgatgat tcttcacct  atgtgtttgt ttctctactg aatttaaaat tatcatgaga   66900
aacttctgtg ttattaacat tgtaatcaa  ccagtttaca aagttagggt tatttttcttc   66960
tgttggtga gctaacttat tcccaatccga taactgtgtt tcccaacctt gaggtaaggc   67020
acctaatttt actgtaggat aaacagttac attccatgat ttttcaccTT ttttagcttt   67080
agcaatatta ataggaatg  catcatcggc tgaaataaag ctgtgtgtag cagtaggtga   67140
tggtgataac attctatctt ttagtcggtc aatcaattga gacagacctg tattagatag   67200
ttccataggt tgaataataa cattaccttg ttcatctgtg ttaggaacta attgaccatt   67260
ttgattaaag tattcaataa catgaatata tgctcgtcgt gcaggtttat tagggaagtt   67320
```

```
actaaattgt acaccttgct ttaaccatgt atttacataa gggtctacaa cagatgagtt   67380
aactttctcg ggtaaagtaa gcatagagaa cttttgtgcc ccatcttttt taacatagtt   67440
aatacctaat gttctaaatt ccttaaagaa ctcattagaa cctgctacag gcggtagtac   67500
acgtacaagt gcagactctt tattaatttg attattgtta acgtccttaa tctttcctaa   67560
tcgcaaaacc ggattctttg gtttgtacgt ctctacctca ttgtcaaaac cacttgattg   67620
tagcttttct gattgctgat taataaattg attaaaatcc ataatatctt ttctcctttt   67680
attttaaaaa ttacttaatt agtataacat gttttctttt gtttgtcaat acctaatgtg   67740
taaatgggtt agtaacacca ccatttttat ttgtttgtct tagttccgca ctaatctgta   67800
ctaacatagt tgtacgtgtt tcaaaagctt ttacgatata atgtaattgt ttttctctat   67860
aattccatgc ttctacaacc tttgcttgct gttgatattc atcagaaaga aatacagcag   67920
actctacttg gtcttttgta ggtttctttc cctgttgttc gtactgagct ctaatttgta   67980
gattaagttg agctcctatt ttttctaact tacgttgctc tgcttcggta taattactca   68040
cacgttcttt taaggaagcc caccatgcaa atttagacga ctgttggtac atttcgtctt   68100
gaattgtata ctcactaagt tttagttcat catgaatatt aaacgtctga gtgtttccat   68160
tattatcttt taaggttagc tcattgaaat ctaatgtatc taaatgtatc tccataatac   68220
cctcctctat tttactgtac tatataactt taaaactgtc aatattattt ttaatatatt   68280
ccgttttttg tttgtattgc tcctcagtta gtttatctga ttcatagtag tctttgattt   68340
gttgtaaggc taatttatac ttaatatatc ctttatacga attaaattgc tttattaact   68400
cttcgttgta ttctaccata tcattatatg ttaatcctat ctctatatct gcatctatag   68460
gatactgtct taactcacca ttaattttta tttttaagaa atcataagga aggttctcca   68520
ttacatggac aataacttta gccataatat taacttcttc aggaggtgag tctactacaa   68580
tactatcatg aacagtagct actaacttcg atttcatatt cttattttga ataaagtcgt   68640
caatataagt aatagccatg ttagtaaggt aaccacctgt accttgaata atcgtgttaa   68700
aggactgtct aagaccctca ttttttaatct ttttatctct agattgtgct gagtgtatat   68760
atcttctgtg tccattcatt gtttctacat atccatgttt tgaacaaac tcatgagttg   68820
catctataga cttcttaata gcaggtttat tagaataaat atttattaat atttcagtag   68880
cttcatcaac tgtcatatta ttttaccctg caaacgaaaa ttccgattca ccataaatta   68940
aaccaaaggc tacagcttta ctggcttgtc tttcttctgc tgttacgtcc ttcatacttt   69000
taccatacat aatacttgcc gtattttat gaatatcttg tcctgttaaa aacatctcta   69060
acatttcttt atcatctgta tatagtgccg taatacgcat ctctaaggca ctgtaatcgg   69120
cttgtaaaat tacaccatct ttaaatctag agataaaaga acgtttaata gggtggtgat   69180
aatcaaactt atttacatca gatgtatgag caggaagatt ctgaaggtta gggttgttac   69240
tagaaagcct gctagtatta tgatttacaa tattattagc tacaaatgaa tggctactag   69300
gaacatgtaa atcaaaaaat tccatatctt ttatttttc aatttttctt attttaccta   69360
ataaaacatt atcatataaa agaataccgt ttcttctgcc taatgccttt agattttctg   69420
atttatactt tactctcatca cgcttaatac tttcaataaa ccctatttca tcgtaaaatt   69480
tatctaatgc atcataagtt atttgtatag aatagcattc attttgtact tttctattaa   69540
tattttata aactttacct atagaatacc tacaatagat acccatattc attagcattg   69600
ttcttatttg taaagccatt ttattagata cagtattata gtacaaacta ggatacttt   69660
tcttttctgt tgcagtatct aaacttaaac ccttaagaaa tgcttgttgt acactttag   69720
ggctatctaa tatttgttgt gggatttctt tatttaatgc tttactttgc atattaaaaa   69780
tatgttctaa ccatctacct aaaccaattg aagaaaattc aatagaatca cttctatctt   69840
tattactaat gtagtatggt gtaatatcaa ataaatcttt agttaggtta aagaatctat   69900
tcctaacttc aagattacta ttagttaatc ttatactgaa tgaaccgtta tttgtagaaa   69960
aagacccatc agctgtatac ataccgtacc attcagcaaa atcttcggat acataattag   70020
gtagtgtata gcttttgtg tttgtaatac ttttttcttt actatatata aaatcttag   70080
tatctaaatc aatataacta ttattataaa gattagaatt ataagacatt tttatataat   70140
cacctatttt taaatcttca gctacaaccc aatcattatc taataaatgc ttagttgttt   70200
gttttgtttt atttagaacc ctaccagtat tactataata attatttcgt aataagggt   70260
ggtttaaagt agtagttaat gtagtaccat cttcaaagt aatctttaat ccatttctta   70320
caccactata ataaaagtgt gaagcttttt ctaaatttcc ctgtctatta acaatacta   70380
catcaatact actaaatact tttctttttc tattatttga taagtcttct atttttttta   70440
tacctttatc agtaataact aaagaatcac ctgtaataca tgcagttcct gtactattat   70500
agttaccatg taaattatgt gtattcttat ttactctttt aggtaaattc ttagtaaaag   70560
aatttctttt agtttgcaaa gaggcataat aaataagtaa gtctagtagc tttttattat   70620
cttcattctc aaccaaagat aatgccatct ttatagactt agtatctgtt ttgtaatctt   70680
tccatgataa ctcatcttct ttagtaccat tactgaaagg tttatcctta actgtctctt   70740
tactataagg taactgtata cctaaaatgc tatacaatac ttcaccttta tggtcacctg   70800
agcttggttt aaacttccaa ccttccatctt taaatttagc tctatactca tgtatttctt   70860
tatttctatc agatggtttc ttctcatgtt ctgctaaggc taattggtat aaattatacc   70920
tagtctcctc aaattcttgg atagcccaat gttctctaat ttcttggtgg gttttttcca   70980
tctcattaat ataaaattca tcattttat gcatgtattc taggtcacaa tgtaaaccat   71040
ttgattgtat tctagctaat gttctaatta atctagggta acttattgac attaagtcca   71100
atgctttagg tctattttgt tctttaact tttcaataac atcacagtat attcttctac   71160
agacatcggt gtcaccactg gcataaggat gcataagctc taatggaatc caatcataat   71220
taaagtcacc tccatctacc tcattaataa ctttagtatt gtcttatac gtgttaatta   71280
aattaataga tgtacctaat acataatctt tagctttgtt agataaactc atatactcag   71340
gtgatgattc ggctacttct ttaaattcag aatccataag catattcttt gtaataacct   71400
caggtgttag tttttaactct aaatatcttt tttgctcttc tgtgatacca taatacttat   71460
cttcatctgt tagttctata tcaatgttat cgagttatt tttcaaccaa gtatcatact   71520
catttgctttt tatgttatat tctttcttag caactttttt attttctttt taatatctt   71580
ttagtttatc tgataagaat cttagtagct tcaatacata ccactcttta aaatcttcaa   71640
ggggtttgtc atatcctcct acatctgtta cttcgtaagc aaggtctgat aatcttagag   71700
actctgcttg tttgttgtt acagctaaat accaacctac cttagtgtct tgattatttt   71760
caaagtctgt gaaaccttgt gttgtcatta gaaaatttat atcataagta gcattatgta   71820
gtaccttaat gtcttctttg ctagctatcc attctttag taaggaaaga atttcatcaa   71880
tatcttgctg tccattctcc caagtaaagt ctgatttata taaaggtatt gtaacacctt   71940
gaccattctc ccaactcatt gatagtacta agggttact tccttctcta tcaggactaa   72000
gtgagttagt ttctaaatcc catgcggtaa tgtctacacc gtcatgatta tcattcttta   72060
```

```
cttctttatt aaatatttct cttacacgct caatacttgt aacaagttca tacttaactt   72120
ctttaggttt aaatacgtct tcaccttgtt ctacaaactt acctaataac ttaaggtctg   72180
ctactacatg acgctcacta ttcttattaa cgtttgtgta ctctatacta taagtaggta   72240
atacccaaac atcatgtttt ttatcttcac tagtaatagt tacttattta ggtacacctc   72300
taactttacc aatagctgat acgtttaata aatatttaac gcctaactta cctaaaggaa   72360
taataatatc atacttatta tttataatta tttgattcat tctttcatag tgaggtttaa   72420
cttcagataa cttaacgtct tggtacttaa ttgttttacc atacttattc ttaataggtg   72480
taggtacttt aggatataaa aaatcaatgt cataatcctt tgtactccta tctcgattaa   72540
taccagaaat attagacaat agttgtttta gtactctaca attaggtgta tttaatagta   72600
cattcttaac actaccatca gtactaactg aaaagtgctc ctctctaata tggtcatata   72660
aaattaaaac tttcatgctg ttaccaatcc cttctttaac ttaaatacag tataacatga   72720
ctattaataa tagtcaataa aaaaagagga atttaatcct gctactaaaa acatacttaa   72780
atatatattt agaaagtttc tctattcaac gaggttgatt gtattaacaa tcaggtctaa   72840
aaacctctcc cagagcgtta attccgatat agcctaccgt atttgtttag acttttaagta   72900
agatactaat tcttagtaac ttctcttttt cttttataat agtattgtat attccttttgc  72960
ttgtttaag ttaatacttg cgtttatatc cctatcttct atcataccac aattatcaca   73020
tttgtaaatt cttttattta aaggcatttt ttgtctattt ccacattgat tgcatatttg   73080
acttgaaggg taaaatctat ctacttgtct tagttctata tcatattgat aacattttcca  73140
tttgagccat tcaataatgt agcctaatcc tatttgttgg aaactattag acaatctttt   73200
attttcatc atacctttaa tatttaaatt ttcaattgtg atagattgtg ggttttcctg   73260
tactatttct agtattttct tttgtttaat atccttctta atgttgctta ttttacgata   73320
taatctttgt acttttaata attgtttaga ccagttagtg gacttctttt gtttcgtga   73380
taatttttctt tgttgtcgtt ttaaagactt atgtaattta actaattttt tattttttcct  73440
taaatctgta atcttaacgc ctgaaggtgt aaatagtgta tctttaaatc ctaggtctat   73500
accaatacct tcagtatgtg gttttttaag tatggtctta ggttcttcat ctactaacac   73560
tgacacataa tatctatcat tttctttaat aatagtagct gatttttatat tgttttccgg   73620
tatatatcct ttttcttta acttaatcca ttttaaatta ggtagtcgta ttctatgacg   73680
ttctacatgt atagtaccta ttaaatagta agaaccgtta ctttgtgtct tcttaaactt   73740
aggaaaacct gatatattat taagaatctc tttatatgca tcctcagcat ttgccatagc   73800
ttgtttagtt gctttagtat ttacttcctt agtccattt ttatctttat tattaggaat   73860
aaaatcatta ttataccaaa cactaaactt tctatggttt aaaaatttca acccgttatc   73920
ataacgaaat ttatttactt caataaattt attataaaca cttctacaag cattaattgt   73980
tttattaatc tcaattattt gttgtttatt tggttttact tctgttttat atgatttcat   74040
tgtatgtcac tattttttctt tactttcttt ttatattttc taagaccata taccctacat   74100
caggtaatgt atcattctta atacatacta caacaatatg taagttatct aaatctttca   74160
ttttcatatt caatcagctc cttatagtta aactataaca taacataaaa aaaaagagtc   74220
aagtataaac ttgactcaat ctctgttaaa taaatagtat ataatagcaa aacatatact   74280
accaactaaa tacatgaaga gtagatacta aatcttatgc tatataaaat atttaactgt   74340
tttcttcctc tttgtttaat acatctataa ctttatctaa ttcagacaaa ggtttaaact   74400
ttagtgcctt tctattaggt aaagtgaagt atgtttttatt tagtccatcc catgcttttt   74460
taccctttacg ctctactact tctatttgaa agtacttatg attctttacc ttatcgtaat   74520
cttcaagtag taattcagaa atagcttttg tttctgcttc tagtatctct tctacgtctt   74580
ggatataata ccctgtactc tcagatatct ttcttgctaa atctcttcta tttgctgtac   74640
tcacaaaatc acctaaatct taatcttct ttgtctttt aattcagtaa gtaggtcttc   74700
tattgtttca taatctttat tttctttact agcaagaata tagatataca ttttccacac   74760
ggacaaagaa acccttaatt tgtctgcaaa gtcaagcgta tacctaggtt ttagtttata   74820
agcttcttta taatacgtgt agtacttacc ttgtttagcg tctatagaac taatacgagg   74880
gaatgataga tgaacctcgt ctacattcgt tttaacatca tataaacttc taataatatc   74940
gtaaggattg acgtaaggaa atacaactga aatatcaata atgactttg ttcccatgaa   75000
actcaaagct atattatcca tctctttgtt actaaactta ctacgcattc tatatacaac   75060
tgatgattta gggtgagctg ataaaatcttt aagcacatag taaggaatta ctgaatcagt   75120
ataaataggtt acttgtccac cgtgcttgca tattttttca atcaacttat cattgttata   75180
cttctcatta aatagcatgt aatgtttatc atctcttagt atataacctag ttgatttatt   75240
agctaagttg tccatatctt tttctatctc atcttcattt aaagttgtaa ctttaatagc   75300
tttagataat tcatctttgt ttttttacatg tatattaaaaa tatctatcac tattatatat   75360
agttaatgtt ttattttttg cgataactat tcatcctttc atgaaaaaac ctactaccttt  75420
ttactaatat aagtatagca taagtagtag gtaattacaa attaaagtaa atctaattcc   75480
attaagtttt taggtgttac ttggtcttcg aacttcttag caagttctcc atctttataa   75540
ccaataagta caggtgtact cataatgtca aataacttga ccgcttttc tctatctaca   75600
tctttatcat ctaagttaat aacataaaca ggtttagtaa tatctccttc tgcttcgaaa   75660
agaggaatca cactttttaa aatttcacat ttagcacact catcttgtgt aaccatgaca   75720
ataacatcct gttttgtct gattgttgta tttaactcta ataaactatt cacttttcc   75780
atttttctgta tcatccttt ctaatgtgtc aataatatct ttaaatgttt caatatcagc   75840
tacatgtgtt aactgctccg taccatcagc tttaaatagc tttaatgtac cttcatatat   75900
aagaatgtac acatatgtat tataaataaa ctctagctga aatttacttg atttactatc   75960
tgctttagta tcatcttccc tattaaacat cttaataggg tcttgtacat tacttacttg   76020
tgagaaaata tcatttgatt tgaatatatc ttcagttcta cttagtaatc caaacgcttc   76080
tttttattc atttagtcac ctcttaggc ttcacaatta atacaaattt tagataaatt   76140
gaattgttgt gatgcatttg taccatgttg ataatacaat gacttaatac cattagacca   76200
tgcaaagaga taaagttcat ttaactcctc tgctgtaaca tgtttagggt taatcataat   76260
gtttatagat tgtccttggt caatatattt ttgtcttgta gaagcttggt ctaatatatt   76320
atattgatta atttcaccat atgttttaaa tacttccttt tcataatcac ttaagaaagt   76380
taggtgttga acggaaccat cattatccct gatactctca ataactttt tattgtcctt   76440
tcctttttct tttaatagtc tttaaggta aggattaatc atagtttttct ttacttagc   76500
agtgtctaca acgtaataat tactcataaa aggttcaatt gatttagaaa cttgacctag   76560
gataaatgag ctcgaagtcg taggagctac cgccatcaaa catgaatttc ttctaccata   76620
accttttaaa atagaaggct ctccataaag tttagctaac tgctcactag ctttataagt   76680
ttttttcttt aataattaa atatctcttc attaattga ctagctttaa tacttcaaa   76740
aggtatgagt tttgattgta ggtatgaatg gtaaccaaga acgcctattc ctaaggctct   76800
```

```
gttctcaaca gaaaagttat aagctctctc cataaattta aatgcttctt gtttatcttt   76860
ttcatctgag tctcttagat attctaagtc tctaataaac tcagacataa cagcatctaa   76920
aaagtaaaca agtgtctcta cagcatccgt gtgtttccat tcatcatact taacaaggtt   76980
catactagat aggtcacata caaatgacca atcttcttta ttaggtaaca ttatttcact   77040
cctacatgtt caatagtggt cgttaatcac taccagttct ctaattaaca atatttatag   77100
ttagggaatt tttcagaatt acatcttctg gttaatgtat ttctgtttat tcctagctct   77160
tcagagcata tacccatatt tttataaact acgccatcaa caataacttt tttagcatta   77220
gcgctttctt taccatacat cggattgttt tttcctcgtc tatccattat attccaccca   77280
aaacctatct ccatattata accttttttt acagattcgt acatgtctat aaaaatttgt   77340
tctaccatgt aagcaaactt tttatcctct gtactaaaag tgtataattc ttctacataa   77400
aaattctctt caccatgttt catcattgat cggtgtaaat tagttgttga gcctatctta   77460
gcttttctaa tatgattttt aaatctatgt tgaactgttt ttgatgtaat tccgatgtat   77520
atttattat tgttttttgtt tgtaaatttta taaatatggt actccatttt cgaccctctt   77580
aattattatt gttaatatga acttctatat gtttccatat agagcagact atatcatctt   77640
ccttaataag gaagtccacc atttcgattt aaataagatt tacttgatta ttactcaata   77700
cttataccac ttggctctaa ccttatccct tcacttatgt gaataggtta cagatagtcg   77760
ttaggcattt acagatttat aatctgattt agcacggtgt tgtcatatat tttaacttag   77820
atattcaccg tttagatgga tttttcgata gtaattactt actaaaggtg caaattttta   77880
cacaaatttg agttattaat agttaaccct ttgtctttat atacatctac tgtattacta   77940
tttgcattat catgaaagaa gatataaggg tatcctattt gtgttcttct tgttaatact   78000
ttagcccatg ttttctttt ttcttatcc ccattaatca tgtctaataa ccagtcatca   78060
gtaactgtta ctgcatgtgt taagttttga attggattac cttcggtacc aatctctaaa   78120
aactcatcaa tatcctcatg ttctataggt aaataaggac taaaacgccc tctacgtgta   78180
gaattaccac aaaactaatgt atgcccttct ccttcttacaa caagtttatg agtaggtact   78240
tcaacacaat atacttacc tttatattgt accgttccca cagtaacatt tgagcctcca   78300
aataattgac cttcagatag atataatttta tacatagtag ctttattagg ttctctttcc   78360
cttaaatcaa ctgatttacg agatttataa cctaccatag aagctatggc ttgaacaatg   78420
tctacattat gttcaaccac actcatgtag ataaatgatt tatccgttct tctactagca   78480
tcccaatgag acaactcgtc aataaaatca taagcccatt gttgtgtgac atttttgtaaa  78540
tttacccatt tactaaattc tttaggtaat tcttcaccca tattaacata aatattatga   78600
ttattgtctt tgtctacatt atatgtgtat tcaactccta gaccatctaa tatccataat   78660
agtctatctt ttttacgttc tttactaaat ctaaacttca aagatttagg gtatttttta   78720
ataatactac catctgcttg caaggctacc aaaagacgtt ctttaaatgt gagtcctctg   78780
ccttctttag caaatgaaga atgtgctaaa taaacgtctc tatgtaatgg catatcttct   78840
gctaatctat ttctatactc aggtactaaa acactttctc tttttcctgt ttctttatta   78900
gtcctttag ttctgtattt aaaaaccata ttatggttct tagtcactaa taagtcaata   78960
tttttactat ctttaaaatg aactaattca ttatcttcag gtacaaattc catataacct   79020
gtaggctcta caaactctat ttcatcatta tctgttacct gtgcaacttt tgttccatct   79080
ttctactaa ctacattaga taataattca tacccatctg ctgtgagtat ttcagtttta   79140
tcatcataac atccttggct tatcgtatct gtcatttgct caaatagctt cataaaatga   79200
acggaaccac ttgtcagtcc attatcagtg atttctgagc ctcgaggtct gatgttaccg   79260
aagtaaccac ttgtaccacc accgtattta ctcatcatac ctacttcact agcagtatta   79320
agtatcgatg gtatagtatc atctacccaa ctaccaaaac aactaatact aaatcctcta   79380
tctttcccga aattagacca tataggactg gataaggaat aataacccttt actcatataa   79440
tcataaaact tgtcagaaaa cccatcaata cctaaaatat cttcagcata atctgcaata   79500
tctttaattc ttttgttctgg tgtttcacca tcacttaaat aaccacgttc tagaaaaact   79560
ctagaatcat tatttaacca ttcaaaatta ctcatctata tacactgcct ttatatcatt   79620
tttagtctta aaatagcgtt tactttatct ttagtaactc gtttaccagt attttcaaaa   79680
tcagattccg ttgaaaaaat agtatcttcc gttacagaat tactaaatttt tgtatagttt   79740
acagaacgtt tagataaaaa gtccgttaac ttagtactaa taacttcatc atcaaaccat   79800
gacacttcac tcagtaactc ttcatcaaca tcaaaaagtt tagtataccc aacagctact   79860
agagagttat taagcctatt tttaataaat tcttgtacta cttttcttagg taagaactcta  79920
agttcccccat cttcatacat ccaatcaagt aaccgtgttt ctgattcata agatttttta   79980
caggctgtgt aaactgcatc ttccatttct tgttgaacc actcaggtct ttcttctcta   80040
agaatattaa tgatttctgt tccaaataat ccatggtctt gctcttcttt agatgtagct   80100
tcaatagcat ttgataaacc tctaaataag tttttatatt tattaaaact catcataatt   80160
aaaaattgac taaataaaga tacatgttca ataaatatag aaaataataa aacagatagt   80220
acgtaatctc tatcatcctc actcttactt agttttacat gcatcgctaa ctcatcaaca   80280
cgttctttaa gagcaggaat atcgtcaatt gttttaaact cctcattcaa acctaaatc   80340
tctaataaat gtgaataagc gtcggcatga cgtgcttcac tctcactaaa agttgcaccc   80400
acagctccag tttcccattt aggcattcta tgatataggt cacccagaa agtctttact   80460
gctacttcta cttgggcaat tgctagcata gcttttttaa tggtcatttg ctcattgtat   80520
ttaacgttat tcttatagtc ttgaatatct gatgtatagt taaactcagt gtgtacccag   80580
taacttttggc gtatagcatc tttatattct aataattcaa ggtattcata gggttttaat   80640
tcttttcttg gtttgaataa gtctctttta cgctctcttt tcttttttatc cctatataaa   80700
ataaaagctt tagcagtatc tttatacata ctactaaata aaacttcttc tactatatct   80760
tgtattaatt ctacagtaat gatagtgtct tgttcttcta gtaaagagtc tacgtcatct   80820
acaagagaat caataacatc ttcaatatat tcttctgttt ctgagttggc tcttaaaata   80880
gcattagtaa ctttacttaa atcataatct acaacggaac catcacgttt ttttatttgt   80940
gtaatcaact agtatcccett ccttatatac catcaagtaa accatcaatc aacttatctt   81000
cttttttact aactttagat attttagact tgacaactct atatggttta atctcttttt   81060
tgttgtagca agatataata taagaaggtg ttaagttagt caacccatct atcgtagtta   81120
taagaacatc ataaaaatgt ttatctttc taacattttc tacaataaaa tccgttctca   81180
ttcttcatct cttaacttaa catatacta ttctatataa ggtaatgcta   81240
catatgactg tgctctattt cttgtaaata ttaaacaagg agttttatta acttgcaaac   81300
tatctccctat aacttgttcc caccatgtat gaggttcttt attattaagt agaacattat   81360
ccataatcca attttctcta tgtttacact ctacaactaa tggaaaatta gattctaaag   81420
gtgctacaat gtcaccgaca gcattattgt tagctcccca tgatgcacct cctgattgtg   81480
gagacctact aaaaggataa ccccaccaat cagaaagttc tttggcaatc tttcttctga   81540
```

```
atacatcacc ttttttttta ctatttgtca tgtttcttca actgcactac tttttcatta    81600
tcttcttttg ctttatgctc ttcttgtttt tttcttactt cttcttgttt ttcttctaaa    81660
tactttcac gttttctt taatttaagt tgcgccttct ctacttgctc agtagttaca       81720
tctaggttat cttccataac aatcattaac aaatcaatag cattaaaagc atcattaaag    81780
gcagatgcat actcttgaac tgtaacggca ttaattgctc gtgcaattct agtagcctca    81840
tctaatgata cactacgtgc tccaatacga tgtaattgct tagcagtttc ctcagttaat    81900
tccttgcctt ctactgttcc ttgtgtaata gcttctaacc acatgtccat atcttttgt     81960
gaaataccttt ttgtatgtgt actaatattt ttttccatta ttcttcatcc ttttcttttg   82020
attcttcaat tgcttcctca atatattta atacgtcatc gttaactaac tcagctttgt     82080
ataaagcatc aattagaatg tttaagttta actctgtatt ttgctctagg tcaaccattt    82140
gtttattaac acctaacaat aagtagtaa tagctttcat aacatctgtt aaagttgctg     82200
tttgttcttt acctaactct tctaattggt gcatacgctg ttcattacct acacgtaatg    82260
ctgtaacata ctcatctaca aaatgtagaa tatctttctc ttccaaaata acacttcctt    82320
tattttata tatgtattgt aacatactat acattataat gcaagattaa agttttaact    82380
tttgttgtaa cttgtaactt tgaatacttt caggtgtaac taaaaatcta ttgtgtttca    82440
aagtactaaa agcttttcc ataccatat cattagcatc ttcattacca tgaggtacta     82500
aatatactac attaaaatgc ataataagtt tactagctaa attaatacta aagtctgtag    82560
cgtccgtatc taacataata tatataggtg tttcttagg aatacttgaa atgaggttat     82620
taacttgtat ctttgaaact tgtttaccaa acgtagctat accatactta tcaaatgtaa    82680
gtgcgtcaaa aacaccttca gttataacaa caatctttg tctactagct atatttaaat    82740
taaatataac atcgctttta ccatactcat taggtttaga aggtgcattt atagatttaa    82800
tatatggatt tgttttcaata cttcttgtat tccagtatat atacttacct tcattgtcat  82860
aagtaaaaaa tataacacta tttcaagta ctattttctt tttctcatta ttaataccat    82920
aagaatagca ataaccattt ataatatacc ctatactata gtctaggatt tgctgtagtg   82980
taatacctct attcttgaga tatcttaaat agggtactac ttctttatta tttaagttat   83040
cttaatcaa tttaaaccct ataggtagtt caggtgcttt tgattttata ctactattat    83100
cttttgtata tccattaagc cttagtaata atttctcact ttcagttaaa tctgtgttat   83160
atatttctaa tgttggtgag aattgtatat caatatctt tgtttctaat aactcaaaag    83220
cttgtctacc tgtaatacta taataagatt tcataaagt aataggatta ccatgttctc    83280
cacacttctt acaatgatac ataccattag tagagtctaa agactgttta acataaaact   83340
tgtattctg ttccccacaa aaaggacaaa aatatcttaa ttcccctaca gtattctctt    83400
tgggtgttcc aatctcttga cttaaaaagt cttcaaacct cattttcagt cacttcctat   83460
atagaaacaa ttttcttcat taatagtaac atattataga tttgacttaa atcactataa   83520
gtatcatcta ccagtgttgt actgtacttg agtacttcat ttaattgata atcctcgat    83580
ttcttactaa aggtgttaat ctcttcaatt gttttatctt ttaagtactc gtttgtactg   83640
attgttttta gcgtttggaa ataacacct aagtcactaa atcctgctt tacatcttta     83700
cttgtgaagg gttcatctat agtaggtaaa ccgtacaact tagctttctc aataattttc   83760
tcattatctt ctttttatttt ttcattatac cataatccta gtttacattt aacagtttca  83820
cctttatata aagttcggtg tgttaatcca taagacatag gtaaactaga gcgtaatctt   83880
tttaactcaa tatatccaaa gtcattacta gctttatact cgtatgcatt acttaaaggg  83940
taccagtcta ctaaagtaga aacaggaata ctatctatat gtaactttgc attgtttgta   84000
taacttactg ttaaagatgc aaactgatta tcattaattt ttagtttcat tgtttaaatc   84060
ctttcttagt gtagctacac cattctcttt tactaccgta attgtgttct caaacaaagg   84120
tgctaaactc ttattgtgtg taataacaaa gatagtacct actgttttta gtctatcctt   84180
aagtagttta acaacgttct cacaaccaat agtgtctagt ccgtcaaagc attcatcata   84240
taacgctatg tttgtagata tatcttcttt actcataatt aagtcttgga tagcaaaact   84300
aatagctaaa tcaatacgct tttgttctcc tgctgaatta gatttgtaag attctccacc   84360
attgttattc ttaacaataa catcgaactt gtctttgagt tctccctttag catttttctac 84420
ttgcgtttgg aattcaattt cgatatctga gcctgctaat atttgtaagt actcgttagc   84480
tttttcattt aagaatggtg taataaagtc taatattaca gaacgtaatc ctttattact   84540
aaatgcgtct acagcttgtt tatattttgt tttcttactt tctaattgta ctatacttc    84600
cttatgtttg tcaatagcat tatcaatatc ttttagttct ttattgtgta attcttcatt   84660
aggttcttct atataagagt aatcatttaa tgttggttct tttaaattag ctttagtgtt   84720
ttctaattgg ctaatttcat catatacttc ttgctgttct ctatattgcc gttgaatatc   84780
atcatcatgt tttttctttt ctatatctc ttgctgtata aattgttgta gttccttaga    84840
tttagttagt agctcttctt tcttattaat tatagcctgc tcattatgtt cgtactgaga   84900
tattttagct tgttcttctt taatttgtaa ttctaagttt tctttttctt ttatttttgtg  84960
tgtattatct ataggagaac cacaaacagg acaatggtca tttgtatcta gtttattaat   85020
agattgtttt aattgattaa ttatatttag agttgtattc ttatttgttg tttcttgact   85080
caataatggc aataatttat cattaatatt tgtgttaatc ttttcaaatac cttggttagc   85140
ttttgtataa ttttcactaa atacaaattc aaagtcttca actttaggaa tactacctttt  85200
acatacacca atctgattgt ctaaatcttt taatttattc tcgtactctt gtttcttttg   85260
attaaactgt tcctcttctt gcttcttacg ctctaataag ttattatatt tatttacttc   85320
attattatat tgttcttgtt ttaggttct tttatattct tttcttgttg    85380
ttctttactt tgtttctctt ctacttcttt aaccttttct ttagctactt cttgggcttg   85440
cttataaaata tcagtcttag taatagattc tagtatttct ttttacctt tgtcggtagc   85500
ttgtgaaaac attggaatgt ctccttgacc atatataata gcatttacat atgtattaaa   85560
aggaatacca aacaattctt gaatttggtt atctgtaaca tcatttgtag agcctgttat   85620
ctctttgtta ttacagaaca gcttaaccttt gttcttgtgt tctttatgtt tacggtatct   85680
ttcgattaaa tactcgtctt tacctatgtt gaaagaaagc ttaacgtagg tgtctttcttt  85740
cttatactta ttaacgacat catctgcctt taaaccttc tcagtttttc caaacagtgc    85800
ataggtaata gaagatatca tgctcgtttt acttgttcca ttactttcaa aactatcatt   85860
tgttttatta atacccttcaa taagtacaag accttgctta ttccagattta gctggatatg  85920
ctcaatgact aaaaagttat tcatctctac ataattaaac tttaaccattt gtaccacctt  85980
cttttaacaa tttaaagaaa cattgatgtg aaccataaac tagaatataa caatcttctt   86040
gttcaataac cctcgtataa taatgagcat agttagcttc ctctaatact tttttaataa   86100
ggtacatcgc atcatcaata ttttaacat tacatacatc atatgttctt ttattatgta   86160
agaactgtaa aataggtta gatttatata tacttggttt aatattcttt ataataatat   86220
ctatcatact acagcaccgc ctttaaacac tctagaatct catcttttgc ttctggatag   86280
```

```
tatttgtctg cataactaga agtaatcgtt atagggctgt cagacacgtc agcgtcgact   86340
ctcttttcta ccgtgtattc tttcttcatt tgtacttgta cattagattc atcttctgtt   86400
ttatctaatt caattacttt agcttgttct ggagtaccaa taaacctaat aaagtgacct   86460
tggtttacta aatcattcat gttatctggt acattgtcac cttgtactgt aataaacttt   86520
ctagtatcta atgaaatgaa cgttgatgtt agcttgtctg tgtctattaa gtgtacgcca   86580
ttagcttctt gttcatctga aaaggattgt tgcattagag aaccaccata catatgatta   86640
gggttattgt ttaaatattg tcttctatga tagtgaccaa gaagaataaa atcatattgt   86700
tctggtaata ggtcttggta accaaatgcg ccttctaatc tatgggagcc tttacctgtt   86760
aaactattct ctacgcctaa atgtgctact agtatattta ctttatcttt ttggtaagat   86820
tttttaatat actccttaat ttcttctgtt tcatctccat aagcacacat agttaattgt   86880
actttactag aaagtgagtc actacgtaaa tctttagtta cttccacatt aggtaatgtt   86940
tcaaagatat caatactaga ttccgtatat aaagaattag acacagcatc atgatttcct   87000
ctaaccatat atactttaac atcttgattc ttagcaaagg tttcaaatac cttattatat   87060
actctagtat ctaccgcatt tctcttatgg aataaatctc ccccaaatat aactttagct   87120
ttattttctc tagctaaatc aaatactttt tgtagtgtct caatttgttc tttaaatcta   87180
tcattaccgt attcttcatc aggtttacta taattcgtaa acatatgaaa atggctatct   87240
gtaaaaaata taaatttcat tagtgccctc ctttagtacg ttatgataaa agtataaccc   87300
ttaacaaaca tgttgtcaag ggtttttgtt taatttgtat tatttagtaa tctatcttgt   87360
gccatactga agtattcttc tgataattca caaccaataa aattcctatt taactttta   87420
catgcgacac ctgttgttcc gcttcccatg aagcagtcta gaacaatgtc tctttcatta   87480
gttaagcgct ctaacaacca ttccatagca tataaaggtt tctgtgttgg gtgtcctttg   87540
ccctgctttt cacttctagg tgttacacta cgtataacat ctttaaattc acagcctaat   87600
gcttccatag tatcaataat aggtgtaaat tgtctcatat cacaaaacac aacgatatta   87660
ccacctttt taacttttgg tatagcttta ttaatccata aagtagattc aaaatttta   87720
tcccactctc caaaatcaat accagctcta cccatagttg taaatctgtt ttcttttgca   87780
atgttatatg gagggtctgt tacaatagca tcgatactat tatcttcaat tgtatctaat   87840
aactctaagc aatcccctg taataatttt atcattattt tactccctct tcactaattt   87900
ctatagcatc atgattagca aactcctgta atttaaacat atgattgtca ttaatctcat   87960
ttagtagctt acttgaataa aaatgtatca attcacatac ctcatctgtg taaggctctc   88020
ctcttaatat atcttcaagg tatccattg cttcttccgt attcctaccttt acatgtctta   88080
aaaattcagt cttatcttgt agttcctgta ttgtcatttt cattgtttag tatctcctta   88140
tgttttccta ttctttcact ggctaaatta tagtattctt cgtctaattc aaaaccaatg   88200
taattgcggt tagtactcat acaagcaata gcagtagtgc cactaccaat aaacccgtct   88260
aaaaccacat ctccttttat actatgcttc ataatacatt gttttattaa atctaatggt   88320
ttttcatttt ggtgtaattg ttttttacca cttaccctat caaattccca tacatcggtt   88380
aatcttctcc cattaaaatg ttttttgccc tttactacta aaaataagat ttcgtatttt   88440
ctaccaaaag aaccttttaa atctcctgct gtatgattgt tttttaccca tataatcata   88500
ttttttattt taaatttctt ctctaaattgt tgtttaaaaa aatctactt gtctgatgag   88560
caaacatat acatggcact attgttttt agtaaccatt aacactcatt tatataatct   88620
ataataagtt gttcgttatt atcgtttaaa ataacttttc caaatctatg ttctttattt   88680
tttctccact tggttctata attaattaaa tagagggtc tgtaacaatt aagtctacac   88740
tattgtcagg tatcttcttc ataccttcta aacaatcttc gttatagatt ttatttaatt   88800
ctaattccat gttaataccc tacttttctta aatgtttaat tttattgttt gttagttcta   88860
attctataat acttctttta ggtctaatgt taaataattt acagtcatac ttatctaata   88920
cgtaattatc taatgtatta aataagtcaa ttgaaacatc ttctaattcc ttttcagaat   88980
actttgtgtc tgtagtttct ataaatccgt gtttattgat aacttgaaag ttttctagtt   89040
ttactttgc ttcatttaag ttcaaatctt accacctctt tattgtttat aataaaagta   89100
taagccttga caaatacatt gtcaaggctt tttctcaatt ttttaactta tattcaattg   89160
ctttaattac ttccttgatgt gtattgcaag gtatagcagg tacttattta gacataacgt   89220
tatacttata tcctgttgta ttattccttg ctatagagtc tagtaatgta acacatacat   89280
tagttccttt taattggaag gttcttaacc ctgtatttgt ataatcccat tctgctttat   89340
tgcgtgtaaa tgttctacgt acttttttat aaagctagt aaagtcatcc attaaaaact   89400
cagcccctcca aaagaattat taatagcttc agctttatta ggttttttctt taaatctact   89460
tttatcttca ccattaaatt ccgctagtat ttgcttatgt tcttctgcct cttctggtgt   89520
ttcatctcta acaaccattt tagtaggctca tactttaaga ttaacaaatc tctcacctgt   89580
gtttgaactg tttcttactt tatctaggta caatcttaag aaaccatttt taaattcttc   89640
atctttttgg ttaacggcaa aagcaacctc tacagcattg acaatctttc tgcttccctc   89700
aacatgctca cttgtaataa tttctgaacc gtaagctgtt ctgtttgttt gtgctaatgt   89760
ccaacaaaca aaattgtatt cttgtgataa ttttcgaata tcttcaaaga tacgaccacc   89820
agcatctgat tcactttgat acttaaggta agggttacgc ataagtttag gataatcaat   89880
aataacaaca tctatatgct tatctttctt aattgttgta ttaactataa tttgttctaa   89940
ttggtttggt gttacctcac caggcatatg tttaacgata taaagttac ctagcagttg   90000
tctattcttt ttatagtgtt cttgtatctt attataagca tctgtgttta aagataagtc   90060
accattaagt aattgattct tttgtacacc taccattgt tgttccgctc ttaataccat   90120
tctatccatc tttttcctcta gggcaatata taaaacattt aaaaccttgtt aacatagtt   90180
cttacctaaa ttacttgcca taagagactt acctctacct gtaggtgcaa taactaatcc   90240
tacttcccct ctacctatac caccttcaat ttgctggtct atagaatgga aacctgtaga   90300
atacttatta atacttaagt tgtttaatag ttctctcttt ttatctacgt cttcaaagaa   90360
atcaataaat tcaccatcag taccattaat gtcactaact tctatttgtt ttaatttctc   90420
tactaattca ggtaagttat ctgagtcctc ttgcttattc tcagctatga acttaactaa   90480
tacttctta gacatttctg ttttaatata cttttctact tcatagttta cagaatcgtc   90540
tttattattc atgtctactg tatataaact atctaaatat tttaatgttt gtgttacttt   90600
ttcatcatct tgttttatcac tacccattaa ttgctctact ttaatagcta aagattcatt   90660
tttttta tcagcaatgt gtgctgttct tttatagct tgtgaataagt aacccatgtc   90720
ttccgattct gtagcaaata gacttttagg taacttatct agtacttctc ttgcaaaatg   90780
tatatccttc atagacttat gtaggataat ctccttaatt cgtttactca tatgtgtcat   90840
cctttactat atcaataacc ttattatagt tcaacatacc ttcttttgtc aatggtattt   90900
tatcaattaa attatatttt tcaattatag acttaacttg ttttaaatta acctcataac   90960
ctaagtaatt actatacatt tgtaaaatat atgatgttga agtaaatctt ctcatatgta   91020
```

```
gataattcat tgttgtttgt tctatattta caatatcttg tttacttaag tctgtagtgt   91080
ttactaaact tataccatt aagtctcttc tatctatacc gccatttaat tctgcgatat    91140
ttgcttata ctcttttgc attaaaaaca tagatagtct agcattatta ggtattgtag     91200
taggtgaata ctcatttaca atacattgtt taataaattt atttaataag ttttatgtt   91260
tactaggtaa ttttcatt agatgttcta tatatttatt atatgataaa agtataatat    91320
gtttcatgcc attaaatata ccataaatag tatcttctat atctaaagct gttttaaaca   91380
ttgtatcaat atcatgtatc tcttcattta aaggtgttgt atatagttga tgtaattgtg   91440
ctacagcagg atttaataag taatcagatg acttaattaa agactctact tccccaattt   91500
gtctatttgt tttatttaca cctcgtttaa tacctttac ataattttca taattagtta    91560
agtatttatc ggaactaaaa aaatttggtg caggtatagg gtaaggttgt gttttattct   91620
caaacccaaa tgtggtattc ttaaaaacat tttgcatgta tttaaaaaca ttaatgttct   91680
tatctttat ctttaagtaa aagttgtaga atgtattaaa tgtcttacta ccaaagaagt    91740
ctttacaaat actatctcgt gataaattct gtaacatttt ctttctgtag tactcagata   91800
aatgcttatg tctatctacg tcttcattac catttgataa tgttaaatgt tgtatatatt   91860
tagcattcat gtgtgctata gcatattggt catataactt acataatata taagctttat   91920
aaaaaccctc agggtcataa gacatattaa aaatatcttt agtagggtaa ggtaagctac   91980
tactataaaa attcatattt gatatttttt cctgtttttt atcttttaata gcattatatt   92040
gaaccattc tagtttttgtt ctacgtttat tttcttttct ttcatatacg taactaggaa    92100
aaaatctatt tcgtaattca gtagcgtatt ctagattaga agtaataaca ttatcatctg   92160
tagcattaaa atgtaagaga ctatctgtat cataatctct tactagtgat ataacaatac   92220
caccttttatt tcctcttta gaaacaacat taattttgtt atcctgttct aatcttttaa   92280
ggtttttaga taaagtagag actgagacat ctagctcctc tgctaactct ttttttagtag  92340
ctatttgata agtattattt tttgatttt tttcaatgta atcatataat cttctttctg    92400
tcttagtcac taccatacc tactttccta attcttttaat ttcaaatttt tcttcttcat   92460
atatttctct acgctcatta gaatgtttat ataaaaactt atgtgtcata tcattaaaat   92520
caaatatctg tgttgtatta tcttcttct tttttacgtaa cgcacgacct acacgttgta   92580
gtgtttgtcg taaagattta ccacctgcac ctaggatta tgaacgaata ccactgatat    92640
caacaccctc atcaataagg cttgtagcaa tcataacttt aagttacca ttacgcattt    92700
catctaactt ttgtttacgc atatctgact ctatttcacc atgtaaaaag aaattctcta   92760
caccattc attcaacata gtggatagta tctcaccatg ttcaacaaaa ttaataaataa    92820
taagcgtagc tttatcttga ttataccatt tagctgttag ttttgcaata agtttattc    92880
taaactcgtt atgtacaata cctttattat atgcatccct gtaatcctta atattatcta   92940
tatcatcagg gttagcaata gggataatat ttattgtagg tctagctgaa tagccattct   93000
cgattaaaaa ctcattagat gttcttacaa taatatctcc gaataatgct tgcatacgca   93060
tccatagtag ctcatcttc atgtctatgg agcctgttaa tgctatcctg tataatgcat    93120
tctcacagga cattaaactt gtataccatg aatctgattt actgtgatgt gcttcatcaa   93180
ctatcattac agctatagag tctaggaact cacgcatttt atgatattta tcatagctct   93240
tttgatttt ctttcttact tctttttgga aaataacatt atgattgttt aatgccatta    93300
atacttcagc atccgtcttt gaattatgat aaatatctg aagtatatca agcacattct    93360
gctctacttt agttttaggt gttgtacttt ctaataataa cttaagtaac ctttttttgat  93420
ttttaccacc ttcaaattta ggaagtatct ctttagctat ctttttactt aagtttactt   93480
tagcagatac ttttactcct tctgtagggt cttttaagtt agagttaaca gtaggaatca   93540
taactacagt tcttgttta acatcaaact taccagaacc tactttacct actggtatat    93600
tcaatcgttc acttaaacgg tcagcagatt gattaaaaat ctcggtagag cttgtaaaga   93660
aagctacacg ctctccttt tctagttgtg gtaaatagttg gtctatgata ccgctagcaa    93720
cctctgtttt caattatgtt acgattaggt tcgttactcc taaccttctt gtagtctcct   93780
acaaagttca gactatatct taaccatatc taatgagact taggttctcc ccgttttccat  93840
ccacttggat gtacataata gtcgttgcac cttcctattt ataggcttgg ctcatgattg   93900
tctcaaatga gagagttccc atgaattaaa ggagtcacac ttataatatt tctactataa   93960
ggggcaaaat ttacctgcat tagtagcttg cttacatata ccattataat tgactagact   94020
attaaataca gcttcgtact gatagtcacg taatgtaatc ttacctacgt tattatctag   94080
tagttgtatt tcatcatcaa tatcttcttc agctaaaaag cttcagatt tttcatcaat    94140
aatttcgtat tgaaagttat gtcttgattg taactcacct agtaatgtta tcatcttagg   94200
taacaaccca ctgggaatt tgttctcaga ataatcatag aaatctacat aaccatccca    94260
cacacctcgt ttaaaagcta agctatgttg ataaccatct tttttagctc ctaatgtttt   94320
atgaacacgc ttaagtatga tatctttaat ataccatca ctttcgtcaa aatctacata    94380
tgtatatata ttctgttgtc ttaactgcat atattctcct ttcttttag tccttttatta   94440
tcttaccata tttattaaag ttagtcaaga aaaaagact aggaattatc ctagtctatg    94500
gtaaagagat acctacaaca cgtgtaacat attggtcttt attattattt actgcactat   94560
ctttaattgt ccaagtatca ccactaatag atagtgttac tctataatac tctactccaa   94620
tattagagtc tcctgataca taagctcctg aacatgtgta aataccgtct ccgtctatat   94680
agaacttatg acatagtgta cctgtttat cagtaccttt tgtattttgt agagctctat    94740
atcttgtgta tacttctaca tactggtagt tagatataga atcagacatg gtttcttttt   94800
tatttgtatc tttaaagtta tgtgcaccat tccacagtct tttaaatcct ggtagtgttt   94860
ttgttgtgtt ccacacatta ccatttacag aaccattaat agttcttcca tcagtaccta   94920
tagcagtata aacaccatat agattagtaa agttagttga atctgatatg aatacacctc   94980
tacaactaac cgaggacgga gaccctacaa cacctccttg tatataaaaa gtaaaaacag   95040
ttcacttgt ttcttcaata tgttagctta ttgcctgttg aaatgttatg ttgtctgtag    95100
tatatacaga taaagagtag ttaattacttt cagcatcacc atctacatta gataacaaat   95160
acttacttat ttttttgtaca tctaaatcag ttttccatgt gccccagcta ccatacgatt  95220
ttttaacatt aagatattct tttcctgtgc taatatccgt taatcttaac attcatttt    95280
cattattgtc tataataacc tgtaaaaacc cttcatatac accatttggc atatccgaca   95340
tactagacac ataataatata ccttgtgtgt taatatcaaa aggacttcca cctattttgag 95400
atgtgtattt attatttggt agactttgta ctctgtcgtt tgtgatgtt tgataattgt    95460
taacaaacct atatagtact tttacttag aatcagcggt agataatgta tgtaatatct    95520
gtactactct atcctcagta tctaaggtta gtacttgaag tagtacatcc atgttttcca   95580
tatcaggttt atcatacata gtagctaatg tacgagctcc tatataatat agacctacct   95640
ttctaatatc tcttaagtaa ttagtataat caatatcttt agctaaccct ctatctgttg   95700
ttaacttaac ttttgtgtt ctacttacat ctgcttgtaa gtctgttgtt acttcaaaga    95760
```

```
catttctgtc ctcagttagt acaccaccta tattattaac ttgttttgtt aaatctgcta    95820
ttgtactatt ttctgtaata ggtgtaaaat ttagtgccat attatttatc ctttcttaga    95880
taacaattct tgtagcattc tttttaattc ttctacttca ctttctagct tttatataatc   95940
ttctttagga acatactctt taggtggttg gtaatcagca tcttcaatac tcttagcatt    96000
atccttaaaa tttttgttat tatattacttc gttagtattc ttatagtata catacttagt   96060
actaacaaac tcagtaaaaa acccgtcagg aagaattgac ctagaaattt ttacgtcacc    96120
gttgttctca tcatatcctc caacaatagt gtaacccatg atatacttac tatcttctaa    96180
atgtaacaca atttcatctt tactaatatc atattttatc atttacaaaa ctccttatta    96240
aatatacgtt agtcctacaa ctcttaatac ttcaatatga ccagtttgat taaactgagc    96300
aacagacata gtatttctat tcccatctat tttatttgtt tttgacattt tagcagtaac    96360
attcactcta tctgtaatgt cacaatacccc ttcaaaaaag tctacactag cattagaacc   96420
atcatttact aagttaaaat ctctaattac aatactagat gtacttgctg ggtacctttt    96480
agttgtatta tgtccagaac ttctagtcca gtatactact tcaataaaat cataattatc    96540
taatgaatcg dataagttta ctgtattacc tgaagctagg tcaagagtac cttcccaaag    96600
actattacta gacatttgaa cttcatatc ttgccaacca ttagtatctt tattatatgt     96660
taaagaatat cttttacctt tagggtcact aaaatccatt tgtattattt tatttgtagt    96720
atttatatta ttattcttat atgctacttg tatcgtacct tgtatagttt tattgttagg    96780
tgttccactt atagagctat cacaataaaa agtataaaaa cctgaggta cagacattgc     96840
taattgttgt aaacttctac cgtttgcgtt ttgataattc catacatatt tgtagtagtc    96900
attgttgtac gtatctacag cactatgtgt ttgaagttca tccttgcttg ttgtctctat    96960
ccaattgctc catatctcat catattttct tttatcataa gtatttgtaa taaatggagt    97020
taccgagtac gattttttcta attttggtag tgcataatat acaatagcac cattattttt   97080
agagttagaa cagttaaatc ttaataatgc tgatatataa ttaacagtgt cattgctagc    97140
ctcttggtta taatactgca atgtaaaagt aaatgagaat tttttccatt ctgtagataa    97200
ctcatagtaa ttaacttctc tccttcctcc tgtgtaaggg ttatttgttt gagatacatt    97260
atcataaccc gctatttcaa agtaagggaa gttaccattc aataaactag tgtcatttac    97320
tttaaggtat acagacattg taactgtatc acctacatat aaataattcc ctaatctaaa    97380
acgtttagat ataacagtag gatatgattc cccccccatca tctaattgaa tagtatttc    97440
acccatatat ctaactgttg aggtagatgc attattagta aaaccccaaa aagatgtatt    97500
atctatataa tccgttctta tattagctac atccgtcatt ggtaatgtga ataaactatc    97560
ccttaacaag ttaggttgtt ggtcttggtg tggtaacttt ctaatcattt taaatgttga    97620
agtagaatta ataggattaa actcagctaa agctgaggta ccattttac tttccttata     97680
atttatccat cctgtgttta aattacttttt aggaggattt atgagtgttg caaattgagt    97740
tgtagactct gttaaatctt ttacattaat tgtatttcct gaatcgtata gtgtaccttc    97800
atctagttta aaactaaccc aatcatagac agtaccatta taataagttt tcacaaacaa    97860
tttatttgtg ttagatgggg cataatataa cttataataa gtactaccct tttatctaa     97920
gtgtaaaaac cccgtagtac ttacaccttg tggggtgttt ctggcttgtg ttacaaagta    97980
gtcacctgag tcttgtatga aatttagaac attatttaag tcaggataac taatcgttta    98040
taaatcagat aagttaactt cttcttttaa gtatttaccc atttcattta cttttaggta    98100
catatccttt aatctttgtg attctgttag aggtgtgtag ttaaacgtca tgtgtgtaat    98160
cacctttcaa ttttttaagc tcatcaataa gctcattaac ttcttgtagt ttatctttat    98220
atgtttgttc catttctttt atagctttt cttctacagt aggaataaag agtttagctt     98280
gtgagtaagg gtctctatat tctgtaggca taatatcact tccttagtta aataaaaaga    98340
gggtatgaaa ccctctcttaa acttactcat ctcttgttgt aaccataagt ctacgtacac    98400
gaggtcttaa gaaactatt tcagttgata agtctaatct tacttgtaat ttgttattct     98460
tagtagattg atttactttc tcatcaataa catatctatt aaagtctcta ttagccttaa    98520
ctacctgagc agacttagta aatgcttttcc aagttttcc atcatcgtct gaatatttag    98580
gaataacatt agtgcccttta ggtaagaatg cttcataact aaatcttatt tgttgtatatg   98640
gagcttctgt catatcaata gctctaccga tataggaacc ttttaactca gttaagaatg    98700
tagtaaacgt taagtcatta gaacttaata aaggtgaaat atatttatta gactcaaatg    98760
tagcttttaa tttaacttgt ttagctaaac ctaataccctc taaatcttgg tagttaccaa   98820
taggttccca ttttaattgg tcaaatgtag tagatgtagc catgtcatct aaaatcttt      98880
taatttccca agtacaacct gttctttcag gggttaagta cgtagacatt aaaactaatc    98940
tatctgctga tacattctta ataggttcaa attcaattgt agctgtttca ttaaacttag    99000
aagtatatac accaaatttt aaatctgaat tttggtgtgg agtccaagta ctagcgttag    99060
atgaactaaa tagaacgcct tgtacatatg gattaccact aataacttca ctaggtttat    99120
caatcttagg ttttgttctt gttccgaccc acatagtata atcactattt tctgtaataa    99180
tgacaatagc atactcttta cctgcttcag ccatcatagg gtcatcaaag tatactctag    99240
tttcagcact agcattatta gatacttttaa tatcatctga gttgattact gtttcagcat    99300
ataccgtctt gttagggtaa cctgtatctc ccataccacg aatttgtaca gttacattac    99360
tagacttatc tcctttacta gcaaagtata aacctaaaga actaatagtt ctactttcat    99420
catattggaa tgattgtgct aatgggtcta ctaagtttac tgtaacacgt gttttgataa    99480
taacatcttg tacagtcttc ttcgtccttt gagctgtata tgttgtagca cttctagagt    99540
tagcattttt caatgttact tctctattac cgcaacgaat acctgctgga attgtaaatg    99600
tacctttagc tgtgccttta gcatcagaca taattgtacc atcttcagaa ccttttctat    99660
aacctgttgc tggtgtaata gcacaacgaa caccatcaaa taaatatac aaattattat     99720
cattaggatt taaccatta acttcgaaag atacgtcacg aacacgaata aattcaatca    99780
tttcttcaag tgtacgctgt cctccagcct ctaatagagt acctgttcta ccatgttctc    99840
tatcatatgc atatgactta ccttttccact cttgtccttt atctaactgt aagttagaat    99900
ataagtaatg ttctgtttct ccataataac tttcattatg tctccagaat cttttcattg    99960
ttactttttt agtttctgt tctgtgattg ttacattctg agtatctatc cagttatctt    100020
cactaggagt taatttaac acaccttgtt tatttggtat attataaggg tttacattta    100080
aagtttctga tgcttgtcct tggtaaattg tacgttcttc tgtaaatggt gcagaaatta   100140
atcgaccca tacatgagct gtagtgtctc cttgaataat cttaggttgg ttcacagctt    100200
ctttatacgc tagagtagcc tctgcatcat caaaactaaa cacaatacca aagtcagggt    100260
gtgtaatatc agctttatct aaagatataa aaccttcact aaatacgaaa cgtaatgtta    100320
atgggttttg ttttccatt gcgcatcat ccaaagcatt aacagcttgg ttatactcta      100380
aattatctac tctagttttt acttttttgta agtcttccat agtaatcta gtaatagcat    100440
atgaaataca tactgcttcg ttagaatcag gtaatactgt tacagtacct aattgtaagt    100500
```

```
tctcagggtc tgtatttaaa ggtggtgtta ctaatctcat aatattaggt tcacctttaa    100560
gaatagcaat atcaccaaac ttattaataa aaacagcatc tttacgagct aagtagtaag    100620
tatagtctac aagtacaaca ctttggtcaa taggcttagt accattaaca ggtgtgaaat    100680
taatagacca acgtttacct actccctcac ctactgtaga tacttcataa tctttaccta    100740
cttccatctt tctgttgtac ttatacgaaa cataataaga tgtacctaca ttaggttctt    100800
gacctgaagg agaccagtct attgtttgac catcagtaag tctatagtct tctccttgtt    100860
tgtattcttt tgttgtctga cctggacttg ttttctgtcca tactctaact acttcaaaag    100920
ctgttttatt agataaatag tcttgagaat ctcctgttga acttcttgta acacgctctt    100980
tatctactaa tacttgcgct gttacacgtt gaacatcttt tacaggggta ttagctaaag    101040
taatattatt tgatgattta ttaaatacag tactttcatt ttctgcttta cctagttccc    101100
ttgacttctc tacactaatt ctagtagaaa ctggtttatc tacttataaa ccttttacat    101160
atgccttacc agcatctaca acaacagata catgattatc atcttcggcg tttccttctg    101220
aaaatagctc aaatccacta actttatatg aacccgactc atcataagta cgctctgcta    101280
atactttgtt gattttatcc atctcagcat tagtagattg gatatagagg tctccatcca    101340
taaaagtata aatagtagca gaagtagggt cattgactgt taaagataac ttctcttcta    101400
gacggtctgc acccttagaa aaataactag gaactccgct tgtttggtct aataagctat    101460
tatcttcatc aggtgtaata attctttctg ttagtttaat acctactgtt tctttaccta    101520
cacccgtaat tttaacagtg tcttcactac tatagtaacg tatcttacca tttatataca    101580
cataacctgg gttaacttgt agtacattat ctttagttaa tgtaaaacct aatcctgatt    101640
gtttatcccc atctttaaaa atagaatccc ctaaatttt taagtaatat tgttcaaatag    101700
actgcatttc atttagttct gattgttgta gtggtctatc tggattaaat agtactcttg    101760
ttctatcttt tgtagggtca aatctatcta agtatgagaa acttttaaaa ttaattgcca    101820
tatattcaat tctcctttt aaacttcaat gataaagcgc tcttttacag ttgtttgttc    101880
acttctattt tggaattgtt tattatcata aaataataaa gttcctgtag attgcacttc    101940
actgggtagt aagttaaatt tagaaatact atctttagct aacaaatcca taacaaatcc    102000
tacttgtcta tatgtaccta agggtaattc atccccaaca atactactt ctaagtacac     102060
ccacttagca ccttcagcaa ctgcattagc tgagtcgatt tctacccatc gttattacc    102120
atatgtaatt tctttttac tttcatcacc tgttgttttt gcaggtctaa ctaatgctac    102180
cttagttgct tttttatc cgataacttc ttgtaatgat gttgctgttt cttcaggttg    102240
aggtgggctt gtttcattag cccacgctgt acttttacca attgttaaat aaatagaatc    102300
agccttactt acaatgtatt tagctaattc tacatgtgaa gcatttgttg ctatagccat    102360
atttttatt ccttcatgt ctagtattct gtattaatat aacaaggtat actataaatac    102420
gcataccta ctatatcata ttaatacttt attgtcaata tatttactgt acttctgtgt    102480
acgtatctat tactttaatt ttattatcta ctgtgaatgt atcacttgat agtaacatat    102540
cccgtaagtc ataaataaat ctatttgaac ctaatgtaat attctcgtta tatagagtag    102600
tagacgttag caatctatct acatcagtat atccttggta tatcttaggt gctaatttta    102660
ttacctgtcc tgttgaacta tcaaatacat taccttcact atcagtaagt atgctcatgc    102720
tacttaatgt agtgttatat atcatatcta cctcttgcca cacagcattg aaatagttat    102780
tactcatgtt agaaaatacta ccttttttat ttgttaaatt attcaagtta gcattccata    102840
tagttttaag tataacccta gagaaaggtg taatacttga ataatctatt gtttctaagc    102900
catataaatc tactaggtta ttaggtgtta ttgtttcacc ttgacttaaa ttacttattg    102960
ttttttaggtt tgtccaatta tccccatagt aagaataact tagctcaata ttttaagag    103020
gtgttgttgt attattcct attgtttgta tatctgttaa tatgttatca aacacaatag    103080
ctttgtctat aacattagtt acatcttcag gtgctaccgt gtagtccttc ttagtagctc    103140
cttcttttag ttgaaggttt gttacttta ccgtattaga agcaataggt gttttagagg    103200
cagtaccatc tgctgtatat ctacctgtgt aaacaacaag tctatggtct gtaattgtag    103260
gtgctgtaaa tgtgatagat acctcaatct tattacctat cttttctttgc atgctttaa    103320
caccattagc aacaatacct ttagtactac tatataaata tatccatga ttgtcagaat    103380
atgtttttaa gtccatatta gcatctgtga tttccatctc gaatgacaaa gtatataatt    103440
tttgtggttc tagtacttta gataaatacg ttgaattata taaggtgtca gcccatgatg    103500
agatataaaa ctcttttgtg cttacaacac ccttgaatat atcatca cctttatatg    103560
attgcaataa gtttctatta gttgtatttt tatataaatc tataggtgta ttattttgta    103620
cctcattatt gctgttttta cctgtaatac ttacaatagg tttagttgaa tcataagtag    103680
catgtaacct taaatatttt atgggttgat atccattttt attaattatg tctccattta    103740
ataatgatgc tactttaaag ccttcaatat aagtatcttt agtcaaatct atgtagtttt    103800
caactagtgc cttaaaaggt ttgatagtat acacatcttt tttataatta taaaaatgta    103860
aatccatgta gttaatactt atatcttttt gctcatcttt acctatatta acctctaatc    103920
ttgtaaataa attaaggtca tcatttaagt aatctcttat ataacctatg tttacaccta    103980
tgttttctc gtaaaagat agttctgttt ctgatacagt taaccattca ttactacgaa    104040
aatcaaatat ttgtaactta atgggtaatg attcatcagc tgaaactaaa gcttttgcaa    104100
agaaatcaat tgttagttct cctataaaat cggatatttg ttttttagca ttatctctag    104160
ttatatctat attaggtttg tatctactga taaactcccc tacattaaag ttattgtata    104220
aataagatac accgtaagca gtttccattg atatattat atcattagta ttctttaagg    104280
atgtatataa gtaataatct aaaggtggtt cttttccttt atcattaaa gaagctatat    104340
gtgtgacggc tgatgtacta gtaggttcat atgcatatgt cgtaacataa gcataattta    104400
taaatctacg tccaatatta gaagagcctg ataagaaatc ttcactattt aatgtactct    104460
tatttgttct gaaccttgtt ttatcagatt gttcagctgt tgcttcactc atgtttaaat    104520
gtccatagaa agtttcatca taacctaata atctatctaa atccgtatag gtttcaatttt    104580
taggtagatt tttaagccat ttaacaacac catcacccttt tatggtagta gcaccatcat    104640
aagttaaata taacttaaca cctgcgggtt taaattcatt tattacatct ataatctcta    104700
aaggaaagta accatcaaca gaaacattta tcacagcaaa tctataataa taacccatta    104760
aataatcttc accattttat tttgatttat tggtataaaa tatattttta aaaggttcat    104820
atacactaac attatattc tcattatcta agtagtcttt aatgacacta atgatagcat    104880
tattagtacc ttctttttcat aataagtatt ttataattct tttctatag ctgtcatcat    104940
tctcatttat tcttctgtat acaccaaacc aatcccaaa cttatctaag taatctcctg    105000
tggcagtttt taatgatgat tgaagtttgc tttaatggt gtctaactct atattgttca    105060
tctcatcatt aagtgctgtt attaaagcat agttagggtc ttggttatct ttattattct    105120
tatttcttct taataaaggg tgtaagtttc ttaaaaaatt agccattgtt tacccccctat    105180
attaattcta ccttaatatc ccctgctcta ataatacctt tcgaagatac ttctatattt    105240
```

```
gtagataaat tcttaaatgc tacatcataa attaaattat catctatatt cataatagct   105300
tgaattaaat cgttaataat taagtcatca gaagtagtca gactatttat gtatcctcta   105360
ataacacttt caatatgtct ttgtaatgtg tcacctatcc tagctttatt agatattgtt   105420
actactgcag acacatctat ttcctctttc tctacaccta caacatctaa ttttatacca   105480
ctaggtctgt aatcttctaa tgccgttatt atgtcatttt ttagagtagc agataaattt   105540
ccgtttttat catgcgcata tacagtaaca tgacctactt cttcataaac ataaacacca   105600
tcaacatcag gtacttgtaa tgtaccatat ctaatagatt tattagtagc tcttcctctc   105660
gattctacaa acatatggaa cctacgttta aaatcctctt gagattcttc ttttgttcct   105720
gtattaaagg aagtcgggtt tgtaattgta cgaattaaac tagagcctga ggctattgta   105780
ttaatgatat cttcaggtat attacctaca ataccaactt ctttacagta aacttctact   105840
gtaatttcag tggttccttc ttcagcatag taatcaacta atgtttcaaa ctgttgaggg   105900
tattcttgcc tagtagatga gaatgtagta cctgcaggta tatacattct catgtctaaa   105960
ggttggtaaa attgaatgtt tacattacca taagcacgct tagcttttct tttttgaaaa   106020
tcaaaagctt caataatccc ttcttgaatg ccccaattaa tgttttctct tgttaatata   106080
taatactgtt ctatttctaa agctactgct tctaaaagag agcgtacagc tgaaccaggt   106140
gtaaagtctg ttattttgct tgtaccttgt atcgtcttat ccattaacct agataatatc   106200
tgtgttaact ttcttgttct catataaatt tcctttctta gtcaaataaa gcaaagacac   106260
ctgaatcatc ttgacctaat acaaagtcta tagattcttc tacggacttg atttctacat   106320
taaatgaccc atagtattca ttaccttttta tctcccaacc ttttaagtta gctgatttaa   106380
ctctactatc tgatgttaga gtctttaata catctacttc aattaacgta gcttgttcag   106440
gtatatttaa accaaataaa ttatgaatgt tagaaccata ttcaggatgt aataataaag   106500
aacctttagg tgtcaaatgt ctagctctta aagattgctt aatattatct atgcctttaa   106560
ctatatcaag gtctcctcta ccatctgaag atagggctaa tatttcatca tctgttccat   106620
gagcgtctat atactcttta ttatccgtca tatttaggtc tctacctaaa gctaattcta   106680
ctaatacatc tttatctctt gatgttattt ctttagaaac cgagtctgtt aactcagcat   106740
ctaaaggtat aataataata tcaccccttag ttattaagtg ttcaggggtc cttttctttt   106800
cttcatctgt atctacaata taaggatatt gtaagttgtt atgttctatt aaatctaacc   106860
aataactaac atcaccataa tacctttgtg atatagcttg taaggtttct tctggttgga   106920
cttcatgctt tctaaatctc attataccac ctcactctta attagtggta gttgtaattc   106980
caaagagcca aaacataagt ctaagtctct taaatcgaaa acaatactat tgtattcttc   107040
ataatcactt aagtagtcag ctacgtagtt aacattactt cttactatag atacatcttt   107100
ttctgttaaa tattttaagt attcaggact ttctacaaag cagtttacaa tagcgtaagc   107160
ttccattacg atagattgca taattaaata cattctaggt gattgtaact ttaaacttgt   107220
ttgttctact ttattaacta ttgtattgtt gttaaatgtt cttttcaaag tagggatatc   107280
agtagactta atctctttta attttattct tgcaagttca cttagttgta tttgtggtgt   107340
ataaaattta gaaacaaaag gtacttcctc atctaataag ttcatatgtg tgtaagacat   107400
gtctaactct aatccattta aaaaccttaa tagtccttgt ggttgaggta tataattatt   107460
cattacctag atacacctcc atcaccgtat cctattttaa gtgccatatc atcaacagta   107520
ctactaagac cgttagtatt ctgtctaggg ttatatatcc ctatattact catccgtct   107580
ctattacctt cagaaccacc tgttcttatg ccactacctc ctcttaatgt tcctgccgtt   107640
ccatatcgtg aaccactact actagaatta gaagagcttt tactacttt atttttcaaat   107700
tgtgatacta tttgattatt cttgtttctt gttttttcgtg cgttactatc taaatcatta   107760
acaccctcat caactctttg tttagcatta ggttttacat taccaaactc agcagatgtt   107820
acggaacctc tatctgcttc agcaaggtta cctatcacaa ctaaagttat ttcatatcta   107880
tataacaagg attcatcttt agaccttgtt attttttaaac cttgcggtgc tagatgtact   107940
ttgtaatatt tatcatcagt aaagttatag aactctatat aagctcctgc tacgctacca   108000
tctccaccct gcttagcata tgcttctact tgttcttgta gttcctctat tttttgtttt   108060
cctgttttag taccatctac ttcttttaca ggtctaaatc cagtagtacc agaaaaagtt   108120
attgtctcta tatcttttacc gtaatcttca acaataatgt ctgatttagt tttagttata   108180
gatgttcttt gtggtgcatc tatttcataa ctttcagggt ttactttgaa acggtacata   108240
ttatatttac cgcttgcggt tggaaaacgt aatgcaatac gtcttattgt attctttcca   108300
tctgattgag gcataactta ccacctttct atatcgtatt atatcatata taggatttaa   108360
atacaactac tttctcaagt ttaatataac atgacatata taaaaagcc ctattaatag   108420
gacttttaaa cttttttaaa ctctaatatt ttatttgttt ctacaccatc tataccatat   108480
aaaataagct tatttataat tcacttgtc atatcaccac tgaatatat agataggtta   108540
ttattatgtg ctgtatttac tgtatcttga gtgatgctag tatataggtag tagtactcca   108600
tatatatttg tatatatacc tttgttaata tctgtatttg ttagatagga agtattatat   108660
aatactggta agttagaaaa attatttaat acttcttgtg tgattgttaa atctttaact   108720
ttcaaataca cttgattcct aggtgctctt ataccaatta aattatattt tttcagtagt   108780
tctactatgt ttgcagtagt tggtaaatta atactatatc taatagaatt tttatattta   108840
gctaatacat cttctaaaga taaaatactc tcaccgttct tagctgaaaa tgactttatt   108900
tgttgtagag tatagtcaga tacattacct ttacctgttg ttatattgtc taatttggaa   108960
tcattaagac agactaattg attgtcttta gtaacttgtg ttgtcaaact caataaatca   109020
acattagaat ttacaagtgt ttgtagttgc ttatctgttt gttcggatac tgtacctaat   109080
aactcagtgt tagtaggtgc taaagtagtt tctaatactt ctatactaaa cattgtatta   109140
tcttgtagta atgtaaggtt aatatcatta tcttgttgta cttctactgt gaatgtatct   109200
ccttgtttaa caggtataac atttgtaatt atattatcgt gtgtattacc attagttata   109260
gttttgtatg tattactatt cttcttgact gtaatagttt ttactttata tgtaatata   109320
tcccatttaa gattaataga aactttaact ttagatacac taacggaat aacaaaagca   109380
tccttagtct tatttacaaa ctcagaatta ttaaaaacta tcttattcca tgtaatacgt   109440
gtaggtgtgt atggataaat agtaaggtta ctatctagtt gcagtaatga acctagataa   109500
ttactactaa aactttgaga actattatta acataggtct tacttgattt ctctaataag   109560
gtattattaa tgttaggtaa tgtaattgta tctagatgat tcaatctact ttttaactca   109620
tttcttt ggttgtattt atttatcata gtagaagcat cttcatataa gcctttaaat   109680
gttttgtctc tgaactcttg aaactgtgta ataatccttc cagctctact acttacatta   109740
gatatttgag atttcatagt cgtaacatca ctacttgctt tactagaaac ttctatagat   109800
ttttttagtct cttggattaa ctcctctaag ttttccttac ctacaccctc aagtaagtag   109860
ttaatgtcat ctaattcttt ctgtacttcc ttaagcctat ctatagactc ggtaatgcta   109920
gcatctaacg tatctaaaat tggcttatca tctaaatata tacctttatc attaaattca   109980
```

```
aacatatgct tagggttttt tatataaaac acattattat catttatacc aaactctacc  110040
catacttgcg ctgagtctaa taataggtca tcatcttgct ttataactct ataagaacca  110100
tcgtgagaca tctcttgtgt tgttcttttt tgtgtgcttt tgtctaatac tgaagctctt  110160
acatcacctt tttcggaaat aaataaagtt gtaacatgat tatcttcgga accatcatca  110220
aagtatagac cctggtgttt aagtaacatg ttaggtgcct tttgtattct aggttctatt  110280
aaattttttgt tactatagta tgatggaaat aagtcttggt attcagtacc tgtataaaag  110340
tctgaagata aaggtttttc tttatcacct gaagtaatgg ataagaaaga tttaccattg  110400
aatgtttttta tagatgtacc ttcaccatct ttatatgtat aagttaggtc aggtaatata  110460
gagtataaag cactgctgta tttataaaca tcatcattac tcattttacc accctctaaa  110520
ggattcgtat ttatgagttg gtttgcttcc gtattaccgt agatagctag tataataggg  110580
taattaatgt catcattaat aaaccctaac agtacagtag ttccttccgt tattaaagta  110640
ttactgccat acatactacc ttcaggtgtt cttcctacat aatctttagg ataaggaaca  110700
gctaacttac catcatcact agggttatgt cctaatgtta aactatttat tttaacttct  110760
acagtttggt acttataatt tattttgctt actgtaccta ataatagacc tttaacatta  110820
agttcttctg agtctatctt ttttaaactt ctacctaaag aagattgtaa tcttaccacc  110880
atgctatatc atcctcatca aacctcataa ccctaccatt aaagtcatcc caataatcgt  110940
ctaactcata ggtactaata gaggtgttat ctttaggaaa tgtacctata agagaaataa  111000
acttcttatc tcctatgtat atccctatat tatcatcact acgtccaaag aatagtatat  111060
cacctatttt gaatttgtca atatcaactt tatatttgtg tcccttacca aatatagtat  111120
agaagctttt acctgtgaag aagtagttaa ctgttaatgg attttttaagc tctacatttc  111180
tcttttttata catccaatat aataagttgt atgtatctaa aggtactata tccttacttt  111240
caaaagggtt tttatccgta ttcccttttaa acatatactg tatatgttta taattattta  111300
aattctcttt caagtctaat gttactaatg tactaactgg aacatcttca tcaaatatat  111360
gctcattctc catgtagcta ccatacagta tgttctgtaa ctcatcaaag taatctataa  111420
caagtacacc atttctttct accatatgca ccatacaagt tgataatgca tcagtaggta  111480
ctgtgagatt atcagtagta taacttattt ttctaaatgt gagtttagct tctatatctg  111540
taccattatt agtaaaacta tcatatgtta cttgtctagg tgttacactt tgtataacac  111600
ctacatatgg tctaatataa acaactttat tgtatacgtc ttctgtagtt atctttttaa  111660
cttccttatc tttttcttca accttttctt tggttaatac ttcaaaattg aaaagattat  111720
ctataaattt atctataaca tctttaactt gtttatccgt tgccatatca attatccttt  111780
atcatatata aattgagcac ctttacctat tgctgaactc atatctattg ttcttgtacc  111840
gtaaccgtta ggagttgcaa agttatgttc tgatataaat atactggctc caccgtctaa  111900
tacttttttct acaaaagcaa catgtccata ctgcgggctt ccgccaggag cgcctctctg  111960
ccatatgaca caagctcctt gtttaggtgt tctacctaca ctataaccag cacttttagc  112020
accaccaatc caatccgccg cgtctcccca taacgaaaca ggaataccta actcaccacg  112080
tctattatag gcataccatg tacattgata cttataatgc ctattgcctg gttgaacaaa  112140
gttagggtca tgtttaggta atttaccatt atatttttct aatgaagcta aagtgcctcc  112200
atcttgtgca ccaccttcgg agtctccatc tttatttcct tttgtttttct tctcggctac  112260
acctttttct tttaattctt tagatgtctc ttcacccata agaccaccca taaagtcaga  112320
tgactgattc catagtcctt taaacctatg tttgcttcct tcaccatctt ttataatagc  112380
atcttttagt cctcttgtta ctcctattgt agtaaagtat ccttgtttat aatcaaactt  112440
atgttctacg gactctatgt aaaactccca tatatccccct cgttgtttat cttttataaa  112500
taaccgttta cctaggtcat ctttagggtc acctaataca acaatattac ctgcataaaa  112560
attagggttt gagtgatacc aattaaatag cattttagta aatataatta aagagtcatc  112620
acttgcgtca gaacctgtat ctctagcaac attagctact ccttctacgg ctttaagata  112680
cttatcataa atatcacctg tggtacttgt cggtgggttg cctttaaatc tagtgtaatc  112740
ctctagtagt ttcttagcat gtgtaggatt accatactta taattcttttg taatatcatc  112800
tattacagct tttgttgttt tcttatttaa atctttatca tcaaaagttt cttttcttatt  112860
aaaacttttcc gctaatatag actttaattt ttctttttgtt agtttggtc tagtatcaga  112920
tactgactct cttgaagtat tgttctttgt tatttttttca tattcttctt tacttagatt  112980
acctttttttt ataaagatt ctaaaatact ctttacttca ggtttagtaa tattgttgta  113040
ttttgatgat atcttactgg agtatttatc taatccttta gatatagact ctctaccata  113100
gttatttaaa tctttaagta gtcgtgtcata agttactcgt tcgtgtccat tatctccacc  113160
tgtagtttca ctatcttctg tagcactacc acttttagtt cctatatata ggttttctgt  113220
ttcatatttta gaatacccgt atctatctac taattcttgg tggaattgtg gtttagagaa  113280
tacatcccct gttaattctt ttaacatacc tgctggtttt actgtaaaga tagagtaggt  113340
ttctacatca ctcttaccta catcctcctc tataaaatca tcagttggta caactatata  113400
ttctaatgct ttccattcag ttggattaaa aggagttttt cttaatacta gctgtgcttt  113460
accttttatgt ttatctgaat ttctaaagaa taactcatta aaaggtctag cagttactaa  113520
gtccattagc tgttttaatg taccatcaaa gttagtaaaa gcggaaactt cagttaactt  113580
ttcatactca tcccaactag ataaatcatc ataatctaag taactctcta atgtgttgta  113640
tgttttatcc gtataattgt acttcatgta aggaataaat cgttgtataa taccttgcat  113700
tacatcttta gcggaactac ctgtaaattt aacctgattc tctccatcgc catcaactaa  113760
ccaaccaaca gttggtaata cagcttgtac ttcttgtata acacctaaac caacttacat  113820
aaaaggtttt acaaatgatt gacctgttat tctaaattgt acttggtcat tgccataact  113880
acctacttta gatacttgag ataccatacc cacttgtata agtttctctt ggtttccctc  113940
tttatcttta gggtcattat taggcgtaat atatatctta ataatatcat ttgccattac  114000
tagcttatcc caatacgtat cccctgacat agttatttgg aatacagcac tatcatcttc  114060
catagcattc ttagtttgaa aactaagtaa ctttgaagca aattgattgc cgttgtaatc  114120
tttagtgtct tcaaacttta atgtaaatgt attatcatct gttactattt ctattcgtat  114180
cttaggtcgt ctaattctat acatatatgt acttcctttta tttttatata aagggtagta  114240
cttaataata ctaccctaat aattacgttt atacgtgttt gagaagatgt ctaaatcgtc  114300
accaaaggta gacttaatac ctttgcttat gccttccgca tcttctttat cgtttactcc  114360
tgtgatgtta acactcacag aaacattgtt ttgagattta ctacttccag atgtactact  114420
aagtatagga tttctcatga ctgaagtata tgacgatggt ataactccgc caccgccacc  114480
acctgactta ccgtatttac taacatagct tttggcattg ttaactctgg tactcatcat  114540
agcttctcca gcaccatac gctcaaaacc ttgtgcaaaa gcttttgtat ttttttctaa  114600
gcttccactt ttactccatc ctgcattttt aagcatatca ctgttttgac cagaactcat  114660
ttctttccat aagaaatcta attgtgcgtc taggtcatta gacttcttac ctttagattt  114720
```

-continued

```
agcaaagcta tcaaggtctg atttcctact acctaaccat tgtgcaaatac caaaagcacc    114780
gctagaggcg ttctttgcat tagggtcaag ccctgattct tgcttaaggt tacccataac    114840
ggcacctact tggttatcgg ataaaccttt acctttaagg aatttgtaaa tcttacccgc    114900
accttctcca tctacatcgg aagctgaacc tcctgaatca gaactactgt ctgaacctcc    114960
tgagtctagc gcttttagcat cttctataat ttgttgtgcc ctatctaata ggttactgta    115020
agtttttaag ttttttagttt ctgatttatt attcttttct cttagttgtt ctgtagacat    115080
tttctgtttt ttattgtttg tacccttttgt taaagtatat aaatattata attgtattct    115140
aaaaattaga ttctaataat tgttttaatt ttctacctat tgctttccct gtttcattag    115200
ggttttact tttaggtact tctatgttat atttaagatt ctttggttga tggtcatttt    115260
ttagagcatg tctaggcata acatcactgc ctccacctcc accacctatg aacttgtctg    115320
aacctttcat aatactggca atcatagtat cccaattacc tgctgttgca tactcatgaa    115380
caccattgtt atgtctcata tcatgtaagt tcttttgtcc tttgttgtag aagttatctc    115440
taatccattt agcaccacca acaatacca atccatagtt aaaaccatta ttaggattgt    115500
tatcaaaagc acctataccg aaccaattac cttttgttagg gtctccacct ttggaaaggt    115560
tcgaggttcc ccagcctgtc tcaacagcac tatgtgccac taagtacctt gggtcaagtc    115620
ctgactcttt acctgctttc atataaagct cacctaaacc acgcattta gaattactag    115680
gtgcttgaga ctcaatccat ttatttaaca tttcggcatt tacaccttta gcagttttac    115740
ctaagtcatg cttagttacg tctttatctg taaagttctt accatcaaga tagtcaagtg    115800
ttcctcctga tgaactattg tcggaactac tgcctttatt tgttagattg tctgctaaat    115860
ggtcaagaa atgtgagtat actgttacat ttccttctct agaatcatta ttcttttctc    115920
ttttttcttc tgcttttttgc ctgtctttac tttgtgattt atcattaata ccataagtta    115980
aaacatataa acaatagtat acttttcatat ataacctatc gtattagtta tgtatattta    116040
tttaataaca agtttacctt acaaaataag aaaggtttat atgcagaagt agaatacaaa    116100
ttttaattat ttatatattt taacaatgtt taaatataca cgctactgta tattctctag    116160
ttatttctag acactaggtt tccctacgtg tgcagactat ttgttatccc tagtttatag    116220
ggtgagtatt ttcttccac caatagcttg tggtttttact tccgtcacct atacggaata    116280
gtcgttgaac gttctccatg ttaaaggagt ttcgatgcta tacacccatt gtacttctcc    116340
ttaggattta accttagagt atctcaactaa tttttttctga tttctcaaca ttcaagctta    116400
gtctttcgac ttacttttgta gtttagttag ctttagtagt ttcatagcag ttaacactcg    116460
gtacttacag attgctctat aagcaaggca attagtatat aactaattat gttaccttt    116520
ttattttttca ctgtttcatc taatttagaa gggtcatctg gtgtgaagaa atctgttatg    116580
ccacccccata gtttacctac aggtgagtct tggaatttat tcttaccatc tttatctcca    116640
ttagcccata atttccaacc atcacctgtc gaagcgcctt ctgctgtttt cgtagcatag    116700
tctcttaatc cgtctccata acctaggttt aatgggtcta tgacacttcc tatagtatta    116760
ccaaatttag aagaagcttc tttagtatct ccttgtatta agaactacc tatatcaaac    116820
gccgatagac ctgcaccaat ccaacctagc ttacttgtaa gaccacctag tttaccaaga    116880
ccacctgcgt tagcagtagg tgcttgtgac ataaaccta aattggaacc tttaccacta    116940
aatttacctt taactttacc aaaagctcct ttacctttgt tccatgcacc tttactaag    117000
tctttggttc ttcccatata ttcaccaaat gtaaagtctc tttttccgaa ggtatcaaat    117060
aggttttac ccataccttt agcagttgt cctgcacctt ttacttggtc tttaaatggt    117120
cggtctccac ctttaagatt atctcctagt atagtgtcag ctaagttttt aagtccacca    117180
aaacgcccac caccgttagg attaccacca gtcttaccta ttgaaccacc tttacggtta    117240
ttaaaccaat cttttagtcc tttttgaccct ttacctaata aagaccacc agccatcatg    117300
gcagtagatt tagctaaaga tgctacaaag gcaagtactg ctcctgaagc taggtataaa    117360
ggagctggca agcttgccat agcactatga acatctctaa taggttgagc taagtcataa    117420
atatcctcgg ctttatcatc tgtcttagct ttgttctggt cattcctacc tgctttagat    117480
tcggaatact tatccctatt cttatctcct gctttggaac cttcttgctc catctttta    117540
gcttactag ctaactcttc tttagatagt ttacctgagg cgtaaagatt atacaactca    117600
tctgtttgct cttgtgttaa attagctccc atgctttcaa agccttttt agctatggct    117660
tgttttcttt ttgttgtact tcctatatta ttagcttggt caaatatatt aactaaatta    117720
ttagggtctg atatacctt atccatttgt gcttgtaagt catgcatacc ttctaatcct    117780
tggtacttag tacccccatcc cattgctagt ctagtgtaag aattacccat accattttta    117840
atacccttggt caatactact taacgcttga gcccccttgag ctccttgtaa accttttacta    117900
cctgtacccg ctacttgagc ttgtaaagaa gtaagattga acatgtctcc tttagataat    117960
gttctaccctt gtcctgactg ctcggcaata gtacttaagg cttttaattg ctcatccttgt    118020
ctaccaacca tatcagattc acgtataccca cctaagaaag catcttgcat agcttttcata    118080
ttatctgaat ttacgccacc tgtatgcata agttgtgaca tagactgttg gtacatttct    118140
tggtcttgta tacctaatga gcgtccacct acagctaact gttagctcc tttgtatgta    118200
tctgcatcac tttatgacc tatagaactt tcatatgatg tgccacttt taacacgtca    118260
gttgaattgt aaccaagctt attatctatg gataaatcac cataagtatt tcttactgca    118320
tctatgtcca tattatctga attctgtcct aatgatgtta ccataggtct atttgcttca    118380
gatagggaag caccacgcat atacataccg cctgcaagag cagttactgc catagtagca    118440
tgtgcaccaa tagaaggtaa cctatcttga aacaattac ccattgttcc tctttgctgt    118500
tctatctcac gctgagcaaa ctgttttta gcactatttt tatagtagtt gattgattg    118560
tctaattcag cacctgtttt tctatagact tcagaaagct tttcactttc atcaatcatc    118620
atttttaatag atgctgattg tttttaatag tcttcagaac tgatttcacc acgagctctt    118680
ttacctacta aatcttgttg ttgctgtcta taacctctat atctatcttg gttttctttt    118740
attcttctat tgtttcttc tcgttgcttt tcaaaagtgt ctactttacc taattcagaa    118800
cgtactctag caccttggtc ataggacatt ctattagagc cttcagacct agatatatga    118860
ccccctaacca tattacgatt agctcttagt tgctttgtgt actccttagc tgaactggca    118920
tcttttacta atttattata ctctctgta acttggttca gtgttttcat ttctttttatt    118980
ctgtttgtta catctgagtc tgaaccaatc ttttgagatg ctactttctc tagttctgtt    119040
tgtgtattgt ttagtgtctt attaagttta ctatatactt tctctacttc agggtcagga    119100
gctatacct ttgtaaatatt aagctgtttgt atgtcattta agtctcctt taggtcattt    119160
atgttcttag ttacattctg tgtagaacta atagcctcgt ccatagcttt tggtgatatt    119220
aaagatttat cactttgctt gtccataata ttttgtacag attttacttc ttttgctatt    119280
acttttagtt tctctaagaa gtttgttaat ggtgcatcta tgttcttaga ctctaacgca    119340
tccatataca tctctatagc ttttaaactt tgttctaaac tagaactatc accggtcaag    119400
accaacctat aatcgtcatt cattgccaaa cagtattcac cacctaatca aaaaataagg    119460
```

```
gtattggtat tataccatta ccctacatgt accaatcatc tacatttttt attgctttgt    119520
ttatatcttc ttgtgttatt tctttactgt caatacctaa actttcatca agctcttttt    119580
gttttttgtct tatgtgttcc atcatagcca aatgttgagt tgttaatcct tcagtttcat   119640
cttctaactc agcttcaact cgtctatctc tttctatctt ttctttctca cttaaacttt    119700
tatctacttg tgtatttaaa tcatctaagt ctaagaaatc aggaacaaca tcaaattcat    119760
ctgtcggcgc ttcgaaccat gatgtgtcta cgtcttccgc tttcatatca tagttttttac   119820
cgtctctagc ttccatcatt tcttttgtat caagattcat gttagctata ataaactcta    119880
tttggtaatc atctaaatct ttaaaacgtt gttcagtagg taatacatta aactcacgca    119940
taatagccca taggtttctt gatagaggct ctttagctat atgtgaaatt ccacctaacc    120000
gttctatatc ttcatttaac tgctttacgt tactagtaac gaaaggacgt cataaagtct    120060
aaccaatcat cccacataat agcaagcgga gttagattat aaatctcctc agggtctcta    120120
aattctttag gtacttctac ccctacttct tgtaaagtag ctaacatctg ataagcatta    120180
ataacttggt cagattggta agcatccatt ccacctaagt atgcagaacg taaagccata    120240
atattacctt gttctctagc attaggtaat ctaattttta ctttgaattt taaatctaat    120300
tcttcaaagt tgtattcttt ctcccataca tcattaacac ctttaattac tttgttaata    120360
acacgctctt tatctttttcg ttgctgtatat tttaactcat caatttcttc aggtgtcata   120420
tctttaatat cttttttgttc ttttttccaat tcttatccaa tccttttatta tgtattcatc   120480
attaatataa cagctaactt atgttttttta tacacataca gtataacata atgtggttat    120540
aactccaaat tacttaacat attcagctac tcttttttca atttcttgta atcttttgttc   120600
aattgtttca ctattttttaa gtaagtaaat atagtaatct tgaagtgagt cataatattc    120660
aaaatcaatc gtcaaaatct cttgaccctc aaaatacttt ttagtgattt tacctgcttg     120720
ttccgttaag gtttttaaact tgtcaagaat ttgattgatt gcgatagcag ttgtcttact    120780
tgttaaatct acattctgtg ggaattttatg taactcaatt ttcatttctt catgaatagc    120840
tcttaattta tttgtcattt ttttattctc ctctttatta atgtaacctt agtatatatt     120900
atgtatttac ttatgtcaat actttattttt taaatttttta tcataataat catttaaatt   120960
taatgttttg tggttatctg taactctgtt ataatacata gttacaactt cacctgtttc     121020
tatctctata actagatatt gataagataa tttattatct acttttacta cataaggatg     121080
tctaacaact accctacgtt gtatttttgtt attatataat gtttcattat attctataat    121140
atctaagttc ttattatgta tgtaatgaac aaacgctttta aaatttactg gtttcttaca    121200
tttaccttttg aagtgattttg ttaacttaaa gtaattgttt ttattgtaag cctcttttaa   121260
taagttccta catataatta tttcttggtt agtcatttgt ttataatgct tcttttacttg    121320
cctgtttttta cttgttgttc ttctgcctga atagaaagtt ttcacagttc atcatctcct    121380
tatataacta tagtattaca gttatttata attgtcaata cctttatgct tatttttttct   121440
agaatatttt gttttatctt ttttaattct tgttgttggt ttaattttcc atgttgccct    121500
tgaattactt acttttaccta ttgttttcct gtttgtcatt tagttcacct ctttttattt    121560
ttaattataa tacagtactt ctaataaaac aagtataaaa aaagacctaa cttttattgt     121620
taggtcttaa tacgaaattt aagttctagc cttatctgat gctgtcctct ataccctatc     121680
tttcgatata ttttaaaggg agtagactat accaaatct taatgtgtaa ctaagactca     121740
cttattatag tcgttgaagc ttcccactct cgtaggcttg cctgcgtatc atctatttta    121800
ctgtacttag ggtttaacct tatactatac tagatatttt ttctgatttc tcaacattca    121860
agcttaccct ttcaggttac tttgtagtta tctagtctttt aagactttca cgcaatttaa    121920
agtgttttct atgcttgtca ccaaacatag cctctattag ttaaaggtag ctaaactcaa    121980
tttcttctgt tacaatttca tttgtctgcc aagtctcgtt gtagttgttt gctgaaccgt     122040
ttataccctca tcttcgatat tattttaagg ggctagacta tgccataatc ttaatatgta    122100
actaagactt acctattata gtcgttgaac cttctccatt ttacaggagc ttggatgcta    122160
attaccaatt atgtagtact taggatttaa ccttataccca tctaactaat ttttctgat    122220
ttctcaacat tcaagcttag tcttttcgact tacttttgtag tttagttagc tttacggtgt   122280
tctagcaatt taaggtatta ttcaatgcac atcactgtac aagggggtctg ttttaattaaa   122340
ccatgatatg aaaataataac ttgtttcgtt aagttatcta ctactaagat atcaataata    122400
tcttttcttaa gaatctcttc accaagtgaa gcatatccta aatctgcgaa gttttctttt    122460
ttcatacgta aacgttctag tgtaattgta ccagcatatt ttaagtaaac atgctcttgt    122520
ggcataatac taccaatttc gtatacacca gtagttccgt attcacgttg acctttagca    122580
gattgtgctc ttccaactgg tttaccttttt accattagca taacggtatt accagtatgg    122640
acagactgct tagcctctga agccatatta attcactctc ctattaaatt taataggagt    122700
acctaaacta ggtactcctt gtcctagttt aggctcttaa tgtttgttgt tggtataca     122760
agctaacaga aattttcttg aagcttctga tagggtatac aaccattgag attctagctt     122820
cattaccctc gacaataact tgtacgtctt caggtgggaa gtcttgaatt tcgttatctc     122880
gtttcttgcg tcctaagaat gactgtacaa agtcttgat aattgaagca cttgtattga     122940
tagtacgagt accaataaag ttattttcaa gctcaagttt taactcagaa cataagaagt     123000
catttgcttc cccaacagcc atttctgact taacagggtc atttttatca ttaaatgtcg    123060
taacatcgtc tgttaatcta agaatgtat tagctctatt acgaacatat tgtacggtga     123120
taataccgtt tcatttaac tcatctaagt ctaatgattc atataattgg tctacattat     123180
taatacgtag ttgcttaaag gtaatagact cacctatagc taaaccactt accaaacctc    123240
cgatacgaga agctaccata taagctggta catgtaactt acgacgttg tccattgtga    123300
atatacctga gttagctact aaagcaactc gtgggctaga taatgatgat tgacgaccaa     123360
acaactgttc tttcgtttca ttaaatcctc cacctagaat agcacgcata ggttcacctg    123420
catcagaacg ttcttaaaca aaagaagcta cttctgcatg aacagattgt ttagatgata    123480
gaggtaccat gtagtatccg ccttcatgtg caaattttt aatttatct gcccatgtag      123540
ctggtggttc accatttgta ccgccagaaa gttttgttaa ttcaaaaggt gtgatttctt    123600
gaattggtga tacagctgtt acagtggcag actcttcgtg tgcgtctact tctacgtttt    123660
taggtgcttg ttcagatact aatcgttcaa atgaaacaag tccgttatag ctgtttgtt    123720
tctctaagtc accaaatact gctttacat actcagcttt atccttaata tcaacatctg     123780
tcatagggtc taataagtaa gactcaagt tcttgtctcc aaaggtgat aacttagctt      123840
caaaatcagg taattggta atatcgttga tgatgcgatt agtagtagg taagctcctc     123900
ctgtcaagtc ataagactta acttctgtgc tattagcttt taatactaat cttttgctt     123960
tttgtgtttc tttatcatgc tctacagaaa aagtagctgt actttcacta cctttatatt    124020
tgatagtgaa gatattacca atattatcat atgtttcatt aaatctatca tcttggaaga    124080
ttaaatgtaa acgtaatgaa ttactgattg tatttttttc taatcctact tgaatgttgt    124140
tagctacgtt accataaatc tgtgaagtaa ctttcaatcc gcctacttca gctgtagctg    124200
```

```
gtttagcatc atctacacgc atagcaaaaa tcttacctgc tgtgtattgt ggattagaac   124260
cccaagctaa ttcaattgca tcaagtaatt cacctgagcg gaatagtctt ttagcttgtg   124320
cgtagtttct taattcatat acggtatcag gtttaccacc ttcagcttgt ccaattaaac   124380
ataaaatctt ttcactggag ctagctgatt taccgatacc tgtactgtct acattaatga   124440
ctgcatgtgg acgagtgaca ggtcttcttg gaaacggttc aactgccatg tataattctc   124500
ctatctctat attaaatttc taattctcta cctaaatact tttctaaaaa tggaataaag   124560
tcttttcat tgaataggta atgtttacct tccatatagg ctttaaaacc tgcaacttgt    124620
gactctttca tattaaacaa ggtctgtgct gttttaaaa atgtatctat atgtacataa    124680
cctgtaaagg ttttacctt aggtgttttc ttagccatta tcttttgct cctttattct    124740
tgaaagtaat cttattaata tctgtgtta ttgtataatc taaatctaat gaacttgtgt    124800
atttaattat agtaggtcta ccaaagatag atgactcacc gtcttggaat ataggtgcga   124860
tatctccaaa tgcaagattt tgtagctgga atgtttgttg ttcttctata ctgtctctca   124920
tagatatcaa tatcattttt aatacggcat ctaaacatct agcaacatct acattatacg   124980
acatacccac aattgttact tgttcttcta tggtaatacc ttttactaac ttttactat    125040
catttgtttt ttctcatatat acaatatttg cgttgtagcc ttcataagtc tcattgttag   125100
tataattaaa agatacagtg ttatccgata ctttaacatc atcgtaagaa tcaaacgcta   125160
tgtcttctac tcttattaca ttagaaatag gtttagatac atgaaatact aaacgattac   125220
cttctctttt agctactgat tgttcactat atgtgttacc cgaagcttct agataagacc   125280
cttgtatact acctaaagag ttttaacct cttgaccttg tcctagttgt attaggtaat    125340
gagcttcgta gttgttttta aagctaggga aattgaaccc taccgttact tcgtgctttg   125400
cgttcttacc gcaaaaagcc tctttgaaca tttcccctagt ttgataatca aagtctttta  125460
aaacttcatc tataatataa caattactta gtactgtatg taatctgggt tttatttgct   125520
ctaataaata tgagtctact gatgttattg ccatcctact tccataacct ttctacatta   125580
aattttaat tttccaattc attaaatttcc taacatattt taatgttgtt ttagagaaat    125640
tattctcgtt aactttgtct ctatttaata tccatgaact tgcaggtgac ttactagaaa   125700
ctgttctaaa cataaaataa ctagattttt taccatttct tacttttgtt attctgccat   125760
tactgctagg tacttttaaa gaaggatggc ttatgttatt acgtctacct tctagataat   125820
cagtaagagt agatactgaa ttacttgaac tgcctatttt taaagacctt aaatcttggt   125880
atgttttatt attcattta cttgttttta ttctaattgg aaccgttaga taccaaccac    125940
catcttttgc tctttttttc ttagatgaac gtgcaaaagc tttttaagg tctattacac     126000
cttcttctc tagtttctgc tcagttattt gtaagtaggg aggcatacgt ttgacactca    126060
cattatctac ttgtaatgct gtagcttgta atctatctaa aatatcagaa cgcatagcat   126120
ctactgttct cttacctaca tttttatagc tcttgtctct aaataactta ggtctagttg   126180
cttttatagg cattatagca ttcccccaaa gaaaccacct gaatgattat ctttagattc   126240
tttttaggg tcttctacct gtatctctaa gtcctcttct ataccatcat taacttaaa    126300
tggctcaggt agtacaataa cgtcttccct tttaataat aacttctgag gtaaatttttc   126360
aaactttgta ttaggttgat taaatttagt atattggtat cgactttctt ttaatatatc   126420
tgatactaca tatcctaagta ccattaaaat atttaaggat atagtttgt tttcaaactt   126480
agcgtccatg aataatctat tgttctctat attatagtca tcttcataaa cattaccatc   126540
gttagatgta ataaaggtta cttctttgac atcatagtat agaggtatac cttttttgtat  126600
acgctcttta gtaacatggt atataagttg ttgtggcatc aatacttcag gaacagtaaa   126660
cctgtctcta taagatactc gttttttcaa ttgtgtagtt cctatagctg taccagtatc   126720
taaaattcct atatctaaat tgttagttcc ttttttcttga gattggatag ccattattgt   126780
ctctttagga ggtaaatagg caataccttt accgtgacac ctaggacaat ctactctagg    126840
atgtcctgtg tcagggttaa ggcaaggaca aaagtaagcc ctttcccaca gtacctttat   126900
acctctatca ttgacaaatc ttctcatatc cttagtgtca aactctagtc tagctgtaga   126960
taacttttgt tcttgttcat ctgcttgtgt tgtagatgta tacatagtag acttattaat   127020
tatattagaa gtattattat tagtacctat cataaaaggt ttttgcattt aatatctcct    127080
tcctactata tgcctatcat attggagcca aagtaagatt ttaacccagc taatagctct   127140
tttatatctt cattaatttg tagtatctga gcacttgctc caccatacat agcagattgt   127200
gtagtaccta ttgtttctgt aataccatct acatctagta tttttgtttgc tattcctgca   127260
ccgataatga gattaccata tgttaattaa attaacttcc tttgtaaaat aaaaggcatt   127320
atacattcgg gttatggaac cctactaaaa gcaaacatat tattggtttt gttctttttaa  127380
ccattgggaa ttatgtaat ttttaaatt aatacttgca tttatatccc tatcttcttc     127440
atatccacaa gcattacatt taaagacatt atcacctaac tgtaattta aagcattct      127500
ttttctttct ccgcaattac tgcatatttg tgatgatgga taataagtac tagctactgt    127560
aaattttata cctctatctt cacatttata ttgtaattgc tgtctaatca tatagaaatt   127620
agaaaactgt atttgttttc ttttttgtcc tgtatatcct ttgtctttta ttaaatcacg    127680
aactcttata tcctctacaa taatcttttt aggatactttt caacaattt cttttgttat    127740
ttcatgtaca tgatttttac ggatatttga cattttttcta taaacttag ctatcttatt    127800
ttctagcttt aaaacattat ttgtttggt gtgattaata tcatattat tacttaatct      127860
tttctgtagg tcagataatt tttttctaa ccttttcatt ttcttggaat aaataatatt     127920
accatatatt tttctgttag aacaaattac gtgtttttta ccactaccta agtctatacc    127980
tatgacttcg ttagtattat ccttttcttt cttgtattga ttctactt caattgaaaa    128040
agatatatac caatatttac catcatagta acatttaggg tttaaaggtt taatgctttc   128100
attctctagt actgatttat tatttttata tgtaccatta gaaattctta agtaacctaa   128160
ttttttcaact ttaacatgtt tttctttgtt aaagtgcatt cggtcatatc taataggaaa   128220
cctcttagat tcccttttct tagacttaaa tttaggttt ctaatttcat gattatgata     128280
ttttattaat gtttctctta agtcatctat tttaccaact aaggttttc tagatacttc    128340
atttaagaaa ctatacttat catcattctt tatttctttt aatatagaaa tcatattttt   128400
atggtctata tatttaccgt tatcgagagc tttccaatat ctttctaaca tataattata    128460
aataaatcta gaatggttta catgtttcca cattaactct tcttgttctt gggtagggtt    128520
tacttttagt gttataacct ctataaaattt attttccgtt tttttcattt actttcacca   128580
cctatatat tatctctata atataacata tacttggggt aattttcaata ggaagttttc    128640
atttaattaa cattgtttcc ttacttacg tactaaataa gtctaggtca attcctagca     128700
ctcctttttca agacgtgtgc agactatttg ttatccctaa gactagggta aagatttttc   128760
ttctcccaat cacttggagc tttacttctg tcgtctatac agaatagtcg ttgaacgtat    128820
tccttatcta ttgacttagg actttcgatg ctaaacttcc attgctcttc tctttaggat    128880
ttaaccttag agtatctaac taattttttc tgatttctca acattcaagc ctatcctttc   128940
```

```
agattacttt gtagtttagt tagcttagg atttcttagc agttaacctt tgaaaatgtg   129000
caacttacgc tacacacagg gtaatatcat cgtaaccca tatttggtaa atctcttta     129060
gtgcatactt aataactaat tgctctaatt ctggtggtac ttcccatggt ttagttctac   129120
ctgctctttg tctaggtaac ataccactaa tataatctaa tgtaatcatt tgaggtgcaa   129180
aagttgctcc acttggtggg tacattcctg ctaattgaag atatccactg aatacagcat   129240
cgtaagacat agattgaccc gtctgcatta aagctgtagg gaataactgt acgtgacctg   129300
ctaaatgctc cactttccac cagttagctg gataatcata cataggtcta ccattaaatt   129360
gtagttgtaa attttctacc tgtaatatag gtttttata tgcgtgtaca aacatataac    129420
tattaaattc tgtttcgtag taatctctca tttcatgttg taagtcaggt aaaatagata   129480
tatctaaagc tctttccgct ttacctatag ctctttctaa tatatatgatta taaaaatcat  129540
cacccatagg ttgtcctgta tcggggtttt gtactgttat accaaacata taggctttca   129600
cagcatctgc tgaccaacca taatcagcta gagtaatact atctaattct cttttatcta   129660
tatgttttgg gtttccagat gggtgataag gatactcata tgataaagag ctttcgtaag   129720
ggtctaaact accaccaaac atactgttta ccattttatc aacctactta tcttcttttt   129780
tagttgtttt tttagttggt ttcttctctt ctttttcttc cttaggcttt acttcttttct 129840
ttgttgtttt cttgtcttcc atatgtgtaa aacctggtaa attagcaaaa tcttttttctt  129900
gtttagcagt tagtcccttta actacgcctt tatcatctac ttctacttga ccatgtacag   129960
tagccatttt aatatttttt aatttataag ttaacattga ttttttagatt cctttcttgt  130020
atactataag tagtaataaa aaaggagcaa cccttaggta tactccttat tctattgtat   130080
tcaatttttta attgtattta ctattttaat gcaaggtaac ttacgttttt aatacgagcc   130140
cattttttag gagcacgtaa cgctaaagca ccataccata atactgcaaa tgtaatacta   130200
gcattaattt gagctaatgg taattcatc atttggtaata actcgaacaa gtgtaatact   130260
tgtggtgaca tttcaccaac gaatacgtct gctgtttcag gtaatgtttc gtttttatca   130320
acgaatacta aagaaccatc ttcttgtgca tctttaagtg ctacacgttt aattaagtag   130380
tacataccatg ttctcttacc ttgacggtaa atagatacga attgtgggct tgttggtac   130440
atagagttaa gtaataatctt taattctact ccatctgtag catttgttac tgtagcaact   130500
tgtgcttctg atggtgctga ttcagcttca tcagagtgaa caactacttt ataagataaa   130560
cctgcacggt cttcttcttt agtaaattta cctttttggt ctgtttttac agtagcagtt   130620
actgtagctg gttgtggtgc atttggttgt gggattaaag tttcatctag gattaattca   130680
ttttccatta cagtagaacc ttataatcta atgaatccac gagatgaata gaatccgtta   130740
acactgaaac cagtatttac attaccacta ttgtctgca ttaattgcat ttgtcgacct    130800
aaaaatattag taacaaagtc agaatgtaca ccgataggca tataagcatc tgtagctgta   130860
ccaaaacctt taccgatttt aactgaagct aagtttaata atttctcatc taagtgagca   130920
cctttagcgt cgataacgtt atcagcatca attaatttag ctaatccatc gaactctaaa   130980
ccttctccac caacttcaga agttaagctt gcgtcaccat agaatgaagc ccattcaatt   131040
gttttagcaa caactgagat agcatcttca gtcaagattt gacctgggtc agcaatgttg   131100
tttactaaac tagatgccaa tgacatattt ttagtatcag aaatatattt cattgtaacg   131160
gtcttttgac ggatattagg gtctgaaact gacgctactc cgatttcacg tacaaaacga   131220
gaatggccta ctttaccatg acgtaagaaa acatcatatt taattactgt tgattcagct   131280
ggtctacgag caacatcacg atagaatact aaatcattat ttccccatgt aagcatagtg   131340
atttggtcgt ctaaaatttc acgacgtaaa gcacctgcat ctacttgtgt ttcaggagtg   131400
atgccatatc cagtttggaa ggatttcgat aattttttctt gtaattcatc agcaactgca   131460
tgttgctttt ttgaaagttc atttttggttc atttatatat atcaccttc atatatgctt    131520
ttttttttatt gttttatttt acacactata atataacaca actttgtttc ttaattaaag   131580
attagcaaat tctttacaa tattaaagtc tttttcactt gcttgctctg gattgttgcg    131640
gatatttaag taagcttgat aagcattcaa tacttctgaa cgattcgtat gtgggttttg   131700
agatttttct ttataggtac tcatgaattt tcacggtct tctacagata agtctctact   131760
ttcttctttta acttctactt cttgttcttc tttatcttct gtagtttctg cttgttcttc   131820
tgtttgtact gatttagcta cataaccaac tacatcttgt tcattcgaag tgttattagt   131880
cgttacggat ttttctactg cttcttcttt atcttcttgg ttgctctcaa ctgatttaga   131940
aacttcttca ttagaattaa ttttatcagt taaatcttga atagatttag ttacttcttc   132000
taaatctgat ttagtcacat attgttcatt ttcttttta atgtcttgga atgatttcaa    132060
gatagtacgg aaaccatcta caatatcttt atcagaaata gatttagatg ttttctcttc   132120
ctcttcttca tctttttctt cttttttgtc tttttattt tttcgtttct cgttgtcttt    132180
gtcttctgtt ttagtatctt ttttatctac agggtctttc gactccttag ctgacttaga   132240
tacttcttct tctagatttt cttcttgttc atgtgcttct ttagcatctt ctttagcatc   132300
ttcttcagta acctttgcag gttcttgtgg ttctcttta gcttctgcta cttgctcttc    132360
tgtagcttct acttcatttt taatttcttc ttttttcttct gttttagtgt cttctgtttt   132420
atcttctttt acttcttctt tagactcttc tacagatttt gatacttctt ctttgtctaa   132480
gttatcatat tcttgtagaa tattttgtaa ttccgtaggc atataatata atccccctatt  132540
ctaaatttttt tttattaata ctcataactg ctatctcagc atcttttctt gatagtcctt   132600
tggctaattg taatgtaata actgattctt cataacccat attattagat ttagttaagt   132660
cctctactac attattccaa atatcattat actctttaac atctttaatt tttgttacat   132720
aggttaaatt agtaatagag cttgctaatg atctctttacg taaggctcct gcatctactt   132780
gtgtgtctgg tgttgtttcc gttccagtaa ggaatgattt aacaaaactc tcccatgtag   132840
cttcaggatt agctgggttt tttactagtg ctacccctgt aatcataagt tcatcaacaa   132900
ttctattgtc atttatgtta cgtttcttaa cagcgccttc tatagaaaac cctaaacgtc   132960
taccactacc tgacttttct agttttctcag ctaggtctaa cattttata acatttttcat  133020
catctttcca tagtttagct tctataaata aacctttttc taaatcaaca taacagttat   133080
ctgtaggtat acctactaca ttatcttgtt gatgttcgta gttaatatat ccattttttt    133140
taaagtattc tatatcaata cctttttggat ttataatgtc attctgcaaa tcaacagctg   133200
gtgtggaagc ccaaccagat acgatagaat atttattgt atcatcttcc gtatctatgg     133260
atttctttaa gtccatagga acaaaagcat taaatttcat ttcttccaaa gtgattatac   133320
acctcactta attgttattt tatatgtaca tacataat acacaaaagt atatcatcaa      133380
cattattcat tactacacac atagtataac atagtataaa tgtagctcca aattaaaaaa   133440
taacaaccta agtattaatt aggttgctaa tattatctac ataaagtcgg aagatttctc   133500
accttttctt ccttgtcctt tatttgatgt ttgtgttcta tatacgttat catcacctt    133560
taactgatta tctgttccta catcttgatt agttgttct tgtttactat catcagtagg    133620
ctcatcagtt tgtggttgtg tataactcat aagtaattga agtctttctt tttgtttagt   133680
```

```
atctaaatat tggtcttttt gtatttcttg tgctgtactt tgtaaaaatg ctgaatcaag    133740
aattacatct ccaccatcta tcggttttaa tccttgttct tctcttgctt catttacagt    133800
tttatatact tgtacttctt tttgtaagat actaagctta tctaattcag acttagtatc    133860
tcctccaaca aattggaaag tatacttatc accaaattca gatataatgt gtctgttaat    133920
taattcttct ataaatctta atagaggttg taaaccttta ttcatagatt gttgttgctt    133980
cttagcaggg tctgactcat tcaatgtaga accgccttt gacctgtag ctcctcctcc      134040
tctattaggg aatcctattt cagaagggtc tataccatac aaagcagaaa taatattgat    134100
taaaaagttt aaccatttct caaattgcat atcatttgct gttggtgtca tattaacaaa    134160
cttaacatca tcagccatca tcacggggac ttgccagcta ccgtttatac ctgaaaaact    134220
agatttccat tctcttttaa aatttttctaa cgcatgttga gattgctgtt ggtctgctct    134280
aatctgtaag atgcctctag ttgttccacc atgactgaag aatctatcgt taaaactttc    134340
agtattatta taagctataa attctttcat tgcaatctct acttctgaca atccataccc    134400
actagagttt aagtctgacc tagggttcct aatacccatg acaagttctc tgcttgtaaa    134460
actagctact acttgcttat ctatgacctg tacaaaacga ttgctacctt taattatctt    134520
accgttttta tcagtagcat aaaaaatggt gctggggtct actgcaataa acttctccat    134580
cttagttttg ttttaggac taaaaacttt tcgaagtta acttggtcgt acgtgtaagt      134640
atctcttact atttttttac aaaactcttg gaatgaatcc ctgtctatat ctttatctgt    134700
acctgtatta agaataaatt cttcaatacg tttcatctgc tctttttctt taataccagg    134760
tgtagcgtct aagtctttta atttaacttc aaaaccgact cctctcttctg aatacctagc    134820
aggtttacag tatgtagata cttgattagc tcttgtaata attatagcat ttagtataga    134880
gttattacca aatttcttta acacttcatg taagttatga gcattcctca tatagctctt    134940
cttatctcta taatcaggat ttgtatccat catttctaaa aatggttctg cataagcttg    135000
ctgtttacca tatagagatt tagtaatttc ttgcatctct tttgtatctt gttctatttg    135060
tctaatgtta gcttgtattc cgtcatctac aggaaccata aggtcttcag tatcttcttt    135120
atacatacta cctaaccta gacttttaaa taaatcaggc aacttttat ttacctcctc      135180
gaatagtagt tagtataaca gtgttattat aggtaatgtc ttggatatgt ttaggaaatat    135240
ttatctttac ttcgaatggt tcttctatat aataaaacat tttccttactt tccataacaa    135300
tatcataatc ctctaacaca atattattat cctatctac caatattact ttattatcct      135360
ttgtagcttc tagtaccata tatttaactt tatcaatagc aataaacata gctacatgtt    135420
taccacctat ctgtctataa taatccacta cttctatcgc attatctgct aatccttgac    135480
cttttataaa gtcttttgct tcatcccatt tatcgtcttt tgaaaatagc aaatgcttca    135540
atcctttaat tttttatttt ttaaattcct agtatttaca atcttcataa ctaaaaacca    135600
aaaactgcct attacagctc caaagaaact tataccaaaa acaattaaag ggttattaaa    135660
ccctacatac tgctctgtat tctcaataga gtctataaca tcatttttta taatgattga    135720
cgtggcttga aacattgtta atactacata agaacctata gaaattatag catatatcaa    135780
gtatagaacc aacttactac ttttttcagt tttaatatac gcaaatacca ttagtgctag    135840
tagacttaca caagcaaaaa ctacggatat agctgtaagt acgtttaatc ctaccaaaaa    135900
atcaccaact ataatgttta ttttattact cttttaatat agcaaaaaaaa ggagaggtta    135960
tccctctcca ttagtatcat tactttcatc tacaggtgtg ctaggttcca atggaactaa    136020
aggtatcgta gtatctgagc taggttttc aggttctata ggttttttcag gttctatagg    136080
tttttcaggt tctataggtt tttcaggttc tataggtttt tcaggttcta taggtttttc    136140
aggttctata gggggt                                                    136156
```

SEQ ID NO: 4      moltype = DNA  length = 17629
FEATURE            Location/Qualifiers
misc_feature       1..17629
                       note = PN1957
source             1..17629
                       mol_type = other DNA
                       organism = synthetic construct
SEQUENCE: 4

```
aatccactta tcatttcttt actaaactta taaaaactgt gcaacttcta ttccaactta      60
tctaacctat tacatattaa tcaaatacat ttattataca tctattgact tttatcaaaa    120
tttatgattg gaacataaaa tctaatttct tctattaaat agtagtttta aattatttaa    180
actttttaa gaaaaactgt tgacaaaact tttaaacgtt tgctatacta attatgtaat     240
caaaacaagg aggtaacaaa atggttaat gttgataatg caccagaaga aaaaggacaa      300
gcctatactg aaatgttgca actattcaat aaactgattc aatggaatcc agcttataca    360
tttgacaatg caattaactt agtagcagct tgccaacaac tattattaaa ctataacagt    420
tctgttgttc aattcttaaa agatgaacta aacaatgaaa ttaaaccaga atcaatatta    480
tcttacattg ctggtgatga ccctatagaa caatggaaca tgcacaaagg attttatgaa    540
acgtataaca tttcgttttt ttagaaaagg aatgatataa taatgaaagc tgatgacatt    600
gttgttttac gtgttaaagg ttatatactt cattacttag atgatgataa tgaatatatt    660
gaggaatttg ttccacttca cgagtatcat ttaactaaaa cgcaagcaaa agagttatta    720
ccagaatcat gtacactatt atccactaca cgtacaacga ccacttaaca gttattactac   780
aatgatttac tacaaatcgc aattgcagaa agcaaataat ttaaataaga ggagaaatta    840
aaatgacaaa cgtaaaagat attttatcaa gacaccaaaa aacattagcg agatttgaat    900
ttgaggaaaa agaaagagta tttatcaaac tatcagaatt agtagaaaaa tacggtatga    960
aaaagagta tatcgttaga gcattattca taaacacaga atcccaattc ggtgaacagg   1020
gtgttattgt cactgacgac tataatgtaa acttaccgaa ccacttaaca gagttaatta   1080
aagaaatgag agcagacgag gacattgttg acattatcaa cgctggtgaa gttcaattca   1140
caatttatga atatgaaat aaaaaaaggtc aaaaaggtta tcaatcaat ttgatcaag    1200
tatcattta atacaatttc ataggggata tttcccct attttatga ggtgctaaac       1260
aatggaaaaa atatacactg ccgtattatt atacaatgta tcaattaatg aaacatatga   1320
acatgaaatt gaacaattcg aaaaaaataa taagttagg tgataatta gttattttga     1380
cgcaaacttt tacaaaaaag gtgcataaa tctttgtgta aaatatatta aggagctata    1440
aaatgaaaat tacaacaaca ttaaacacaa acaaattaat taattacatt ttaactaata   1500
gagagtgttt tataaataaa ataacaaat ttacatcact aagtgataaa tgtgtcgttt    1560
ttgttagata cggtgatatt tctattgaat actatgatag tgatacaaaa acaataatg    1620
atttatttac tttagacatt gacgttgata ttaataaaca tgttttaat tttccttgtgg   1680
```

-continued

```
tttttttatcg agaacattta aacccactat ataaaaaaga agttttcacg ggatgtacta    1740
ttgatgatgt attagaacat tttgagaaac cattagaaag ttatattact attatatacc    1800
aaaaaaaagt catatacggt aatgggaaag tgattgaaca tgaataacct attaaacata    1860
gccattgtat tccttttagc atttttaatt acactgatta tacttatgac actgcatata    1920
cgcgtgtcat ttggtgtttt attcactaca ttgattatat tctatattat cttttttaatg   1980
gttatttacg ctttatatgg aggttgatat taatgccaag acatacgtct gaaatggata    2040
aatgaaaaaa agaaagagaa gctagaaaag agcaagaaaa agatttattt ttaaacgatt    2100
ttagtactgt taattttaaa tttgatgata aagatttaca agaggcgtat atagacgcat    2160
ggaaacattt cgcacatctt ccctattttc caaaagaaag atacgtatca tatgcaaatg    2220
ctgtatcatt ggtaagaggt aaaagacatg acaaattaaa tcatatactt gaaatatata    2280
accgtaaaga tgaatctaat aataaaaacg ctaaaaagca taaatacgct ttatatgatt    2340
tacaagctaa aaataataat tcttcaatgt ataaatatat taaagaaatt gatactttat    2400
ataaagaaat tggtaaatct gatagaccag tgacaactat cgatgatgaa gatgtgaggt    2460
ataactttt atattatgca acatttgact aataaattta atactgtaaa cgatatcata    2520
aactattaca aggagcaaaa acatggtaaa acaaaaccgt ttagacatgg taagagatta    2580
tcaaaatgct gtcaatcatg tcagaaaaaa aataccagat aactaaatc aaatagaatt    2640
agttgatgaa ctcatgaatg atgatataga ctattatata tctatttcaa accgttctga    2700
cggaaaatca ttcaactatg tttcattttt tattttattta gctattaaac ttgatataaa    2760
atttacttta ttatcacgtc attatacatt acgtgacgct taccgtgatt ttattgagga    2820
aatcatagat aaaaacccac tattcaaatc taagcgtgtc acgttcagaa gtgctaggga    2880
ctatttagct attatctatc aagataaaga aattggtgtg attacagatt tgaatagtgc    2940
cactgattta aaatatcact ctaacttttt aaaacactac cctattatta tatatgatga    3000
atttttagca cttgaagatg actatttaat tgatgagtgg gataagttaa aaacaattta    3060
tgaatcaatc gaccgtaacc atggtaatgt tgattatatt ggttttccta aaatgttttt    3120
actaggtaat gctgtcaact tttcaagtcc tatattatct aatttaaata tatacaattt    3180
attacaaaag cataaaatga atacatcaag acttacaaa aacattttt tagaaatgcg    3240
acgaaacgat tacgttaatg aaaaacgtaa tacacgtgct tttaattcta atgatgacgc    3300
tatgacaact ggagaatttg aatttaacga atataatttg gcagatgata atttaagaaa    3360
tcatatcaac caaaacggtg attttttcta tattaaaact gacgataaat atataaaaat    3420
tatgtataac gttgatactt ttaatgctaa tattattgtt ataccttata caaaacaata    3480
tgaatttgt actaaaatca aagatataga tgcaatgtt atttatttaa gagaagatat     3540
gtttataaaa gaaaacatgg agcgttatta ttacaatcca agcaatttac attttgataa    3600
cgcttactca aaaaattacg ttgttgataa tgatagatat ttatatttag atatgaataa    3660
aattataaaa tttcatataa aaaatgaat gaagaaaat atgagtgaat ttgaaagaa     3720
agaaaaaata tatgaagata actatataga gaatacaaaa aaatatctta tgagacaata    3780
tgaattataa aggtgtgtac gattatgggg ttactagaat gcatgcaata tcataaacat    3840
gaacgtcgaa tgattttata ctgggatata gaaacattag cgtacaataa agttaacgga    3900
cgaaaaaac caaccaaata taaaaacgta acgtattcag tagcaattgg ttggtttaat    3960
ggttatgaga ttgatgtaga agtatttcct agttttgaat cgttttatga cgcattttat    4020
acgtatgtga aacgacgtga tacaatcact aagtcaaaaa caaatattat catgattgca    4080
cataactgta ataagtatga caaccatttt ttacttaaag ataccatgcg ttatttttgat   4140
aatatcacac gtgaaaatat atatttaaaa tctcagaaag aaaacgaaca cacactaaaa    4200
atgcaagagg ctactatttt agctaaaaat caaaatgtga tttagaaaa acgtgtgaaa    4260
tcgtctatta atttagactt aaccatgttt ttaaatggat ttaaatttaa tattattgat    4320
aactttatga aaaccaatac atcaattgca acattaggta aaagttgct tgacggtggt    4380
tatttaacag acgaccaact taaaacagat tttaattaca cgatatttga taaagataac    4440
gatatgaatg atagtgaagc atacgactat gcagcgaaag gttttttcaaa actcacacct    4500
gaacaactta catacattca taatgacgtg attatattag gtatgtgcca tattcattat    4560
agtgatatat ttccaaattt tgactataac aaaattaacat tttcattgaa tattatggaa    4620
tcgtatttaa ataatcaaat gacacggttt cagttactca atcaatataa agatattaaa    4680
atatcatata cacattatca tttccatgat atgaattttt atgactatac caaatcattt    4740
tatcgtggtg gtttaaatat gtaaacact aaatacataa acaaactat tgatgagcct    4800
tgttttctta ttgatatcaa ttccagttat ccttatgtga tgtatcatga gaaaattcca    4860
acatggttat acttttacga acattattca gaaccaacgt taatccctac tttttttagat   4920
gatgcaaatt attttttcatt tataagatt gataaagatg tatttaacaa tgattattta    4980
attaaaatca aatcacgtgt attacgtcaa atgattgtta aatactataa caatgataat    5040
gattacgtta atatcaatac aaaatacatta agaatgattc aagacattac gggtattgat    5100
tgtacgcata tacgtgttaa ttcgtttgtg atatatgaat gtgaatattt tcatgctcgt    5160
gatatttattt ttgaaaacta tttttataaaa acacaaggta aattaaaaaaa taagattata    5220
atgacatcac catatgatta taaaattact gatgatatca acgaacaccc tactctcaaat    5280
gaggaggtta tgttatctaa aatcgtttta aatggattat atggcatacc tgcattacgt    5340
tcaaattta acttattccg tttagatgat aacaatgaac tatacaatat cattaacggt    5400
tacaaaaaca ctgaacgtaa tatattattc tctacatttg tcacatcacg ttcattgtat    5460
aacttattgg ttcctttcca atacttaacg gaaagtgaaa ttgacgacaa tttttatttat    5520
tgcgatactg atagtttgta tatgaaatcc gttgttaaac ccttattgaa ccccgattta    5580
ttcgacccga ttgccttagg taaatgggat attgaaaacg aacagataga taagtgttt    5640
gtactgaatc ataagaaata tgcatatgaa gtgaatggaa agattaaaat agcttctgct    5700
ggtataccga aaacgccctt tgatacaagc gtcgattttg aaaccttttgt acgtgaacaa    5760
ttctttgacg gtgccattat tgaaaacaat aaaagtatct ataatgagca aggtacaata    5820
tcgatatatc cttctaaaac tgaaattgta tgtggtaatg tatatgatga atatttttact    5880
gatgaactta atatgaaacg tgaatttata ttaaagacg ctagagaaaa tttcgaccat     5940
agtcaattta atgatattct ttatattgaa agtgacatcg gttcattctc acttaatgac    6000
ttattttccag ttgaacgttc agtgcataat aaatctgatt tgcatatatt aaaacgtgaa    6060
catgatgaat taaaaaaaagg caactgttaa gcttttttcg gccttttttcg tttgagataa    6120
catgaaaaat gtgtacgaaa attgattatg ttttgtattt tatttactag cattactagc    6180
atgttttcat tataccacag ttaattaagc tataccacta aagaatacaa tattatcacc    6240
tgcattatgt ggtacaccat taatgagtgt atataatact acacgtgacg gtgcaacgta    6300
cggcggtaca ttatagttag cgactaagaa tgacccatca tcaaatactg ccacgacaac    6360
accagtgtga ccaataccat aagcagttgc ttgtaagtag ggtggtttac tagagaaacc    6420
```

```
atatccaaca gttggattat gtgttgtttt tgctcctaac ttttttataga cgtaccatac  6480
acgttgaccg tttgtcactt gaccgtcgtc tgtcggttgt cttttaccat gtaattgtga  6540
catatacgcc catgttaatt ctgtacactg acctgcatta cccgtttgag gaaatatgtt  6600
acctgatttg tataaatatt ctttttttgaa taaaggtaca ccaattgctt ttttatattt  6660
ttctggtaac tgtgcgtacg tccagttacc accaatcaca cgaccacttt ttccatttgg  6720
tttgactgat ttaccactaa ttggtttatg gtcaccgtca tcatcagtag gattagaact  6780
actacccccca ctatctactt gcacgctatc aatcagtttt tttaatgaat cgagtagacc  6840
aatcgtcatt ttaatatgat atgtgttgtt aaatgttttt tgtaatgtaa aataatcatt  6900
actaaaaaat ttgtcactac ctatactgtg tacatcccat tttaatgcgt cttgtacttt  6960
ttttaataat tcttgcatag cttgtttttgc taaagcgagc agtgaactac cactgtcacc  7020
attactacca ctgtcagacg aatcactagg tgaaccacct ttaccgtcta atttaccacc  7080
ccatgctaaa atagtatttg caccgtctaa aaaggatta ccatagtttt gtactttatt  7140
atatgacgct ttcaaaccta gggggtaata tgccgcccaa gtagccgctg ctgttaatgg  7200
aatatacgca cgtccgattg tacctgcttt catattttta gcaaaatcgt cattaccttt  7260
tctttgtacg tcttgaggta caaagtgaac gatgttacct gcgtcatacc aagacggttg  7320
tcctgctgt tttgattgtg atactaattt tcttgcaatg aatttagcgt ctgttaaata  7380
gtcacctcgt gcagatgtat ggttcaacca acctaaacca gcgctatacc cttcattttt  7440
ttcataaca gcaaaagag taggcgacac acctatctct tttactgctt ttaatacttg  7500
tcttatttta ctttcattac caccaagcca tacattaaag cgtccatacc cttttacttt  7560
agggactaac tggtcaatgg ttaaaccgaa atcgtcatta ataggaat gtgtaaattt  7620
atctatcttc tcttggtcgt tcattttat cactctttc agaatcattt ttaattactc  7680
ttaatttatc tttaatttgt tctggcacta atacgtccat ttcagcgcaa ttttccacga  7740
tagatagccc ctcatttgcg atataataga aaatcgtaat catgagtaaa ccacctttta  7800
attgtaaaat ttggtcgatg atgttagcta aaatgataat gcagaatatg agtaattttt  7860
tagcgaaacc tttcattgat ttttagacc atagattatt atttttaatt gctttagcaa  7920
aaccagttac aacatcaaca caataacaaaa atatagtaac tttaaatctc  7980
ctgcatatat gaacatatga aatgcttctg tgtccgtaaa tcttaatttt acctcattca  8040
ttttttataca cctgctctaa atttattatt taacggttc tgtaacattg gattacctga  8100
accgtcatta tgccaaaatc tcacgccaga ttccaaaatt gcttttaatt gctccattaa  8160
catcgggtcg atgtcacgta tagtatacgt acctgtacat tttaaatagt tgcaaacggt  8220
catactgtta attggttcaa taaatgcgtt atagtcattg acttcaaaac caaataacat  8280
ataatattt tgtaagaatg tgatttcttt tggtgacggt acactaatct tcatcgttaa  8340
accattaata ctatttgcga tttggaatgc gttgccatt tctgattctg tcactgatgg  8400
aggttgtaag gctaaatctt tatattctgc ttgttgttgt ttgtagaaat tatattctt  8460
attaaactta ccaaataaag cagtaggact taaattactt gctacactca cagcgtcata  8520
aaatcgtgat ttcgggtcac tgccatttaa tacattatca atacgatttg taattaattg  8580
actttctgca ttcttctgtc tatttgcttg ttgtgattgt cctaagatac cattattgat  8640
taatattggc acttgtgcaa aactattaaa tgtgatattt gtgtttaaga atgaacctgt  8700
atcaatcaat atatctttat tctttttgcaag atcggtccta tcattttctg cactgttata  8760
atctactgga tatacacgta cttcattatg ataaccaatg attgactttg tacgtaactt  8820
aacacctgtt ttttgtgata ttttaccagc gtcaagcaac attgtatttc cattccaatc  8880
ataaaattca atggtcatgt actcattacg tatcatatgc ttaaattcat cttttttaga  8940
caacatcatt tcttgaagct ttgtgaaact taatgataaa tcgtttaaac tccattcttt  9000
tgattttcca ccttgttttta acgtcttttaa tccagtaatt ttttcacttg ttttaacgtc  9060
ctctaaatct tttgtattaa taaagtcttt aggtaacatt tgaaccttt gaaagttttg  9120
tgtaatccac ggataagcac tcattttatc cataaaattg ataaaatccc cgtattccat  9180
gacgtataag ttaactggtg atgtgatatt gtcatatatc gtaccccttag acgtatccaa  9240
gttcggttct tttttttgtac caaatttctt tgataaatca gcactggatt gaaataaaaac  9300
taaatttttct aaatactgtt gcatttggtt atacacatag ttttttattcg atactttttaa  9360
cacatcatca ttgttacgta acattggtaa catatagtta tacgtgcgtt ttgataaatg  9420
ttggcgttcg atattaacgt ttgtgagttg ctctaataca ttgcctttgtg tatacgtcat  9480
aatagtatca ataacaaaat atattttaac cacaacgtca ttcacgtatt cgatttggtt  9540
cacaaatgcg taataacgtc tgtcctcaaa atctgataaa aacgtcatat agttaatccc  9600
ttgtgcgtca tgccactgca tatcaacatt gatttccatt ctatcacgta taaaattata  9660
cggttgtttt gaatagtcta acgatttaaa atgacgacca tttaaaaaat aatcatcacg  9720
ttctttatta ctattaaaat gaatcgtatt ttgatagtct gtaaacggtg tgttatagaa  9780
aaacttaaaaa ttcgttaact ttctcatatt ttcctcctaa taaaaaatag tcgtataaat  9840
aatttatacg actattatat catttttatt caatgatttg tgtatctatt gcaaaacgtt  9900
tatcaccatt tgttaaatca ctatcactat aatttgatgt aacaaaatgt aattcattat  9960
taaagtttaa ataatctct gtattaatca ttttattatc aatcgcacat tgtgtgtagt 10020
gatgtgttga tttaaaatta gcattaatcg tacctaattt aatatcaccg tttttcttaa 10080
tcccttttaa tacccctttt aattgtatgg ttttaacacc attaattgtg acaatacgat 10140
attgcggtgc cggataacca ccgttgctat cacttgcaac tataccactt tctagcgata 10200
tatcttgcca acctgtatcg ttaaattgta attttgcact gttaattttt tgatcaaaat 10260
tttgttcaat ttctgtttta gattgtgcaa tttttgtatc aatatttaag ttatccactt 10320
ttgttgataa actgttaata tttgattcat ttttagatgt ttttttgtttt aaatcactaa 10380
tatcattatc gtatttagat aagtcaatat gaccgttttcc gtcaacaact ggtctatctt 10440
ttaattcttg aatatctttt tcaatttttg atatttttgt attattttgt ttaaagtag 10500
cgatgtcaga tttaataaga ttaatatcct gtgtataatc tttttggtta atgttattaa 10560
tttttgtttc taattctcta attttatcaa ggttagcatt tgttttaata tcattaatgg 10620
attgttctaa cgcttcaagt ttcccagcac ttgaatttg tttaactga ttaatatcct 10680
gttgcatttc ttgtatagta ttgtcgtttg ttggttttga ttttaatgat tcgatttgtt 10740
gttcaatatc tttttatttta tcaaggttga cactctttt aacctcagct aattctcttt 10800
ttaacgcgtc aatgtttca gcaccagtat tgctttaat taaattaatt tcatctgtgt 10860
tacgccctac actatcttta gtagcgttta atgattgtgt aattgtatga tatttctcat 10920
catactgtaa cattgatttt tcaaattcat ttaattgtgt ttgatgttgt tctaaacttt 10980
cacttaatat gatatctttt tcttttaatg cgtcaatgtc attttattta ctatcaatca 11040
ttggttggaa ttttttttatc ttctctaaaa atgttgatat tttctctttg ttatcattaa 11100
ttgcaatatc atgtttatct atttgaccac tgtatttatc aatcaatgtt tttaaatcat 11160
```

```
tataaaatgt caatttataa taacttgaat cagtacggac ataaatatgc ccgtctgatg   11220
tactgattaa gtcattttct tctgttaaaa aatctgctaa acggtctata tcttcgacac   11280
gtcttaaact tcttacgatt ctatcagcca ttgtttacac ctcttattta tatcgtttcc   11340
aactaaaact aaagaaaaaa cctaaaatac ccattatgag aacaccccc acggaatatc    11400
aacactgtaa ctattacctg ttttaccatt ccattgcctt actggtaaat aataacgtgt   11460
accttgccag ttgtaaccaa tccaaactaa cccatctgat aaacatactt cgtcatatgg   11520
tgtatatcca ccaggttgaa accagtagcc gttaggttct gataatttag gactaccaac   11580
atgtgcaaat attggtaaaa agccacatgt aaatgttgca ttttcatttc tgtaatatgt   11640
gccgtattga ttttgtttcc agttgttagt tttttgaata ttttttttcta atactttact   11700
atcactattt gaaaattttg gacgaataaa gtgtgttaca ccgtcataat aatgtgttct   11760
tattgttgct ttttcccatc cgtcaaaacc tccacctaac cagttttgtt ctaaacatgt   11820
gtaataatct aaattgccac ttgttacgca ttgaatatga ccatattgag aattagtgta   11880
tactgcaatg tcacataatt gaggtttaaa gcttggtgta ttttcataca cctttgctaa   11940
acctttaaag tcattattaa tcgcgtcttt ggcattaccc cacatacgaa cttttaccgtc  12000
tgtaatgtaa taaacataag caactgctaa gtccatacat tgaaaaccat atgcaccatc   12060
aaagtcaaca cctacaccct catgattata tatccattct tttgcttgtt gttgtgattt    12120
catttatatc actcctattt tttatgtttt gctacccaac catactcacg atgtttggtt   12180
tcagcattaa cattactaaa aaattcttta tattcggaaa catttgcctc taatgtttgt    12240
cttacttcac ctacagcgtt accactcgac acgcgtaacc atgcacctac tttttttaatt 12300
tcttctggtg cgtctctaaa caattccatt tggtttccag taatataata ttcacctggt   12360
gctgtaacgt aagcaatcca attattgtac tgacttgcct ccaaatattc ttggtatggt   12420
gcgtcctgttt tgatggttgt ccataaacca taatcccatt ttagcgtgaa cacgtctaac  12480
gtcataccac gcaccatttt aaccatttta cgacctgttg aaaaacgcgt taattcttgt    12540
actgtaccta atgtttgtgt tgtagggtat acattgatga aacaaccagc gtctataatt   12600
ttttttactac cattcattgg catattttta agttactag ctgtaccacc gtcaatataa   12660
tagaaccctg cttgtgttaa gtcattttaag tcgtcgatag ggtctggaat agataacgca  12720
cgtccatcgt cttttgttaa tttatagttt tgtgaacctc ttgcgcgtaa tgcttcaaaa   12780
tgttcatatt ctccaagttg gaaaaaacca tataaattat tgaatcgttt tccgccgccg   12840
ccatttgtca tagcaagtaa taaagattta cgttttgttt ttgggttagt ataaatacaa   12900
ataccctcag gctctttaaa gttatcacgt ggaaaattaa ttccgtcttg atatgataat   12960
ttaaacggat aatcataaat cttttttacct gttgttaatg aatatttacc tatttgaacg  13020
tgtgaattaa ctgaactgtt accacttagc cagtacaaat catctccgtc aactgcaatc   13080
ccttgcatcc aacggtcatc gttattctca gaattgtcaa ttgtcatttc tttttctaca   13140
ttatcaatgt gattttttac gtctgctctt gaacgtacct gtattgtccc gtcaccgaat   13200
cttaaaacga ttttgtcatt tgcttcatca attaacggtg taaatgtatg tttgtttaaa   13260
agtgactgtg gtgtataatc tgttaaacct ttagcctctt ctaaatctaa aacataatta   13320
tctttatatg caacttgtaa caattttgat acaccgtcat gatgtaaccaa tattttcatt  13380
tctccattag attgacgttc taatccgatt gttgtaccat gaccacccctg tacaatacgc   13440
atgctagaaa ttaagtcacc actaggcgtt aatttattta tccaaaatcc ttctggtttt   13500
tgtgagtcgg attgtgtaga gtacatgtga ttagtctctt tatcaatatt aatagattgg   13560
ttaacagcat tacgaatacc accaaagccc ataacaaact ttggttcaag ctcatttaat   13620
tcaaaccat taacgaaacg gtcaatatct tttattaagt ctttcacttc ttctttaaag    13680
tcattcattt gtttcatttc tgcaacttta aataaagcaa atgcagatgt taaaccagca   13740
ctatatttt taaactcatc atgaataata ctgtcaatcg taccgtcgtt taaccaacct   13800
ctgaataagt ctttcgcttg ctctggaaat gctttcatta agtcgtccca gtttctaaaa   13860
cgttttttta actaccgtc atagtcccaa atacgacgtg ctaatacttc aatgagtttt   13920
gataatcttg aaatataatc ataatacgat tttgaatttg tattataatc tgctcatca   13980
tcgtaaaacg gtgtataacg ttctctcgtt ttataaattt cgtctaaaaa tggacgaatg   14040
tcatcaaaat atttaaaatc gttttcatta tatccataaa ttttccacct ttaccaaatt   14100
tgtaaaaaac attttttatc aaattcattt aaaaattttct ttcttaaatc gtatacttta  14160
tcaatattat caattaaata ctgttttgaa aattgtgtac ctttcgcatt acctttttga   14220
ttttgattac gttttgcgtt ttgattactt tcgttacttg atttattgac ggatttaccg   14280
ttatcaatag tgttattgtc tgcaaattgt aacgttgttt tatctacatc aatgttaacc   14340
tcgctttgtg gtaatgacgc ataagcattt ctgtttgctg tcatacctgt tgaattgtct   14400
aatgaagtag cattttgatt tgacgtttca tcagtgttgc ttgttgtatc ttcattgtgt   14460
tctgtaaagc cttgtgattg tagatatttt tcaacttcgc ttgatgaata aaccacattc   14520
aaataatcct catgtgtgat acatacagta atcacttgca tgccaaaagc ttcaactgtt   14580
tgtctgttga tttctctatc taaaaagtgt attgtaaatg attttttaaa aagtaagtca   14640
gataagtcat ctttaagttt aaaaccttta aacacttttt cattaacgat ggctaaaacg   14700
tctttgtcaa acttcaacat tttttgcatg aattgaaatt catcatcata aaacgttaat   14760
ttatcattat ttacaaattc attaaaacct tttttaatta attctgattt aataaaatca   14820
aataaagtca ttgtatatct agccattgta ttcactactt tcatcattag acaatgtatc   14880
tatcattgtg atttctgaag taacttcatc gtcgtaaac ggtttaatat ctaaaccata   14940
acgttttgat aagaatgtaa tcggttcacg acctttaaa taaatattac tatttgatgt   15000
ggtaaaacct cggttgcttt ttgcctcttc gtccgaaacg ccgctttcct tatccactgc   15060
tagtgaatta ataccctaaat agttacttaa ttcactaatt ttattttggt attcgcgttt   15120
catctccagtt agtgctggaa tcacactatt actggttaaa tctataatat catcatcggc   15180
gttaaacata ggtgacattt taacaaatgg tgcaccgtta tatatttccg atacaagttg   15240
attaactgac tcatcattaa tgtctgattt aaatattttg ctaaattttg cttgcataat   15300
taatgaaaat cgagataaaa caaccctcaga taattcatca gtataatgtt ctatgatttc   15360
tatatcacta ttatattgaa ttggtttatt ttgcataaca acaaagttac cactcataca   15420
gttatcatat attttatgaa tctgtaagca ttcatctggt attaaatagt ctgggacaat   15480
gaaataaata tcatcttttg ttaatcgttt ttgaattgaa agttaaagt ttgatgaaaa    15540
atttggtgct tgattaaagt aagtattatt tacgtaacga agaatcataa tttgttcatt   15600
tcttgctttg ccaaccacta cattgatgtt ttgtcttaat gctgattcta attgaataaa   15660
atctatacca accgtatcac gattggtata gttgatgagt agtggtaaaa attccaaata   15720
acgattaaac ataagacgtt taatctgtt gcgatgttca acaactcttt tgttgatttc    15780
ttttgataat tcacctgta cgcctttatt atgtttagtc atttatagca cctctattat    15840
tctgttcttg atgttacatc ttggtcagta attaaaattt tattaaagaa tgggctaatg   15900
```

```
gctttaaatg aatagtaatg aatccagtgt gtgacttcat caaattcacc attatagaat  15960
ggttgtttta acataccttt tgtgtaacgt ttatatttaa ttgaattaat atccaaaata  16020
aacgcgtata aatctgattt tggtttaatt tcttcaacac tatctttaaa ctctgatagt  16080
tttgacacat cataagtgaa tactgaacca actggaattg tatcaccttt atgagtttga  16140
taatcaccat aagcacgcaa gaaagctact gaatcatcac ttgaaacgac aatgtcttta  16200
gtaactttaa acacaccacc taaatcatca aaactaatga cgtggtctgt gaaatcaatt  16260
ccagcaattt ggaaggtatt cgcaatcttt gtatctaaaa gataagattt taatgaatct  16320
gttgttaaaa tcacaatatc ttttaatttt gagactgttg tatattgtcc aatagcacca  16380
cctgaagcac gatgaacttc attatattta gcactgttgt tttgtaagtt aagaatagct  16440
tcaaaaactt tacttgctaa atcctctttt gatgttgctt tacgtacatt tgattcagat  16500
aattgattca atgagtaatc aactaacatt gcacgcattt cttttttcttc taatacgtta  16560
atatcagaaa ttttctttt atagacacct aatgcataat tagttgcgtc tgctaatgtt  16620
tggaaattga aacgtgtatc attgttattt aatgtgaatt tttgtttctt cacaatacca  16680
ctaccatata acttagttgc catacgtgga taattacgtt ttaacattaa ttcttcattt  16740
ttagataaat ccatgttaat aggtactgta tccataatta catattcttc actgtattga  16800
cctataaagt cctgctcttt agctaaccaa ttaaaacgat tacctaatgc aatatcgatt  16860
aataacgttt cattaatctt agggaataaa aatttattta caaatgtttc aaacattgta  16920
ttagaattat cccacttatc gccaaacgtc catgattttg aataagtatg attaaagtct  16980
tgtaatgcag atttagctga ctgtgcaact aatagtgctg tttcgttttt tgtactcttt  17040
tctgccatga tttattattc ctcctctaca tcgccagtaa atgactgttt tgaaagtgaa  17100
tgaatttgta caccataact atcttcactt ttatttgtat caattgacat attttcattt  17160
aattctgttc gtttatttaa tcttgaatct tcatatgatg tacccatcat agaacgcata  17220
ttgttaccct catacatgtt taaattcctc ctaatctaaa tctaacttat cgactaattc  17280
ttcatctgaa tagtctttat cattatcatc tggttcagta acatctggtt gtgtttgttg  17340
tacttgttgc gattgttgca tttgtgaaga taaaaaagta gtcacttgtt gttctaatga  17400
agcaatacgt tgttctaata caacagggtc aaatttcgaa ctatcttcat ctgttgtagt  17460
aggttctaat ttgtttttcat tttcttcttc gattgtttct actgttttat cttcagttga  17520
ttcttcagtt gattcttcag ttgattcttc agttgattct tcagttgatt cttcagttga  17580
ttctttgtcg tctggtttta cgatttcatc aaattctgtc atttagaca              17629
```